(12) United States Patent
Tendulkar et al.

(10) Patent No.: US 12,257,064 B2
(45) Date of Patent: Mar. 25, 2025

(54) PERSONALIZED SKIN CARE FROM SKIN SCANNING

(71) Applicant: Sephora USA, Inc., San Francisco, CA (US)

(72) Inventors: Prasad Tendulkar, Foster City, CA (US); Nelly Mensah, San Francisco, CA (US); Anna Teresa Nicholas, Hazelton, PA (US); Jillian Bertone, Lafayette, CA (US); Lisa Zhu, Belmont, CA (US); Jennifer Stokes, Seattle, WA (US); Witono Liujanto, San Ramon, CA (US); Aaron Oelckers, Pleasant Hill, CA (US); Marc McCotter, Hana, HI (US); Harsha Haddar, Livermore, CA (US); Fiona Kavanagh, San Francisco, CA (US); Amit Adiraju, Santa Clara, CA (US); Naroju Janardhan, San Ramon, CA (US)

(73) Assignee: Sephora USA, Inc., San Francisco, CA (US)

( * ) Notice: Subject to any disclaimer, the term of this patent is extended or adjusted under 35 U.S.C. 154(b) by 278 days.

(21) Appl. No.: 17/931,111

(22) Filed: Sep. 9, 2022

(65) Prior Publication Data
US 2023/0120602 A1  Apr. 20, 2023

Related U.S. Application Data

(60) Provisional application No. 63/261,060, filed on Sep. 9, 2021.

(51) Int. Cl.
*G06V 10/00* (2022.01)
*A45D 44/00* (2006.01)
(Continued)

(52) U.S. Cl.
CPC ............ *A61B 5/441* (2013.01); *A45D 44/005* (2013.01); *A61B 5/0064* (2013.01); *A61B 5/442* (2013.01);
(Continued)

(58) Field of Classification Search
CPC ............ G06N 3/08; G06N 3/02; G06N 3/042; G06N 3/045; G06N 3/047; G06N 3/049;
(Continued)

(56) References Cited

U.S. PATENT DOCUMENTS

| 4,648,718 A | 3/1987 | Sadamitsu et al. |
| 4,989,079 A | 1/1991 | Ito |

(Continued)

FOREIGN PATENT DOCUMENTS

| WO | 2012/065037 A1 | 5/2012 |
| WO | 2015/126988 A1 | 8/2015 |
| WO | 2017/181293 A1 | 10/2017 |

OTHER PUBLICATIONS

Alexander, Antoinette, "Virtual Mirror Kiosks Make Beauty Shopping 'EZ'," 2009, Drug Store News, Feb. 9, 2009; vol. 31, No. 2, 66 pages.

(Continued)

*Primary Examiner* — Amir Alavi
(74) *Attorney, Agent, or Firm* — Aka Chan LLP

(57) ABSTRACT

Various techniques pertain to a user interface that includes an instructional display portion comprising one or more textual or graphical instructions pertaining to preparing for a body scan for body care of a client and a scan initiation display portion that includes a scan initiation widget which, when interacted by the client, invokes execution of a scan process and an analysis process for a respective body area of the client. The user interface further includes a scan result display portion including interactable textual or graphical (Continued)

information pertaining to a result of the body scan for the body care and an adjustment display portion having a plurality of adjustment widgets that transform at least a color index or value into a transformed color index or value in a L*A*B* color space or a Lch color space.

20 Claims, 72 Drawing Sheets

(51) Int. Cl.
*A61B 5/00* (2006.01)
*G06Q 30/0601* (2023.01)
*G06T 7/00* (2017.01)
*G06T 7/90* (2017.01)
*G06V 10/26* (2022.01)
*G06V 10/56* (2022.01)
*G06V 10/764* (2022.01)
*G06V 10/774* (2022.01)
*G06V 10/776* (2022.01)
*G06V 10/82* (2022.01)
*G06V 40/10* (2022.01)
*G06Q 30/01* (2023.01)

(52) U.S. Cl.
CPC ..... *G06Q 30/0621* (2013.01); *G06Q 30/0631* (2013.01); *G06Q 30/0633* (2013.01); *G06T 7/0012* (2013.01); *G06T 7/90* (2017.01); *G06V 10/26* (2022.01); *G06V 10/56* (2022.01); *G06V 10/764* (2022.01); *G06V 10/774* (2022.01); *G06V 10/776* (2022.01); *G06V 10/82* (2022.01); *G06V 40/10* (2022.01); *A45D 2044/007* (2013.01); *G06Q 30/01* (2013.01); *G06Q 30/0641* (2013.01); *G06T 2200/24* (2013.01); *G06T 2207/20081* (2013.01); *G06T 2207/30088* (2013.01); *G06T 2207/30201* (2013.01)

(58) Field of Classification Search
CPC ...... G06N 3/082; G06N 3/092; G06N 3/0475; G06N 3/0454; G06N 3/0464; G06V 10/26; G06V 10/56; G06V 10/774; G06V 10/776; G06V 10/764; G06V 40/10; G06T 7/90; G06T 7/0012; G06T 2200/24; G06T 2207/2008; G06T 2207/3021; G06T 2207/30088; A61B 5/441; A61B 5/442; A45D 44/005; G06Q 30/01; G06Q 30/0621; G06Q 30/0631; G06Q 30/0633; G06Q 30/0641
See application file for complete search history.

(56) References Cited

U.S. PATENT DOCUMENTS

| | | | |
|---|---|---|---|
| 5,483,339 A | 1/1996 | Van Aken et al. | |
| 6,437,866 B1 | 8/2002 | Flynn | |
| 6,522,977 B2 | 2/2003 | Corrigan et al. | |
| 6,603,550 B1 | 8/2003 | Flynn et al. | |
| 6,908,608 B1* | 6/2005 | Huglin | C11D 3/28 424/59 |
| 7,180,524 B1 | 2/2007 | Axelrod | |
| 7,285,264 B2* | 10/2007 | O'Brien | A61K 8/64 514/20.7 |
| 7,648,364 B2* | 1/2010 | Dauga | A45D 44/005 601/17 |
| 7,738,032 B2 | 6/2010 | Kollias et al. | |
| 8,182,091 B2 | 5/2012 | Foster | |
| 8,252,847 B2* | 8/2012 | Veeger | A61K 8/37 514/937 |
| 8,564,778 B1 | 10/2013 | Igarashi | |
| 8,673,879 B2* | 3/2014 | Thoerner | A61K 8/733 514/54 |
| 8,784,853 B2* | 7/2014 | Wagner | C07C 69/757 568/717 |
| 9,019,296 B1 | 4/2015 | Abraham | |
| 9,064,279 B1 | 6/2015 | Tuan et al. | |
| 9,519,927 B1 | 12/2016 | Tuan et al. | |
| 10,045,820 B2 | 8/2018 | Youngquist et al. | |
| 10,387,937 B1 | 8/2019 | Tuan et al. | |
| 10,825,567 B1* | 11/2020 | Wala | G16H 10/60 |
| 11,154,878 B2* | 10/2021 | Luo | B05B 15/00 |
| 11,547,219 B2* | 1/2023 | Park | G06N 20/00 |
| 11,948,668 B2* | 4/2024 | Burger | G16H 80/00 |
| 2002/0036778 A1 | 3/2002 | Wagner et al. | |
| 2002/0059248 A1 | 5/2002 | Farchione | |
| 2002/0062263 A1 | 5/2002 | Katou | |
| 2002/0065452 A1 | 5/2002 | Bazin et al. | |
| 2003/0058261 A1 | 3/2003 | Challa et al. | |
| 2003/0065578 A1 | 4/2003 | Peyrelevade et al. | |
| 2003/0065636 A1 | 4/2003 | Peyrelevade | |
| 2003/0149504 A1 | 8/2003 | Iwaki et al. | |
| 2003/0151611 A1 | 8/2003 | Turpin et al. | |
| 2003/0235544 A1 | 12/2003 | Kishida et al. | |
| 2004/0010333 A1 | 1/2004 | Baker | |
| 2005/0146531 A1 | 7/2005 | Rice et al. | |
| 2006/0022994 A1 | 2/2006 | Hussie | |
| 2006/0066629 A1 | 3/2006 | Norlander et al. | |
| 2006/0095297 A1 | 5/2006 | Virik | |
| 2006/0178904 A1 | 8/2006 | Aghassian et al. | |
| 2006/0179045 A1 | 8/2006 | Grinsfelder et al. | |
| 2006/0253176 A1 | 11/2006 | Caruso | |
| 2007/0058860 A1 | 3/2007 | Harville et al. | |
| 2007/0071314 A1 | 3/2007 | Bhatti et al. | |
| 2008/0003547 A1 | 1/2008 | Woolfe et al. | |
| 2008/0046410 A1 | 2/2008 | Lieb | |
| 2008/0079843 A1 | 4/2008 | Pote et al. | |
| 2008/0194928 A1 | 8/2008 | Bandic et al. | |
| 2008/0281728 A1 | 11/2008 | Gomez | |
| 2008/0311061 A1 | 12/2008 | Heuer | |
| 2010/0020095 A1 | 1/2010 | Reynolds et al. | |
| 2010/0183528 A1 | 7/2010 | Maloney et al. | |
| 2010/0185064 A1 | 7/2010 | Bandic et al. | |
| 2010/0322878 A1 | 12/2010 | Stella et al. | |
| 2011/0093361 A1 | 4/2011 | Morales | |
| 2011/0106650 A1 | 5/2011 | Stone | |
| 2011/0184837 A1 | 7/2011 | Biro | |
| 2011/0246284 A1 | 10/2011 | Chaikin et al. | |
| 2012/0045121 A1 | 2/2012 | Youngman et al. | |
| 2012/0096380 A1 | 4/2012 | Wagner | |
| 2012/0123759 A1 | 5/2012 | Cho et al. | |
| 2012/0203668 A1 | 8/2012 | Howard et al. | |
| 2012/0253224 A1 | 10/2012 | Mir et al. | |
| 2012/0269743 A1 | 10/2012 | Smith et al. | |
| 2013/0092805 A1 | 4/2013 | Funk et al. | |
| 2013/0117137 A1 | 5/2013 | Klein et al. | |
| 2013/0177137 A1 | 7/2013 | Eichhorn et al. | |
| 2013/0250322 A1 | 9/2013 | Kawabata et al. | |
| 2013/0300761 A1 | 11/2013 | Ahmed | |
| 2014/0323873 A1 | 10/2014 | Cummins et al. | |
| 2015/0356661 A1 | 12/2015 | Rousay | |
| 2019/0038211 A1 | 2/2019 | Rattner | |
| 2019/0125249 A1 | 5/2019 | Rattner et al. | |
| 2019/0318505 A1 | 10/2019 | LaSalle et al. | |
| 2020/0043053 A1* | 2/2020 | Jeon | A61B 5/0077 |
| 2020/0226657 A1 | 7/2020 | Ji et al. | |
| 2022/0138972 A1 | 5/2022 | Rattner et al. | |
| 2023/0074782 A1* | 3/2023 | Tendulkar | G06V 10/56 |

OTHER PUBLICATIONS

Weisstein, Eric W., "Subset," MATHWORLD, retrieved from http://mathworld.wolfram.com/Subset.html, dated May 16, 2013, retrieved from the Internet Archive on Jul. 12, 2015, 1 page.

Hastie, Trevor, et al., "The Elements of Statistical Learning Data Mining, Inference, and Prediction," Springer Series in Statistics, 2nd ed., Chapters 14.3-14.6 and 16, Jan. 13, 2017, retrieved from

(56) References Cited

OTHER PUBLICATIONS https://hastie.su.domains/ElemStatLearn/printings/ESLII_print12.pdf, 78 pages.

Goodfellow, Ian, et al., "Deep Learning," MIT Press book, 2016, Part I, Chapters 7 and 10, Part III, Chapters 14 and 20, retrieved from https://www.deeplearningbook.org/ 196 pages.

PCT International Search Report and the Written Opinion of the International Searching Authority for International Application PCT/US2022/043155 dated Mar. 26, 2023, 14 pgs.

Molnar, Christoph, "Interpretable Machine Learning—A Guide for Making Black Box Models Explainable," Aug. 26, 2021, Chapters 4.1 and 5, retrieved from https://web.archive.org/web/20210828033303/https://christophm.github.io/interpretable-ml-book/, 27 pages.

* cited by examiner

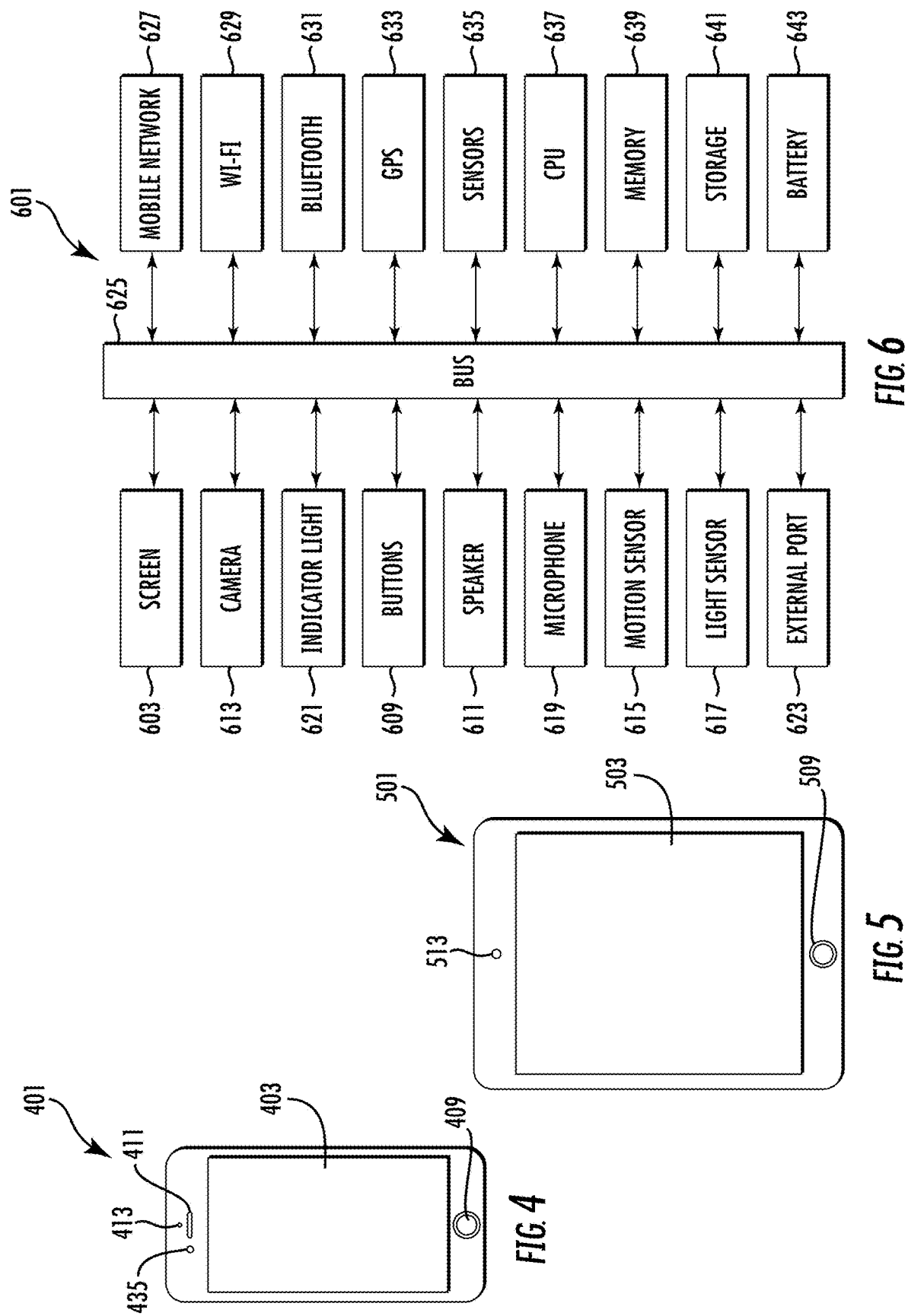

| VARIABLE | VALUE | DESCRIPTION | UPDATED |
|---|---|---|---|
| lOFFSET | 19.5 | STARTING POINT OFFSET FOR L | |
| lSEGMENTSIZE | 7.5 | DISTANCE OF L PER SEGMENT | |
| lSUBSEGMENTSIZE | 2.5 | DISTANCE OF L PER SUBSEGMENT | |
| lSEGMENTSMAX | 9 | MAXIMUM L SEGMENTS | |
| lSEGMENTGROUPING | [0,0,0,1,1,1,2,2,2] | LINK DEPTH SEGMENTS TO | |
| cOFFSET | [6,6,6] | STARTING POINT OFFSET FOR C | |
| cSEGMENTSIZE | [12,12,12] | DISTANCE OF C PER SEGMENT | |
| cSEGMENTSMAX | 3 | MAXIMUM C SEGMENTS | |
| hOFFSET | [39,39,39] | STARTING POINT OFFSET OF H | |
| hSEGMENTSIZE | [5,5,5] | DISTANCE OF H PER SEGMENT | |

FIG. 12A

| SEGMENT | ENGLISH | FRENCH | RANGE |
|---|---|---|---|
| 1 | DEEP | | L < 27 |
| 2 | DARK | | 27 ≤ L < 34.5 |
| 3 | TAN | | 34.5 ≤ L < 42 |
| 4 | MEDIUM DARK | | 42 ≤ L < 49.5 |
| 5 | MEDIUM | | 49.5 ≤ L < 57 |
| 6 | LIGHT MEDIUM | | 57 ≤ L < 64.5 |
| 7 | LIGHT | | 64.5 ≤ L < 72 |
| 8 | FAIR | | 72 ≤ L < 79.5 |
| 9 | VERY FAIR | | 79.5 ≤ L |

| hGROUP | H RANGE | ADD'TL INFO |
|---|---|---|
| 1 | H < 44 | HIGH PINK |
| 2 | 44 ≤ H < 49 | MEDIUM PINK |
| 3 | 49 ≤ H < 54 | LOW PINK |
| 4 | 54 ≤ H < 59 | NEUTRAL |
| 5 | 59 ≤ H < 64 | LOW YELLOW |
| 6 | 64 ≤ H < 69 | MEDIUM YELLOW |
| 7 | 69 ≤ H | HIGH YELLOW |

FIG. 13E

| cSEGMENT | hSEGMENT | ENGLISH | FRENCH |
|---|---|---|---|
| 1 | 1 | COOL 3 - INTENSITY 1 | COOL 3 - INTENSITY 1 |
| 1 | 2 | COOL 2 - INTENSITY 1 | COOL 2 - INTENSITY 1 |
| 1 | 3 | COOL 1 - INTENSITY 1 | COOL 1 - INTENSITY 1 |
| 1 | 4 | NEUTRAL - INTENSITY 1 | NEUTRAL - INTENSITY 1 |
| 1 | 5 | WARM 1 - INTENSITY 1 | WARM 1 - INTENSITY 1 |
| 1 | 6 | WARM 2 - INTENSITY 1 | WARM 2 - INTENSITY 1 |
| 1 | 7 | WARM 3 - INTENSITY 1 | WARM 3 - INTENSITY 1 |
| 2 | 1 | COOL 3 - INTENSITY 2 | COOL 3 - INTENSITY 2 |
| 2 | 2 | COOL 2 - INTENSITY 2 | COOL 2 - INTENSITY 2 |
| 2 | 3 | COOL 1 - INTENSITY 2 | COOL 1 - INTENSITY 2 |
| 2 | 4 | NEUTRAL - INTENSITY 2 | NEUTRAL - INTENSITY 2 |
| 2 | 5 | WARM 1 - INTENSITY 2 | WARM 1 - INTENSITY 2 |
| 2 | 6 | WARM 2 - INTENSITY 2 | WARM 2 - INTENSITY 2 |
| 2 | 7 | WARM 3 - INTENSITY 2 | WARM 3 - INTENSITY 2 |
| 3 | 1 | COL 3 - INTENSITY 3 | COL 3 - INTENSITY 3 |
| 3 | 2 | COL 2 - INTENSITY 3 | COL 2 - INTENSITY 3 |
| 3 | 3 | COL 1 - INTENSITY 3 | COL 1 - INTENSITY 3 |
| 3 | 4 | NEUTRAL - INTENSITY 3 | NEUTRAL - INTENSITY 3 |
| 3 | 5 | WARM 1 - INTENSITY 3 | WARM 1 - INTENSITY 3 |
| 3 | 6 | WARM 2 - INTENSITY 3 | WARM 2 - INTENSITY 3 |
| 3 | 7 | WARM 3 - INTENSITY 3 | WARM 3 - INTENSITY 3 |

| cSEGMENT | hSEGMENT | ENGLISH | FRENCH |
|---|---|---|---|
| 1 | 1 | COOL BLUE 3 | |
| 1 | 2 | COOL BLUE 2 | |
| 1 | 3 | COOL BLUE 1 | |
| 1 | 4 | NEUTRAL OLIVE | |
| 1 | 5 | WARM OLIVE 1 | |
| 1 | 6 | WARM OLIVE 2 | |
| 1 | 7 | WARM OLIVE 3 | |
| 2 | 1 | COOL 3 | |
| 2 | 2 | COOL 2 | |
| 2 | 3 | COOL 1 | |
| 2 | 4 | NEUTRAL | |
| 2 | 5 | WARM 1 | |
| 2 | 6 | WARM 2 | |
| 2 | 7 | WARM 3 | |
| 3 | 1 | COOL RED 3 | |
| 3 | 2 | COOL RED 2 | |
| 3 | 3 | COOL RED 1 | |
| 3 | 4 | NEUTRAL BRONZE | |
| 3 | 5 | WARM GOLDEN 1 | |
| 3 | 6 | WARM GOLDEN 2 | |
| 3 | 7 | WARM GOLDEN 3 | |

1304G

| cSEGMENT | hSEGMENT | ENGLISH | FRENCH |
|---|---|---|---|
| 1 | 1 | COOL OLIVE 3 | |
| 1 | 2 | COOL OLIVE 2 | |
| 1 | 3 | COOL OLIVE 1 | |
| 1 | 4 | NEUTRAL OLIVE | |
| 1 | 5 | WARM OLIVE 1 | |
| 1 | 6 | WARM OLIVE 2 | |
| 1 | 7 | WARM OLIVE 3 | |
| 2 | 1 | COOL 3 | |
| 2 | 2 | COOL 2 | |
| 2 | 3 | COOL 1 | |
| 2 | 4 | NEUTRAL | |
| 2 | 5 | WARM 1 | |
| 2 | 6 | WARM 2 | |
| 2 | 7 | WARM 3 | |
| 3 | 1 | COOL ROSEY 3 | |
| 3 | 2 | COOL ROSEY 2 | |
| 3 | 3 | COOL ROSEY 1 | |
| 3 | 4 | NEUTRAL PEACH | |
| 3 | 5 | WARM GOLDEN 1 | |
| 3 | 6 | WARM GOLDEN 2 | |
| 3 | 7 | WARM GOLDEN 3 | |

| cSEGMENT | hSEGMENT | ENGLISH | FRENCH |
|---|---|---|---|
| 1 | 1 | COOL BEIGE 3 | |
| 1 | 2 | COOL BEIGE 2 | |
| 1 | 3 | COOL BEIGE 1 | |
| 1 | 4 | NEUTRAL BEIGE | |
| 1 | 5 | WARM OLIVE 1 | |
| 1 | 6 | WARM OLIVE 2 | |
| 1 | 7 | WARM OLIVE 3 | |
| 2 | 1 | COOL 3 | |
| 2 | 2 | COOL 2 | |
| 2 | 3 | COOL 1 | |
| 2 | 4 | NEUTRAL | |
| 2 | 5 | WARM 1 | |
| 2 | 6 | WARM 2 | |
| 2 | 7 | WARM 3 | |
| 3 | 1 | COOL PINK 3 | |
| 3 | 2 | COOL PINK 2 | |
| 3 | 3 | COOL PINK Y 1 | |
| 3 | 4 | NEUTRAL PEACH | |
| 3 | 5 | WARM YELLOW 1 | |
| 3 | 6 | WARM YELLOW 2 | |
| 3 | 7 | WARM YELLOW 3 | |

FIG. 13H

SKINCARE CONSULTATION ✕

6 OF 7

WHICH OF THE FOLLOWING BEST DESCRIBE YOUR RACE OR ETHNICITY? (SELECT ALL THAT APPLY)

- CAUCASIAN / WHITE
- AFRICAN AMERICAN / BLACK
- EAST ASIAN
- SOUTH ASIAN / INDIAN
- MIDDLE EASTERN
- PACIFIC ISLANDER
- NATIVE AMERICAN / AMERICAN INDIAN
- OTHER / PREFER NOT TO SAY

BACK | NEXT

FIG. 14G

SKINCARE CONSULTATION ✕

7 OF 7

PLEASE SELECT AT LEAST 2 OF YOUR FAVORITE FOUNDATION BRANDS THAT ARE SOLD AT SEPHORA.

FOUNDATION #1

| BRAND | |
|---|---|
| SELECT BRAND | ▽ |

| PRODUCT NAME | |
|---|---|
| SELECT PRODUCT NAME | ▽ |

| SHADE | |
|---|---|
| SELECT SHADE | ▽ |

FOUNDATION #2

| BRAND | |
|---|---|
| SELECT BRAND | ▽ |

| PRODUCT NAME | |
|---|---|
| SELECT PRODUCT NAME | ▽ |

| SHADE | |
|---|---|
| SELECT SHADE | ▽ |

FOUNDATION #3 (OPTIONAL)

| BRAND | |
|---|---|
| SELECT BRAND | ▽ |

| PRODUCT NAME | |
|---|---|
| SELECT PRODUCT NAME | ▽ |

| SHADE | |
|---|---|
| SELECT SHADE | ▽ |

[ BACK ]   [ NEXT ]

*FIG. 14H*

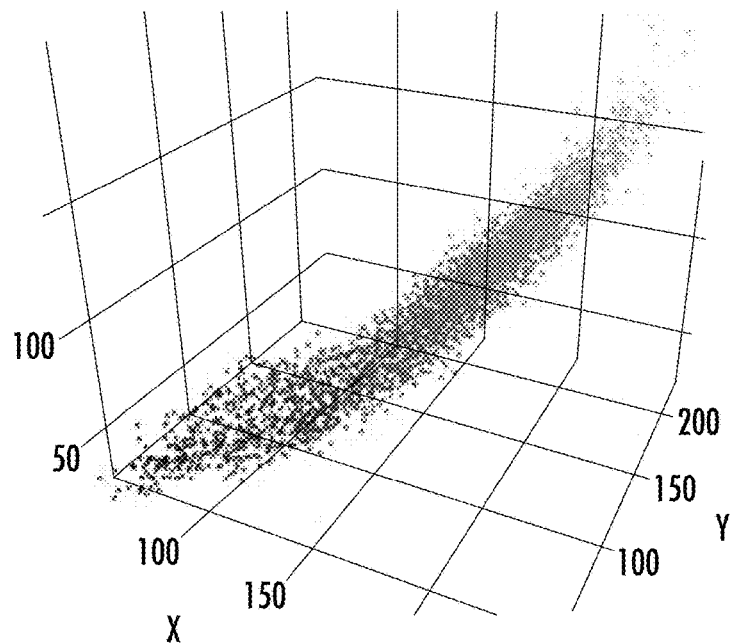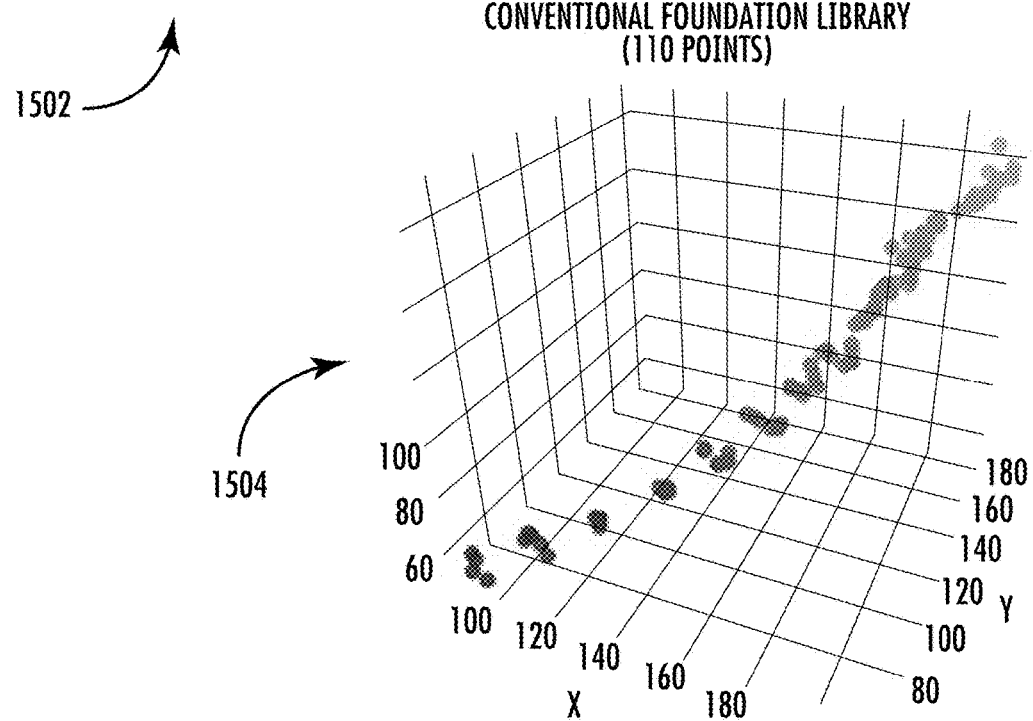
FIG. 15B

PERSONALIZED SKIN CARE FROM SKIN SCANNING

CROSS-REFERENCE TO RELATED APPLICATIONS

This patent application claims the benefit of U.S. patent application 63/261,060, filed Sep. 9, 2021. This application is incorporated by reference along with all other references cited in this application.

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

BACKGROUND OF THE INVENTION

This invention relates to cosmetics and more specifically, to techniques for selecting one or more cosmetic products based on the individual requirements of a specific user.

For people in the market for cosmetic products, the process can be daunting. Cosmetic products are intensely personal, since the right or wrong choices may have dramatic impacts on the outward appearance of a person. This makes it important for customers to select cosmetic products that are suitable for themselves.

However, although selecting cosmetic products may be of importance, there are many roadblocks in selecting the right products. The process goes beyond matching a customer's skin tone with what color a product looks like when it leaves a manufacturer, how a color appears before it is applied on skin, or what a color was intended by the manufacturer when creating the cosmetic product. Additional factors that influence whether a cosmetic product is suitable include how a product looks in natural light, after the product oxidized on the skin, and many other factors.

Further, the problem in finding suitable cosmetic products is even more difficult for customers who have been traditionally underserved by the cosmetic industry, such as those with certain skin types, skin colors, or skin conditions. For example, certain minority groups may have a smaller set of suitable cosmetic products, even when considering their purchasing potential in the cosmetic product marketplace.

Although manufacturers have made substantial efforts in expanding their cosmetic product portfolios to be more inclusive, since these cosmetic products may be newer or target smaller sets of customers, outreach remains difficult. Without the proper outreach, customers may never become aware of suitable products, and it is difficult to find an advisor or expert who may understand all the options available.

Also, because of the difficulty in selecting cosmetic products, retailers of cosmetic products face a particularly difficult set of challenges. A retailer may have problems with customer loyalty, when the customer has a bad experience with the retailer because they were unable to find a suitable product or purchased a product that was not suitable for them. Further, since most cosmetic retailers have generous refund policies, refunds from unsatisfied customers have a large impact on a cosmetic retailer's finances in dealing with returned merchandise.

Therefore, there is a need for a better method to determine what cosmetics are best suited for a person.

BRIEF SUMMARY OF THE INVENTION

A cosmetic matching system allows people to more easily find cosmetic products that are suitable to them. The cosmetic matching system includes a wide variety of cosmetic products that may be suitable for a customer indexed by an extensive color space. The cosmetic matching system may use color measurements taken by a scanning device of a customer in determining which cosmetic products are suitable.

A skin care product matching system allows people to more easily find skin care products that are suitable to them. The skin care product matching system includes a wide variety of skin care products that may be suitable for a customer indexed according to skin condition and skin health, which can include, for example, skin type, oiliness or oil balance, fine lines or wrinkles, or hydration, or a combination. The skin care product matching system uses skin measurements (e.g., pore size, size or number of wrinkles or lines, and moisture level, or others, or a combination) taken by a scanning device of a customer to determine which skin care products are suitable. This system can improve the health and appearance of the skin.

An embodiment of the cosmetic matching system includes Sephora's new Color iQ or Mobile Color IQ (MCIQ) technology which helps customers find their perfect foundation, concealer, pressed powder, or tinted moisturizer. It takes into account three attributes of color: depth, undertone, and saturation-versus the industry standard, which currently only consists of depth and undertone, not saturation. The MCIQ increases conversions and results in sixty-three percent of customer purchasing a product (as opposed to an average of forty-eight percent in-store conversion). The MCIQ increases purchase amounts by customers who try the cosmetic matching system and reduce the number of returns of products. When clients purchased a product after an MCIQ session with a scan and product added to list, returns reduced from fourteen percent to around ten percent.

Scanning a person's skin allows one to more easily find products that match their skin tone and skin condition. A skin scan can assist one to determine what products are appropriate for them and then purchase them from a retailer. A scanning device is used to scan one or more locations of a person's skin. For example, two different locations of a person's face can be scanned, such as the forehead and cheek. An additional third scan may be near the person's eyes. The scan determines skin tone and skin condition results for the person's skin. These results can be used to determine and present a listing of products that are appropriate for the person's skin tone and skin condition.

Skin condition scanning allows one to more easily find products that match the condition of their skin. Based on a skin condition scan, a person can view products appropriate for their skin condition such as skin type, oiliness or oil balance, fine lines or wrinkles, or hydration, of a combination. A scanning device is used to scan two or more locations of a person's skin. For example, three different locations of the face can be scanned, such as the forehead and check and near the eyes. The scan determines a skin condition result for the person's skin.

Scanning a person's skin allows one to more easily find products that match their skin tone. Cosmetic products are organized or classified using a three-dimensional skin tone color space. A skin scan determines a person's skin tone in the same skin tone color space. This allows customers to determine which products are appropriate for their skin tone that they can purchase form a retailer. A scanning device is used to scan one or more locations of a person's skin to obtain a skin tone identifier. For example, two different locations of a person's face can be scanned, such as the forehead and cheek. There may be an additional third scan. The scan determines a skin tone result in the skin tone color space.

Various techniques pertain to a user interface that includes an instructional display portion including one or more textual or graphical instructions pertaining to preparing for a body scan for body care of a client and a scan initiation display portion that includes a scan initiation widget which, when interacted by the client, invokes execution of a scan process and an analysis process for a respective body area of the client. The user interface further includes a scan result display portion including interactable textual or graphical information pertaining to a result of the body scan for the body care and an adjustment display portion having a plurality of adjustment widgets that transform at least a color index or value into a transformed color index or value in a L*A*B* color space or a Lch color space.

The CIELAB color space, also referred to as L*a*b*, is a color space defined by the International Commission on Illumination (abbreviated CIE) in 1976. It expresses color as three values: L* for perceptual lightness, and a and b* for the four unique colors of human vision: red, green, blue, and yellow. HCL (Hue-Chroma-Luminance) or LCh refers to any of many cylindrical color space models that are designed to accord with human perception of color with the three parameters. Lch has been adopted by information visualization practitioners to present data without the bias implicit in using varying saturation. They are, in general, designed to have characteristics of both cylindrical translations of the RGB color space, such as HSL and HSV, and the L*a*b* color space.

Various techniques pertain to a system having multiple mobile computing devices that includes a unified front end computing device and a mobile computing device of a client, a first artificial intelligence model operatively coupled to the multiple mobile computing devices and predicting a predicted body characteristic of a part of a body of the client for providing body care to the client, a second artificial intelligence model operatively coupled to the multiple mobile computing devices and predicting a list of products or services for the body care at least by executing a recommendation service on the list of products or services, and a data lake that is integrated with multiple application programming interfaces across multiple computing nodes and stores multiple types of data for predicting the list of products or services by the first artificial intelligence model and for predicting the personalized recommendation by the second artificial intelligence model.

Various techniques for predicting a matching product and recommendation for a body characteristic of a client receive an input pertaining to a body complexion characteristic of a client at a computing system and predict, by a first artificial intelligence model, a body complexion index via executing an extraction task on at least the input to obtain an extraction result and executing a classification task on the extract result. These techniques further predict, by at least a second artificial intelligence model, a list of products or services at least by executing a recommendation service based at least in part upon the body complexion index for the client. Information pertaining to the list of products or services may then be displayed in a user interface of the computing system.

Various techniques predict body complexion characteristics at least by predicting one or more objects in a plurality of first inputs via executing an object extractor. These techniques receive and classify the one or more objects into one or more respective classes, where a class of the one or more respective classes corresponds to a color index or value in a L*A*B* color space or a Lch color space. A body complexion index or value may be predicted for the at least one subject area based at least in part upon the class, where the body complexion index or value represents a body complexion characteristic of the at least one subject area. Textual and graphical information pertaining to the body complexion index or value may then be presented in a user interface of the mobile computing device that captured at least some of the plurality of first inputs.

Various techniques identify multiple objects that includes multiple user objects, multiple product or service objects, and multiple relationship objects. Textual embeddings, visual embeddings, and relationship embeddings may be determined for the plurality of objects. Based at least in part upon the textual embeddings, the visual embeddings, and the relationship embeddings, a plurality of product or service latent representations may be determined. A plurality of user latent representations may be determined for the plurality of user objects. A personalized, ranked recommendation may be predicted for the client based at least in part upon ranking measures pertaining to at least the aforementioned latent representations where the personalized, ranked recommendation includes information pertaining to one or more recommended body care products or services from the plurality of products or service for the client.

A kiosk system for predicting a body characteristic of a client and recommending products or services to the client includes a banner or signage describing information pertaining to determination of body shades for body care products or services to clients and a mobile computing device having one or more sensors that capture data from the body of a client and transmit the data as a data stream to the processor that processes the data for display on the display. The memory of the mobile computing device stores a sequence of instructions whose execution causes the performance of several acts including invoking execution of a first artificial intelligence model that predicts a body complexion index, invoking execution of a second artificial intelligence model that predicts a list of products or services, and displaying, in the user interface of the mobile computing device, information pertaining to the list of products or services.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIGS. 4-5 show examples of mobile devices, which may be mobile clients.

FIG. 6 shows a system block diagram of mobile device.

FIG. 12A illustrates some example configuration variables as well as their respective values and descriptions for a system for cosmetic product matching and recommendation in one or more embodiments.

FIG. 13E illustrates an example hue table that may be utilized in a method or system for cosmetic product matching and recommendation in one or more embodiments.

FIG. 13F illustrates an example undertone table that may be utilized in a method or system for cosmetic product matching and recommendation in one or more embodiments.

FIGS. 13G-13H illustrate three example undertone table that may be jointly utilized in a method or system for cosmetic product matching and recommendation in one or more other embodiments.

FIG. 14G illustrates an example user interface for a client interview process to collect various pieces of data or information that may be utilized in subsequent product matching and recommendation service or services in one or more embodiments.

FIG. 14H illustrates an example user interface for a client interview process to collect various pieces of data or information that may be utilized in subsequent product matching and recommendation service or services in one or more embodiments.

FIG. 14O illustrates an example user interface screen that includes textual and/or graphical information and/or instructions to guide a client to more correctly place a scanning device for a second particular area of a client's skin and/or how to perform the scan for the second particular area with a scanning device for the selected skin scan in one or more embodiments.

FIG. 14AA illustrates another example user interface screen showing the results of a skin guide scan session in one or more embodiments.

FIG. 14AB illustrates another example user interface screen showing the results of a skin guide scan session in one or more embodiments.

FIG. 14AC illustrates another example user interface screen showing the results of a skin guide scan session in one or more embodiments.

FIG. 14AD illustrates another example user interface screen showing the results of a skin guide scan session in one or more embodiments.

FIGS. 14AE and 14AF respectively illustrate summary screens of a skin guide scan session in an example user interface in one or more embodiments.

FIG. 15B illustrates an example comparison between a new foundation library utilized in one or more embodiments described herein and a conventional, industry-standard foundation library.

DETAILED DESCRIPTION OF THE INVENTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computer systems, server computers, or communications networks, or a combination. have not been shown or described in detail to avoid unnecessarily obscuring descriptions of the embodiments.

It shall be noted that, unless the context requires otherwise, throughout the specification and claims which follow, the word "comprise" and variations thereof, such as, "comprises" and "comprising" are to be construed in an open, inclusive sense, that is as "including, but not limited to."

It shall be further noted that Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Furthermore, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Figure 1:
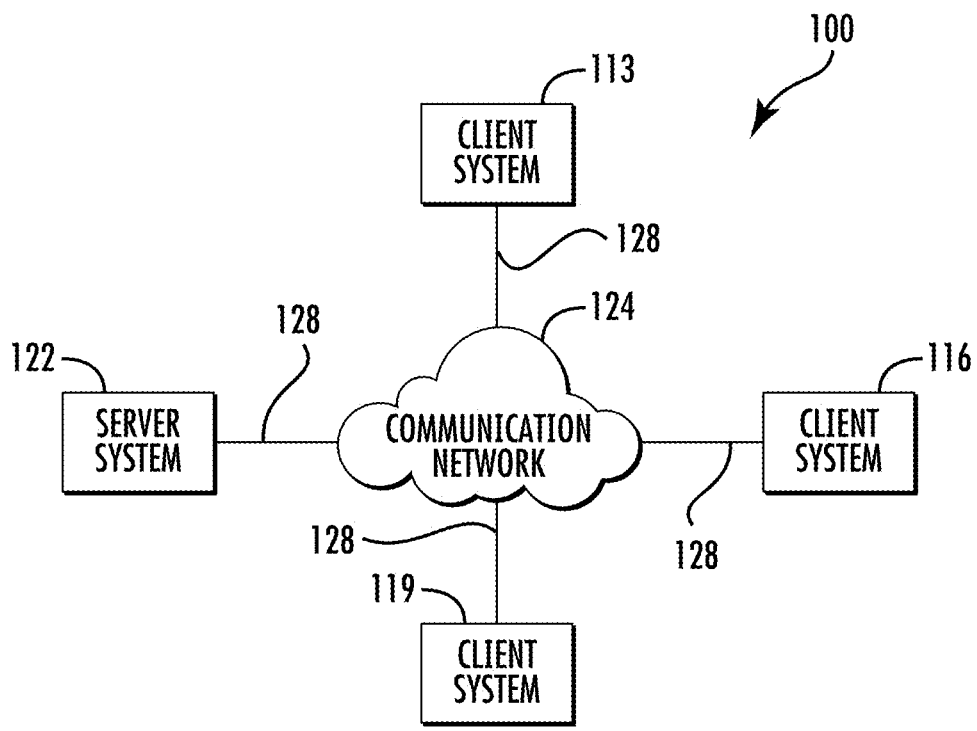
FIG. 1 shows a simplified block diagram of a client-server system and network in which an embodiment of the invention may be implemented.

FIG. 1 is a simplified block diagram of a distributed computer network 100 which embodiment of the present invention may be applied. Computer network 100 includes a number of client systems 113, 116, and 119, and a server system 122 coupled to a communication network 124 via a plurality of communication links 128. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information.

Various communication protocols may be used to facilitate communication between the various systems shown in FIG. 1. These communication protocols may include TCP/IP. HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, an intranet, a private network, a public network, a switched network, and combinations of these, and the like.

Distributed computer network 100 in FIG. 1 is merely illustrative of an embodiment incorporating the present invention and does not limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server system which provides the information. For this reason, server systems typically have more computing and storage capacity than client systems. However, a particular computer system may act as both as a client or a server depending on whether the computer system is requesting or providing information. Additionally, although aspects of the invention have been described using a client-server environment, it should be apparent that the invention may also be embodied in a stand-alone computer system.

Server 122 is responsible for receiving information requests from client systems 113, 116, and 119, performing processing required to satisfy the requests, and for forwarding the results corresponding to the requests back to the requesting client system. The processing required to satisfy the request may be performed by server system 122 or may alternatively be delegated to other servers connected to communication network 124.

Client systems 113, 116, and 119 enable users to access and query information stored by server system 122. In a specific embodiment, the client systems may run as a standalone application such as a desktop application or mobile smartphone or tablet application. In another embodiment, a "web browser" application executing on a client system enables users to select, access, retrieve, or query information stored by server system 122. Examples of web browsers include the Internet Explorer and Edge browser programs provided by Microsoft Corporation, Firefox browser provided by Mozilla, Chrome browser provided by Google, Safari browser provided by Apple, and others.

In a client-server environment, some resources (e.g., files, music, video, or data) are stored at the client while others are stored or delivered from elsewhere in the network, such as a server, and accessible via the network (e.g., the Internet). Therefore, the user's data may be stored in the network or "cloud." For example, the user may work on documents on a client device that are stored remotely on the cloud (e.g., server). Data on the client device may be synchronized with the cloud.

Figure 2:
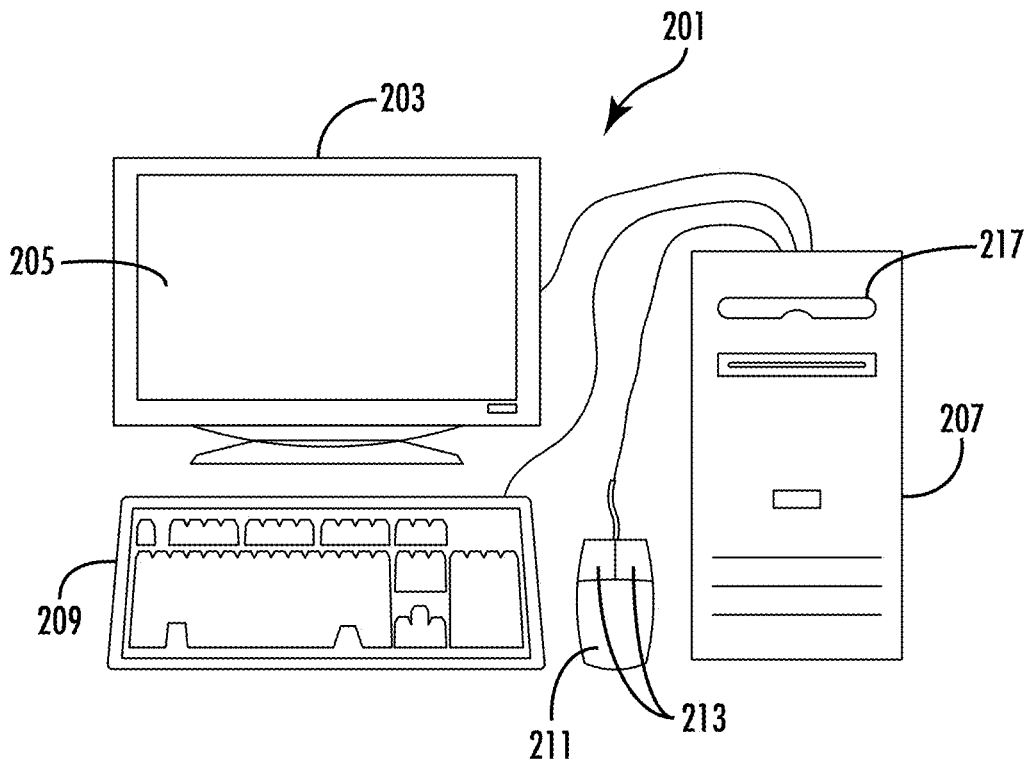
FIG. 2 shows a more detailed diagram of an exemplary client or server computer which may be used in an implementation of the invention.

FIG. 2 shows an exemplary computer system (e.g., client or server) of the present invention. In an embodiment, a user interfaces with the system through a computer workstation system, such as shown in FIG. 2. FIG. 2 shows a computer system 201 that includes a monitor 203, screen 205, enclosure 207 (may also be referred to as a system unit, cabinet, or case), keyboard or other human input device 209, and mouse or another pointing device 211. Mouse 211 may have one or more buttons such as mouse buttons 213.

It should be understood that the present invention is not limited to any computing device in a specific form factor (e.g., desktop computer form factor), but may include all types of computing devices in various form factors. A user may interface with any computing device, including smartphones, personal computers, laptops, electronic tablet devices, global positioning system (GPS) receivers, portable media players, personal digital assistants (PDAs), other network access devices, and other processing devices capable of receiving or transmitting data.

For example, in a specific implementation, the client device may be a smartphone or tablet device, such as the Apple iPhone (e.g., Apple iphone 12 and iPhone 12 Pro), Apple iPad (e.g., Apple ipad Air, Apple ipad Pro, or Apple iPad mini), Apple iPod (e.g., Apple ipod Touch), Samsung Galaxy product (e.g., Galaxy S series product or Galaxy Note series product), Google Nexus, Google Pixel devices (e.g., Google Pixel 5), and Microsoft devices (e.g., Microsoft Surface tablet). Typically, a smartphone includes a telephony portion (and associated radios) and a computer portion, which are accessible via a touch screen display.

There is nonvolatile memory to store data of the telephone portion (e.g., contacts and phone numbers) and the computer portion (e.g., application programs including a browser, pictures, games, videos, and music). The smartphone typically includes a camera (e.g., front facing camera or rear camera, or both) for taking pictures and video. For example, a smartphone or tablet may be used to take live video that may be streamed to one or more other devices.

Enclosure 207 houses familiar computer components, some of which are not shown, such as a processor, memory, mass storage devices 217, and the like. Mass storage devices 217 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

A computer-implemented or computer-executable version or computer program product of the invention may be embodied using, stored on, or associated with computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media may also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software of the present invention may also be stored or reside on mass storage device 217 (e.g., hard disk, magnetic disk, tape, or CD-ROM). As a further example, code of the invention may be transmitted via wires, radio waves, or through a network such as the Internet.

Figure 3:
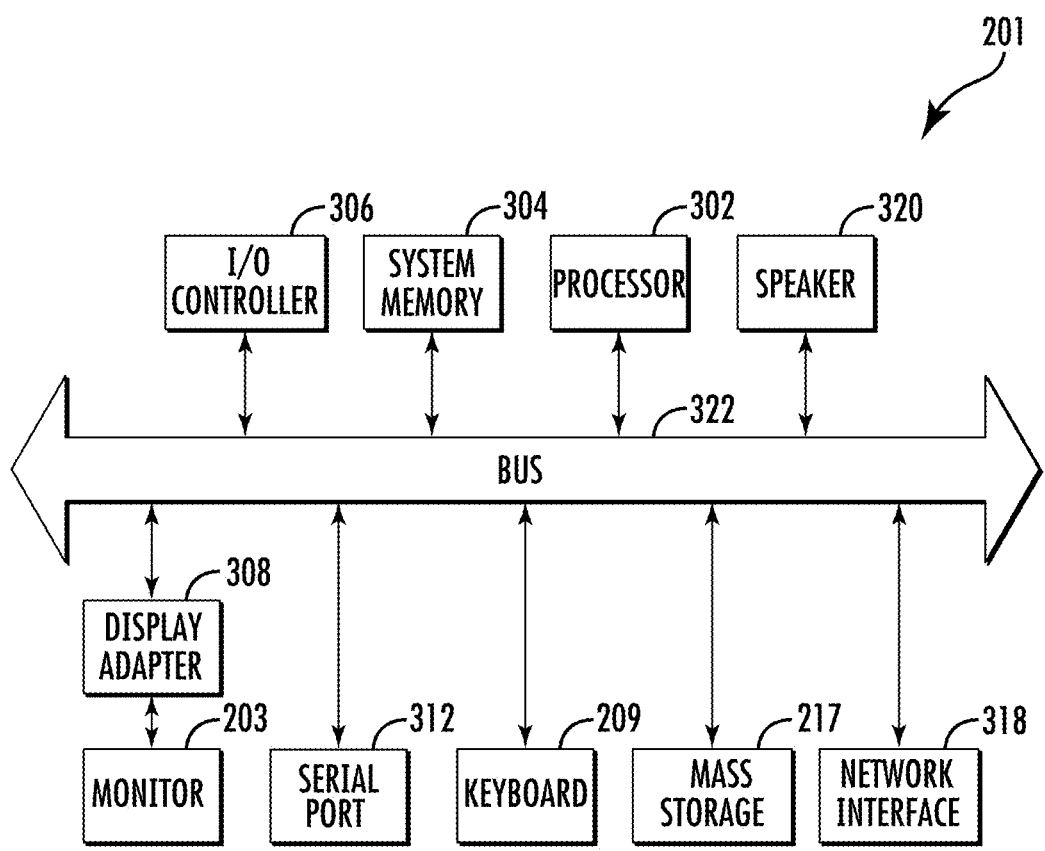
FIG. 3 shows a system block diagram of a client or server computer system used to execute application programs such as a web browser or tools for building a explore and exploit cohort optimization engine according to the invention.

FIG. 3 shows a system block diagram of computer system 201 used to execute the software of the present invention. As in FIG. 2, computer system 201 includes monitor 203, keyboard 209, and mass storage devices 217. Computer system 201 further includes subsystems such as central processor 302, system memory 304, input/output (I/O) controller 306, display adapter 308, serial or universal serial bus (USB) port 312, network interface 318, and speaker 320. The invention may also be used with computer systems with additional or fewer subsystems. For example, a computer system could include more than one processor 302 (i.e., a multiprocessor system) or a system may include a cache memory.

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. The processor may include multiple processors or a multicore processor, which may permit parallel processing of information. Computer system 201 shown in FIG. 2 is but an example of a computer system suitable for use with the present invention. Other configurations of subsystems suitable for use with the present invention will be readily apparent to one of ordinary skill in the art.

Computer software products may be written in any of various suitable programming languages, such as C, C++, C#, Pascal, Fortran, Perl, Matlab (from Math Works, www.mathworks.com), SAS, SPSS, JavaScript, AJAX, Python, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows 7, Windows 8, Windows 10, Windows 11, Windows CE, Windows Mobile), Linux, HP-UX, UNIX, Sun OS, Solaris, Mac OS X. Apple IOS, Android, Alpha OS, AIX, IRIX32, or IRIX64. Other operating systems may be used. Microsoft Windows is a trademark of Microsoft Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11c, 802.11 g, 802.11i, 802.11n, 802.11ac (e.g., Wi-Fi 5), 802.11ad, 802.11ax (e.g., Wi-Fi 6), and 802.11af, just to name a few examples), near field communication (NFC), radio-frequency identification (RFID), mobile or cellular wireless (e.g., 2G, 3G, 4G, 5G, 3GPP LTE, WiMAX, LTE, Flash-OFDM, HIPERMAN, iBurst, EDGE Evolution, UMTS, UMTS-TDD, 1xRDD, and EV-DO). For example, signals from a computer may be transferred, at least in part, wirelessly to components or other computers.

In an embodiment, with a web browser executing on a computer workstation system, a user accesses a system on the World Wide Web (WWW) through a network such as the Internet. The web browser is used to download web pages or other content in various formats including HTML, XML, text, PDF, and postscript, and may be used to upload information to other parts of the system. The web browser may use uniform resource identifiers (URLs) to identify resources on the web and hypertext transfer protocol (HTTP) in transferring files on the web.

In other implementations, the user accesses the system through either or both of native and nonnative applications. Native applications are locally installed on the particular computing system and are specific to the operating system or one or more hardware devices of that computing system, or a combination of these. These applications (which are sometimes also referred to as "apps") may be updated (e.g., periodically) via a direct internet upgrade patching mechanism or through an applications store (e.g., Apple iTunes and App store, Google Play store, Windows store, and Blackberry App World store).

The system may run in platform-independent, nonnative applications. For example, client may access the system through a web application from one or more servers using a network connection with the server or servers and load the web application in a web browser. For example, a web application may be downloaded from an application server over the Internet by a web browser. Nonnative applications may also be obtained from other sources, such as a disk.

FIGS. 4-5 show examples of mobile devices, which may be mobile clients. Mobile devices are specific implementations of a computer, such as described above. FIG. 4 shows a smartphone device 401, and FIG. 5 shows a tablet device 501. Some examples of smartphones include the Apple iphone, Samsung Galaxy, and Google Nexus family of devices. Some examples of tablet devices include the Apple iPad, Samsung Galaxy Tab, and Google Nexus family of devices.

Smartphone 401 has an enclosure that includes a screen 403, button 409, speaker 411, camera 413, and proximity sensor 435. The screen may be a touch screen that detects and accepts input from finger touch or a stylus. The technology of the touch screen may be a resistive, capacitive, infrared grid, optical imaging, or pressure-sensitive, dispersive signal, acoustic pulse recognition, or others. The touch screen is screen and a user input device interface that acts as a mouse and keyboard of a computer.

Button 409 is sometimes referred to as a home button and is used to exit a program and return the user to the home screen. The phone may also include other buttons (not shown) such as volume buttons and on-off button on a side. The proximity detector may detect a user's face is close to the phone, and may disable the phone screen and its touch sensor, so that there will be no false inputs from the user's face being next to screen when talking.

Tablet 501 is similar to a smartphone. Tablet 501 has an enclosure that includes a screen 503, button 509, and camera 513. Typically, the screen (e.g., touch screen) of a tablet is larger than a smartphone, usually 7, 8, 9, 10, 12, 13, or more inches (measured diagonally).

FIG. 6 shows a system block diagram of mobile device 601 used to execute the software of the present invention. This block diagram is representative of the components of a smartphone or tablet device. The mobile device system includes a screen 603 (e.g., touch screen), buttons 609, speaker 611, camera 613, motion sensor 615, light sensor 617, microphone 619, indicator light 621, and external port 623 (e.g., USB port or Apple Lightning port). These components may communicate with each other via a bus 625.

The system includes wireless components such as a mobile network connection 627 (e.g., mobile telephone or mobile data), Wi-Fi 629, Bluetooth 631, GPS 633 (e.g., detect GPS positioning), other sensors 635 such as a proximity sensor, CPU 637, RAM memory 639, storage 641 (e.g., nonvolatile memory), and battery 643 (lithium ion or lithium polymer cell). The battery supplies power to the electronic components and is rechargeable, which allows the system to be mobile.

This application describes some specific flows, but it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data.

A specific implementation of the system is Sephora's MobileColor IQ (MCIQ) system. All public published content by Sephora, including Web pages available at www.sephora.com, to the filing date of this patent application is incorporated by reference along with all other cited references in this application. This published content includes Web site pages, user guides and manuals, white papers, and other on-line and paper publications and documentation (including material related to Sephora's MCIQ system).

The following is an outline of a basic flow of the cosmetic matching system in operation:

1. An advisor (e.g., Sephora's Beauty Advisor) learns about a customer, such as desired finish and formulation.

2. Prepare the customer for scanning, by removing the customer's makeup, cleaning a scanning device, or other. Alternatively, a reverse lookup may be performed to identify a preferred color.

3. Use the scanning device to take scans from the customer.

4. Read a skin tone identifier from the scanning device.

5. Use machine learning to provide a machine learning adjusted skin tone identifier. This is discussed in further detail below.

6. Allow further manual adjustment to the machine learning skin tone identifier. An advisor or customer may make adjustments, based on skin tone skin and scan results.

7. Enter the skin tone identifier into a tablet computer.

8. Use machine learning to determine a customer's product match. This is discussed in further detail below.

9. View the customer's product matches.

10. Filter the customer's results to find the right foundation. For example, the system may show only liquid foundations or products that are formulated for sensitive skin.

11. Allow the customer to test their selections. A sample may be given to the customer.

12. E-mail matches to customer. The e-mail includes a link to each product for easy purchasing.

Headings are used in this written specification. Features discussed following each heading do not limit the features as being required by a specific embodiment identified by each heading and do not limit the features as solely belonging to any specific embodiment identified by each heading.

MCIQ Color Space

Human beings come in many different skin tones. For products such as cosmetics that are individualized to a person's skin tone, it is often a difficult and time-consuming task to select a product that is the correct color match to a person's skin tone. Some examples of cosmetic products for which color match to skin tone is important includes foundation, concealer, pressed powder, and tinted moisturizers.

A person's skin tone or skin color is determined a pigment called melanin. Two forms of melanin are eumelanin and pheomelanin, which are naturally occurring. Eumelanin comes in primarily brown and black hues. Pheomelanin appears as red and yellow hues. Melanin is produced by a specialized group of cells called melanocytes. Skin color depends on the amount and mixture of eumelanin and pheomelanin.

For cosmetic products, the color of these products is achieved by the use of pigments, typically not eumelanin or pheomelanin, but rather chemicals, compounds, dyes, metals, aggregates, composites, or a combination, or synthetic pigments.

A person's skin color or skin tone is mapped into a three-dimensional skin tone color space. And the cosmetic products are also mapped to the same three-dimensional skin tone color space. Then based on this mapping, a system can recommend appropriate products for the person's skin tone.

The skin tone color set may be referred to as a unified, uniform, or reference skin tone color set (e.g., MCIQ Color Space, skin tone color space) against which products are mapped. A database of products across different manufacturers is mapped to the reference skin tone color set. As an example, there may be manufacturers A, B, and C that manufacture foundation using their own color schemes and names. Some examples of cosmetics manufacturers include Amazing Cosmetics, bareMinerals, Clinique, Dior, Korres, and many others. These manufacturers produce a variety of products. These products are further divided by these manufacturers and their products will often use proprietary labeling and naming for their products. For example, manufacturer A may call their foundation colors called cocoa, toffee, honey, and sand. Manufacturer B may use different names such as rich coffee, southern tan, warm sunset, and light sunset.

The cosmetic matching system evaluates and maps the products of the different products, usually having different color names, of the different manufacturers to the reference skin tone color set. Each product is evaluated in a laboratory to determine a primary and secondary skin tone match. These skin tone matches indicate the skin tone which the product is compatible with color wise. For some products, they may be suitable for only a single skin tone color match. Other products, such as a tinted moisturizer may match a more than one skin tone. A number of skin tones may be listed in the secondary match. This may be defined as a range of possible values or values otherwise chosen from a skin tone color set. A system may include any number of skin tone matches for a product, one, two, three, four, five, or more. The laboratory skin tone matches may be verified manually by applying the product on a person. This verification of the laboratory results is optional.

In an implementation, the cosmetic matching system uses one or more color spaces to represent colors in the cosmetic matching system. Some examples of color spaces that may be used by the cosmetic matching system include Lab, LCH (lightness, chroma, hue), YUV, HCL (hue, chroma, lightness), Cielab, CMYK (cyan, magenta, yellow, and black), RGB (red, green, blue), TSL (tint, saturation, and luminance), RG Chromaticity, or a combination of any of these color spaces. For example, a scanning device may produce results in a first color space (e.g., Lab) and products are indexed using another color space (e.g., LCH).

The skin tone color space of the cosmetic matching system may have benefits over other color spaces. For example, other color spaces for skin tones may have been developed back in the 1970's or 1980's, and unfortunately, as a reflection of historical times then, was centered almost entirely around Caucasian skin tones. This left large segments of customers for cosmetic products without even a usable measure of their skin tone, since they simply could not be represented by colors found in these color spaces.

As one example, despite being a common undertone, olive shades are not addressed by most color spaces. This leads most foundation brands that use these color spaces to also not address these skin tones. For example, some color spaces describe medium tones in Middle Eastern and Hispanic women as olive undertones. However, customers may have skin colors across all depths, not just medium. Olive may be warm, cool, or neutral.

Further, some color spaces include disadvantages when used to represent skin tones. For example, cosmetic products may be matched onto a color space that does not include enough granularity, so that skin tones found in the general population could not be accurately classified. Additionally, skin tones that were "on the fringe" or represented by colors at the outer edges of possible colors included in those other color spaces resulted in clustering of products for a small set of fringe colors since these color spaces did not include enough possible colors to match the clustered products.

In an implementation, the cosmetic matching system accounts for saturation, a measure of skin tone that traditional color spaces did not account for. A more accurate skin tone color space including saturation provides advantages. Some advantages include:

Results using the skin tone color space may use plain English. This allows a common language between customers and advisors when discuss scan results.

Convey full depth information (shade range) and undertone in a digestible and inclusive way.

Demonstrate high accuracy of the scan to inspire confidence.

Be easy to understand by advisors and make intuitive sense.

Allow advisors to easily adjust the scan to accommodate client preferences.

Easier reverse lookup when not a customer is not at a retailer location (e.g., online).

Potential integration with other platforms (e.g., Influenster, social media, shared directly with friends).

Supports foundation sampling programs.

In an implementation, the cosmetic matching system may use a specific color space to represent a color, but only a subset of the color space is used by the skin tone color space (MCIQ color space) to form the cosmetic matching system's useable color space. For example, there are colors that do not exist in human skin. The cosmetic matching system may represent colors in a color space that may include a spectrum green color, but the MCIQ color space or skin tone color space would not include the color.

In the implementation of the skin tone color space represented using LCH values, the skin tone color space includes depth represented by the lightness value and undertone represented by the chroma and hue values. Warmth/coolness may be represented by the hue value and the saturation represented by the chroma value. Further specificity in the color space may be achieved by further dividing depth into levels with sub-divisions, and undertone into parts based on values on a C-axis and B-axis. Additional details on this implementation of the skin tone color space are provided following:

Depth (Lightness). Depth is based on the L value in LCH. Cosmetic products typically fall within a range of 18 to 88 on a lightness scale. The cosmetic matching system may represent the lightness values as a set of depth values with fewer possible values than the lightness scale. In an implementation, depth is represented using nine different depth levels. This allows the cosmetic matching system skin tone color space to represent a wide variety of skin tones found in a general population but grouping lightness values that are very similar or would generally require similar colors in their cosmetic products. Further, this allows the cosmetic matching system to divide the number of cosmetic products in each depth level to make sure there are a sufficient number of cosmetic products in each depth level. The depth level may be represented in plain English for easy of understanding by a customer. For example, names for depth levels may include deep, dark, tan, medium dark, medium, light medium, light, fair, and very fair.

Within each depth level, there may also be a sublevel. The sublevels allow additional granularity in the lightness results. The depth sublevel may be represented as a number. For example, a customer's skin tone identifier representing their depth may be "light medium 2."

Undertone (Chroma, Hue). Undertone may be based on A and B values. C (chroma) relates to the saturation, with higher values being more saturated. H (hue) relates to color. For the skin tone color space, red represents cooler values and yellow represents warmer values within the Hue area. The chroma value may be represented as a c-group value and there may be three possible c-group values. A conversion may be needed to transfer a chroma value to its associated c-group value. The c-group value may be represented in plain English for easy of understanding by a customer. For example, names for c-group values may include low saturation, medium saturation, and high saturation.

The hue value may be represented as a h-segment value and there may be seven possible h-segment values. A conversion may be needed to transfer a hue value to its associated h-segment value. The h-segment value may be represented in plain English for easy of understanding by a customer. For example, names for h-segment values may include high pink, medium pink, low pink, neutral, low yellow, medium yellow, and high yellow.

In an implementation, the cosmetic matching system may be represented as a three-dimensional color space. Instead of including only colors represented on an x-axis and y-axis, the skin tone color space may include a a-axis. For example, the axes may represent lightness, chroma, and hue.

Cosmetic Product Database

In an implementation, the cosmetic matching system stores data on cosmetic products meant for a diverse array of skin tones. Color information is stored for the cosmetic products. Although cosmetic products may relate to one or more skin tone identifier in the cosmetic matching system's skin tone color space, the cosmetic products include a color value for the cosmetic product that does not have to be in the skin tone color space. The color space used may be any of the color spaces as described in this specification. This allows the cosmetic products to be easily remapped to a new skin tone color space as needed, as well as allow adjustments to be made to an existing skin tone color space without needing to completely rescan all cosmetic products to see where they correspond to in the adjusted skin tone color space.

Scanning Device

The cosmetic matching system may use different scanning devices to capture skin tone information from customers. For example, customers or retail locations may have limited access to certain scanning devices, some scanning devices may be more difficult to use, or some scanning devices may not be as accurate as other types of scanning devices. Therefore, the cosmetic matching system includes a validation procedure to reconcile scans from different devices, as well as scans made by different people, during different lighting conditions, and other factors that may affect scan quality.

In an implementation, the cosmetic matching system may use scanning devices such as Nix™'s color sensor, AramHuvis™'s 3-in-1, or FitSkin®. FitSkin provides a scanning device that attaches onto a mobile device such as a mobile phone that allows accurate measurements of color using the mobile device's camera. The FitSkin scanning device may include optical or digital magnification, polarized lighting, blue lighting, infrared lighting, or any combination of these. Nix's color sensor includes a scanning device that may be placed on any surface to find digital color codes (e.g., sRGB, CMYK, CIELAB, HEX, LCH (ab), LRV, and Hue). The cosmetic matching system may include algorithms that consider the variability of different devices when processing skin tone color data from each specific device.

A scanning device of the cosmetic matching system may be selected for scanning accuracy and usability. Different form factors for the scanning device may include different positives and negatives. For example, when the scanning device includes a lens coupled to a mobile device:

Issue 1: Scanning Hardware Accuracy. Many scanning devices produce results that are too red/dark. The scanning devices' lens hardware design makes scanning accurately challenging for novices and produce inconsistent accuracy across devices. This has detrimental impact on stores:
  a. thirty-eight percent of scans are adjusted
  b. twenty-one percent of scans result in undertone adjustment
  c. thirty percent of all scans result in a shade adjustment
  d. twelve percent of sessions have a rescan Issue 2: Usability & Adoption. Many scanning devices require continual training, increasing rollout costs. Scanning devices produce a result that would be finetuned by an advisor or a customer and making the finetuning was not easy. Further, stores expect a skin tone identifier to provide a customer's ideal foundation number, not their exact skin color. This has had a detrimental impact on stores:
  a. Stores are trended at approximately fifteen percent toward session goals
  b. Low Volume stores have higher adoption
  c. High volume stores are facing challenges due to lower advisor coverage Some of these issues are related to components of the scanning device. For example, the act of scanning makes skin redder. Further, when the scanning device includes a mobile device and an image is captured using in part a camera on the mobile device, camera hardware and operating system native image processing prevent access to raw color or image data.

For example, when the scanning device includes a stand-alone device with a lens, or a mobile device encased with an included lens some positives included:
  a. The cosmetic matching system produced higher accuracy values when scanning paper color swatches.
  b. Additional diagnostic opportunities became available.
  c. Some scanning devices, particularly the stand-alone lens device, were highly accurate and could be used as an internal benchmark for accuracy.

User Interface

The cosmetic matching system may include a user interface that allows a customer or an advisor assisting the customer to see what products may be suitable for them based on their skin tone identifier. The cosmetic matching system may be adapted for use on a tablet, personal computer, smart phone, or a variety of devices.

An example flow of adjustments made to a skin tone identifier are described following:

On a first screen, the cosmetic matching system may present a visual swatch of a color associated with a skin tone identifier. For example, a customer may have a skin tone identifier already associated with them. This may be a result obtained from a scanning device, manual entry by a customer, or from a scan result associated with a customer.

Included with the visual swatch are options to change different dimensions of the skin tone identifier. In an implementation, there are three different dimensions that the customer may adjust (depth, undertone, saturation). For each dimension that may be adjusted, a visual sample of how the shown visual swatch would change is shown. A bar may be used to visualize how adjusting a dimension would affect the visual swatch. For example, for a depth dimension, adjustments may be made to make the visual swatch lighter or darker. For an undertone dimension, adjustments may be made to make the visual swatch cooler or warmer. For a saturation dimension, adjustments may be made to make the visual swatch less saturated or more saturated. The customer or advisor may choose to make adjustments in one, two, three, or none of the dimensions.

On a second screen, the cosmetic matching system adjusts the visual swatch according to any adjustments (if any) were made. The updated visual swatch may also include the original visual swatch before adjustments, so that the customer or advisor may see how their adjustments have changed from the color associated with the original skin tone identifier to a new skin tone identifier resulting from the adjustments made.

On a third screen, based on an updated skin tone identifier determined based on the adjustments, one or more cosmetic products may be presented that are suitable for the adjusted skin tone identifier.

In an implementation, the cosmetic matching system includes a quiz to allow a user to determine suitable cosmetic products and prepare for scanning. The scan flow quiz may be presented to a customer on a mobile device with a scanning device attachment. An example flow of a scan flow quiz may include:

On a first screen, prompt a customer for a general description of their skin type. Some choices may include dry, oily, normal, or combination.

On a second screen, prompt the customer for their age range.

On a third screen, prompt the customer for whether they have any skin concerns. Some skin concerns include acne & blemishes, anti-aging, dark spots, pores, dryness, fine lines & wrinkles, and dullness/uneven texture.

On a fourth screen, prompt the customer to begin the scan.

On a fifth screen, prompt the customer to perform initialization steps to perform the scan. For example, the scanning device may need to be cleaned or the customer may need to clean their skin of any existing makeup on their face.

On a sixth screen, prompt the customer to place the scanning device on the correct portion of skin to be scanned. Instructions on how to find the correct portion of skin are provided. For example, to find a forehead portion to scan, the customer is instructed to use imaginary lines from the center of their nose to the center of their forehead. The screen also alerts the customer that, when the scan is being performed and they are unable to see the screen of the mobile device, the mobile device will vibrate when the scanning device has captured the color data.

On a seventh screen, a preview photo of the scan result is shown. The photo may be accepted or rejected, if the customer believes that the photo is of poor quality (e.g., not representative of area, lighting was poor, blemishes were included).

On an eighth screen, prompt the customer to place the scanning device on the correct portion of skin to be scanned with instructions on how to find the correct portion. For example, to find a check portion to scan, the customer is instructed to use imaginary lines from the outer corner of their eye and the corner of their nose. The screen also alerts the customer that, when the scan is being performed and they are unable to see the screen of the mobile device, the mobile device will vibrate when the scanning device has captured the color data. A preview photo screen of the scan result may be shown, similar to the seventh screen.

On a ninth screen, prompt the customer to place the scanning device on the correct portion of skin to be scanned with instructions on how to find the correct portion. For example, to find a neck portion to scan, the customer is instructed to hold the scanner on the center of their neck. The screen also alerts the customer that, when the scan is being performed and they are unable to see the screen of the mobile device, the mobile device will vibrate when the scanning device has captured the color data. A preview photo of the scan result may be shown, similar to the seventh screen. Various embodiments of the cosmetic matching system may include fewer or more scans, and at different locations of a customer's face. For example, a customer's jawline may be helpful finding suitable products. However, if a customer has facial hair, this location may not be suitable for use in determining suitable products.

In an implementation, the cosmetic matching system includes additional questions for a scan flow quiz. For example, in addition to the screens as previously described, the cosmetic matching system may include:

On a first screen, prompt the customer for a secondary skin concern. This skin concern may be the same list of skin concerns as previously prompted.

On a second screen, prompt the customer for whether they are of Hispanic or Latino origin.

On a third screen, prompt the customer to best describe their race or ethnicity.

On a fourth screen, prompt the customer to enter cosmetic products they already use that they like. Multiple products may be entered.

Machine Learning

In an implementation, the cosmetic matching system uses machine learning techniques to improve the process of finding a suitable cosmetic product for a customer. Machine learning is a process where the cosmetic matching system is trained to perform operations, without explicitly being programmed on how to do so. For example, instead of solely using color data information from a customer's skin tone, the cosmetic matching system may use data from other customers, an advisor that assists customers, the customer themselves, or any combination of these, to learn and find suitable cosmetic products.

The cosmetic matching system may use machine learning at one or more stages of finding a suitable cosmetic product. In an implementation, the cosmetic matching system employs machine learning techniques at a color adjustment stage and a recommended product matches stage. Alternate embodiments of the cosmetic matching system may use machine learning techniques at only one of these stages or in combination with machine learning techniques at other stages of finding a suitable cosmetic product.

Color adjustment stage. A customer provides their color information from a scanning device. The scanning device may be any scanning device as described in this specification. This is raw color information, since it represents the result as captured by the scanning device. When this raw color information is presented to the customer or an advisor assisting the customer, a manual shade adjustment may be made to the raw color information, based on the subjective determination of the customer or advisor as to what is most suitable for the customer. For example, the advisor may feel that, based on the concerns of the customer, they would prefer an adjustment to the raw color information based on one or more of the dimensions of color. Some examples of why the manual shade adjustment would be necessary are that the customer believes they will be spending more time outdoors, adjustments in light exposure based on seasonal changes, concerns based on experience with past colors, or many other factors. Some factors considered using machine learning include:

a. Previous MCIQ scans
b. Use Client return/purchased shades LAB
c. Other client preferences from other sources, such as interviews with an advisor or quiz regarding factors (e.g., skin concerns, preferences skin type, skin tone, conditions).
d. Client profile attributes (e.g., geography)

The cosmetic matching system may store manual shade adjustments over a large set of customers for use by other customers, different than the customer who made the initial manual shade adjustment.

Recommended product matches stage. After a customer has determined their shade preference (whether using a manual shade adjustment, using machine learning, or otherwise), the cosmetic matching system provides a list of cosmetic products the customer may be interested in. The cosmetic matching system may use more than the customer's shade preference to determine the cosmetic products. For example, the cosmetic matching system may consider any of the following factors using machine learning: product attributes (e.g., brand, price), client profile attributes, prior client purchases, prior client replenishment purchases, client returns, client affinities (e.g., brand loyalty), advisor suggestions, or any combination of these.

In an implementation, the recommended product matches stage includes an algorithm that aims to predict a set of foundation products, for example a top 5 list, which a customer taking a matching session using the cosmetic matching system has the highest likelihood of purchase. This algorithm may consume multiple foundation products (approximately 100) which are with 2.8 deltaE, of a customer's LAB. The "top 5" products are identified as those, which a customer has most likelihood of interacting with. Interaction, in this context means purchasing a foundation product. For example, when foundation products are recommended to a customer after a session, most of the times customers take home, a sample portion of foundation product, try it on their skin for a brief period (approximately 2 months) and only if they liked it, they eventually purchase the foundation. The cosmetic matching system may not always have an explicit signal from the customer that they like a certain recommendation made to them, so the cosmetic matching system approaches this as a "Implicit Recommendation" problem (more details follow). Some different models that may be used alone or in conjunction by the cosmetic matching system include:

A. Implicit Recommendation (Pure Recommendation). The cosmetic matching system may use Alternating Least Squares (ALS) with an implicit feedback algorithm, provided by the spark machine learning library. The cosmetic matching system may include a standard Collaborative Filtering technique, which aims to find patterns between similar users and similar products in the data set.

The inputs to this model are pure identifiers (e.g., customer_id, sku_id) and the target for prediction is "No. of Purchases/Returns" on the combination of customer_id and sku_id. In an implementation, the customer_id may be anonymized or pseudo anonymized to protect the identity of a customer whose data is being used. ALS with implicit feedback tries to predict the preference to each product, for a given customer. A traditional ALS tries to predict the actual count of interactions (interactions may be number of purchases/returns).

Interpretation of Outputs for Model: If predicted score from the model, say 0.001, is on the lower end, then a customer does not have high preference in purchasing this product, it could also be thought as high preference to return the product. A higher value, say 1.56, means customer has high preference to purchase the product. At the end, all products are sorted by the scores, in descending order, to identify top 5 products.

Apart from predictions, this model also provides other useful data (or data bi-products) such as: User Features— Unique numeric representation of each user; Product Features: Unique numeric rep of each product. These other useful data could be used in downstream machine learning tasks, or even to segment customers based on purchase patterns.

B. Bi-Products+Re-Ranking through Classification aka Enhancement: This model uses bi-products of the MVP model (user & sku features) as inputs, along with some additional dimensions like skin type, concerns of a user, season, location for scan, and other. In a first version of the model, the model provides a point of view that, an upstream recommendation system will act as a "high-level" filter, which selects say top 30 out of 100 products and, there will be a downstream classification model, which re-shuffles the top 30 products by the "Likelihood of Purchase" and returns only the top 5 based on predicted probability, acting as more "granular/specific filter" based on other dimensions than purchase history alone. The user and sku features from an upstream recommendation model, encapsulates all the purchase trends for each user and product. This representation is richer than plain attributes which gives purchase history of customer like frequency, number of purchases, and other.

In a second version of the model, the model instead takes all the products with 2.8 deltaE (approximately 100) and predicts Likelihood of purchase for each customer; acting as a lone model. Inputs to this model may include: customer_id [biAccountId/bicmail]; user_features sku_id sku_features skintype (user) skin concerns (user) scan month (month when MCIQ scan took place) storeId (proxy for location); and target for prediction, is "Likelihood of Purchase" which is between 0 and 1.

Interpretation of Outputs for Model: Since the model is a binary-classification model, the closer the predicted value is to 1, the higher chances that this customer will end up purchasing the product and vice versa. At the end, all products are sorted by the probabilities, in descending order, to identify top 5 products.

Some examples of skin tone color spaces, scanning devices, databases, user interfaces, and related systems are described in U.S. patent applications 61/826,488, filed May 22, 2013, and Ser. No. 13/924,549, 13/924,550, 13/924,551, and 13/924,552, filed Jun. 22, 2013. These applications are incorporated by reference along with all other references cited in this application.

Figure 7:
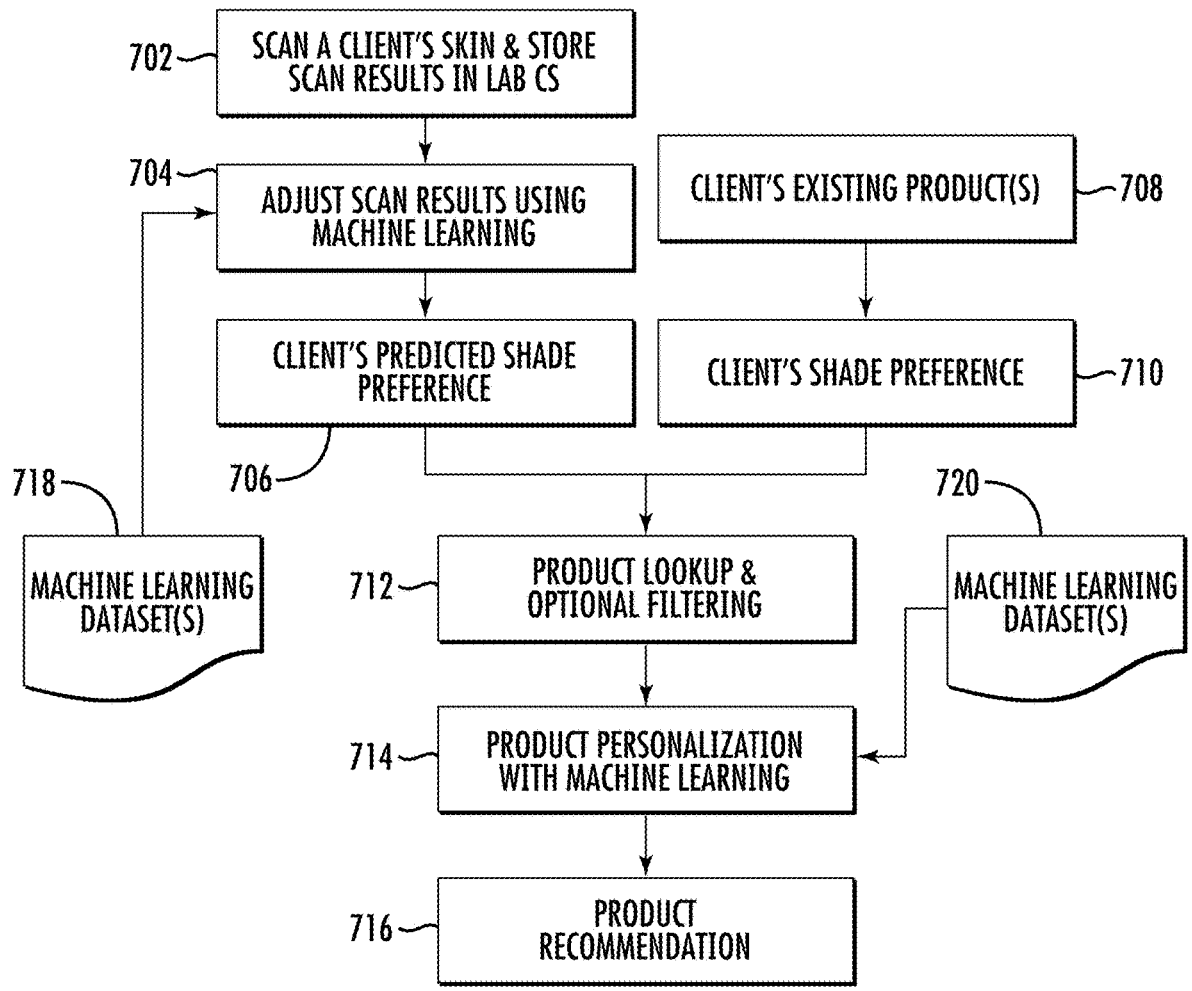
FIG. 7 illustrates an example high-level block diagram of a flow for cosmetic product matching and recommendation in one or more embodiments.

FIG. 7 illustrates an example high-level block diagram of a flow for cosmetic product matching and recommendation in some embodiments. More particularly, FIG. 7 illustrates a lookup service for determining and recommending one or more matching cosmetic products. In some these embodiments, a lookup service may be performed by a store digital app (which may also referred to as an Advisor Assistant app) that is an integral part of a system for cosmetic product matching and recommendation. A lookup service determines one or more products for a particular user (e.g., a client or a prospective client of cosmetic product or products) and presents pertinent information in the form of a personalized recommendation with sufficient textual or graphical examples, or a combination, descriptions, explanations, and additional auxiliary information to convince the particular user to try or purchase at least one of the recommended products. In some embodiments, cosmetic products include foundations, concealers, products for lips. In some of these embodiments, cosmetic products may further include all skincare products such as moisturizers, products for exfoliation, products for eye puffiness, dark circles, and others, skin hydration products, and others. A personalized recommendation differs from a general recommendation in that a personalized recommendation includes a form of personalization that is custom tailored to a specific client by at least accounting for one or more specific attributes, characteristics, habits, preferences, and others, that are known, not inferred or implied to be related to the specific client. It shall be noted that although multiple clients may have an attribute or characteristic in common (e.g., same age, same ethnicity, even same skin tone, and others), a personalized recommendation differs and deviates from a general recommendation with the consideration of more personally specific attributes, characteristics, habits, preferences, and others.

In some other embodiments of these embodiments, a lookup service may be performed by a mobile app installed on a user's mobile computing device (e.g., a client's or prospective client's mobile phone or tablet, a beauty advisor's mobile phone or tablet, a wearable artificial intelligence hardware such as a virtual/augmented/extended reality or VR/AR/XR goggles, smart glasses, and others, having an image capturing device) Each of the aforementioned store digital app or the mobile app, or a combination, may function individually and independently in some embodiments or may be connected (e.g., via a cellular or wired network) to a server owned and operated by a cosmetic product manufacturer in some other embodiments.

In some of these embodiments illustrated in FIG. 7, product information pertaining to user's one or more existing cosmetic products (e.g., concealer, foundation, lip, and others) 708 or the user's preference, or a combination, (e.g., shade preference, care preference such as skin care, hair care, and others, styling, hair treatments, skin treatments, scalp treatments, oily hair treatments, hair dryness treatments, hair color preservation or alteration, nail treatments, and others) 710 may be received for a lookup service. The product information 708 may include, for example, the brand name or names, the product name or names, the shade or undertone reference or references, or any other information that may be used to identify a particular cosmetic product.

Some embodiments characterize and address the nuances of skin undertones or shades using depth, hue, and saturation not only to address the deficiencies of the current, industry-leading foundation color system (e.g., Pantone) but also to address olive undertones that are not addressed by most, if not all foundation and concealer brands of cosmetic products. Olive undertone represents medium tones in, for example middle eastern and Hispanic persons and has been observed across all depths (e.g., warm, neutral, cool), not just medium tones. Further, the color system and techniques characterizing undertones account for saturation that is often ignored by most, if not all, foundation and concealer brands. More details about the color system and the color space are described below.

The product information 708 or the user's preference 710, or both, may be received at a matching and recommendation system or module 712 that performs a product personalization service using the received data (e.g., 708 or 710, or both) and machine learning at 714. In some of these embodiments, the matching and recommendation system or module 712 may perform optional filtering to generate a first plurality of matching products (e.g., 100 matching products) based at least in part upon one or more first filtering criteria. These one or more first filtering criteria may include, for example, the particular user's affinities to specific brand or brands and product or products, or a combination, the particular user's purchase history or trend of purchase, or a combination, the particular user's replenishment purchases, one or more product attributes, the particular user's profile attributes, one or more previous beauty advisors' product recommendations, the particular user's product return history, the skin type (or hair type such as straight, wavy, curly, and others, for hair scans) or skin condition, or a combination, of the particular user, or any other appropriate criteria, and others. This first plurality of matching products may then be further filtered at 714 with the product personalization service with machine learning. More details about the multi-stage filtering for matching and recommending one or more products are described below with reference to FIGS. 11A-11F.

The product personalization service may be enforced with artificial intelligence techniques. In some embodiments, the product personalization service may be trained using one or more machine learning or deep learning datasets 720. These one or more datasets 720 may include data such as client brand or product affinities, or a combination, or loyalty data, user's prior purchases or purchase trend or trends, or a combination, user's prior returns, product attributes such as prices, brands, and others, user's profile attributes such as age, ethnicity, preferences, and others, prior product recommendation or recommendations, any combination, or any other suitable data, or a combination. The product personalization service performed by the matching and recommendation system at 712 may determine a plurality of matching product (e.g., one or more products of the manufacturer that develops and owns the matching and recommendation system, one or more products from one or more competitors, and others) and recommend one or more of the plurality of matching cosmetic products for the particular user based at least in part upon the data or information specific to the particular user at 716. A dataset may be transmitted to a model as a data stream for training the model where a data stream is the transmission of sequence of digitally encoded coherent signals to convey information.

In some embodiments, the data input to product lookup and optional filtering at 712 may come from scanning the particular user's skin 702. In some of these embodiments described herein, skin scan results are processed and stored in a CIELAB color space (also referred to as L*a*b or L*A*B* color space or LAB color space in short) defined by the International Commission on Illumination (CIE) in some embodiments, a color space based on the CIELAB color space (e.g., CIELch color space that uses polar coordinates C* for relative saturation or chroma and h for hue angle) in other embodiments, or any other device-independent color space in yet some other embodiments. A CIELAB color space lies in the Cartesian coordinates and defines the lightness value (L*) ranging from 0 (black) to 100 (white), the green-red values (a*) with unbounded values where negative values toward green and positive values toward red, and blue-yellow values (b*) with unbounded values where negative values toward blue and positive values toward yellow. That is, CIELAB is an opponent type color system where L* describes the lightness or darkness, a* describes the redness or greenness and b* describes the yellowness or blueness of a color. CIELAB color space is a device independent color space recommended by the CIE (International Commission on Illumination, which is commonly abbreviated CIE for its French name, Commission internationale de l'éclairage) that was developed based on the human visual system as opposed to a particular display or printing device. In some embodiments where certain data is not represented in a select color space (e.g., CIELAB, LIELch, and others), such certain data may be converted into the select color space as various databases, knowledge bases, and others, store data in the select color space. A color space is a useful model for understanding and characterizing the color capabilities of a particular device, digital file and even the human visual system. One of the basic functions of a color space is to define reproducible representations of colors.

Scanning the particular user's skin 702 may be performed by using a scanning device such as any of the scanning devices described above in the Scanning Device section or an equivalent thereof in some embodiments or by using a mobile computing device having or coupled to an image capturing device such as a mobile phone, a tablet, a laptop, a desktop, and others, in some other embodiments. Various techniques described herein may include a plurality of image capturing device profiles so that when a particular scanning device is used for scanning a user's skin, the corresponding image capturing device may be referenced for various calibration to render the scan results to more accurately represent the color of the user's skin tone. An image capturing device profile may include settings for a specific image capturing device. The settings may include, for example, lighting condition (e.g., bright sunlight, overcast, fluorescent, incandescent, tungsten, and others), one or more factors of the image capturing device (e.g., vignettes including hue, saturation, tint, and others, image sensor geometric characteristics, lens optical characteristics, or any other appropriate factors that may affect the accuracy of representing the subject (e.g., a user's skin) in images and others. In some embodiments, an image capturing device is configured to capture raw image information in a raw image format that contains minimally processed data instead of other more heavily processed image data format such as JPEG, TIFF, and others to preserve the image data.

The scan results may be adjusted at 704 in some embodiments. In some embodiments where a CIELAB or CIELch color space is adopted, adjusting scan results may including altering one or more of a L* value, an a* value, and/or a b* value in the scan results. The adjustment may be achieved by a user (e.g., the user whose skin is scanned, a beauty advisor, and others), by various programmatic techniques described herein, or a combination of both a user and various programmatic techniques described herein. For example, a beauty advisor having professional training may manually adjust the scan results for a particular user based on the beauty advisor's in-person observation of the user's skin and the beauty advisor's experiences. In some embodiments, these programmatic techniques include an artificial intelligence module that uses, for example, one or more machine learning datasets 718 to train the artificial intelligence model for image recognition and classification (e.g., recognition of skin features such as freckles, wrinkles, other color spots, hairs, and others, and classification of skin tone under one or more colors in the LAB color space) in a supervised mode, an unsupervised mode, or a hybrid mode include a supervised mode and an unsupervised mode. A freckle denotes a small pigmentation spot usually having a brownish or reddish color on the surface of the skin while a wrinkle denotes a small furrow, ridge or crease in an otherwise smooth surface. Spots with varying sizes and colors other than brownish or reddish may be categorized as other colored spots such as a white spot due to loss of color pigmentation. The one or more datasets 718 may include data such as other scan results (e.g., prior scan results), adjustment or adjustments made to scan results, the color attributes of user's or beauty advisor's preferred product or products, user's preferences such as user's skin concern or concerns or skin condition, or a combination, user's skin type (e.g., dry, oily, neutral, and others), user's prior product history for purchases, trials, returns, and others, or any combination, or any other appropriate data. In some embodiments where a beauty advisor adjusts the scan results, the actual scan results before the adjustment and the adjusted scan results may be stored as a reference pair that may be subsequently utilized to further train or fine-tune the artificial intelligence model.

In some embodiments, the artificial intelligence model predicts the particular user's shade preference and/or complexion at 706 based at least in part on the scan results or the adjusted scan results if adjustment has been made to the scan results. The predicted shade preference for the particular user may then be forwarded to matching and recommendation system or module 712 that performs a product personalization service using the received data (e.g., 708 and/or 710) and machine learning at 714 in an identical or substantially similar manner as described above.

Figure 8A:
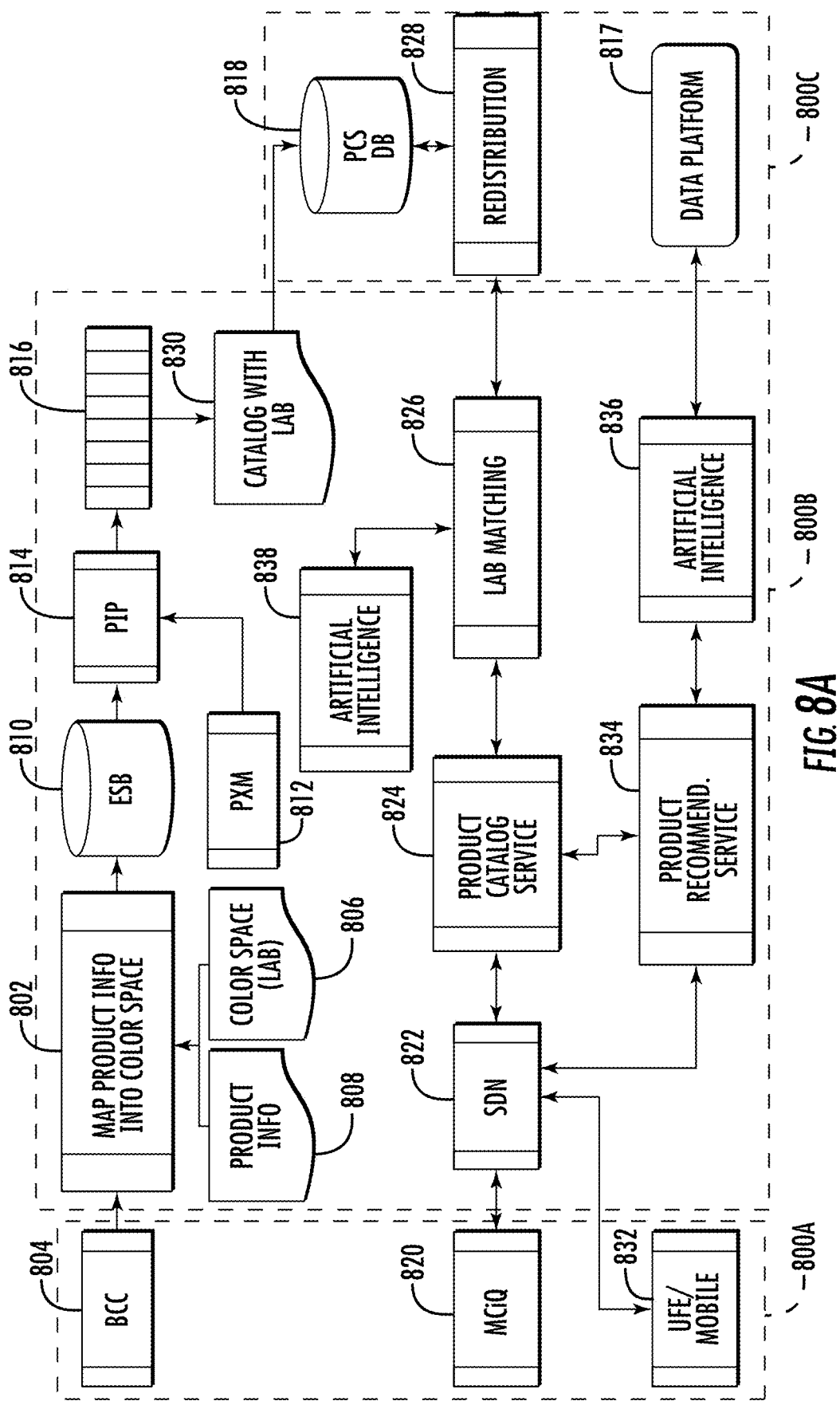
FIG. 8A illustrates an example high-level block diagram of a system for cosmetic product matching and recommendation in one or more embodiments.

FIG. 8A illustrates an example high-level block diagram of a system for cosmetic product matching and recommendation in one or more embodiments. More specifically, FIG. illustrates a three-tire structure of a system for cosmetic product matching and recommendation: a source tier 800A, a middle tier 800B, and a target tier 800C. In some of these embodiments, the source tier 800A may include one or more business control center (BCC) databases 804, MCiQ (Mobile Color IQ app) or CiQ (Color iQ) devices such as a store digital app capturing data 820, and/or devices capturing and transmitting data using UFE (Ultra-Fast Ethernet)/mobile communication network (e.g., a cellular network) 832. The mobile app installed on a client's mobile computing device is referred to as mobile color iQ app or simply mobile app herein.

An app includes an application program or application software that is a computer software package that is installed on a mobile computing device and performs one or more specific functions directly for an end user or, in some cases, for another application in one or more embodiments. An app may be self-contained or a group of programs that may be implemented as a monolithic software application, a set of services, or a collection of loosely connected microservices.

An app may be implemented using software as a service (Saas) with a set of services or as a collection of microservices. In some embodiments where an app is implemented as a set of services in a service-oriented architecture, the service-oriented architecture utilizes BASE (basic availability, soft-state, eventual consistency) transactions, rather than ACID (atomicity, consistency, isolation, and durability) transactions for monolithic implementations. Service-oriented architectures for SaaS have distinct and formal service taxonomy in terms of the type of service and the role of that service in the overall architecture with any number of service types in a service-oriented architecture. For example, enterprise services include concrete, enterprise-level, coarse-grained services that implement the functionality defined by services while application services are fine-grained, application-specific services bound to a specific application context, and infrastructure services implement nonfunctional tasks (e.g., security, authentication and authorization, logging, and others)

An app may also be implemented as a collection of microservices. Unlike service-oriented architectures, microservices are devised to share as little as possible, whereas services are generally devised to share as much as possible and thus often require processing logic to be replicated across multiple service components each of which is required to discern, for example, where and how retrieve data (e.g., replicated services accessing respective, different databases). Microservices, on the other hand, may often be devised using a domain-driven design such as a bounded context that refers to the coupling of a microservice and its associated data as a single closed unit with no or minimal dependencies. Therefore, a microservice with such minimal or no dependencies may be considered as self-contained and only expose well-defined interface and may thus be designed, altered, tested, and deployed nearly completely independent of other microservices (with few exceptions where there may exist some dependencies although much less than the dependencies required for services). One of the advantages of microservice implementations is that the code required for design, modification, testing, and deployment is much smaller and is less likely to negatively impact other parts of a software application implemented as microservices than monolithic implementations or services.

Another distinction between services and microservices is that services favor service orchestration over service choreography, and that microservices favor service choreography over service orchestration. Service orchestration includes coordinating multiple services through a centralized authority such as a service consumer or a hub although whether service orchestration or choreography may not necessarily be a bright-line division between services and microservices. Service choreography includes coordinating multiple service calls (e.g., calls among microservices) using inter-service communication and more importantly, without using a central authority. In some embodiments, an app may be implemented by using both services and microservices. For example, a portion of the app (e.g., a more complex portion) may be implemented with services in a service-oriented architecture while the remain portion (e.g., less complex portion) may be implemented as microservices.

The target tier 800C may include one or more databases 818 operatively coupled to one or more product catalog database (PCS) 818, a redistribution layer 828 operatively coupled to the product catalog database (PCS), and data platform 817. The middle tier 800B includes a model 802 that maps product information or data (e.g., product identifiers such as a product stock keeping unit (SKU), bar code, QR code (quick response code), or other equivalent identifiers into a color space. In some embodiment, production information or data is mapped to a CIELAB color space. In some other embodiments, production information or data is mapped to a CIELch color space or other equivalent color spaces. In some embodiments, the color space adopted by various embodiments described herein exclude the CMYK color space, the CMYK+ color space, the RGB (red green blue) color space, spot colors (e.g., spot colors adopted by Pantone), and/or any variants thereof (e.g., by adding the fifth, sixth, and/or seventh color to the CMYK or CMYK+ color space).

In some embodiments, the model 802 may include or may be Kafak (or other equivalent module) 816 that stores records (data) in topics. For example, records are produced by producers (e.g., users and/or beauty advisors) and are consumed by consumers such as a downstream process (e.g., a recognition process, a classification process, a matching process, a recommendation process, and others). Producers send records to Kafka brokers. Each worker node in an HDInsight (HDI) cluster may constitute a Kafka broker. In some embodiments, records are partitioned based at least in part on topics across multiple brokers. When consuming records, a process may use up to one consumer per partition to achieve parallel processing of the data. In some embodiments, replication may be employed to duplicate partitions across nodes, protecting against node (broker) outages. In some of these embodiments, a partition may be designated as the leader for the given partition. In some embodiments employing Kafka, a Producer API provided by Kafka may be used for publishing (writing) records to a Kafka topic, and a consumer API may be used when subscribing (reading) to a particular topic.

In some of these embodiments that employ an HDI cluster, HDI allows for changing the number of worker nodes (which host the Kafka broker) after cluster creation. In some embodiments, upward scaling may be performed from, for example, the Microsoft® Azure portal, Azure PowerShell®, and other Azure® management interfaces. In these embodiments employing Kafka, partition replicas (e.g., produced or replicated by using Kafka's MirrorMaker utility) may be rebalanced after scaling operations to allow Kafka to take advantage of the new number of worker nodes. In these embodiments, in addition to serving as a message broker, Kafka may partition the streams across the multiple nodes in the HDInsight cluster. Consumer processes may be associated with individual partition or partitions to provide load balancing when consuming records. Further, within each partition, records may be stored in the stream in the order that records were received.

By associating one consumer process per partition, records may be guaranteed to be processed in-order. Moreover, activities may be tracked or even recreated by using, for example, Kafka's in-order logging of records. For example, user actions on a web site or within an application. In some of these embodiments, Kafka may be used with Apache Storm or Spark for real-time stream processing and for building streaming solutions without requiring Storm or Spark. The stream processing capability of these embodiments enables aggregating information from different streams to combine and centralize the information into operational data as well as combining and enriching data from multiple input topics into one or more output topics in some embodiments.

The middle tier 800B further includes a mapping model 802 that receives product information or data 808 and color data 806 (e.g., L*, a*, and b* values in the CIELAB color space) and maps the product information or data 808 to color data 806 or vice versa and stores the correlated/mapped results (e.g., products SKUs with respectively associated color values or color identifiers such as rosy, tan, and others) into a database 810 (e.g., ESB 810). The database 810 may be operatively coupled to and sends one or more catalog files including information pertaining to one or more cosmetic products to a management module (e.g., PIP or Product Ingestion Processor 814) that is further operatively coupled to a product/user experience management module (PXM) 812. The product/user experience module (PXM) 812 transforms the data in the one or more catalog files received at 814 into transformed data (e.g., data incorporated or associated with information pertaining to user specifics or experiences) and feeds the transformed data into a distributed system 816 (e.g., Kafka or other equivalent module or modules).

The distributed system 816 in turn processes the transformed data that is transmitted as one or more streams of data as the data occurs or retrospectively and further infuses associated color data in, for example, the LAB color space into the corresponding data in the one or more catalog files. In some embodiments, the distributed system 816 transforms the one or more catalog files into one or more corresponding modified catalog files or other data structure or structures to correlate product data or information with corresponding color data. In some embodiments, the distributed system 816 comprises a platform that is responsible for establishing and managing a plurality of pipelines for data and execution of applications or services. The clients in the distributed system 818 allow writing distributed applications and microservices that read, write, and process streams of data in parallel, at scale, and in a fault-tolerant manner even in the case of network problems or machine failures.

The one or more catalog files with associated color data (e.g., LAB data) 830 may be stored in one or more separate databases 818 (e.g., a database coupled to a PCS or process control system database 818). A product/user experience module (PXM) 812 includes one or more models that are devised to capture, learn from, and enhance experiences and/or interactions with a product or a user when utilizing a system for cosmetic product matching and recommendation described herein. A process control system (e.g., 818) may monitor and adjust one or more processes on the system based at least in part upon one or more objectives such as quality maintenance of the system for cosmetic product matching and recommendation or a portion thereof, performance improvement of the system for cosmetic product matching and recommendation or a portion thereof, user experience (UX) enhancement, and others by, for example, load balancing, resource re-allocation, setting reconfigurations, adjusting various set points in execution of one or more processes, and others.

The middle tier 800B may further include a development network (SDN) 822 that includes a collection of application programming interfaces (APIs) for interfacing with 820 and 832 and is operatively coupled to (e.g., reading, writing, or both reading and writing) the MCiQ (Mobile Color IQ) or CiQ (Color IQ) devices 820 and/or the devices capturing and transmitting data using UFE (Unified Front End)/mobile communication network (e.g., a cellular network) 832 in some embodiments. The SDN 822 may be further operatively coupled to a product catalog service 824 and a product recommendation service 834.

The product catalog service 824 performs a matching service 826 by referencing data stored in the one or more separate databases 818 coupled to a process control system in some embodiments. For example, the matching service 826 may receive skin scan results in the LAB color space and determine a list of products whose color attributes (e.g., L*, a*, and/or b* values) exactly and/or approximately match those of the skin scan results. In some embodiments, the matching service 826 may be operatively coupled to an artificial intelligence model 838 that may be trained for feature recognition and classification (e.g., predicting the color index or color code for a skin tone and/or undertone of a client) to facilitate the determination of matching cosmetic products by the matching service 826. A color index or color code may comprise a number, a string, an alphanumeric representation, a hexadecimal representation, a symbolic representation, a graphical representation, a triple (e.g., light medium 3-neutral-intensity 2, {light medium 3, neutral, intensity 2}, or other triples in appropriate formats showing the respective levels and/or sublevels of lightness/depth, undertone, and saturation, not necessarily in the aforementioned particular order). It shall be noted that although various embodiments are described with reference to color index/value or even skin tone color index/value, various techniques are not limited only to scanning and determining skin tone color index/value. Therefore, the term skin tone color index or value or its variants or equivalents may be used interchangeably with body complexion index or value or simply body complexion index or value or complexion index or value and generally refer the complexion of a part of a client's body (e.g., part of the client's skin, nails, hair, and others) Complexion may generally include the color, undertone, texture, size, shape, location, or any other general aspect or characteristic of a client's appearance unless otherwise specifically claimed or described.

Some of these embodiments may also predict the accuracy of a predicted or recommended skin tone or undertone color index or value. As a working example for predicting a skin tone or undertone color index or value in the LAB color space, an artificial intelligence model (e.g., AI model 838 in FIG. 8A or 8B) may generate the predicted skin tone or undertone color values:

TABLE A

{
"67.255: 35.658: 12.355"
}
based on the following input to the AI model:
{"visited": "s0058cdiphone01NX359]CL2", {
"primaryConcern": {
"dullness": 0,
"dryness": 0,
"acne":0,
"finelines": 1,
"antiAging": 0,
"darkspots": 0,
"pores": 0),
"ageRange": "40",
"biAccountEmail": "UserName@DomainName.com",
"storeId": "1186",
"skinType": "Dry",
"atgId": "7027413029",
"biAccountId": "23000000012483439",
"labs": [
{"area": "forehead", "lab": "67.055: 10.499:16.298", "sort": 1},
{"area": "cheek", "lab": "61.523: 14.083: 18.207", "sort": 2},
{"area": "neck", "lab": "63.815: 12.071:16.684", "sort": 3 }
]
}

As another working example, for predicting a skin tone or undertone color index or value in the LAB color space, an artificial intelligence model (e.g., AI model 838 in FIG. 8A or 8B) may generate the predicted skin tone or undertone color values:

TABLE B

```
{
"rankedSkusList": [
{
"'skuId": "789123",
"rank": 1,
"overAllRating': 2
}
]
}
based on the following input to the AI model:
{
"storeId": "8",
"atgId": "89856",
"loyaltyId": "123456",
"biAccountId": "500002221236",
"biAccountEmail": "UserName@DomainName.com",
"ageRange": "20",
"skinType": "combination",
"matchedLabSkuids": "789123",
"matchedLab": 46.17595137483466:14.231242541255863:
21.632915339226052",
"PrimaryConcern": {
   "acne": 1,
   "antiAging": 0,
   "darkspots": 1,
   "pores": 1,
   "dryness": 0,
   "finelines": 0,
   "dullness": 0,
   "moles": 1,
]
}
```

In some embodiments, a data redistribution layer 828 may be invoked to reshuffle data in the one or more separate databases 818 into shuffled data to optimize or improve one or more objective functions (e.g., indexing data, rearranging data according to indices, fetching frequently accessed data and/or data types, retrieving a certain amount and/or types of data according to a static or dynamically configurable accuracy requirement, a performance objective, and others) for the matching service 826 and to provide such shuffled data to the matching service 826. In some of these embodiments, the redistribution layer 828 may also shuffle the matching service results to optimize or improve one or more separate objective functions (e.g., arranging the matching service results according to indices or column identifiers in the one or more database 818, deduplication of the matching service results, denoising the matching service results, and others) for storing the matching service results into the one or more databases 818.

The product recommendation service 834 may be operatively coupled to the development network (SDN) 822 as well as an artificial intelligence model 836 that assists in or performs the identification of matching products through the product catalog service 824 (which in turn receives the matching service results from the matching service 826) and recommends one or more of the identified products. In some of these embodiments, the development network 822 may relay color adjustment data (e.g., a beauty advisor's adjustment to scanned results at a Mobile Color IQ station 820) to the product recommendation service 834 that generates and forwards a list of recommended products to the product catalog service 824 that in turn relays the list back to the Mobile Color IQ station 820 or the mobile computing device 832.

In some embodiments, the artificial intelligence model 836 may be operatively coupled to a data platform 817 to receive data (e.g., a particular user's data such as the particular user's preference for shade, the particular user's purchase and/or return histories, the particular user's skin concern or concerns, the particular user's skin condition and/or type, the particular user's product/brand affinities, and others) from the data platform 817 to generate a personalized recommendation for a particular user or other artificial intelligence models described herein. The artificial intelligence model 836 may further receive additional data (e.g., data from mobile color IQ 820 and/or data from devices capturing and transmitting data via UFE/mobile network 832) relayed by the development network 822 and the production recommendation service 834 to further fine-tune or calibrate one or more model parameters of the artificial intelligence model 836 (e.g., one or more hyper parameters, one or more model parameters such as one or more weights in a kernel, bias parameter value or values, and others)

In FIG. 8, the processes initiated at 820 (mobile color IQ) to the matching service 826 and the product recommendation service 834 may be deemed as an offline mode for product reverse lookup with color information in some embodiments. For example, a user may enter his or her skin tone color identifier or identification data (e.g., color IQ referred to herein) in a mobile app, and the mobile app may use this skin tone color identifier or identification data to "look up" one or more matching products (e.g., one or more foundation products, one or more concealer products, one or more lips products, or any combinations thereof, and others) via various processes described herein in an offline mode (e.g., not connected to the Internet).

In some embodiments, the offline mode may be performed completely by the mobile computing device on which the mobile app is installed by referencing at least a portion of the aforementioned one or more catalog files with associated color data 830 that has been downloaded to the mobile computing device. In some of these embodiments, the aforementioned at least a portion of the one or more catalog files with associated color data 830 may be stored on a mobile computing device in an encrypted format. In some of these embodiments, the skin tone color identifier or identification data (or body tone color identifier or identification data that may be used interchangeably with skin tone color identifier or identification data unless otherwise explicitly distinguished) of a user may be obtained by a scan process using the image capturing device or sensor of a scanning device at a store site having a system for cosmetic product (or body care product that may be used interchangeably with cosmetic product unless otherwise explicitly distinguished) matching and recommendation or simply by entering the skin tone identifier or identification data into the system for cosmetic product matching and recommendation located at a site having such a system. In some embodiments where a reverse lookup is initiated at 832, the skin tone color identifier or identification data of a user may be obtained by a scan process using the image capturing device or sensor of a user's mobile computing device or by directly entering a previously known skin tone color identifier or identification data into the mobile app installed on the mobile computing device.

In some other embodiments, the processes initiated at 820 (mobile color IQ) to the matching service 826 and the product recommendation service 834 may be deemed as an online mode where a mobile computing device having the aforementioned mobile app installed thereupon transmits the aforementioned skin tone color identifier or identification data via the Internet to a server maintained or owned by the developer of the mobile app or manufacturer of certain cosmetic products for accessing the aforementioned processes such as the product catalog service 824, the matching service 826, the product recommendation service, and others. In these embodiments, the one or more catalog files with associated color data 830 are accessed remotely by the mobile app so that no catalog files with associated color data are stored on the mobile computing device, and the aforementioned mobile app provides one or more application programming interfaces (APIs) to communicate various processes, modules, and models, all of which may be implemented as services or microservices, in the middle tier 800B and/or the target tier 800C. In some embodiments, a product may be associated with its corresponding body tone color identifier or other form or forms of identification data. For example, the corresponding body tone color identifier or other form or forms of identification data may be printed on the packaging, the container, a separate tag attached to or placed on a shelf, and/or on a label affixed to the packaging or container of a body care product on a shelf in a store or a section of the store in some embodiments. In these embodiments, such a tag or label for a product is deemed as coupled to a shelf upon which the product is displayed. In some embodiments, information pertaining to a specific body care product in a predicted recommendation may also be associated with the corresponding body tone color identifier or other form or forms of identification data. For example, information pertaining to a product in a list of predicted or recommended products or services may include a link to or statically embedded information of its body tone color identifier or other form or forms of identification data in some embodiments. In some of these embodiments, the information pertaining to the product may further include the inventory status (e.g., in stock, available online only, out of stock, or others) In addition or in the alternative, when a user is on premise of a retail store (e.g., when the store's network detects user's mobile device with sufficient received signal strength and/or the mobile device's GPS data), the information pertaining to a product may further include the product's inventory status and the location (e.g., shelf number of the shelf on which the product is displayed, in storage, or any other location-related data, etc.) when the product is available in the particular store in which a user is in.

Figure 8B:
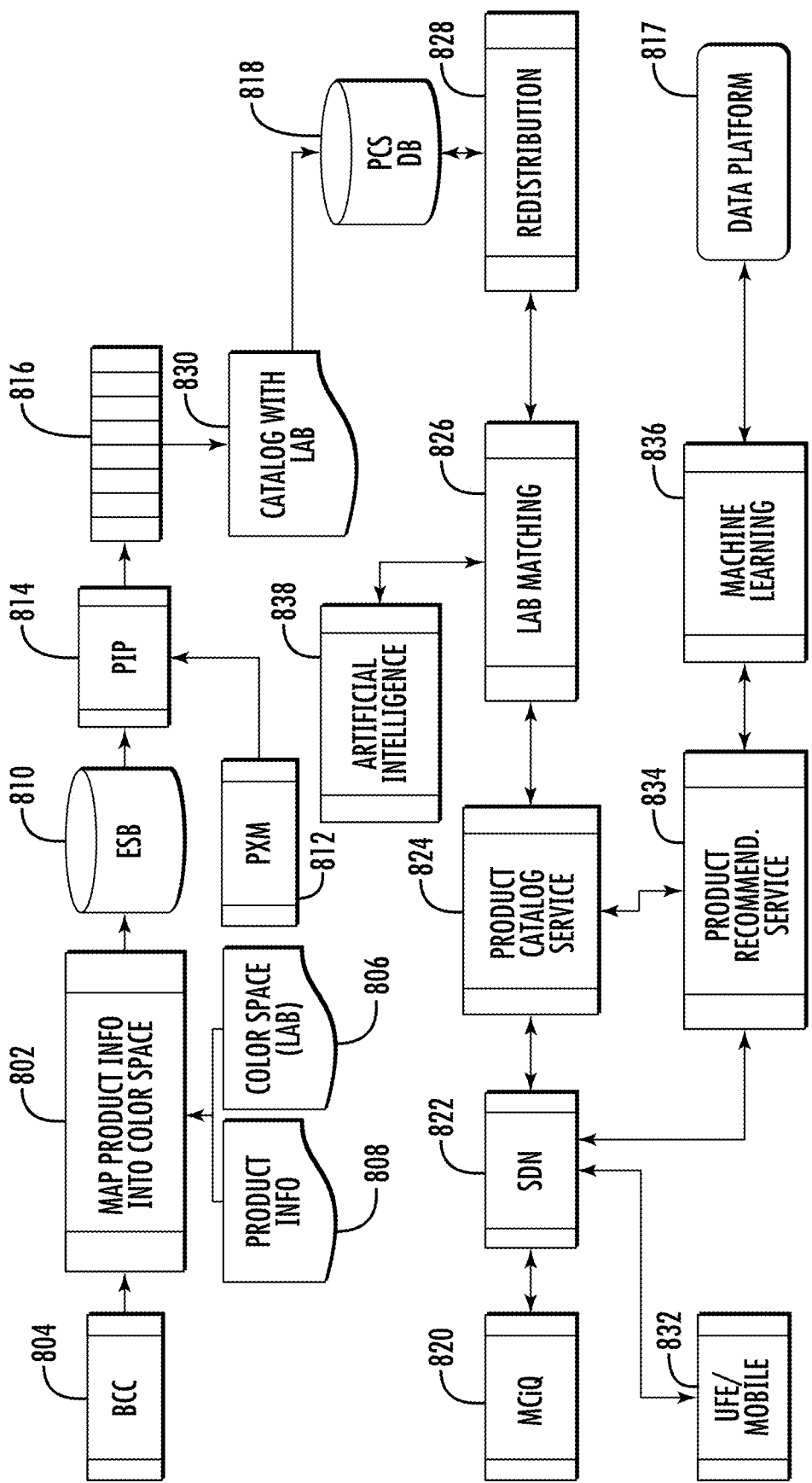
FIG. 8B illustrates an example high-level block diagram of a system for cosmetic product matching and recommendation in one or more embodiments.

FIG. 8B illustrates an example high-level block diagram of a system for cosmetic product matching and recommendation in one or more embodiments. Various components depicted in FIG. 8B are substantially similar or even identical to those depicted in FIG. 8A. Nonetheless, the example high-level architecture illustrated in FIG. 8B differs from that in FIG. 8A in where certain components are located. More specifically, the architecture in the embodiments illustrated in FIG. 8A includes three platforms—the source platform 800A, the middle tier 800B, and the target tier 800C where each platform includes respective components as illustrated in FIG. 8A and described above, and these three platforms are more likely located in different geographic locations with communication networks connecting these three platforms to facilitate the performance of product matching and recommendation. A platform or a computing platform includes an environment in which a software application is executed and comprises multiple abstraction levels, including a computer architecture, an operating system (OS), and/or runtime libraries. A platform may include components, for example, the hardware or the operating system (OS), a web browser, associated application programming interfaces, and/or other underlying software for the program code of the software application to be executed with. A platform may reside entirely on a single computing node (e.g., a computing device) or on multiple computing nodes interconnected via one or more wired and/or wireless networks. Two different platforms may reside on the same computing node (e.g., a server computer) in some embodiments or on two or more computing nodes in some other embodiments.

In contrast, the boundaries between these components in FIG. 8B are not as clearly defined as those in FIG. 8A. More specifically, although some components such as those in the target platform 800C and certain components in the middle platform 800B may still respectively below to such target platform and middle platform as described above with reference to FIG. 8A, certain other components, which are part of the middle platform 800B in FIG. 8A may now be part of the source platform (e.g., now an implementation of a part of the one or more business control center (BCC) databases (804), a part of the mobile color iQ app 820, and/or a part of the unified front end (UFE) mobile app (e.g., a store digital app installed in a system for cosmetic product matching and recommendation at a cosmetic product retail site).

For example, the one or more databases 818, the data platform 817, and the data redistribution layer 828 in the target tier 800C in FIG. 8A as well as the enterprise service bus 810, the development network (822) which includes a collection of APIs to interface with various mobile computing devices (e.g., clients' mobile computing devices having MCiQ 820 installed thereupon, the unified front end (UFE) mobile computing devices 832 installed on systems deployed at cosmetic product retail sites, and others), some or all of the product information 808 and color space data 806, some or all of the catalog files 830, the a distributed system 816 (e.g., Kafka or other equivalent module or modules), and the product catalog service 834 may still be deployed in the middle platform. A unified front end (UFE) mobile computing device 832 installed on a system deployed at a cosmetic product retail site may include a mobile computing device such as a smart phone, a tablet, a laptop computer, or a desktop computer (e.g., the mobile computing device illustrated in FIG. 17A-17B and described below). It shall be noted that although a desktop is generally not considered as a mobile computing device, a desktop computer installed on a system deployed at a cosmetic product retail site may nevertheless be considered as a mobile computing device in some embodiments because a desktop computer may be attached to a kiosk (e.g., a kiosk described below with reference to FIGS. 16B-D) that may exhibit certain mobility in these embodiments.

Similarly, the components in the original source platform such as the one or more business control center (BCC) databases (804), the mobile color iQ app 820, and the unified front end (UFE) mobile apps (e.g., a store digital app installed in a system for cosmetic product matching and recommendation at a cosmetic product retail site) may still belong to the source platform. Nonetheless, some embodiments may implement certain components or at least a portion thereof into the source platform such as implementing such certain components or a portion thereof on a client's mobile computing device 820 or the unified front end mobile computing device 832. Such components include, for example, one or more of the artificial intelligence model 836 or the artificial intelligence model 838 in some embodiments. In some of these embodiments, one or more of the product recommendation service 834, the matching service 826, the product/user experience management module (PXM) 812, the product ingestion processing 814, or the model 802 that performs mapping between product information and color information may also be implemented, at least partially, on a client's mobile computing device 820 or the unified front end mobile computing device 832. In some of these embodiments where a smaller portion of a model or module is implemented on a client's mobile computing device 820 or the unified front end mobile computing device 832, the remaining portion of the model or module may nevertheless be implemented in one or more computing systems in the middle platform.

For example, an artificial intelligence model (e.g., 836 or 838) that is implemented entirely in the middle platform 800B in FIG. 8A may be partially or entirely implemented on a client's mobile computing device 820 or the unified front end mobile computing device 832. Some mobile computing devices such as smart phones, tablets, or smart devices (e.g., VR/AR/XR goggles, smart glasses, and others) may only possess fixed-point processing capabilities whereas a computing system such as a server computer in the middle platform or the target platform may possess both fixed-point and floating-point processing capabilities, although some more powerful mobile computing devices such as laptop computers may also have both fixed-point and floating-point processing capabilities. Moreover, mobile computing devices may have not only less powerful compute power and storage capacity but also much shorter execution time due to the restrictions of battery life.

To accommodate those mobile computing devices with less compute power, storage, and execution time, some embodiments implement a model (e.g., an AI model 836 or 838) with optimized code for execution on more powerful computing devices such as desktop computers or even server computers so that the model provides sufficient accuracy within reasonable runtime due to the vast processing capacities of such more power computing devices. In order to deploy such a model onto a less power computing device such as the mobile computing devices described above with less compute power, storage, and execution time, the model (or at least a portion thereof to be ported to such a less powerful mobile computing device) may be modified into a fixed-point processing model.

In an example with an AI model having a convolutional neural network, some embodiments may decompose the original convolution with a larger kernel size in the original optimized code for more powerful computing devices with smaller kernels. Some embodiments may adopt the strip convolutions (e.g., 1×M or M×1 convolutions) while some other embodiments may use depth-wise separable convolution that replaces standard convolution may be replaced by a depth-wise convolution for feature maps filtering and then by a point-wise convolution for feature maps combination or aggregation.

Some embodiments may further employ one or more network pruning techniques or regularization techniques (e.g., dropout techniques) to remove connections corresponding to weights that are less important (e.g., below a threshold). The pruned or regularized model may be subject to additional training using explainable AI techniques to determine which connections may be subject to removal.

Some embodiments may use quantization techniques to convert, for example, 32-bit floating-point (FP32) representations into fixed-point representations (e.g., 8-bit integer representation). Some embodiments may adopt even more aggressive quantization techniques such as binary quantization (e.g., XNOR network with XNOR and bit counting) that replaces floating-point arithmetic operations with bit-wise operations and floating-point representations with binary representations (e.g., $\{-1, 1\}$ or $\{0, 1\}$). Some embodiments may adopt the ternary network that applies ternary-valued weights (e.g., $\{-1, 0, 1\}$) that provides better accuracy at the expense of more compute power utilization, more storage, and more power consumption.

In some embodiments where one or more of the aforementioned network reduction or transformation techniques are utilized, the process to port the original more complex model to the aforementioned reduced model may be retrained until the reduced model achieves a reasonable balance between performance and accuracy.

Figure 9A:
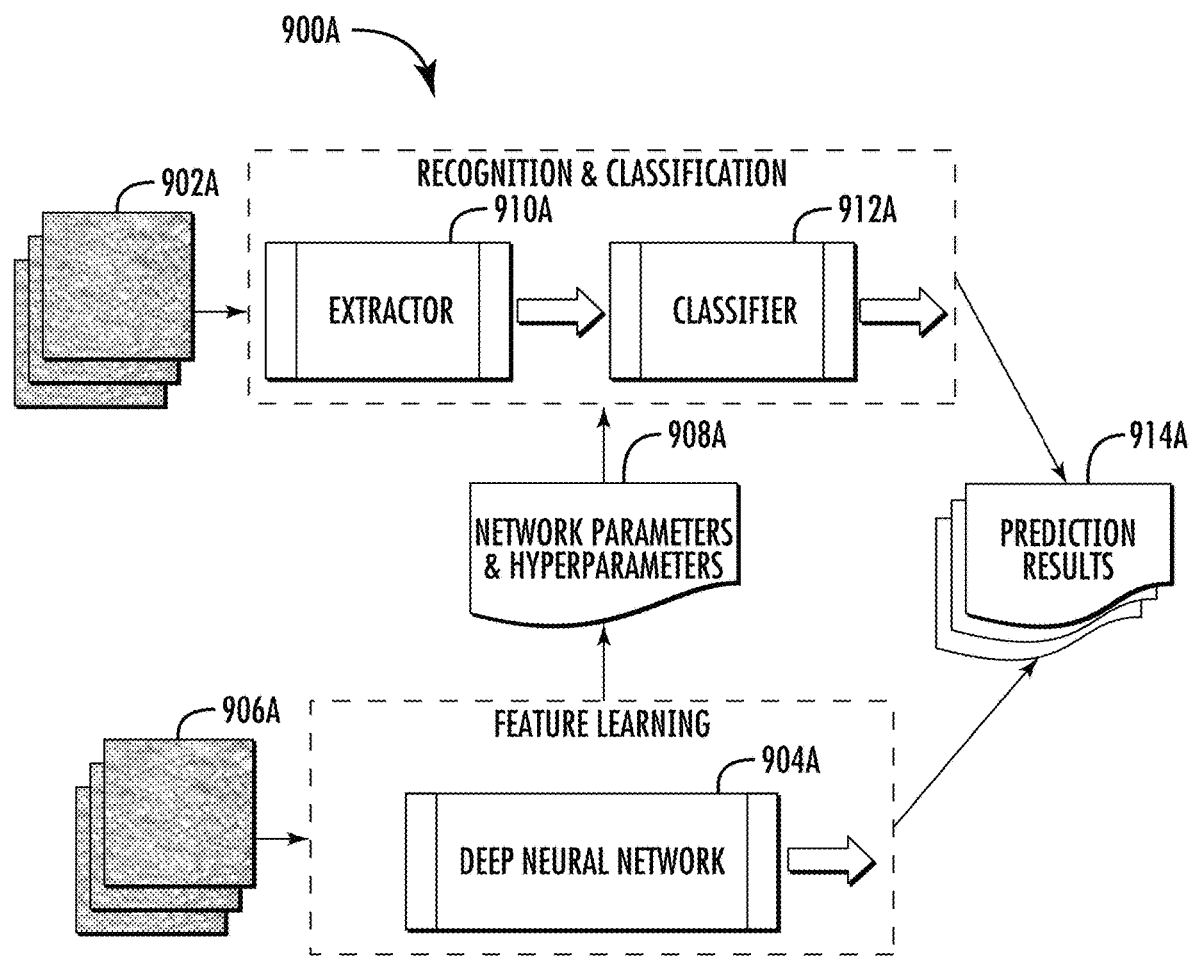
FIG. 9A illustrates an example high-level block diagram for a classification model that may be utilized to implement various features and functionalities described herein in one or more embodiments.

FIG. 9A illustrates an example high-level block diagram for a classification model that may be utilized to implement various features and functionalities described herein in one or more embodiments. More specifically, FIG. 9A illustrates more details about an artificial intelligence module that recognizes objects and predicts the color of an input image (e.g., a image obtained by scanning a user's skin using the image capturing sensor of a mobile computing device of an end user or a Mobile Color IQ device in a system for cosmetic product matching and recommendation located at a site carrying one or more cosmetic products. In these embodiments, the artificial intelligence module may include a deep neural network 904A that includes at least two hidden layers in addition to an input layer and an output layer.

The deep neural network 904A may be trained, tested, and/or validated in a supervised, unsupervised, or hybrid mode using a plurality of datasets 906A (e.g., a plurality of scanned images of one or more users, a plurality of synthetic, artificially created images, or a combination of scanned image or images and synthetic, artificially created image or images) for feature learning (e.g., whether an input image 906A include hairs, freckles, wrinkles, moles, pre-malignant skin growth, malignant skin growth, other colored spots, capillaries, and others) For example, a plurality of datasets may be first identified and then partitioned into two or three subsets where one subset (e.g., about 40 percent of the plurality of datasets) may be used for training the deep neural network 904A, another dataset (e.g., about 30 percent of the plurality of datasets) may be used for testing the trained version of the deep neural network 904A, and the other data set (e.g., about 30 percent or the remainder of the plurality of datasets) may be used for validating the trained version of the deep neural network 904A.

A synthetic, artificially created image may be generated by making an imperceivably small change to an actual image (e.g., a scanned image of a user's skin) in such a way that a human without aid cannot discern the actual image from the synthetic, artificially created image. For example, a synthetic, artificially created image may be created by altering the lightness value (or other values such as chroma value or depth value) with such an imperceivably small amount that human eyes cannot distinguish between the actual image and the synthetic, artificially created image, yet the classifier will misclassify the synthetic, artificially created image (e.g., predicting a different, incorrect skin tone than the ground truth skin tone of the actual image).

In some embodiments, the deep neural network 904A may be trained with one or more such synthetic, artificially created images to improve its accuracy (e.g., better capability in discerning small changes). Such a small change may or may not necessarily apply to the entire frame of an actual image. In some embodiments, a visually imperceivably small change may be made to a small portion of an actual image (e.g., by changing the depth of a hair or a small colored spot in an actual image to make the hair or the small colored spot appear lighter) to generate a corresponding synthetic, artificially created image, and such synthetic, artificially created image may also be used to train the object recognition and/or feature extraction capability of the deep neural network 904A.

In some embodiments, validation of a trained version of the deep neural network 904A may be skipped and ignored. In these embodiments, the plurality of datasets 906A may be partitioned into a first subset (e.g., about 60 percent of the plurality of datasets) for training the deep neural network 904A and a second subset (e.g., about 40 percent or the remainder of the plurality of datasets) for testing the deep neural network 904A.

Training the deep neural network 904A may include learning one or more parameters 908A of the deep neural network 904A. The one or more parameters to be learned may include, for example, one or more network parameters, one or more hyperparameters, or a combination of one or more network parameters and one or more hyperparameters of the deep neural network 904A.

A hypermeter is a variable that determines the structure of the underlying deep neural network 904A and/or how the deep neural network 904A is to be trained. In some embodiments, these one or more hyperparameters may include, for example but not limited to, the learning rate of the deep neural network 904A, the number of hidden layers, the number of neurons in one or more layers, whether and which specific layer or layers and/or whether and which specific neuron or neurons may be dropped out or regularized (e.g., whose output is ignored by assigning the corresponding weight to zero) for improving the accuracy of the deep neural network 904A while conserving computation resources, or any combinations thereof, momentum of the deep neural network 904A, the total number of epochs for the deep neural network 904A, one or more batch sizes, or any combination thereof, and others.

Dropout is regularization technique to avoid overfitting (increase the validation accuracy) thus increasing the generalizing power. Some embodiments use a small dropout value of 20 percent to 50 percent of neurons with 20 percent providing a good starting point. A probability too low has minimal effect and a value too high results in under-learning by the network. For a larger neural network, the neural network's performance may be improved when dropout is used on the network, giving the model more of an opportunity to learn independent representations.

A hidden layer denotes a layer between the input layer and the output layer of the deep neural network 904A. In some embodiments, training the deep neural network 904A may include repeatedly adding a layer to the deep neural network 904A until the error no longer improves or is within an acceptable or desirable threshold. A larger number of hidden units within a layer with regularization techniques may increase accuracy while a smaller number of units may cause underfitting in some embodiments. The momentum may be used to know the direction of the next step with the knowledge of the previous steps and ma assist to prevent oscillations. In some embodiments, the momentum may be set between 0.5 to 0.9.

In some embodiments, the learning rate of the deep neural network 904A defines how quickly the deep neural network 904A updates its parameters. A low learning rate may slow down the learning process but converges smoothly. A larger learning rate speeds up the learning but may not converge. In some embodiments, a decaying learning rate may be used in the deep neural network 904A. The number of epochs denotes the number of times the entire training data is shown to the network while training. The number of epochs may be increased until the validation accuracy starts decreasing even when training accuracy is increasing (overfitting). A batch size is the number of sub samples given to the network after which parameter update happens. In some embodiments, a batch size may be set to 32, 64, 128, and/or 256, and others.

A network parameter denotes a parameter that is actually accounted for during the operation of the deep neural network 904A. In some embodiments, these one or more network parameters include, for example but not limited to, one or more weights in one or more kernels (also referred to as a weight matrix or a filter hereinafter), one or more biases in the deep neural network 904A, initial values of weights in one or more kernels, one or more activation functions for the deep neural network 904A, or any combinations thereof, and others.

An activation function may be used to introduce nonlinearity to models, which allows deep learning models to learn nonlinear prediction boundaries. In some embodiments, a rectifier activation function (e.g., a rectified linear unit or ReLU) may be used. In some other embodiments, sigmoid may be used in the output layer while making binary predictions. Yet in some embodiments, softmax may be used in the output layer while making multi-class predictions. In some embodiments, different weight initialization schemes may be utilized according to the activation function used on each layer. In some of these embodiments, uniform distribution of initial weights may be used.

Learning one or more parameters of the deep neural network 904A may include iteratively computing an error in the prediction 914A (e.g., recognized object or objects in an input image, predicted class such as the predicted skin tone of an input image, a matching product, and others) produced by the deep neural network 904A and backpropagating the computed error through each layer in the deep neural network 904A using, for example, a gradient descent algorithm (e.g., a stochastic gradient descent algorithm or other similar or equivalent algorithm). With the backpropagated error, parameters (e.g., hypermeters and/or network parameters) may be iteratively updated until a cost or objective function (e.g., a cross-entropy function) is satisfied.

In some embodiments, once the deep neural network 904A is trained, this trained deep neural network may be used as, for example, the feature extractor 910A for object recognition and/or classification using these learned parameters 908A. The feature extractor 910A may include a convolutional neural network (CNN) that receives input images 902A (e.g., scan results from a scan at a mobile color IQ scanning device, from an end user's mobile computing device, and others) and computes feature vector or feature maps in each layer of the feature extraction 910A for each input image 902A. The feature vector or vectors or feature map or maps generated by the feature extractor 910A may be forwarded to a classifier 912A that predicts an output 914a (e.g., the color or skin tone of the skin as presented in an input image, one or more recognized objects such as hair, freckles, wrinkles, other colored spot or spots, and others) based at least in part upon the input feature vector or vectors or feature map or maps. In some embodiments, the trained deep neural network 904A may also be used as the classifier 912A. In some of these embodiments, the classifier 912A may be determined by replacing one or more fully connected layers in a trained deep neural network 904A with support a vector machine model. In some embodiments where the classifier 912A predicts skin tones, the last layer of the classifier 912A may include a software having the same number of neurons as the number of skin tones to be predicted. More details about the deep neural network 904A will be described later with reference to FIGS. 9B-9K.

Figure 9B:
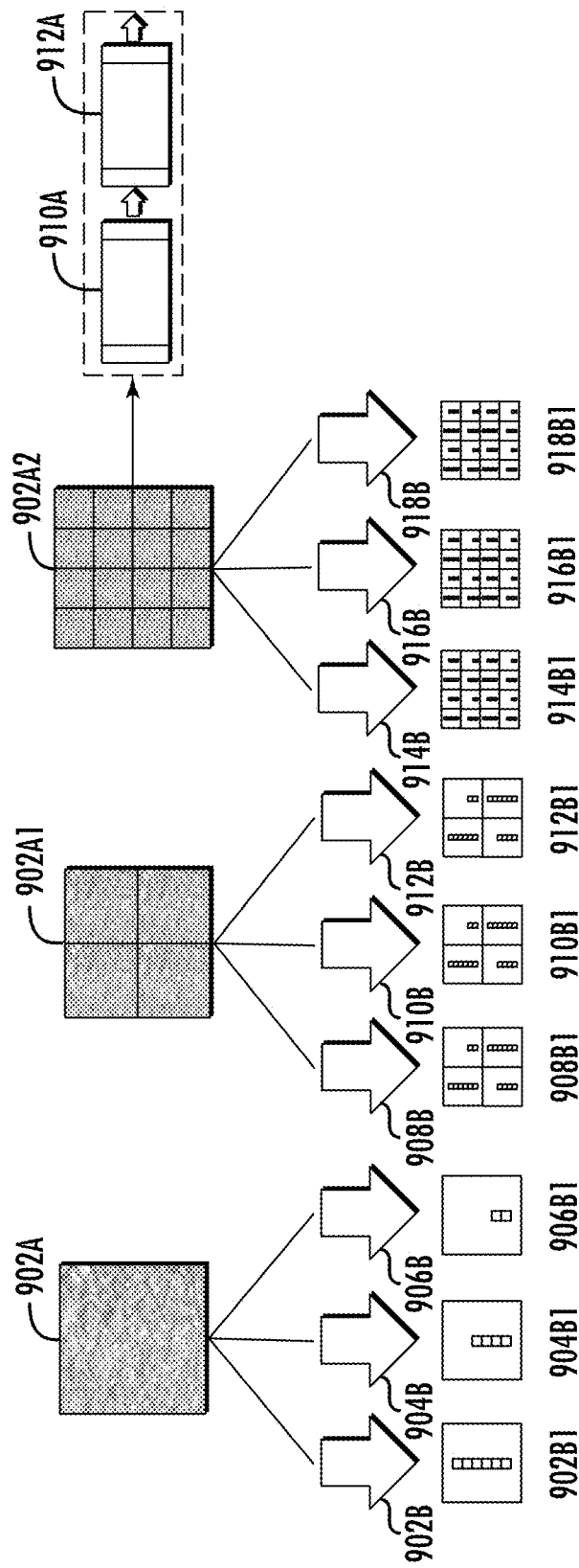
FIG. 9B illustrates more details about a portion of FIG. 9A in some embodiments.

FIG. 9B illustrates more details about the feature extractor 910A of FIG. 9A in some embodiments. More specifically, FIG. 9B illustrates more details about color prediction and recognition (e.g., predicting skin tone of a user's skin) using a modified, trained deep neural network with N levels of hierarchies to represent features in each of an input image. These embodiments incorporate spatial information by successively partitioning each input image into a grid of subregions at each hierarchy of a plurality of hierarchies (e.g., a three-hierarchy, five-hierarchy, and others, partitioning), performing object (e.g., features such as hairs, freckles, wrinkles, other colored spots, and others) recognition in each subregion, and aggregating (e.g., concatenating the respective results of subregions) the result of each of a plurality of subregions to represent the input image.

The artificial intelligence model may include a modified, trained deep neural network such as a modified version of the trained deep neural network 904A. In some embodiments, the output of the modified version of the trained deep neural network may be generated by softmax. In some other embodiments, the output of the modified version of the trained deep neural network may be generated by a number of fully connected layers. In some of these embodiments, only the last N layers (e.g., the last three layers) of the neural network (e.g., 912A in FIG. 9A) are used for color recognition because outputs of earlier layers in the network have been found not to be very informative from analyses (e.g., entropy analysis). Yet in some other embodiments, the output of the modified version of the trained deep neural network may use a support vector machine (SVM) model, rather than the aforementioned fully connected layers or softmax in the final layer or layers of the deep neural network 904A to avoid overfitting because softmax may tend to overfit in some cases. Each layer (other than the input layer) in the modified version of the trained deep neural network receives outputs (e.g., feature vectors or feature maps) of the preceding layer (e.g., a convolution layer, an input layer, and others)

A support vector machine model may reshape the response maps generated by preceding convolutional layers into feature vectors that are then forwarded to the successive classifier (912A) for training or testing. Further, selecting support vector machine over fully connected layer or layers may be based at least in part upon one or more factors including, for example but not limited to, a support vector machine's performance is better than corresponding fully connected layer or layers because the regularization constraint may help combating overfitting that is usually a main issue with FC layers; or the number of parameters of support vector machine is less than that of corresponding fully connected layers and thus makes changing configuration and subsequent tuning, learning, training easier.

The modified, trained deep neural network is aimed at extracting features from different subregions of an input image and aggregating the extracted features of all the subregions together to describe the input image. Moreover, the modified, trained deep neural network computes features at a fixed resolution, varies the spatial resolution at which the computed features are aggregated, and produces results in a higher-dimensional representation that preserves more information (e.g., finer features such as thin hairs, thin freckles, and/or thin wrinkles retain two modes at every level of the hierarchy in some embodiments). In these one or more embodiments, an input image is successively subdivided into subblocks, and the artificial intelligence model computes a color attribute (e.g., a histogram or a histogram statistic, and others) for each of the subblocks. Compared with these embodiments, conventional bag of features (BoF) technique may be widely used to depict a scene of a whole picture or determine that an image contains an object but disregard all info about the layout of the features so they are incapable of capturing shape or of segmenting an object from its background. In contrast, these embodiments segment a hair, a freckle, or a wrinkle from the background-skin. Further, other conventional approaches attempt to build structural object descriptors that have been proven to be challenging at least.

Some embodiments compute the feature or features of each region in convolutional layers in the learned deep neural network architecture (e.g., 904A after training). The feature or features includes a set of response maps generated by the learned filters or kernels in the convolutional layers. Unlike some conventional approach that employ pooling to combine all local features yet lose the information of some pixels that are ignored during pooling, some embodiments consider the information of each pixel in the feature or features of an input image.

During operation, an input image 902A (or 906A during training, but FIG. 9B illustrates that a version of the trained deep neural network 904A may be deployed as the feature extractor 910A or even the classifier 912A) may be successively partitioned into finer grids at each of a plurality of hierarchies. For the case of illustration and explanation, FIG. 9B illustrates three hierarchies at which an input image is respectively partitioned into a 1×1 grid, 2×2 grid, and 4×4 grid. It shall be noted that although FIG. 9B illustrates the use of three hierarchies for partitioning an input image into respective square grids, other embodiments may use a different number of hierarchies and/or different grids such as rectangular grids (e.g., 4×3 grid, 16×9 grid, and others). In some of these other embodiments, the partitioning scheme may be determined based at least in part upon, for example but not limited to, the aspect ratio of the input image.

The number of feature types may be determined. For skin tone recognition and prediction, the number of features may include, for example but not limited to, hairs of varying colors, freckles, wrinkles, other colored spots, and others, in some embodiments. The number of features may be referenced during feature extraction (e.g., by 910A) and/or classification (e.g., by 912A) to categorize features into the corresponding bins (e.g., a first bin for hairs of varying colors, a second bin for freckles, a third bin for wrinkles, a fourth bin for other colored spots, and others) At each hierarchy, an image is partitioned into a grid. Each successive partitioning results in a lower resolution. For example, the input image 902A is partitioned into a 1×1 grid (or no partitioning) having a first resolution (e.g., a 224×224×3 input image) at the first hierarchy. At the second hierarchy, the input image is partitioned into a 2×2 grid as shown in 902A1 having four subregions, and each of the four partition represents a 112×112×3 sub-image with hence a lower resolution than that of 902A. At the third hierarchy, each of the four sub-regions in 902A1 in the input image is further partitioned into a 2×2 grid to result in a total of 4×4 grid (16 subregions) as shown in 902A2, and each of the sixteen partition represents a 56×56×3 sub-image with hence an even lower resolution than that of 902A1.

The feature extractor 910A may then perform feature recognition for each of the subregion (for the entire image at the hierarchy) at each of the plurality of hierarchies and place each type of features into a corresponding bin. For an example with three feature types such as a freckle feature type, a hair feature type, and a colored spot feature type for the case of illustration and explanation, at the first hierarchy, recognized features corresponding to different feature types will be assigned to or associated with respective bins. For example, recognized hair features are assigned to or associated with the first bin 902B1; recognized freckle features are assigned to or associated with the first bin 904B1; and recognized colored spots are assigned to or associated with the first bin 906B1.

At the second hierarchy where an input image is partitioned into a 2×2 grid (with 2×2 subregions) 902A1, for each subregion, recognized features corresponding to different feature types will be assigned to or associated with respective bins. For example, recognized hair features are assigned to or associated with the first bin 908B1; recognized freckle features are assigned to or associated with the first bin 910B1; and recognized colored spots are assigned to or associated with the first bin 912B1. Similarly, at the third hierarchy where each subregion in 902A1 is further partitioned into a 2×2 grid (with 2×2 subregions) 902A2, for each subregion in 902A2, recognized features corresponding to different feature types may be assigned to or associated with respective bins. For example, recognized hair features are assigned to or associated with the first bin 914B1; recognized freckle features are assigned to or associated with the first bin 916B1; and recognized colored spots are assigned to or associated with the first bin 918B1.

In this manner, these embodiments illustrated in FIG. 9B compute features (e.g., recognized features of each type, histogram with different types of features in different bins, and/or a histogram statistic) at a fixed resolution for each subregion, vary the spatial resolution at which the computed features are aggregated by successively partitioning an input into finer grids, and produce a higher-dimensional representation that preserves more information (e.g., fine features such as thin white and thin black lines retain two modes at every level of the spatial hierarchy in the invention but may be represented as uniform gray in all but the finest level of multiresolution histogram). This is in sharp contrast with conventional approaches using multi-resolution features or histograms that are obtained by repeatedly subsampling an input image and computing a global histogram of pixel values at each new level and thus result in loss of information due to discarding information about the layout of the features so that these conventional approaches are incapable of capturing the shape or segmenting an object from its background.

In other words, these embodiments present a much superior approach to feature extraction and color recognition in at least that these embodiments accurately segment features (e.g., hairs, freckles, wrinkles, other colored spots) from the background (a user's skin) so that the skin tone of the skin is more accurately determined by ignoring the recognized features and focusing on the skin to determine the skin tone. For example, the presence of hairs and features having colors different from the true skin tone may obscure the computed histogram due to the presence of different color or colors in an image and thus produce less accurate skin tone prediction. Further, the segmented features may be separately processed (e.g., recognizing a colored spot having an off-white color) so that different product or products may be recommended (e.g., concealer) for this colored spot.

Although the feature extractor and classifier will be described in greater details below with reference to FIGS. 9C-9K, a high-level introduction is presented below in view of the data preparation illustrated in FIG. 9B and described above. In some embodiments, the feature extractor (910A) performs matching in a two-dimensional image space and uses clustering techniques in the feature space. In some of these embodiments, feature vectors may be quantized into N discrete feature types. The feature extractor 910A may then cluster features of the same type into a bin so that features of the same type are matched to one another. Each channel N provides two sets of two-dimensional vectors, XN and YN, respectively representing the coordinates of features of type N recognized in the respective images. The kernel may then be the sum of the separate channel kernels. In addition, the feature extractor computes a feature in each sub-region in convolutional layers in the deep neural network architecture (e.g., 904A after training). This feature may include, for example, a set of response maps that is generated by the learned filters/kernels in the convolutional layers. Some embodiments may employ pooling to combine all or some local features yet loses the info of some pixels ignored during pooling. These embodiments may employ pooling (e.g., max pooling, average pooling, and others) in earlier convolutional layers (e.g., all convolutional layers but the last three convolutional layers) to avoid unacceptable degradation in accuracy. Some other embodiments consider the information of each pixel in the image is considered in the feature.

In some embodiments, the classifier 912A may employ softmax having the same number of neurons as the total number of skin tones to predict. Some other embodiments may employ one or more fully connected layers for generating prediction outputs. Yet in other embodiments, the classifier 912A may include a support vector machine (SVM) that reshapes the response maps generated by convolutional layers into feature vectors that are sent to the successive classifier (912A) for training or testing. These embodiments adopt the support vector machine because SVM's performance is better because the regularization constraint in SVM may help combating overfitting that is usually a main issue with fully connected layers and further because the number of parameters of SVM is less than that of fully connected layers and thus makes changing configuration and subsequent tuning, learning, training easier.

The classifier 912A is devised to perform at least two functions either alone or in tandem with the feature extractor 910A: (1) determination of skin tone (depth, saturation, and undertone); and (2) recognition and correct classification of speckles, hair, existing foundation/concealer, and others. As explained above, separate classification for speckles and/or colored spots for additional recommendation. For example, separate foundation and/or concealer product or products may be determined for speckles and colored spots after segmenting and processing such speckles and color spots. Further, exclusion of speckles, hairs, and colored spots leads to more accurate determination of skin tone. Moreover, if a user's skin is not cleaned or not sufficiently cleaned before scanning, the classifier (after training) is capable of scanning the foundation or concealer covered skin area and induce or predict the correct skin tone by using the characteristics (e.g., depth, saturation, and hue) of existing foundation/concealer.

Figure 9C:
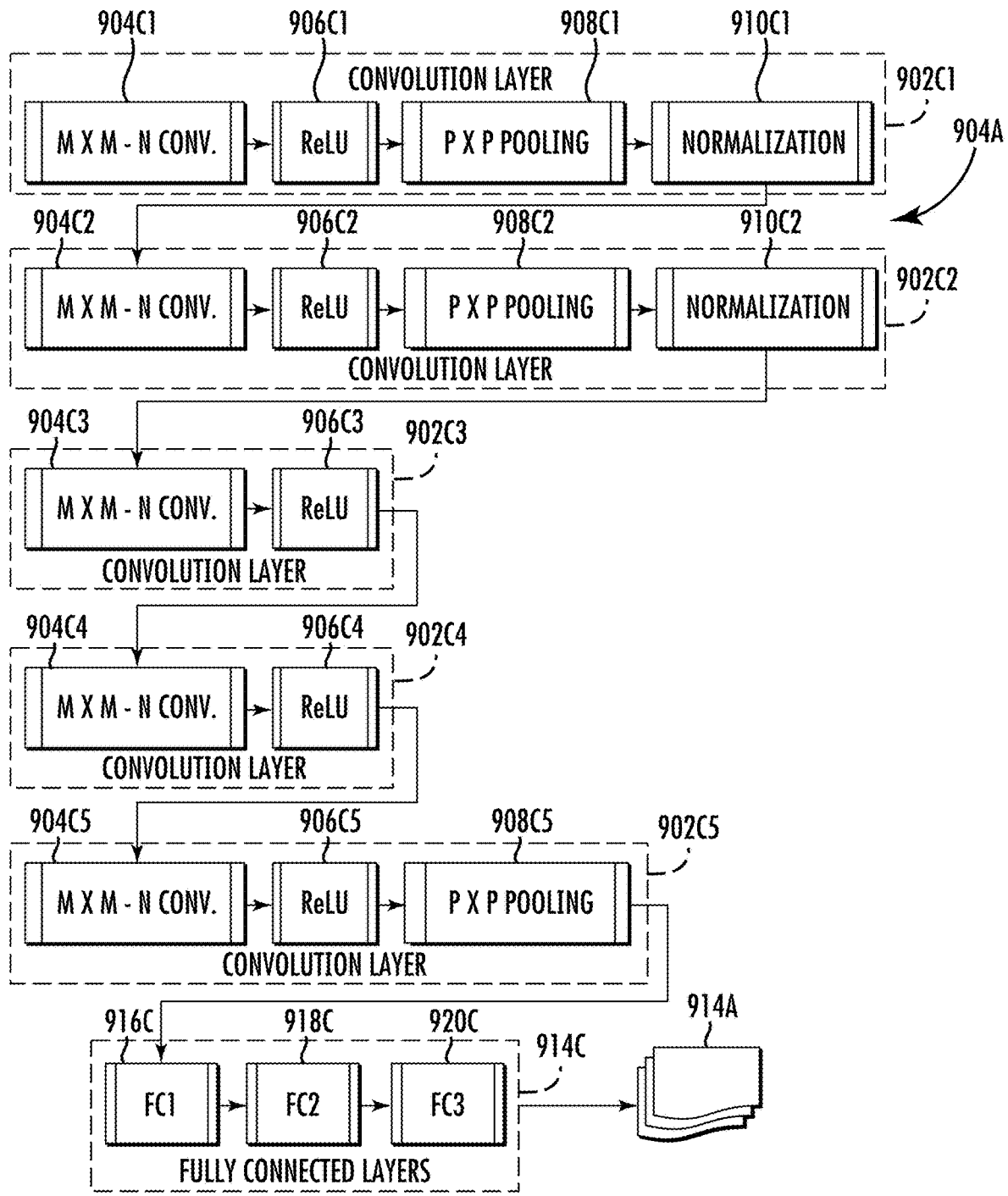
FIG. 9C illustrates more details about an example model of a portion of FIG. 9A in some embodiments.

FIG. 9C illustrates more details about an example model of a portion of FIG. 9A in some embodiments. More particularly, FIG. 9C illustrates more details of the deep neural network 904A that is the subject of training with one or more datasets 906A illustrated in FIG. 9A. In these embodiments, each filter (or kernel or weight matrix) is learned during training. For filters receiving LAB data (or data in other color space such as RGB) as input, each of these filters includes 3 channels. In addition or in the alternative, one or more edge filters (e.g., half-white edge filter, half-black edge filter) may be learned because edge filters may aid in color classification.

The deep neural network 904A may include a first convolution layer 902C1 having an M×M filter with a stride of N convolution layer 904C1 whose output is forwarded to a first activation function 906C1 (e.g., an ReLU or other type of activation function). The activated output of the first activation function 906C1 is passed to a P×P first pooling layer 908C1 (e.g., a max pooling layer, an average pooling layer, and others) that aggregates the activated output into a pooled output that is then forward to a first normalization layer 910C1. The deep neural network 904A may further include a second convolution layer 902C2 having an M×M filter with a stride of N convolution layer 904C2 that receives the output of the first normalization layer 910C1. The convolution layer 904C2 generates and forwards an output to a second activation function 906C2 (e.g., an ReLU or other type of activation function). The activated output of the second activation function 906C2 is passed to another P×P second pooling layer 908C2 (e.g., a max pooling layer, an average pooling layer, and others) that again aggregates the activated output into a pooled output that is then forward to a second normalization layer 910C2.

The third layer of the deep neural network 904A is a third convolution layer 902C3 that includes an M×M kernel with a stride of N convolution layer 904C3 that receives the output of the second normalization layer 910C2 and generates and forwards an output to a third activation function 906C3. In the embodiments illustrated in FIG. 9C, the third and fourth convolution layers do not have pooling layers to avoid loss of details that is a common issue with pooling layers.

The fourth layer of the deep neural network 904A is a fourth convolution layer 902C4 that includes an M×M kernel with a stride of N convolution layer 904C4 that receives the output of the third activation function 906C3 and generates and forwards an output to a fourth activation function 906C4. The fifth layer of the deep neural network 904A is a fifth convolution layer 902C5 that includes an M×M kernel with a stride of N convolution layer 904C5 that receives the output of the fourth activation 906C4 and generates and forwards an output to a fifth activation function 906C5 that activates the output of the convolution layer 904C5 into an activated output. The activated output is pooled with a P×P pooling layer 908C5.

The last layer in the deep neural network 904A includes a number of fully-connected (FC) layers or sub-layers that are connected in series. In some embodiments, the number of FC layers and/or the respective number of neurons in one or more FC layers may be the target of training. For example, the fully connected layer 914C may include a first FC layer 916C that receives the output of the pooling layer 908C5 as an input and generates and forwards its output to a second FC layer 918C. The second FC layer 918C receives the output of the first FC layer 916C and generates and forwards its output to a third FC layer 920C. The third FC layer 920C receives the output from the second FC layer 918C and generates the final output 914A.

As a practical example deep neural network may include 224×224×3 input images for the first convolution layer 902C1 having 96 kernels of size 11×11×3 with a stride of 4 pixels. The pooling layer 908C1, 908C2, and 908C5 are used to reduce the size of the output of the preceding layer to shorten the computation time and may include a 2×2 pooling. The second convolution layer 904C2 may include 256 kernels of size 5×5×48 with a stride of 1. The third 904C3, fourth 904C4, and fifth 904C5 convolution layers are connected to one another without any intervening normalization or pooling layers (e.g., max pooling, avg. pooling, and others). The third convolution layer 904C3 has 348 kernels of size 3×3×256 with a stride of 1 connected to the normalized, pooled outputs of the second convolution layer 904C2. The fourth convolution layer 904C5 has 384 kernels of size 3×3×192 with a stride of 1. The fifth convolution layer 904C5 has 256 kernels of size 3×3×192 also with a stride of 1.

The number of neurons in at least the last FC layer (920C) may be determined based on the total number of classes to be predicted. For example, each of the first, second, and third FC layers (916C, 918C, and 920C) has 4096 neurons in some embodiments where the total number of different skin tones to be predicted is fewer than 4096. With the current library covering more than 5,000 or even more than 10,000 shades for foundation/concealer products, the number of neurons in at least the last FC layer (920C) may be 8,192 neurons and 16,384 neurons, respectively. In some embodiments, the last FC layer (920C) may be replaced with N-way softmax where N denotes the number of nodes (neurons) to cover the total number of skin tones to predict. For each of the three FC layers, the respective output Yi may be represented as Yi=Wi-1*Yi-1+bi-1 where* denotes the element-wise product and summation (e.g., inner product between the kernel Wi-1 and the input Yi-1. It shall be noted that this eight-layer deep neural network 904A (five convolution layers and three FC layers) merely represents an example implementation in some embodiments while other embodiments may use more or fewer layers. For example, a deep neural network having two convolution layers and one FC layer may also be utilized for expedient performance although deeper neural networks provider better accuracy at the expense of higher computational costs.

Figure 9D:
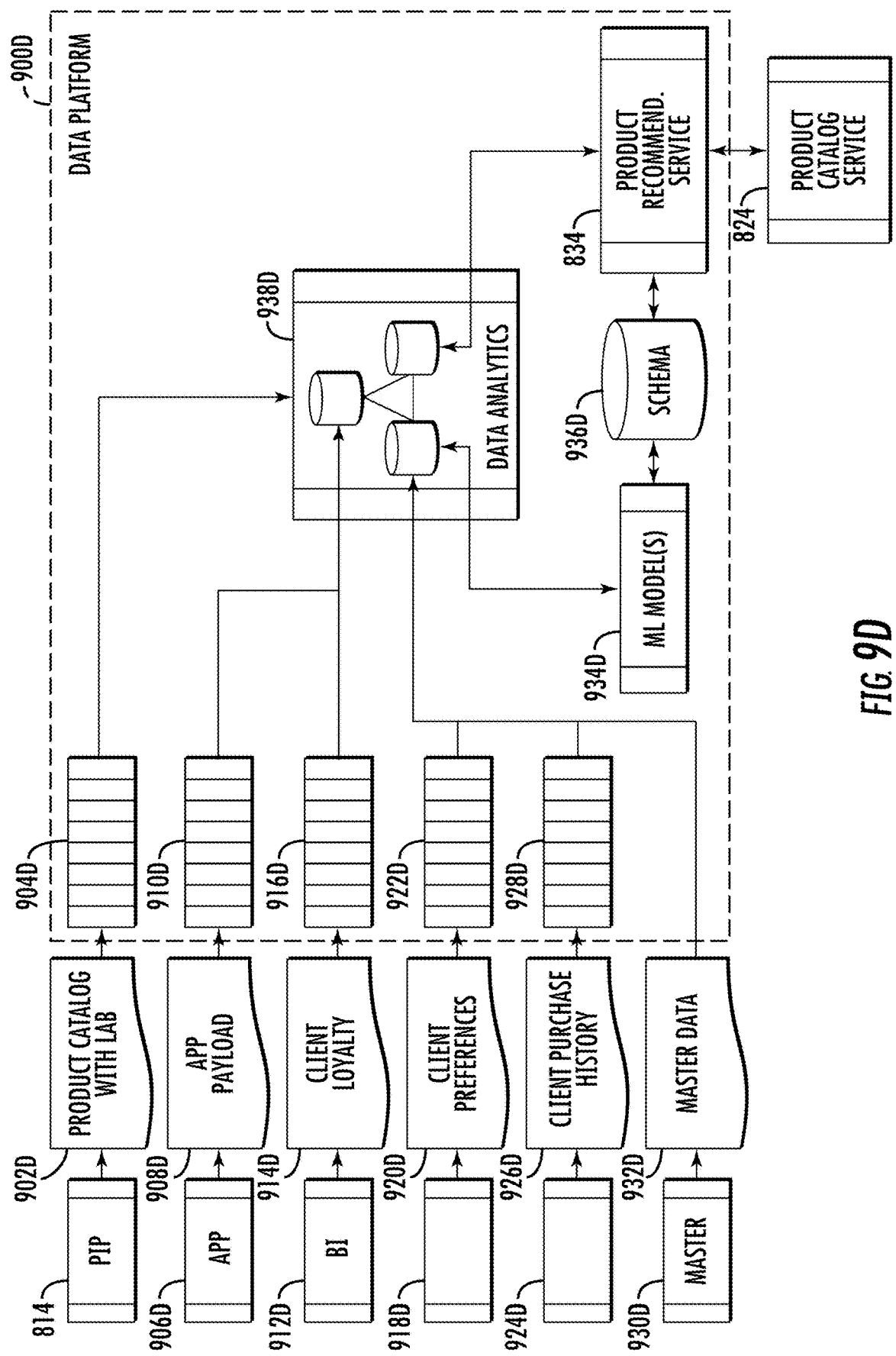
FIG. 9D illustrates an example platform for cosmetic product matching and recommendation with artificial intelligence techniques in one or more embodiments.

FIG. 9D illustrates an example platform for cosmetic product matching and recommendation with artificial intelligence techniques in one or more embodiments. More particularly, FIG. 9D illustrates an example data platform 900D that receives various streams of data from multiple sources for various analytics that may be utilized and/or updated by various models, modules, services, microservices, and others (e.g., one or more artificial intelligence models 934D, the product recommendation service 934, and others) in a system for cosmetic product matching and recommendation. In some of these embodiments, these multiple sources may include one or more of a product ingestion processing module 814, one or more apps or applications 906D (e.g., one or more mobile apps, one or more store digital apps for use by beauty advisors installed at respective sites carrying cosmetic products, and others), a beauty insider (BI) model or system 912D, a data source 918D pertaining to acquiring and/or storing client preferences, a data source 924D pertaining to acquiring and/or storing client purchase and/or return histories, or a master source 930D storing master data for a system for cosmetic product matching and recommendation.

The product ingestion processing module 814 may provide, for example, product catalog or catalogs with associated color data 902D (e.g., color data in the LAB color space for each of a plurality of products). The one or more apps or applications 906D may provide, for example, payload data 908D that may be used to enhance user experiences (UX). The business intelligence module or system 912D may provide various business intelligence data 914D such as client's affinity or loyalty data. The data source 918D may provide, for example, client preference data 920D. The data source 924D may provide client purchase and/or return histories 926D. The master data source 930D may provide master data 932D in, for example, libraries, databases, performance monitoring data and statistics, and others. Such data from one or more of the aforementioned data sources may be forwarded into the data platform 900D.

The data platform 900D may provide various functionalities and services to various modules, processes, models, services, and/or microservices, and others, for application management and integration with data centers. In some embodiments, the data platform 900D may be implemented as a cloud computing service providing software as a service (SaaS), platform as a service (PaaS), and/or infrastructure as a service (IaaS). In these embodiments, the data platform 900D supports a plurality of different programming languages, tools, and frameworks. In some of these embodiments, the data platform may be implemented using Microsoft Azure® cloud computing service and/or HDInsight Kafka having a cluster 938D that provide analytics functionality and services for processing vast amounts of data. These analytics functionality and services encompass, for example but not limited to, data mining, computational analysis of data or statistics, report generation, relational databases, business reporting for sales, marketing, management reporting, business process management, budgeting and forecasting, financial reporting, and others. The cluster 938D may include a data lake for storing data such as clients' preferences, clients' purchase and/or return history, and others in some embodiments or a more general data warehouse architecture supporting OLAP (online analytical processing) or other business intelligence architecture or architectures in some other embodiments. A data lake may comprise a single store or multiple sores of data including raw or natural copies of source system data, sensor data, social data etc., and/or transformed data used for tasks such as reporting, visualization, advanced analytics, business intelligence, and machine learning. A data lake may include structured data from relational databases (rows and columns), semi-structured data (e.g., CSV, logs, XML, JSON, and others), unstructured data (e.g., emails, documents, PDFs, messages, and others), ASCII data, and/or binary data (e.g., images, audio, video, and others).

The cluster 938D may be integrated with one or more artificial intelligence models 934D such as various artificial intelligence models described herein, the product recommendation service 834 described herein, the matching service described herein, and/or other required or desired processes, modules, services, and/or microservices so that these integrated processes, modules, services, and microservices may retrieve data from the cluster 938D to utilize the various services and functionalities provided by the cluster 938D and provide data to the cluster 938D to facilitate or assist the cluster 938D in providing such various services and functionalities. At least one of the one more artificial models 934D may utilize one or more schemas 936D. A schema is a collection of units of understanding that may be hierarchically categorized as well as webbed into complex relationships with one another in some embodiments.

In some of these embodiments, one or more processes, models, modules, services, or microservices, or a combination (e.g., the one or more artificial intelligence models 934D, the product recommendation service 834, the matching service 826, or the product catalog service 824, and others) may utilize the one or more schemas 936D that enables fast access to various types of data provided by the data platform 900D. Further, as described above with reference to FIG. 8, the product recommendation service 834 may be operatively coupled to the development network (SDN) 822 as well as an artificial intelligence model 836 that assists in or performs the identification of matching products through the product catalog service 824 (which in turn receives the matching service results from the matching service 826) and recommends one or more of the identified products.

Figure 9E:
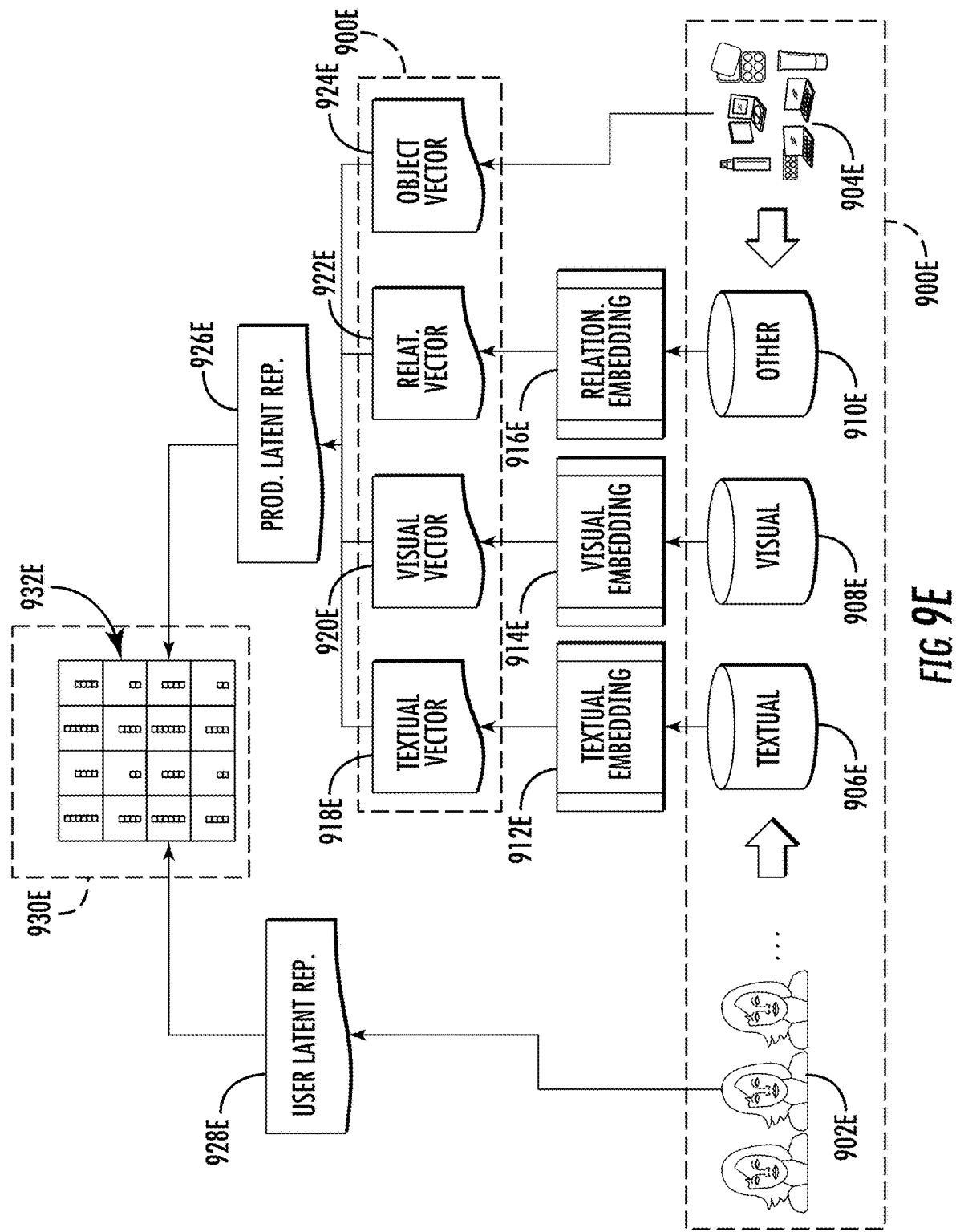
FIG. 9E illustrates an example recommendation model that may be utilized to implement various features and functionalities described herein in one or more embodiments.

FIG. 9E illustrates an example recommendation model that may be utilized to implement various features and functionalities described herein in one or more embodiments. More specifically, the example recommendation model (e.g., the product recommendation service 834) illustrated in FIG. 9E generates a recommendation at least by invoking the processes or services of two major components-knowledge base embeddings (e.g., embeddings via 912E, 914E, and 916E for knowledge bases 906E, 908E, and 910E) and joint learning 930E that utilizes at least the embedding representations described below and a latent offset representation (e.g., a latent offset vector) for each of a plurality of objects (e.g., users, products, and others) Both knowledge base embeddings via respective network embedding processes or services (e.g., deep networks) and joint learning will be described in greater details below with reference to FIGS. 9F-9K.

These embodiments illustrate a multilayer perceptron (MLP)-based hybrid deep network that predicts general as well as personalized recommendations. In some embodiments, the convolutional neural network (CNN) portion in an MLP-based hybrid deep network models the non-linear interactions between users and items and extracts local and global representations from heterogeneous data sources (e.g., textual and visual information or data sources), while the recurrent neural network (RNN) portion in the MLP-based hybrid deep network models enable the recommender system to model the temporal dynamics and sequential evolution of information such as information or data pertaining to user-product interactions, product purchases, product returns, histories thereof, and others.

In these embodiments, a recommendation model such as a product recommendation service 834 described above may receive a plurality of datasets 900E that includes user datasets 920E pertaining to various users (e.g., clients, prospective clients, beauty advisors, cosmetics professionals, developers, and others) and product datasets 904E pertaining to various attributes of cosmetic products. These user datasets 902E and product datasets 904E may be stored in one or more databases or knowledge bases (e.g., 906E, 908E, 910E). In some embodiments, these user datasets 902E and product datasets 904E may include data of multiple data types such as a textual data type, a visual data type (e.g., images, videos, and others), or other data types (e.g., symbols, links, and others) In these embodiments, data having different data types in the user datasets 902E and product datasets 904E may be separately stored into separate databases or separate knowledge bases. For example, textual data may be stored in one or more textual databases or knowledge bases 906E, visual data may be stored in one or more visual databases or knowledge bases 908E, and other types of data may be stored in one or more other databases or knowledge bases 910E.

In some embodiments, such other types of data may include structural data, linkage data, links, symbols, and others of a heterogeneous collection of information with multiple types of objects (in the sense of object-oriented programming) and multiple links to express the structure of the knowledge base for such other types of data. In these embodiments, the aforementioned links describe relationships between these objects (e.g., product types-foundation, concealer, specific type of users, rating, user behaviors, and others) and may thus be used to represent some similarity among objects.

The data stored in the one or more databases or knowledge bases (e.g., 906E, 908E, 910E) may be processed into embeddings (also referred to as embedding representation or embedding vectors). In some embodiments, an embedding is a relatively low-dimensional space into which high-dimensional vectors may be translated. In these embodiments, embeddings facilitate machine learning on large inputs like sparse vectors representing words much more easily. For example, textual data stored in a textual database or knowledge base 906E may be processed by a textual embedding process or service 912E to for a plurality of textual vectors 918E; visual data stored in a visual database or knowledge base 908E may be processed by a visual embedding process or service 914E to for a plurality of visual vectors 920E; and other types of data stored in a database or knowledge base 910E may be processed by a relationship embedding process or service 916E to for a plurality of relationship vectors 922E. In addition or in the alternative, one or more product datasets 904E may also be processed (e.g., via quantization) into object vectors 924E. More details about embeddings will be described below with reference to FIGS. 9F-9I.

The user datasets 920E may be processed into a plurality of user latent representations 928E (e.g., latent vectors or embedding vectors in one or more latent spaces). A latent representation includes an abstract multi-dimensional representation which includes feature values that cannot be directly interpreted or measured, but which encodes a meaningful internal representation of externally observed events or data in some embodiments. User datasets 902E include, for example, users' explicit or implicit feedback captured in structured and/or unstructured, heterogeneous forms or formats of textual (e.g., textual reviews, textual comments, textual descriptions, purchase histories, return histories, loyalty and affinity data, preferences, transaction data, and others), visual (e.g., images and/or videos pertaining to users' experiences with, comments on, and/or reviews of cosmetic products), and/or other formats (e.g., symbolic ratings, emojis expressing users' take on cosmetic products, and others)

These heterogeneous forms or formats of data may nevertheless exhibit some relationships, interactions, and/or linkages among each other. In addition, user data may further exhibit relationships, interactions, and/or linkages with product data (e.g., data in the product datasets 904E). Similarly, the product datasets 904E may also be processed into corresponding latent representations 926E (e.g., latent vectors or embedding vectors in one or more latent spaces). With the user latent representations 928E and product latent representations 926E respectively generated for the user datasets 902E and the product datasets 904E, joint learning 930E generates a final recommendation 932E at least by utilizing at least one of these latent representations (e.g., a textual latent vector, a visual latent vector, and a relationship latent vector for an object such as a particular user or a product) and a latent offset representation therefor (e.g., a latent offset vector).

Figure 9F:
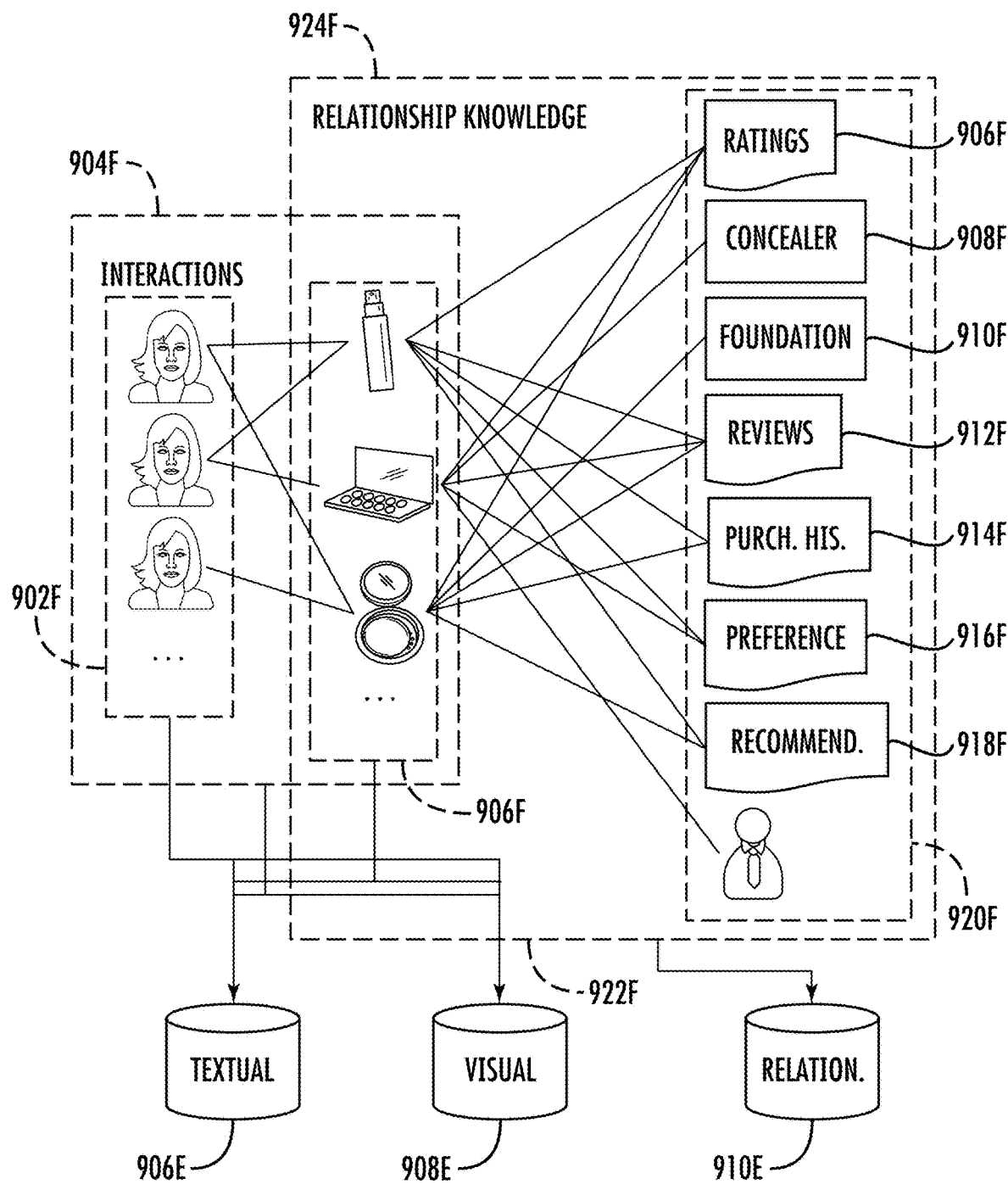
FIG. 9F illustrates some example types of knowledge bases or sources of knowledge that may be utilized to implement various features and functionalities of the example recommendation model in FIG. 9E in one or more embodiments.

FIG. 9F illustrates some example types of knowledge bases or sources of knowledge that may be utilized to implement various features and functionalities of the example recommendation model in FIG. 9E in one or more embodiments. More specifically, these example types of knowledge bases or sources of knowledge may include user knowledge or data 902F pertaining to a plurality of users including, for example but not limited to, clients of cosmetic products of a particular manufacturer or brand such as the manufacturer that develops the processes and systems described herein, prospective clients of cosmetic products of one or more competitors of the aforementioned manufacturer, beauty advisors, cosmetic product sales representatives, professionals following, reviewing, analyzing, evaluating, and others, various cosmetic products, and/or developers who develop various cosmetic products. The knowledge (e.g., data or information) corresponding to a user may be modeled as an object in the sense of object-oriented programming or a user object more precisely.

The plurality of users (or the plurality of objects) may be grouped or clustered into a plurality of clusters by one or more attributes. These one or more attributes may include, for example, types of users (e.g., clients, prospective clients, professionals, beauty advisors, sales representatives, developers, and others) in some embodiments. These one or more attributes may include as one or more additional or alternative attributes of ethnicity, gender, age or age range, and/or relative affinities or loyalty towards a brand, and others. It shall be noted that any two clusters of users may or may not necessarily be exclusive of each other. For example, a user may fall within more than one cluster (e.g., in both the client cluster and the developer cluster) so that multiple clusters into which the user falls may overlap to some extent. In some embodiments, clustering users may be done in a nested or hierarchical manner to form a tree-like structure where each level or hierarchy corresponding to a clustering criterion or attribute.

These example types of knowledge bases or sources of knowledge may also include product knowledge base or sources or sources of knowledge 906F that may include information or data such as attributes or characteristics (e.g., color attributes or characteristics in the LAB color space), types of products (e.g., concealer, foundation, lips, and others), demographic distribution data for a specific product (e.g., data pertaining to ethnicity distribution, age distribution, geographic distribution, types of users, and others of a specific product), product identifiers (e.g., SKU code), price, a list of competing products and corresponding attributes thereof for a specific product, and others. The knowledge about a specific product may also be modeled as an object in the sense of object-oriented programming or a product object more precisely.

The plurality of products (or the plurality of objects) may be grouped or clustered into a plurality of clusters by one or more other attributes. These one or more other attributes may include, for example, types of products (e.g., foundations, concealers, lips, and others) in some embodiments. These one or more attributes may include as one or more additional or alternative attributes such as color attributes (e.g., color index or mobile color IQ (MCiQ) described herein), manufacturers, prices or price ranges, affinity or loyalty pertaining to ages, age ranges, ethnicity, geographic locations, and others, competing product information, sales records, and others. It shall be noted that any two clusters of products may or may not necessarily be exclusive of each other. For example, a product may fall within more than one cluster (e.g., in both the foundation cluster and again in the age range of 20-29 cluster) so that multiple clusters into which the product falls may overlap to some extent. In some embodiments, clustering products may also be done in a nested or hierarchical manner to form a tree-like structure where each level or hierarchy corresponding to a clustering criterion or attribute.

There may be additional data referred herein as interactions 904F that link the user knowledge base 902F and the product knowledge base 906F. For example, a user may provide an explicit or implicit feedback (e.g., positive reviews, negative reviews, comments, metaphors, and others) in a textual form, a visual form (e.g., images of using products showing positive or negative results without textual description), or other form or forms (e.g., a symbolic rating or evaluation such as using emojis, star or stars, and others for a particular user's take on a specific product). In some embodiments, such interactions 904F may be stored in a data structure such as an m×n array where m and n respectively denotes the dimensionality of the plurality of users and the dimensionality of the plurality of products. For example, if an interaction is identified or detected between a user A and a product X, but no interaction is detected between user A and product Y, the field in the m×n array corresponding to user A and product X may be assigned a value of 1 indicating that at least one interaction exists. On the other hand, the field in the array corresponding to user A and product Y may be assigned a value 0 indicating the absence of any interactions. In this example, each field may be represented by using a single bit. In some other embodiments, each field in the aforementioned array may be represented by using multiple bits to capture more fine-grained information (e.g., positive review, negative review, neutral review, and others)

These example types of knowledge bases or sources of knowledge may also include relationship knowledge base or source or sources of knowledge 924F. Relationship knowledge captures the links between product objects 906F and various types of data or information. These various types of data or information may include, for example but not limited to, product ratings 906F, information pertaining to the specific product type of concealers 908F (e.g., research articles or benchmark reports concerning concealers), information pertaining to the specific product type of foundations 910F (e.g., research articles or benchmark reports concerning concealers), product reviews 912F, purchase history data 914F, user preference data 916F, product recommendations 918F (e.g., recommendations by beauty advisors, sales representatives, professionals, etc.), celebrity endorsement data 920F (e.g., a specific celebrity's endorsing a particular product or a particular brand of products), any other appropriate or suitable data or information, and/or any combinations thereof. Data pertaining to these linkages may be captured as a relationship knowledge base 924F.

In some embodiments, each of the user knowledge base or sources of knowledge 902F, the product knowledge base or sources of knowledge 906F, the various data or information (e.g., 906F through 920F), and the interactions 904F may be stored in a textual knowledge base or database 906E and/or a visual knowledge base or database 908E. The relationship knowledge base or sources of knowledge may be separately stored in a relationship knowledge base or database 910E although the underlying data (e.g., 906F through 920F) may be stored in the textual knowledge base or database 906E and/or the visual knowledge base or database 906E as described above.

Figure 9G:
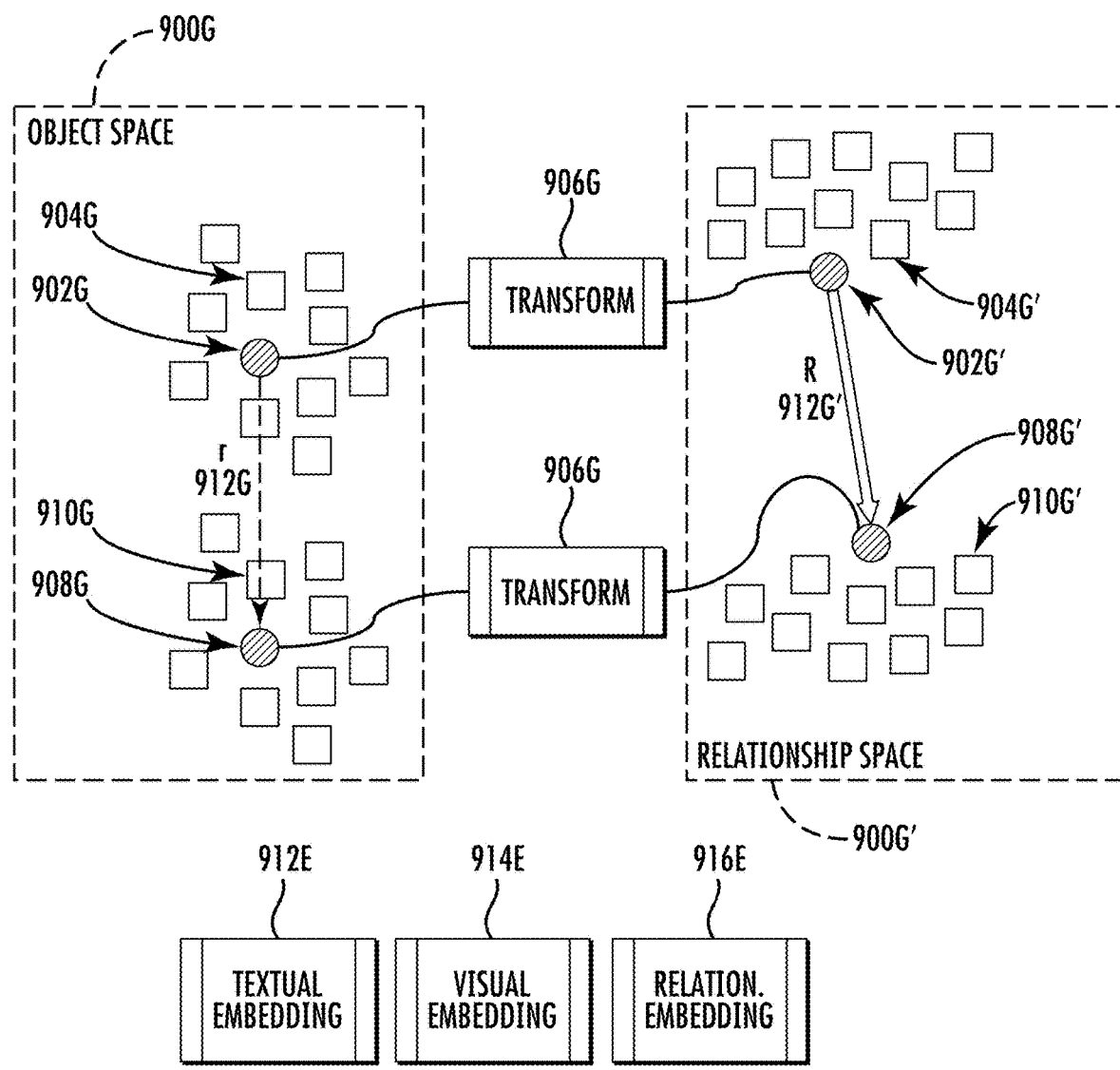
FIG. 9G illustrates more details about a portion of FIG. 9E in one or more embodiments.

FIG. 9G illustrates more details about a portion of FIG. 9E in one or more embodiments. More specifically, FIG. 9G provides a simplified graphical illustration about how relationship embedding 916E functions in FIG. 9E. In these one or more embodiments, the techniques described herein embed a knowledge graph (e.g., objects in an object space or a graph structure) into a vector space (e.g., a continuous or discrete vector space) with a transform or mapping subject to one or more constraints in order to identify relationships among objects. It shall be noted that such relationships are generally implicit in the aforementioned knowledge graph or object space in the sense that such relationships are usually not directly observed or measured. In these embodiments, a plurality of user objects 902G and 904G and a plurality of product objects 906G and 908G may be identified in an object space 900G. Assuming a relationship (r) 912G exists between the user object 902G among the plurality of user objects and the product object 908G among the plurality of product objects. Nonetheless, such relationships usually cannot be directly measured or observed, at least not without substantial amounts of efforts and time.

The relationship embedding may be used to identify such relationships by, for example, transforming each user object (e.g., 902G, 904G, etc.) of the plurality of user objects in the object space 900G into the relationship-specific object space (or relationship space) 900G' with a transform or mapping 906G. For example, user object 902G and 904G in the object space 900G may be respectively transformed into object 902G' and 904G' in the relationship space 900G'; and user object 908G and 910G in the object space 900G may be respectively transformed into object 908G' and 910G' in the relationship space 900G'. Similarly, each product user object (e.g., 908G, 910G, etc.) of the plurality of product objects in the object space 900G' may also be transformed or mapped into the relationship-specific object space (or relationship space) 900G' by using a transform or mapping 906G.

Both the object space (may also be referred to as a knowledge graph) 900G and relationship space 900G' may be vector spaces (e.g., continuous or discrete vector space formed by, for example, quantization or other suitable techniques) or any other measurable spaces so that the knowledge graph, which is generally not directly observable or measurable (hence the implicit relationship "r" 912G is represented in dashed line in FIG. 9G), may be transformed into a measurable graph.

In some embodiments, objects in the object space 900G may be transformed individually. In some other embodiments, a plurality of triples (O_u, O_p, r_u-p) may be formed where O_u, O_p, r_u-p respectively denote a user object, a product object, and a relationship between the user object and the product object. The transform 906G may be applied to transform each triple (e.g., (902G, 908G, 912G)) in the object space 900G into a transformed triple (e.g., (902G', 908G', 912G') or (O'_u, O'_p, r'_u-p)) in the relationship space 900G'. The transform or mapping 906G may be devised to satisfy the constraint that (O'_u+r'_u-p) is approximately (O'_p) when (O_u, O_p, r_u-p) holds (e.g., a relationship does exist between O_u and O_p), where O'_u, r'_u-p, and O'_p are vector representations in the relationship space 900G'.

Moreover, the transform or mapping 906G may further be devised that when a relationship r (912G) exists between the user object 902G and the product object 908G, the corresponding user object 902G' and the product object 908G' will be transformed or mapped closer to each other than to the other objects in the other category in the relationship space 900G'. For example, the transformed user object 902G' will be closer to the transformed product object 908G' than to the remaining product objects (e.g., 910G') in the relationship space 900G'; and the transformed product object 908G' will be closer to the transformed user object 902G' than to the remaining user objects (e.g., 904G') in the relationship space 900G'. In a supervised mode, learning new relationships among objects to complete the object space with newly learned relationships is supervised by existing relationship facts in the object space (or knowledge graph). In an unsupervised mode, learning new relationships among objects to complete the object space with newly learned relationships may be accomplished by using iterative approaches with scoring or objective functions.

In these embodiments described herein, the objects (user objects and product objects) in the object space 900G may be referred to as source objects, and the transformed objects in the relationship space 900G' may be referred to as target objects. The user and project objects may be classified/grouped/clustered first to group the objects into classes/groups (e.g., group of existing clients, group of prospective clients, group of beauty advisors and sales representatives, group of developers, group of professionals, group of foundation products, group of concealer products, etc.) so that a single relationship vector may be used to transform between a user object and a product object. Moreover, the object space (or the knowledge graph) may encode structured information of objects and the relationships. One of the challenges with such a rich data space is that a typical knowledge graph may have millions of objects and billions of relationship facts, such a knowledge graph is usually far from complete. Various techniques described herein predict relationships between objects under the supervision of the existing knowledge graph in some embodiments or in a completely unsupervised mode in some other embodiments and thus find new relationship facts. That is, various techniques described herein which is an important supplement to relation extraction from plain texts.

These techniques described herein vastly different from link prediction in social network analysis in at least two aspects. Firstly, nodes in the aforementioned object spaces are objects having different types and attributes; and secondly, edges in the aforementioned object spaces are relationships of different types. These techniques are devised to find the relationship between two objects by finding a translation between the embeddings of objects, (O'_u+r_'u-p) is approximately (O'_p) when (O_u, O_p, r_u-p) holds where u stands for user, p stands for product, and u-p denotes interaction between user u and product p. It shall be noted that the objects in the object space 900G and the relationships may or may not necessarily be in the same space. Further, an object may have multiple aspects or attributes, and there may exist various relationships that focus on different aspects or attributes of objects. It shall also be noted that some objects are similar in some aspect or attribute and may thus be closer to each other in the object space, but these same objects may be comparably different in some other aspect or aspects or attribute or attributes and may thus be far away from each other in the corresponding relationship space or spaces.

Figure 9H:
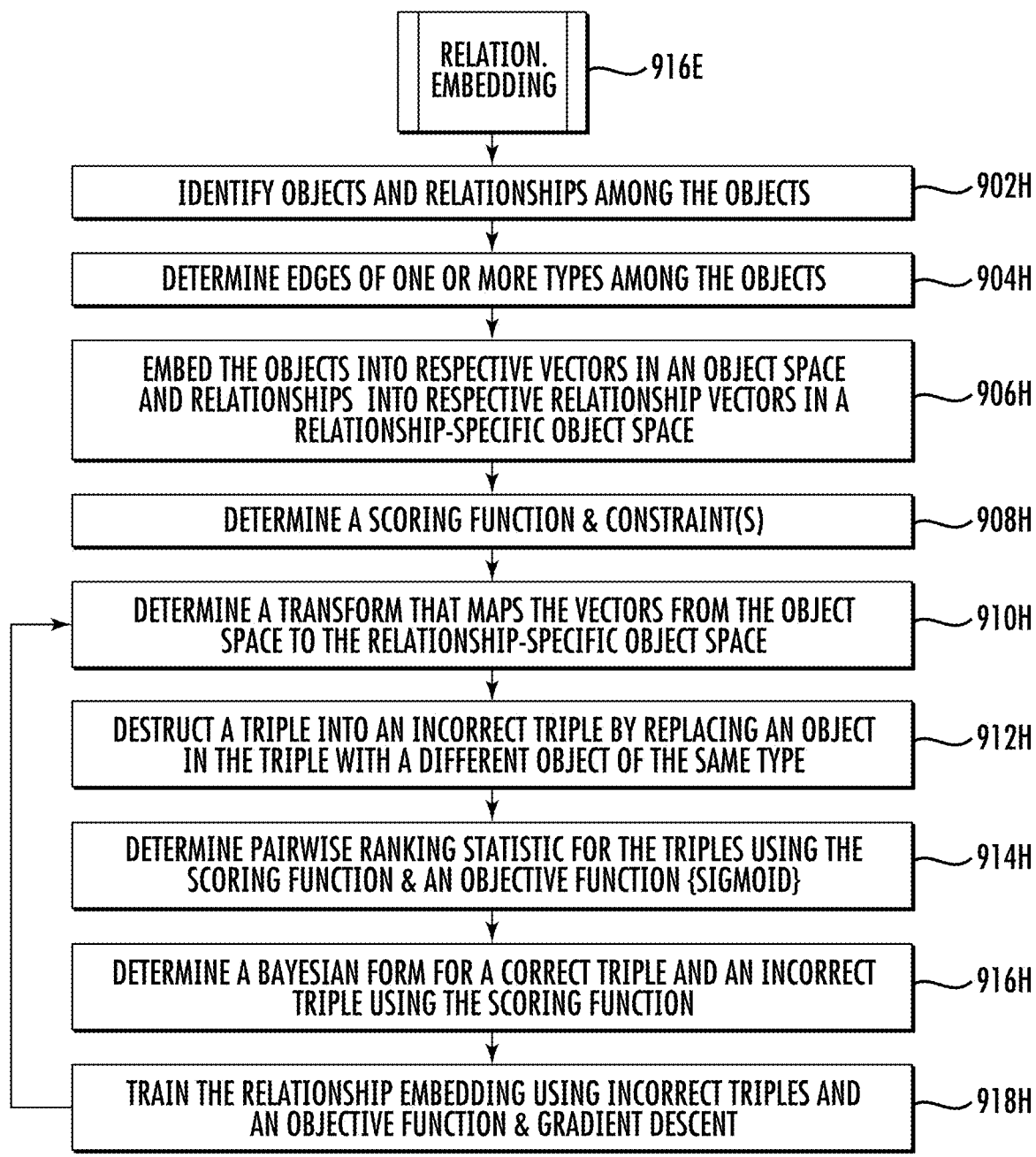
FIG. 9H illustrates an example block diagram for a process for relationship embedding that may be utilized in a portion of the example recommendation model illustrated in FIG. 9E in one or more embodiments.

FIG. 9H illustrates an example block diagram for a process for relationship embedding that may be utilized in a portion of the example recommendation model illustrated in FIG. 9E in one or more embodiments. In these one or more embodiments, a plurality objects (e.g., one or more user objects and one or more product objects) may be identified at 902H. Each of these one or more user objects may represent a user where users may include clients of cosmetic products of a particular manufacturer or brand, prospective clients of the cosmetic products of the particular manufacturer or brand, beauty advisors, sales representatives of cosmetic products, cosmetics professionals, developers, etc.

One or more edges (e.g., ru-p of one or more types between object Ou and object Op that represent respective relationships among the plurality of objects may also be determined at 904H. In some of these embodiments, these objects identified at 902H and edges determined at 904H may be populated into a graph. In one embodiment, relationships have multiple types (e.g., reviewed, purchased, returned, commented), and each type may have multiple sub-types (e.g., positive, neutral, negative). In another embodiments, each relationship type is codified to distinguish from other similar relationship types (e.g., negative review vs. neutral review vs. positive review).

The plurality of objects identified at 902H and the plurality of edges determined at 904H may be respectively embedded or transformed into corresponding vector representations at 906H. The plurality of objects and the edges may or may not necessarily have the same dimensionality due to the differences in their attributes. For example, user objects and products may be modeled or converted into an object space of dimensionality M, while relationships (edges) may be modeled or converted into a relationship space of dimensionality N where M and N are not necessarily equal. Embedding or transforming objects and edges may include identifying a relationship, r_u-p, between a user object O_u and a product object O_p, where the suffices u, p, and u-p respectively denote user, product, and between user and product. All object pairs (e.g., (O_u, O_p)) may be represented with their vector offset (O_u-O_p) for clustering and subsequent operations in some embodiments.

In some embodiments, one or more triples (O_u, O_p, r_u-p) may be generated for the plurality of objects. In some embodiments, a relationship indicates that there has been an interaction between the particular user and the particular product although the existence of a relationship/interaction does not necessarily breathe positive or negative connotations. In one embodiment, relationships have multiple types (e.g., reviewed, purchased, returned, commented), and each type may have multiple sub-types (e.g., positive, neutral, negative). In another embodiments, each relationship type is codified to distinguish from other similar relationship types (e.g., negative review vs. neutral review vs. positive review).

The plurality of objects or the one or more triples may be converted or embedded into respective vectors based at least in part upon their respective dimensionalities. For example, user objects and product objects may be converted or embedded into corresponding vectors in an object space having M dimensionality (e.g., the object space 900G) while relationships may be converted or embedded into corresponding vectors in a relationship space having N dimensionality (e.g., the original vector space in which the relationship is captured or modeled), where M and N may or may not necessarily be equal. With the example dimensionalities of M and N provided above, a relationship may be projected, transformed, or mapped into a relationship space having a dimensionality of M×N (e.g., the relationship space 900G') by using a transform, a mapping, etc. (e.g., a projection transform).

An objective or score function may be determined at 908H for evaluating (e.g., ranking) the plurality of triples. In some embodiments, the objective or score function may be generated by using the L2 norm pertaining to the embeddings (e.g., transformation or mapping of objects and edges (or triples) to the relationship space) although it shall be noted that other objective or score functions may also be used. For example, the objective or score function may be based on $\|O\_u\_r - O\_p\_r + r\_u\text{-}p\_r\|^2$ where O_u_r, O_p_r, and r_u-p_r respectively denote the user object, the product object, and the relationship in the relationship space, and $\|\|$ denotes L-2 norm. For example, a score function (fr( ) may include $fr(O\_u, O\_t) = \|O\_u\_r,c - O\_p\_r,c + r\_u-p\_r\|22 + epsilon\|ru-p\_r,c - ru-p\_r\|^2$ where the suffix c denotes clustering, and the suffix r denotes the relationship space, $\|r\_u-p\_r,c - r\_u-p\_r\|^2$ is used to control that the clustering-specific relationship (ru-p\_r,c) and the original relationship (ru-p\_r) are bound within some threshold distance (e.g., not sufficiently far from each other), and epsilon is used to control the effect of $\|r\_u-p\_r,c - r\_u-p\_r\|^2$ and may also be learned during training.

One or more constraints may be determined on the aforementioned objective or score function. In some embodiments, the one or more constraints may include:

$\|O\_u\| <= 1;$ $\|O\_p\| <= 1;$ $\|r\| <= 1;$ $\|O\_u\_r\| <= 1;$ and $\|O\_p\_r\| <= 1.$ A transform, T, may be determined at 910H based at least in part upon the relationship, r\_u\_p, between a user object O\_u and a product object O\_p. That is, O\_u\_r=T*O\_u; O\_p\_r=T*O\_p; and r\_u-p\_r=T*r\_u-p where the suffix "r" denotes the relationship space. The objects (or object vectors) O\_u and O\_p may be respectively transformed or mapped, with the transform T, from the object space into O\_u\_r and O\_p\_r in the relationship space by using: O\_u\_r=O\_u*T; O\_p\_r=O\_p*T, where O\_u\_r and O\_p\_r in the relationship space. A plurality of triples (e.g., (O\_u, O\_p, r\_u\_p)) may be generated for the objects and the relationships.

A triple may be destructed into a destructed or incorrect triple at 912H. In some embodiments, a destructed or incorrect triple may be determined at 912H by replacing an object (e.g., a user object or a product object) in an original triple where a relationship does exist between the user object and the product object in the original triple so that the aforementioned relationship in the original triple no longer exists in the destructed or incorrect triple. For example, a user U had one or more interactions or relationship R with a product U in the original triple (U, P, R). A destructed triple may be generated by replacing the user U with a different user object U' so that there is no interaction (or relationship) between the user object U' and the product object P. The destructed triple may then be generated as (U', P, R). Similarly, another destructed triple may be generated by replacing the product object P with a different product object Ps with which the user object U had no interactions or relationship. This destructed triple may be generated as (U, P', R).

In some sense, a destructed triple represents an adversarial example that is synthetically generated by altering the corresponding original example (O\_u, O\_p, r\_u-p) into a synthetically fabricated record (O\_u, O'\_p, r\_u-p). Further, due to the fact that most, if not all, of the data is not directly measurable or detectable by humans (at least not without expending substantial amount of time and effort), this non-measurability or detectability of the aforementioned destructed or incorrect triples is also similar to the non-visibility of adversarial examples. In some embodiments, a destructed example may also be synthetically generated by replacing the user object with a different user for which no relationship exists between the different user and the product, whereas a relationship does exist in the existing triple between the original user object and the product object. A nonlinear function (e.g., a logistic sigmoid function. 1/(1+exp(−x)), a margin-based function, etc.) may be determined and used in computing the objective or score function for determining the pairwise triple ranking measure.

A pairwise triple ranking measure (e.g., a probability of a user object O\_u and a product object O\_p having a relationship ru-p or p (O\_u. O\_p| r\_u-p)) may then be determined at 914H based at least in part upon the aforementioned destructed triple and the objective or score function. More particularly, determining a pairwise triple ranking measure for a triple may include destructing the triple (O\_u, O\_p, r\_u-p) to generate a destructed or incorrect triple (O\_u, O'\_p, r\_u-p) where the relationship r\_u-p does not exist between the user object O\_u and the product object O'\_p (and hence "destructed" or "incorrect" triple). In some embodiments, a pairwise triple ranking probability or measure may be computed based at least in part upon the aforementioned objective or score function.

A Bayesian form for a correct triple and an incorrect triple may be determined at 916H by using a nonlinear function. Such nonlinear functions that may be used to determine the Bayesian form may include, for example but not limited to, a logistic sigmoid function, 1/(1+exp(−x)), a margin-based function, or any other suitable or appropriate functions, etc. In some embodiments, the embedding module described herein may be trained at 918H by iteratively using a plurality of correct triples and the corresponding plurality of destructed, incorrect triples with an objective or cost function and a gradient descent (e.g., a stochastic descent algorithm, the Newton-Raphson method, the steepest descent method, or other appropriate algorithms or methods) by populating errors backward through the network for the embedding module to distribute the errors according to a gradient of the errors and by updating the network accordingly. In some embodiments, the objective or cost function may include:

$$\sum_{O\_u,O\_p,r\_u-p} \left\{ \sum_{O'\_u,O'\_p,r'\_u-p} \{\text{Max}(0, fr(O\_u, O\_p)) + \text{lamda} - fr(O'\_u, O'\_p)\} \right\},$$

where lambda denotes the margin, (O\_u, O\_p, r\_u-p) denote the correct triples, and (O\_u, O'\_p, r\_u-p) and (O\_u, O'\_p, r\_u-p) denote the incorrect triples.

In these embodiments, representing objects as vectors (e.g., by quantization or other appropriate techniques), various parameters (e.g., weights, the objective or cost function described immediately above, the score function fr ( ) the one or more constraints, the coefficient 2 described above with reference to the objective or cost function, etc. may be learned during training. Training the embedding module or model may involve an iterative process where one or more parameters or entities are updated in an iteration, and the training returns to, for example, 910H to update the module or model with the one or more modified parameters or entities in the previous iteration and repeats the steps until a convergence criterion is met (e.g., the reduction in errors between two successive iterations is smaller than a convergence threshold, a limit of the number of iterations to be performed or time for iteration has been reached, or any other suitable or appropriate criterion).

Figure 9I:
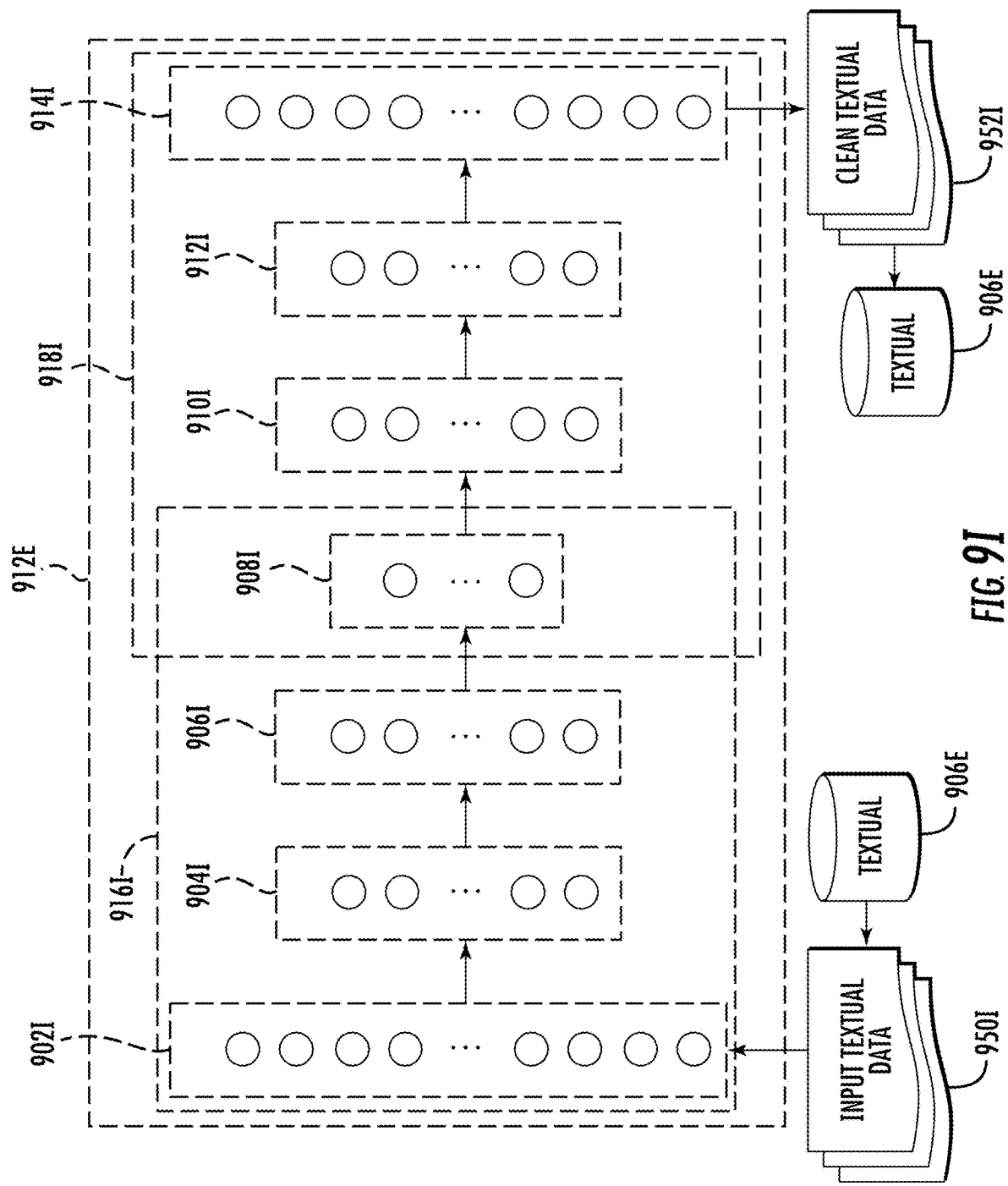
FIG. 9I illustrates more details about textual data embedding that may be utilized in a portion of the example recommendation model illustrated in FIG. 9E in one or more embodiments.

FIG. 9I illustrates more details about textual data embedding that may be utilized in a portion of the example recommendation model illustrated in FIG. 9E in one or more embodiments. More specifically, FIG. 9I illustrates more details about textual embedding illustrated as 912E in FIG. 9E. These one or more embodiments utilize a neural network for learning the representation of the input data, which is often, if not always, contaminated with noise, non-informative information, etc., by learning to predict a clean (e.g., denoised) version or content.

The example neural network 912E illustrated in FIG. 9I may include a total of L layers (seven layers are shown in FIG. 9I for the case of illustration and explanation although a more or fewer number of layers may also be utilized in other embodiments). These L layers may be approximately divided into two portions where the first about ½ (L) layers 916I (including layers 902I, 904I, 906I, and 908I) represent an encoding part that maps the input data 950I received at the input layer 902I from, for example, the textual knowledge base 906E into a textual vector (e.g., 918E in FIG. 9E) and then to a latent representation (e.g., 926E in FIG. 9E). The input data received at the input layer 902I may include contaminated data with noise, non-informative information, etc. as described above. Such noise, non-informative information, etc. may cloud the accuracy of the vector representation and hence the latent vector to correctly represent the informative information in the original input data.

The encoding portion 916I may include a plurality of hidden layers (e.g., 904I, 906I) that successively process their respective input to eventually generate a textual embedding vector 908I. For example, hidden layer 904I may receive the output of the input layer 902I to generate a first output by performing an inner product between the input and a kernel (also referred to as a kernel or a weight matrix); and hidden layer 906I may receive the first output of the hidden layer 904I as its own input and generate the textual embedding vector 908I by performing a separate inner product between the input (the output of hidden layer 904I) and the corresponding kernel. For a hidden layer (e.g., a convolution layer), the out [Yj] generated by the hidden layer for the input [Xi] may be expressed as Yj=sigma (Wij*Xi+bj). where Yj, Wij, Xi, bj, and sigma respectively denote the output, the kernel, the input, the bias, and learning rate. The kernel and the bias may also be learned during training.

The remaining about ½ (L) layers 918I (e.g., including 908I, 910I, 912I, and 914I) represent the decoding portion of the neural network 912E. More specifically, the hidden layers 910I and 912I respectively receive their inputs from the immediately preceding layers to generate respective outputs. For example, hidden layer 910I receives the textual embedding vector 908I to generate a first output that is received by hidden layer 912I as an input. Hidden layer 912I generates a second output that is then received by the last layer 914I that in turn generates a clean, more compact output embedding (e.g., clean textual data 952I) for the original input textual data 950I that may be further stored in a textual knowledge base or database 906E.

In some embodiments, the weight parameters for the kernel (also referred to as a weight matrix or filter) may be drawn from the Gaussian distribution N(0, (lambda_W^(−1))*I, where I denotes an identity matrix, and lambda_W denotes a model-specific regularization parameter that may be learned during training. In some of these embodiments, the weight parameter may be expressed as a more generalized normal distribution with zero mean and variance-covariance matrix. The use of N(0, (lambda_W^(−1))*I) may reduce the total number of unknown hyperparameters in some embodiments. The other entities such as the objects (O), relationships (r), bias parameter (b), etc. may also be determined similarly. For example, the bias parameter, b, may be drawn from the Gaussian distribution N(0, (lambda_b^(−1))*I, where I denotes an identity matrix, and lambda_b denotes a parameter that may be learned during training; a relationship, r, may be drawn from the Gaussian distribution N(0, (lambda_r^(−1))*I), where I denotes an identity matrix, and lambda_r denotes the aforementioned model-specific regularization parameters that may be learned during training; and an object, O, may be drawn from the Gaussian distribution N(0, (lambda_O^(−1))*I), where I denotes an identity matrix, and lambda_O denotes a parameter that may be learned during training. In some embodiments, the aforementioned parameters (e.g., lambda_W, lambda_b, lambda_r, and lambda_O may be learned during training based at least in part on the datasets used in training (e.g., different datasets may provide different, optimized parameter values). In some of these embodiments, these parameters may be learned from a range between 0 and 0.5 (e.g., lambda_W=0.01, lambda_b=0.01, lambda_r=0.001, and lambda_O=0.005), and the learning rate, sigma, may be set to 2 or 3.

For the output Y of an L-th layer, Y may be drawn from a Gaussian distribution, N, as YL~N(sigma (WL*YL-1+bL), (lambda_Y^(−1))*I), where I denotes an identity matrix, lambda_Y denotes a parameter, sigma denotes the learning rate hyperparameter, WL denotes the L-th layer kernel, YL-1 denotes the output of the (L-1)-th layer, all of which may be learned during training. These techniques may thus determine a user latent vector or representation and the product latent vector or representation accordingly. For a triple, (O_u, O_p, r_u-p) showing i-th user O_u,i prefers j-th product O_p, j over the j'-th product, O_p, j, its probability, p (j>j') may be determined by sigma (transpose (O_u,i)*Zj-transpose (O_u,i)*Zj-transpose (O_u,i)*Zj'), where sigma, transpose (O_u,i), Zj, Zj', and the operator "*" respectively denote the learning rate hyperparameter, the i-th user object's vector representation, the latent representation capturing the j-th product's latent and the i-th user object, the latent representation capturing the j'-th product's latent and the i-th user object, and matrix multiplication.

Figure 9J:
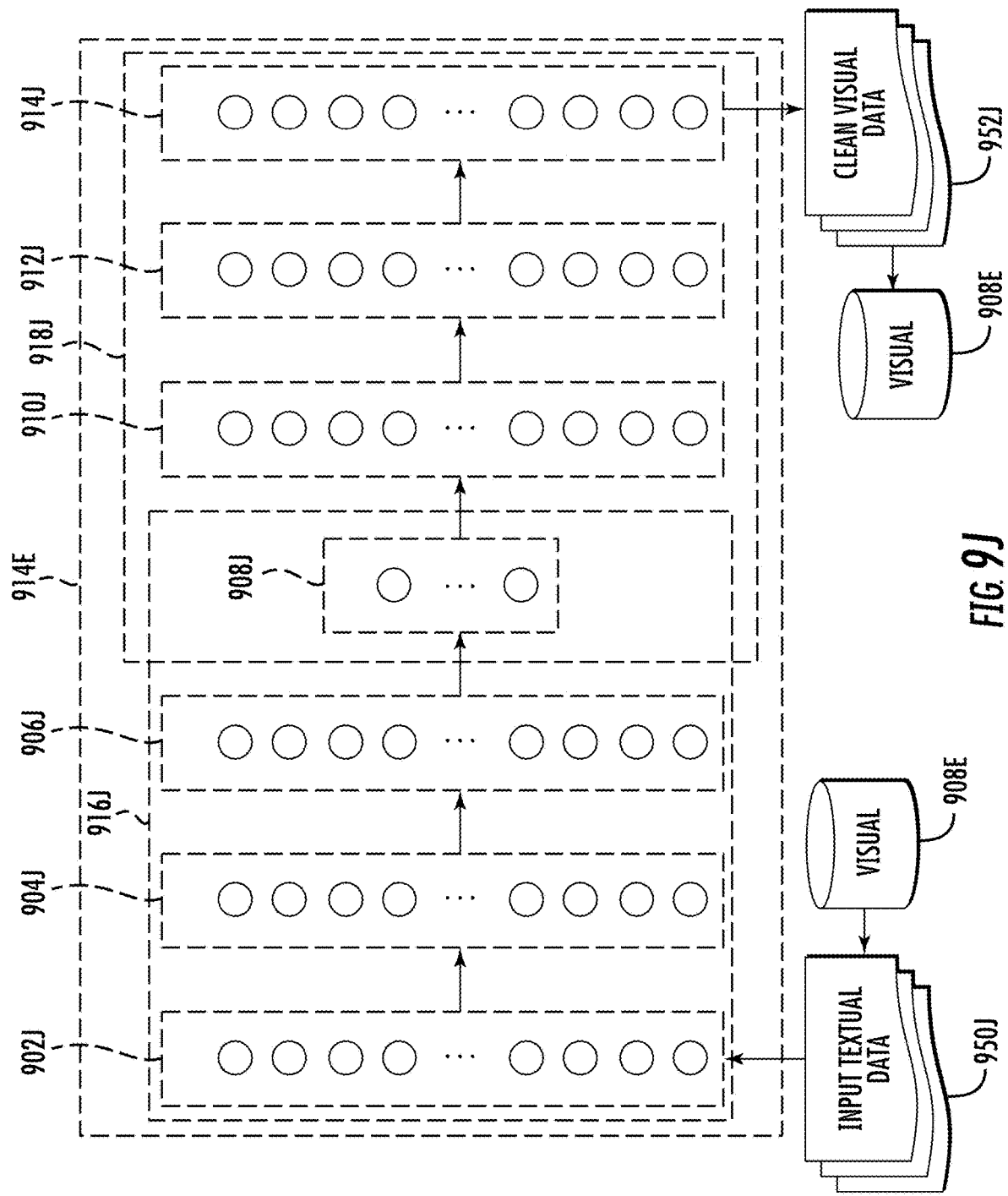
FIG. 9J illustrates more details about visual data embedding that may be utilized in a portion of the example recommendation model illustrated in FIG. 9E in one or more embodiments.

FIG. 9J illustrates more details about visual data embedding that may be utilized in a portion of the example recommendation model illustrated in FIG. 9E in one or more embodiments. More specifically, FIG. 9J illustrates more details about visual embedding illustrated as 914E in FIG. 9E. These one or more embodiments utilize a neural network for learning the representation of the input data, which is again often contaminated with noise, non-informative information, etc., by learning to predict a clean (e.g., denoised) version or content.

The example neural network 914E illustrated in FIG. 9J may include a total of L layers (seven layers are shown in FIG. 9J for the case of illustration and explanation although a more or fewer number of layers may also be utilized in other embodiments). These L layers may be approximately divided into two portions where the first ~½ L layers 916J (including layers 902J, 904J, 906J, and 908J) represent an encoding part that maps the input data 950J received at the input layer 902J from, for example, the visual knowledge base 908E into a visual vector (e.g., 920E in FIG. 9E) and then to a latent representation (e.g., 926E in FIG. 9E). In some embodiments, layers 902I, and 904J may be convolution layers, and layer 906J may be a fully connected layer receiving the output (e.g., feature vectors or feature maps) from layer 904J. The outputs of layers 904J and 906J are feature vectors or feature maps based on the respective input to these two layers from their immediately preceding layers. The visual embedding vector 908J represents a collection of all objects' visual embedding vectors in some embodiments. The input data received at the input layer 902L may include contaminated images with noise, non-informative information, etc. as described above. Such noise, non-informative information, etc. may cloud the accuracy of the vector representation and hence the latent vector to correctly represent the informative information in the original input data.

The encoding portion 916J may include a plurality of hidden layers (e.g., convolution layers 904J, 906J) that successively process their respective input to eventually generate a textual embedding vector 908J. For example, hidden layer 904J may receive the output of the input layer 902J to generate a first output by performing an inner product between the input and a kernel (also referred to as a kernel or a weight matrix); and hidden layer 906J may receive the first output of the hidden layer 904J as its own input and generate the visual embedding vector 908J by performing a separate inner product between the input (the output of hidden convolution layer 904J) and the corresponding kernel. In some embodiments, hidden layer 910J may be a fully connected layer generating a feature vector or feature map as output. Hidden layers 912J and 914J may be convolution layers each receiving respective input from the immediately preceding layer to generate a feature vector or feature map as output. For a hidden layer (e.g., a convolution layer), the out [Yj] generated by the hidden layer for the input [Xi] may be expressed as Yj=sigma (Wij*Xi+bj). where Yj, Wij, Xi, bj, and sigma respectively denote the output, the kernel, the input, the bias, and learning rate. The kernel and the bias may also be learned during training.

The remaining about ½ (L) layers 918J (e.g., including 908J, 910J, 912J, and 914J) represent the decoding portion of the neural network 914E. More specifically, the hidden layers 910J and 912J respectively receive their inputs from the immediately preceding layers to generate respective outputs. For example, hidden layer 910J receives the textual embedding vector 908J to generate a first output that is received by hidden layer 912J as an input. Hidden layer 912J generates a second output that is then received by the last layer 914J that in turn generates a clean, more compact output embedding (e.g., clean textual data 952J) for the original input textual data 950J that may be further stored in a visual knowledge base or database 908E.

In some embodiments, the weight parameters for the kernel (also referred to as a weight matrix or filter) may be drawn from the Gaussian distribution N(0, (lambda_W^(−1))*I), where I denotes an identity matrix, and lambda_W denotes a model-specific regularization parameter that may be learned during training. In some of these embodiments, the weight parameter may be expressed as a more generalized normal distribution with zero mean and variance-covariance matrix. The use of N(0, (lambda_W^(−1))*I) may reduce the total number of unknown hyperparameters in some embodiments. The other entities such as the objects (O), relationships (r), bias parameter (b), etc. may also be determined similarly.

For example, the bias parameter, b, may be drawn from the Gaussian distribution N(0, (lambda_b^(−1))*I), where I denotes an identity matrix, and lambda_b denotes a parameter that may be learned during training; a relationship, r, may be drawn from the Gaussian distribution N(0, (lambda_r^(−1))*I), where I denotes an identity matrix, and lambda_r denotes the aforementioned model-specific regularization parameters that may be learned during training; and an object, O, may be drawn from the Gaussian distribution N(0, (lambda_O^(−1))*I), where I denotes an identity matrix, and lamda_O denotes a parameter that may be learned during training. In some embodiments, the aforementioned parameters (e.g., lambda_W, lambda_b, lambda_r, and lambda_O may be learned during training based at least in part on the datasets used in training (e.g., different datasets may provide different, optimized parameter values). In some of these embodiments, these parameters may be learned from a range between 0 and 0.5 (e.g., lambda_W=0.01, lambda_b=0.01, lambda_r=0.001, and lambda_O=0.005), and the learning rate, sigma, may be set to 2 or 3.

For the output Y of an L-th layer, Y may be drawn from a Gaussian distribution, N, as YL is about N(sigma (WL*YL-1+bL), (lamda_Y^(−1))*I), where I denotes an identity matrix, lambda_Y denotes a parameter (e.g., a model-specific parameter), sigma denotes the learning rate hyperparameter, WL denotes the L-th layer kernel, YL-1 denotes the output of the (L-1)-th layer, all of which may be learned during training. These techniques may thus determine a user latent vector or representation and the product latent vector or representation accordingly. For a triple, showing i-th user O_u,i prefers j-th product O_p, j over the j'-th product, O_p, j, its probability, p (j>j') may be determined by sigma (transpose (O_u,i)*Zj-transpose (O_u,i)*Zj'), where sigma, O_u,i, Zj, and Zj' respectively denote the learning rate hyperparameter, the i-th user object's vector representation, the latent representation capturing the j-th product's latent and the i-th user object, and the latent representation capturing the j'-th product's latent and the i-th user object.

Figure 9K:
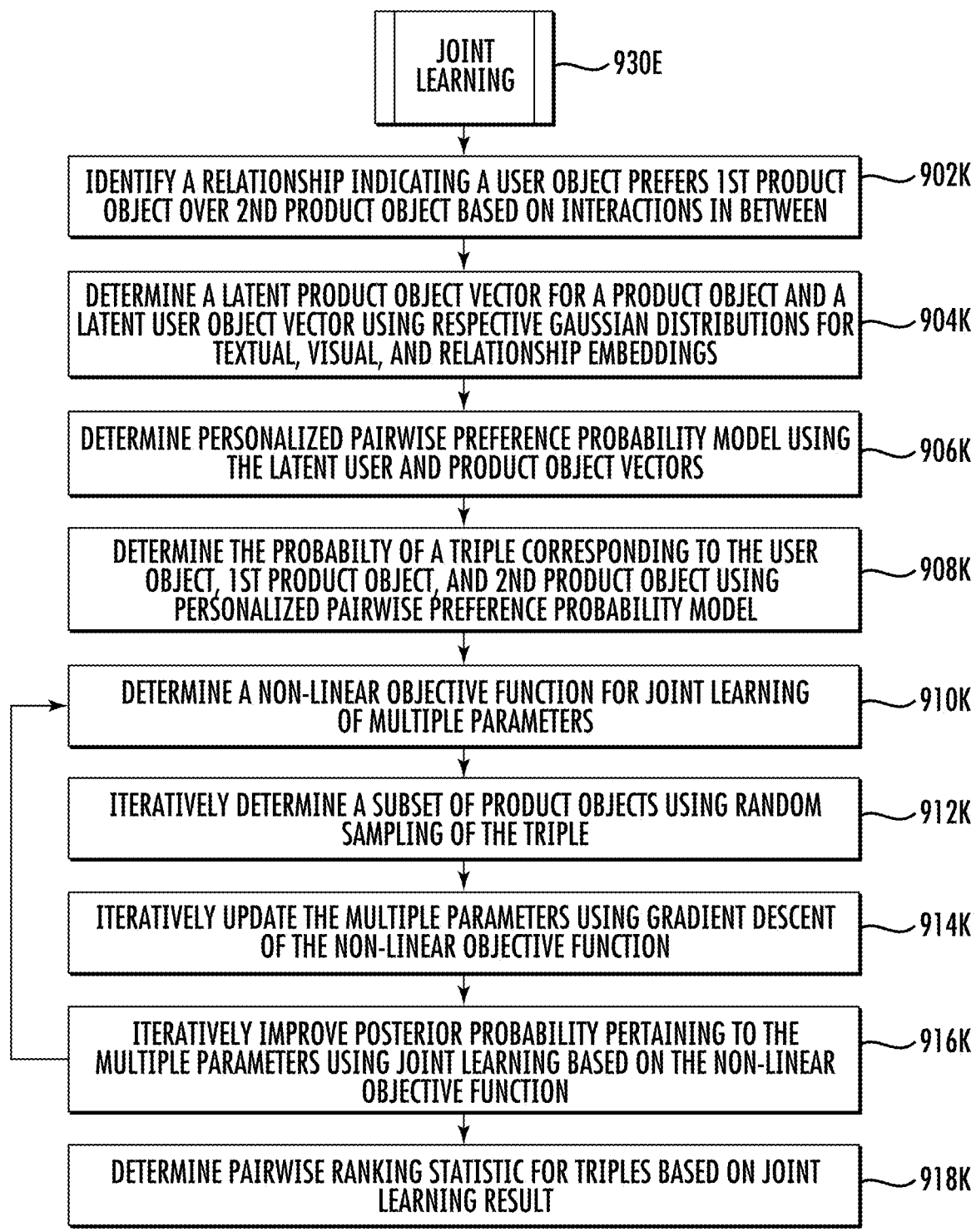
FIG. 9K illustrates more details about joint learning that may be utilized in a portion of the example recommendation model illustrated in FIG. 9E in one or more embodiments.

FIG. 9K illustrates more details in a block diagram for joint learning that may be utilized in a portion of the example recommendation model illustrated in FIG. 9E in one or more embodiments. In these embodiments, a relationship may be identified at 902K where the relationship indicates that a user object prefers a first product object over a second product object based at least in part upon one or more interactions between the user object and the first and second product objects. For example, an i-th user object of a total of M user objects may have one or more interactions with the j-th product object but not with the j'-th product object of the total of N product objects. In some embodiments, an array having M×N dimensionality may be used to store such interactions. For example, the field corresponding to the i-th user object and the j-th product object may be assigned a value of 1 to indicate the existence of the one or more interactions between the i-th user and the j-th product; and the field corresponding to the i-th user object and the j'-th product object may be assigned a value of o to indicate the absence of any interactions between the i-th user and the j'-th product.

A latent product object vector or representation for a product object, a latent user object vector or representation for the user object, and a relationship latent vector or representation may be respectively determined at 904K at least by using respective normal distributions for textual, visual, and relationship data embeddings. In the examples described above for FIG. 9J, the latent representation, Zj, capturing the j-th product's latent and the i-th user object may be determined as: Zj=O_u,j+O_p,j+Psi_L,j+Omega_L, j, where O_u,j, O_p,j, Psi_L,j, and Omega_L,j respectively denote the i-th user's latent representation with respect to the j-th product object, the j-th product object's latent representation, the output of the textual knowledge embedding by the layer L, and the output of the visual knowledge embedding by the layer L.

As described in the embodiments illustrated in FIG. 9J, O_u,j may be determined by drawing from the Gaussian distribution (normal distribution with zero mean) using the expression: $N(0, ((\lambda\_u^{(-1)}))*I)$, where I denotes an identity matrix, and lambda_u denotes a model-specific parameter (e.g., a user object embedding model) that may be learned during training. In some of these embodiments, the weight parameter may be expressed as a more generalized normal distribution with zero mean and variance-covariance matrix. The use of $N(0, ((\lambda\_u^{(-1)}))*I)$ may reduce the total number of unknown hyperparameters in some embodiments.

Further, may be determined by drawing from the Gaussian distribution using the expression: $N(0, ((\lambda\_p^{(-1)}))*I)$, where I denotes an identity matrix, and lambda_p denotes a model-specific parameter (e.g., a product object embedding model) that may be learned during training. In some of these embodiments, the weight parameter may be expressed as a more generalized normal distribution with zero mean and variance-covariance matrix. The use of $N(0, ((\lambda\_p^{(-1)}))*I)$ may reduce the total number of unknown hyperparameters in some embodiments.

Moreover, Psi_L,j represents the textual embedding of textual input and may be determined by drawing from the Gaussian distribution (normal distribution with zero mean) using the expression: about N(sigma (WL*Psi_L-1+bL), (lambda_Psi^(-1))*I), where I denotes an identity matrix, lambda_Psi denotes a parameter (e.g., a model-specific parameter), sigma denotes the learning rate hyperparameter, WL denotes the L-th layer kernel, L-1 denotes the output of the (L-1)-th layer, all of which may be learned during training.

In addition, Omega_L,j represents the visual embedding of textual input and may be determined by drawing from the Gaussian distribution (normal distribution with zero mean) using the expression: about N(sigma (WL*+bL), ((lambda_Omega^(-1))*I), where I denotes an identity matrix, lambda_Omega denotes a parameter (e.g., a model-specific parameter), sigma denotes the learning rate hyperparameter, WL denotes the L-th layer kernel, Omega_L-1 denotes the output of the (L-1)-th layer, all of which may be learned during training. It shall be noted that the learning rate parameters for textual, visual, and relationship embeddings may or may not necessarily be the same and may thus be learned separately in some embodiments or jointly in some other embodiments.

A pairwise preference probability model may be determined at 906K at least by using the latent user object vectors and latent product object vectors. In some embodiments, a triple (O_u,i, O_p,j, O_p,j') may be constructed for the i-th user object latent vector, the j-th product object latent vector, and the j'-th product object latent vector. The pairwise preference probability, p (j>j'), may be determined using sigma (transpose (O_u,i)*Zj-transpose (O_u,i)*Zj'), where T, sigma, O_u, I, Zj, Zj', and the operator "*" respectively denote the transpose operator, the learning rate hyperparameter, the i-th user object's latent vector, the latent vector capturing the j-th product's latent and the i-th user object, the latent vector capturing the j'-th product's latent and the i-th user object, and the matrix multiplication operator.

The probability of a triple corresponding to the user object, the first product object, and the second product object may be determined at 908K at least by using the above pairwise preference probability model. For example, the aforementioned probability may be determined for the triple (O_u,i, O_p,j, O_p,j') by drawing from the above probability sigma (transpose (O_u,i)*Zj-transpose (O_u,i)*Zj') at 908K where the triple satisfies that there exists one or more interactions between the user object (e.g., O_u,i) and the first product object (e.g., O_p,j), but there exists no interactions between the user object (e.g., O_u,i) and the second product object (e.g., O_p,j').

An objective function may be determined at 910K for joint learning of multiple parameters such as the aforementioned hyperparameters, the user and product object embeddings, the relationship object embedding, the kernel, the bias, the learning rate, etc. The process may be iteratively performed between, for example, 910K and 916K until a convergence criterion is satisfied. At 912K, a subset of product objects may be iteratively determined by using, for example, random sampling of a plurality of triples (e.g., (O_u,i, O_p,j, O_p,j') described above for one or more user objects and a plurality of product objects). These techniques described herein are aimed to determine a subset of product objects where for a randomly sampled triple (O_u,i, O_p,j, O_p,j'), the subset that satisfies the constraint that the subset includes product object j or product object j'. At least one of the aforementioned multiple parameters may be iteratively updated in each iteration at 914K by computing an error in the output and propagating the computed error backward through the network structure of the pertinent model or models or network or networks based at least in part upon a gradient pertaining to the error. For example, a stochastic gradient descent algorithm may be utilized. At this step, the error may be computed using a supervised training mode or an unsupervised training mode.

The posterior probability pertaining to the multiple parameters may be iteratively improved or optimized at 916K at least by using joint learning techniques based at least in part upon an object function (e.g., a cross-entropy cost function). For example, joint learning may be performed for the user latent vector, the product latent vector, the relationship latent vector, the mapping from the user/product objects and the relationship objects to the relationship space, various model parameters described herein, various hyperparameters described herein, various embedding related variables, or any combinations thereof. With the posterior probability improved at 916K, a pairwise ranking statistic may be determined for the triple (e.g., (O_u,i, O_p,j, O_p,j') described above) based on the results of joint learning.

Figure 10:
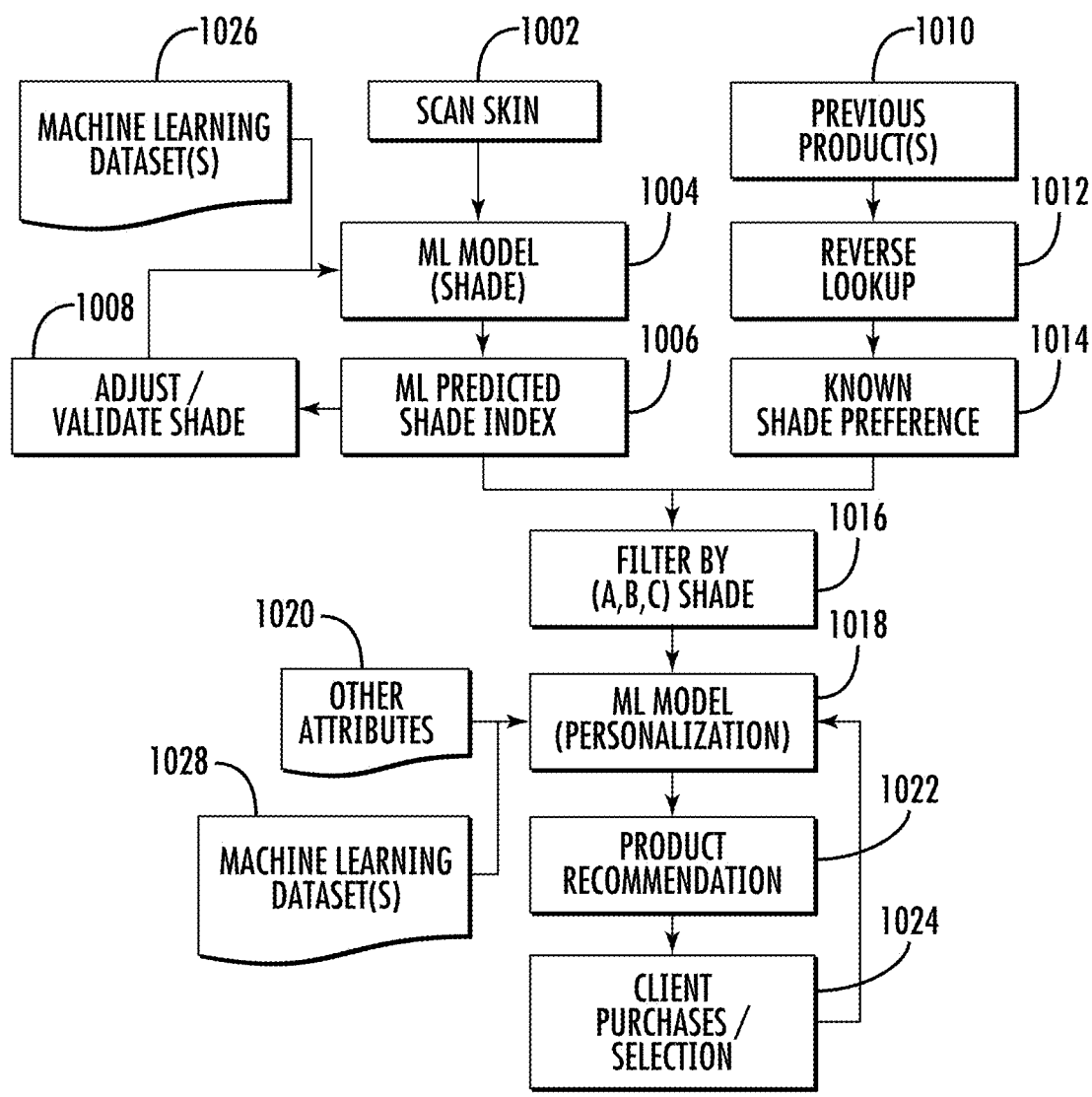
FIG. 10 illustrates an example high-level block diagram for a method or system for cosmetic product matching and recommendation using artificial intelligence techniques in one or more embodiments.

FIG. 10 illustrates an example high-level block diagram for a method or system for cosmetic product matching and recommendation using artificial intelligence techniques in one or more embodiments. More specifically, FIG. 10 encompasses two major approaches for cosmetic product matching and recommendation using artificial intelligence techniques. The first approach applies to cosmetic product matching and recommendation with scanning a client's or prospective client's skin while the second approach applies to cosmetic product matching and recommendation with reverse look up using certain information pertaining to a client or prospective client (collectively a client or clients) or to a product.

In some of these embodiments, a client may use a mobile computing device having a mobile app (e.g., a mobile color IQ app) installed thereon and an image capturing device including a camera lens and an image sensor or visit a cosmetic product retail location having a system with at least a store digital app and a scanning device to scan the client's skin at 1002. In some embodiments, the lens used in scanning the client's skin includes a telephoto lens having a magnification power (e.g., optical magnification power, digital magnification power, or optical and digital magnification power, etc.) greater than one to capture finer details of a client's skin. In these embodiments, the distance between a client's skin and the telephoto lens is more likely within the focal length of the telephoto lens to result in blurry images from a scan session. Such blurry images may be corrected into sharp images (e.g., scan image of an area of a client's skin using a scanning device having a telephoto lens in FIG. 14M) by using an SDK (software development kit) that corresponds to a specific imaging capturing device and/or its telephoto lens and is embedded in the scanning software (e.g., the store digital app or the mobile color iQ app described herein).

In some embodiments, the image capturing device of a modern client mobile computing device (e.g., a smart phone such as iPhone 6S® or later models) and/or the scanning device in the system deployed at a cosmetic product retail site may be configured to capture raw data for images (e.g., DNG files or digital negative files) to preserve the completeness of data in the captured images, and the aforementioned SDK may be embedded within the mobile color iQ app and the store digital app or may be a separate piece of software that functions in conjunction with the mobile color iQ app and the store digital app.

In some other embodiments, the lens used in scanning the client's skin may include a macro lens for creating close-up, macro images, a wide-angle lens, a standard lens (e.g., lens having focal length or lengths falling between 35 millimeters and 85 millimeters), or a specialty lens such a fisheye lens, a tilt shift lens, an infrared lens, etc. A lens may be a fixed-focal length lens having a single focal length value in some embodiments or a variable focal length having a range of focal length values in some other embodiments. Different lenses may have different fields of view. For lenses having larger fields of view, the client's skin may be scanned only once per target area (e.g., forehead area, check area, neck area, jawline, outer eye area or areas, or others) For lenses having smaller fields of view, the client's skin may be scanned more than once per target area to obtain a better representation of a reasonably large skin area for subsequent processing. In some embodiments, each area of interest may be scanned more than once, and the better scan result may be selected for further processing, or the average of these multiple scans may be computed for further processing (e.g., to determine the final skin tone scan result and/or the final skin guide scan result that may or may not include some or all of the final skin tone scan result). In some embodiments where multiple areas of interests are scanned, each scan of these multiple scans generates an intermediate result, and these multiple intermediate results are subsequently aggregated or combined (e.g., an average, a weighted average, or any other linear or non-linear combinations with learnable, respective coefficients or weights that are learnable via various machine learning techniques described herein) to generate a final result (e.g., a final skin tone scan result, a final skin guide scan result, etc.) In some of these embodiments, one or more of these multiple intermediate results are not made available or presented and hence invisible to a client for whom these multiple scans are performed, but the final result is presented to the client. In some embodiments, the final scan result is unavailable for display to the client before the last scan is performed. In some embodiments where multiple scans are performed on respective areas of the body of a client, one or more respective intermediate results for one or more of these multiple scans may not be utilized to determine the final scan result. For example, a skin tone scan may be performed on a forehead area, a check area, an outer area or areas of eye or eyes, and a neck area of a client. The final skin tone scan result may be determined based on the intermediate results of all of these scans in some embodiments or the intermediate results of some but not all of the areas. For example, the intermediate result for the neck area scan may not be utilized in determining the final skin tone scan result due to the client's preference for finding matching products for the client's face area or due to the client's habit of wearing collared dresses, or any other pertinent factors. In some of these embodiments where an area of interest is scanned multiple times, the corresponding intermediate results of these multiple scans may or may not be entirely used. For example, the intermediate result of one scan of these multiple scans for the same are may not be utilized in determined the final scan result.

In some embodiments, the client may use a lens on the image capturing device or the scanning device to scan one or more areas (e.g., forehead area, check area, neck area, etc.) In some embodiments where multiple areas of a client's skin are scanned, the result of each area of the multiple areas may be averaged or weight averaged (e.g., heavier weights for the forehead scan and/or the cheek area scan and lighter weight in the neck area scan; heavier weight in the cheek area scan, medium weight in the forehead scan, and lighter weight in the neck area scan; etc.) The scan results (e.g., images) may be provided to an artificial intelligence model 1004 that performs various processes (e.g., simple linear regression, multivariate linear regression, other linear approach for modeling the input and the output, neural network, deep learning, etc.) to recognize features in the scan results (e.g., hairs, freckles, moles, pre-malignant (e.g., pre-cancerous) skin growth, malignant skin growth, other colored spots, fine lines or wrinkles, characteristics of fine lines and/or wrinkles such as depth or depths, characteristics of pores such as pore size or sizes or appearance, skin health properties or conditions such as dryness, moisture levels (e.g., with a moisture sensor described below with reference to FIGS. 17A-17B), follicle or follicles, bacteria infection (e.g., using a ultraviolet (UV) light source such as one or more UV-A and/or UV-B light sources in 1716 of FIG. 17B to illuminate a skin area of interest to produce, for example, corneform and proprioni bacteria florescence), dead skin buildup, pores, swelling, cracking, scaliness, and others) and to predict one or more characteristics (e.g., skin tone, undertone, etc.) pertaining to the skin scan results.

In some embodiments, various techniques described herein are not limited only to scanning a user's skin for skin care product matching and recommendation. Rather, some embodiments apply various techniques to scan a user's skin and use various artificial intelligence techniques to recognize various types of objects on the user's skin to produce dermatological grade scan results and recommendations. For example, some embodiments may utilize the object and/or feature recognition and classification techniques described herein to recognize pre-malignant skin growth, the size and/or shape of a mole, malignant skin growth, bacteria fluorescence (e.g., corneform and proprioni bacteria florescence), or any other type of skin concerns to predict whether a skin concern may correspond to a specific type of disease and make corresponding recommendation (e.g., a visit to a medical specialist's office) accordingly. In some embodiments, the term "body scan" may be used to encompass using various methods and/or systems to scan a part of a client's body, and "body care" may be used to encompass various care instructions, information, products, services, etc., unless otherwise specifically recited in the claims to refer to which specific part (e.g., skin, hair, nails, or others) of a client.

Some embodiments may further apply various techniques (e.g., scanning, object and/or feature recognition, prediction, classification, and recommendation, etc.) to areas or features other than a user's skin. For example, these areas may include eyes, hairs, nails tongue, or any other suitable parts of a user for which images may be captured and analyzed using various techniques described herein), and various techniques descried herein provide prediction or predictions or recommendation or recommendation of pertinent information or product or products or even personalized prediction or predictions or recommendation or recommendations for a specific user based at least in part upon one or more attributes of the specific user. For example, various object and/or feature recognition, classification, prediction, and/or recommendation techniques may be applied to hairs to predict, for instance but not limited to, hair color, hair condition, hair health, scalp health and/or condition, or any other attributes and/or conditions to hairs and/or scalp, etc. Similarly, such techniques may be applied to analyze images of nails of a user to predict concern or concerns, condition or conditions, or others of the user (e.g., predicted color of a nail, recognized object or objects or feature or features that suggests possible issues with, for instance, trauma, anemia, dietary deficiencies, heart or kidney diseases, poisoning, liver hepatitis, thyroid disease, lung disease, diabetes or psoriasis, lung problem, such as emphysema, some heart problems associated with bluish nails, inflammatory arthritis, fungal infection, skin cancer, infection, injury, etc., or any combinations thereof). Such techniques may also predict and provide recommendations the user (e.g., seek medical help) with information to explain the recommendations.

In some embodiments, the artificial intelligence model predicts the skin tone or undertone value, or a combination, or index for skin tone or skin tones (e.g., a shade value or index having L* value, a* value, and b* value in the CIELAB or CIELch color space) of the client based at least in part upon the scan results at 1006. The predicted skin tone and/or undertone value or index by the artificial intelligence model may be adjusted by a beauty advisor or a sales representative operating the system for cosmetic product matching and recommendation. For example, a beauty advisor may review the scan result and the predicted skin tone and/or undertone value or index (e.g., a color index representing the client's skin tone or shade value or index) and adjust the predicted skin tone and/or undertone value or index (e.g., by altering the L* value, a* value, and/or b* value of the predicted skin tone and/or undertone value or index) at 1008 to modify the predicted skin tone and/or undertone value or index into a modified, predicted skin tone and/or undertone value or index. In some embodiments, the predicted skin tone and/or undertone value or index or the modified, predicted skin tone and/or undertone value or index may be validated by, for example, a more sophisticated AI model running on the system for cosmetic products matching and recommendation or in a backend system (e.g., a store digital (SD) backend) remotely connected to the system for cosmetic products.

In some embodiments, the artificial intelligence model may be trained using one or more training datasets 1026. The training may be done before deploying the system for cosmetic product matching and recommendation to the field in some embodiments. In some of these embodiments, the training may continue after deploying the system for cosmetic product matching and recommendation to the field by periodically, repeatedly, or continuously receive data (e.g., client's predicted skin tone or undertone value or index, or modified, predicted skin tone or undertone value or index, or others) The artificial intelligence model may also be trained repeatedly, periodically, or continuously by using, for example, clients' purchase data, clients' return data, sales records, professionals' and/or clients' reviews, comments, or other responses pertaining to cosmetic products of interest, new or updated information pertaining to cosmetic products (e.g., color characteristics, information about ingredients, key feature of features, or others), or any other suitable or appropriate information or data to further enhance the accuracy and/or performance of the artificial intelligence model.

With the predicted shade value or index (also referred to as skin tone and/or undertone value or index) or the modified, predicted shade value or index, if available, the system for cosmetic product matching and recommendation may generate a list of matching cosmetic products (e.g., foundations, concealers, products for lips, moisturizers, products for exfoliation, products for eye puffiness, dark circles, etc., skin hydration products, etc.) at least by filtering various products stored in a data structure (e.g., a database or knowledge base) into a filtered list at 1016 based at least in part upon the predicted shade value or index or the modified, predicted shade value or index, if available.

For example, the system may compare the predicted shade value or index or the modified, predicted shade value or index to the corresponding shade values or indices of various cosmetic products and identify the shade values or indices that exactly match or approximately match (e.g., with a range of shade values or indices) to generate the aforementioned filtered list of cosmetic products at 1016. In some these embodiments, the system adopts a hierarchical filtering or nested scheme where the filtering performed at 1016 represents the first level filtering. In some embodiments, the first level filtering ranks the products based at least in part upon, for example, scan results, shade index or value, skin type, skin concern or concerns, scan location and/or time, without considering other user-specific data such as history. In contrast, the second level filtering described below predicts interaction probability for each (client, product) pair and rank each pair accordingly by accounting for more user-specific data or information.

In some embodiments, the filtered list of products may be provided to a separate artificial intelligence (AI) model at 1018 that invokes various artificial intelligence techniques that shuffle and re-rank and/or further filter the filtered list of cosmetic products to generate a personalized recommendation having at least a personalized list of cosmetic products at 1018. In some embodiments where the system adopts the aforementioned hierarchical filtering or nested scheme, this personalization performed at 1018 represents the second level filtering. In some embodiments, the separate AI model receives additional information 1020 such as information or data pertaining to the particular client whose skin has been scanned at 1002.

Such information or data may include, for example, client's skin concern or concerns, client's skin condition (e.g., discoloration, acne, or others), client's personal preference (e.g., client's preferring cosmetic products providing a warmer appearance, or others), client's affinity or loyalty to certain brand or brands or specific cosmetic product or products, client's purchase history or trend (e.g., seasonal trend, changes in product or products or brand or brands over time, or others.), or a combination, client's product return history and/or trend, client's prior scan result or results, client's prior inquiries, client's prior product recommendation or recommendation, prior scan conditions (e.g., time, location, lighting conditions such as halogen, incandescent, natural light, direct sun light, or others), client's skin type (e.g., dry, oily, neutral, or others), or any other suitable data or information pertaining to the particular client, or any combinations thereof. Some of such data or information pertaining to the particular client may be stored in one or more databases, one or more knowledge bases, or a combination of one or more databases and one or more knowledge bases.

The separate AI model may then generate a personalized product recommendation at 1022 that may facilitate the selection or purchases, or a combination, of particular cosmetic products by the particular client at 1024. The particular client's selection and/or purchase information or data (data may refer to processed information in some embodiments) of one or more particular cosmetic products and optionally some additional information (e.g., the particular client's comments on the personalized product recommendation or a portion there of) may be sent back to the separate model executed at 1018 or to the database or knowledge base 1028 storing datasets for training the separate AI model in some embodiments for further training, tuning, or validating the separate AI model and/or for storing such information or data for future reference or processing.

In the second approach that applies to cosmetic product matching and recommendation with reverse look up using certain information pertaining to a client or prospective client, information or data pertaining to a product or the client may be received at 1010. Such information or data pertaining to a product may include, for example, the shade value or index for the product, price, SKU code, type (e.g., foundation, concealer, etc.), inventory status (out of stock, in stock at certain store or stores, or others), similar product or products of the same manufacturer or brand or different manufacturer or manufacturers or brand or brands, any other product specific information or data, any combinations thereof, etc. Such information or data pertain to a user may include, for example but not limited to, client's previous shade index or value (e.g., previous mobile color IQ index or value), client identifier, client brand and/or product affinities or loyalty data, client's prior purchases and/or purchase trend or trends, client's prior returns, client's profile attributes such as age, ethnicity, preferences, or others, prior product recommendation or recommendations, any combination thereof, or any other suitable data, or combination.

A reverse look service may be invoked at 1012 based at least in part on the information or data pertaining to the product or the client, and the process proceeds through 1016 through 1028 based at least in part upon the information or data received at 1012 in a similar manner as described above. In some embodiments, if the client's skin tone preference is known such skin tone preference may also be provided for the reverse lookup portion of processing at 1014. In some embodiments, any specific data pertaining to the particular client such as those described above may also be utilized in the reverse lookup portion of processing. Such specific data may be provided by the client (e.g., during a current or prior consultation with a beauty advisor or through an online interview process integrated into the mobile app) or induced from other data pertaining to the particular client (e.g., prior interactions, prior purchases, prior returns, prior consultation, prior scan or scans, or others).

In some other embodiments where there is no or insufficient specific data or information about the particular client, the system or method may identify the data to correspond to one or more similar clients. For example, the method or system may identify other clients of similar age, in the same or similar profession or professions, of the same or similar ethnicity, in the same or similar geographical area or areas, or any other suitable similarities, or any combinations thereof, etc. The method or system may then use identify corresponding information or data pertaining to these similar users and use such information or data for the particular client in the reverse lookup portion of processing. In some of these embodiments, the method or system may identify such other similar clients based at least in part upon their respective similarity scores (e.g., via cosine similarity) above a certain threshold score.

Figure 11A:
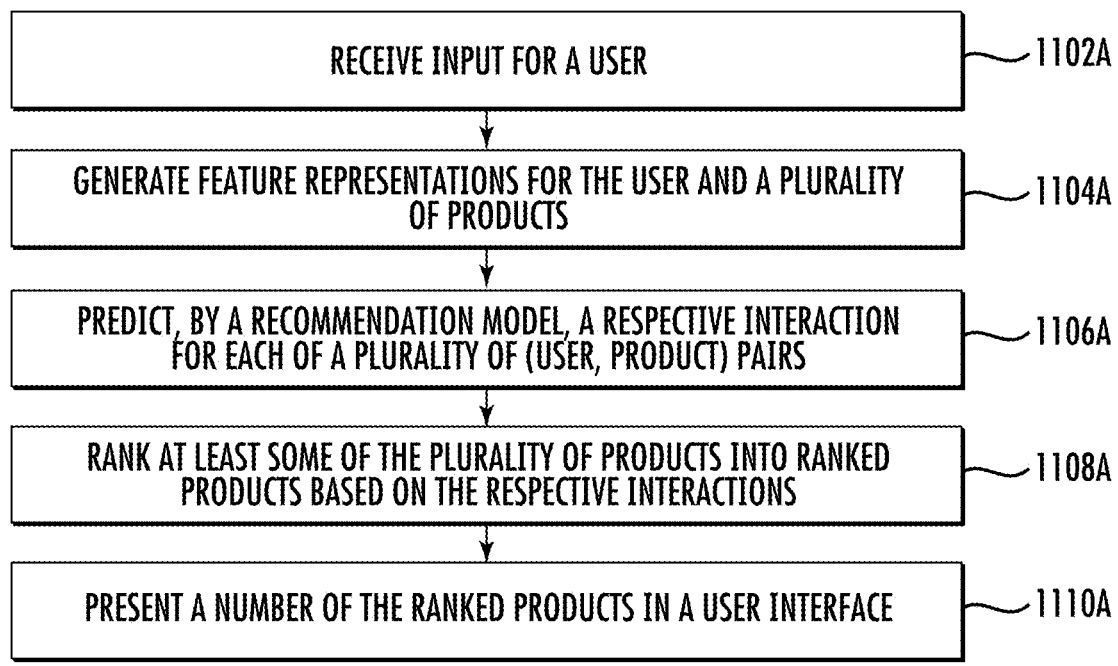
FIG. 11A illustrates another example high-level block diagram for a method or system for cosmetic product matching and recommendation using artificial intelligence techniques in one or more embodiments.

FIG. 11A illustrates a simplified example high-level block diagram for a method or system for cosmetic product matching and recommendation using artificial intelligence techniques in one or more embodiments. In these one or more embodiments, input data for a client or user may be received at 1102A. It shall be noted that the terms client and user may be used interchangeably in this description unless otherwise specified. The input data may pertain to a client and one or more products. For example, the input data may include client identifier, product identifiers (e.g., SKU codes), store identifier or identifiers, store location, client's scan data, lighting conditions for client's scan data, client's current and/or prior scan results, client's brand and/or product affinities or loyalty data, client's prior purchases and/or purchase trend or trends, client's prior returns, client's profile attributes such as age, ethnicity, preferences, etc., prior product recommendation or recommendations, client's skin type, concern or concerns, or condition, or any combination thereof, or any other suitable data, or combination.

Feature representations may be generated for the received input data at 1104A. In some of these embodiments, a client feature representation may be generated for the client, and a product feature representation may be generated for each of the one or more products by using, for example, quantization techniques. In addition or in the alternative, one or more pairs of (client, product) may be generated for the client and the one or more products where each product corresponds to a particular pair. With the feature representations generated, these one or more pairs of (client, product) are effectively transformed into one or more pairs of (client feature representation, product feature representation).

An artificial intelligence (AI) model (e.g., a recommendation model) may then predict a respective interaction for each of the one or more (client, product) pairs at 1106A. In some embodiments, an interaction represents the likelihood of a client's purchasing the product in the (client, product) pair. In some of these embodiments, the interaction may also be referred to as pairwise pair ranking measure to compare with a pairwise triple ranking measure described above. In some embodiments, the AI model may utilize, for example but not limited to, alternating least square (ALS) with implicit feedback (e.g., relationship data described above) with a learning library (e.g., a Spark Machine Learning Library) or some filtering techniques (e.g., collaborative filtering, joint learning, etc.) to find patterns or matches between similar clients and similar products in one or more datasets in the learning library. In some embodiments, the AI model may predict preference to one or more specific products (e.g., a product with a specific SKU code) for a particular client.

In some embodiments, the AI model may rank at least some of the one or more products in the one or more determined (client, product) pairs at 1108A based at least in part upon the one or more respective interactions predicted at 1106A. In some of these embodiments, the AI model may further compute and associate prediction scores with the one or more specific products for the particular client in the one or more (client, product) pairs. For example, a low prediction score for a (client, product) indicates that the client may have lower preference in purchasing the product in the (client, product pair). On the other hand, a high prediction score for a (client, product) indicates that the client may have higher preference in purchasing the product in the (client, product pair).

In some embodiments, the AI model may generate additional data for further processing (e.g., for a downstream AI model). For example, the AI model in 1106A may identify and generate purchase patterns (e.g., identities, prices, timing, quantities, etc. of products purchased), return patterns (e.g., identities, prices, timing, quantities, etc. of products returned), frequency data (frequency of purchase, frequency of return, etc.), client's affinity or loyalty data (e.g., currently favored brand or brands or product or products, previous favored brand or brands or products or products, duration therefor, or others), or any other analytical data that one or more downstream AI models may utilize. The AI model may present a number of ranked products in a user interface (e.g., a graphical user interface provided by a mobile color IQ app) to the particular client at 1110.

Figure 11B:
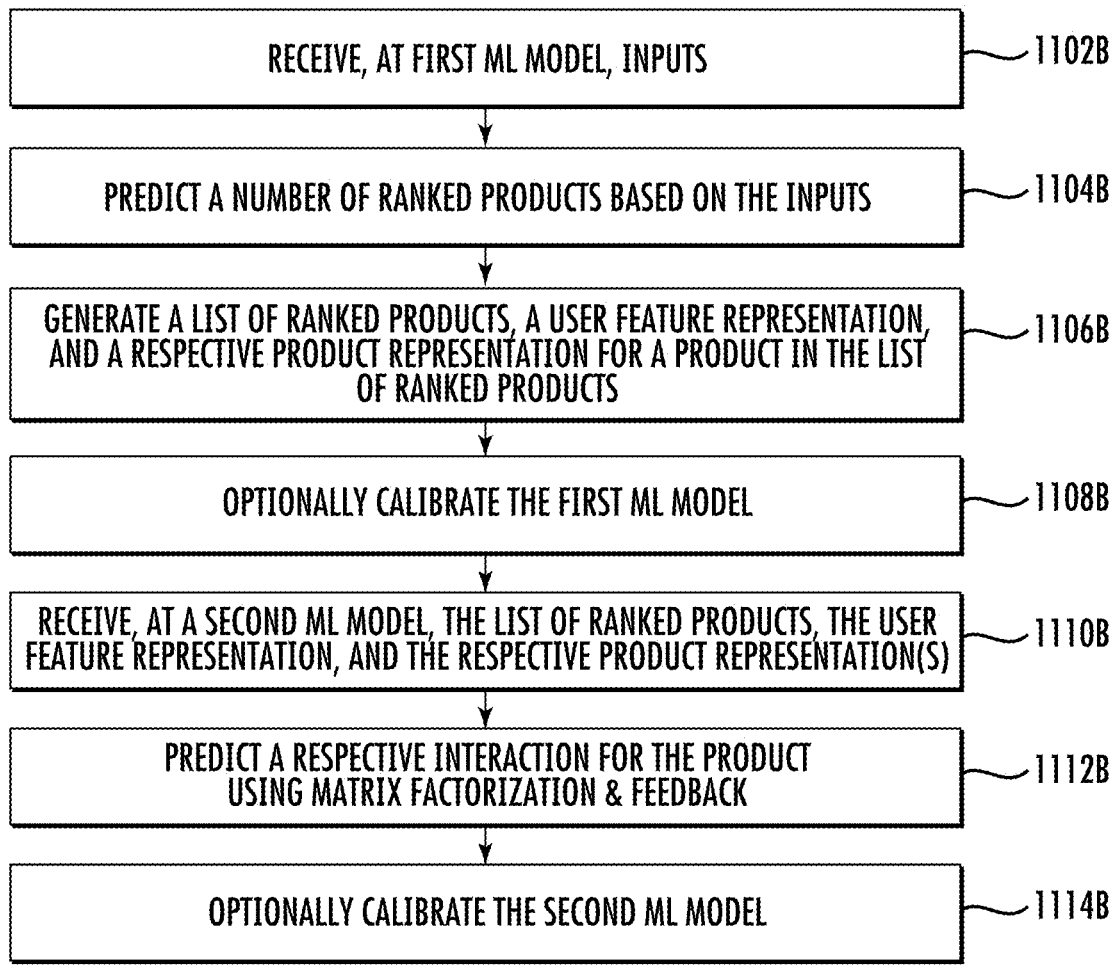
FIG. 11B illustrates another example high-level block diagram for a method or system for cosmetic product matching and recommendation using artificial intelligence techniques in one or more embodiments.

FIG. 11B illustrates another example high-level block diagram for a method or system for cosmetic product matching and recommendation using artificial intelligence techniques in one or more embodiments. In these one or more embodiments, input data may be received at a first artificial intelligence (AI) model at 1102B. The input data may pertain to a client and one or more products. For example, the input data may include client identifier, product identifiers (e.g., SKU codes), store identifier or identifier, store location, client's scan data, lighting conditions for client's scan data, client's current and/or prior scan results, client's brand or product affinities or loyalty data, client's prior purchases and/or purchase trends, client's prior returns, client's profile attributes such as age, ethnicity, preferences, etc., prior product recommendations, client's skin type, concerns, or condition, or any combination thereof, or any other suitable data.

A number of ranked products may be predicted at 1104B based at least on the input data. In some embodiments, the AI model utilizes various AI techniques (e.g., machine learning, deep learning, convolutional and/or recurrent neural networks, support vector machines, various prediction models using techniques such as alternating least squares, or any other suitable techniques or models, or any combinations thereof) to predict a number of ranked products. A list of ranked products, a user feature representation (e.g., a user vector), a product feature representation may be determined at 1106B based at least in part upon the number of ranked products. For example, the AI model may generate 100 ranked products at 1104B and selects the top N (e.g., five or ten or all 100) ranked products from the 100 ranked products for a particular client.

Optionally, the first AI model may be calibrated at 1108B. In some embodiments, the first AI model may be calibrated by executing the first AI model over a validation dataset that is distinguishable from one or more training datasets used in training the first AI model or the one or more testing datasets used in testing the first AI model. In some embodiments where calibration is performed, the calibration may include receiving labeled data (e.g., ground truths) and/or adjustment data for the skin scan result and/or the ranked list of products. An accuracy or error measure of one or more rankings of the plurality of products may be determined based at least in part upon the adjustment data and/or labeled data. The accuracy or error measure may be propagated backward through the first AI model to distribute the accuracy or error measure to various levels or portions of the first AI model based on, for example, the gradient pertaining to the accuracy or error measure (e.g., by using a gradient descent algorithm such as the momentum or heavy ball algorithm, the stochastic gradient descent algorithm, fast gradient algorithms such as the optimized gradient method (OGM), the fast proximal gradient method (FPGM), etc., the forward-backward algorithms, or any other suitable algorithms that may be used in or as an extension of training artificial intelligence networks.

A second AI model may receive the list of ranked products, the client feature representation, the product representations at 1110B and predicts a respective interaction for each product in the list of ranked products for the particular client at 1112B. In some embodiments, the second AI model may generate such predictions by using, for example but not limited to, matrix factorization techniques with feedback. The prediction at 1112B represents the second level prediction that operates on the output of the first level prediction at 1104B or 1106B in these embodiments illustrated in FIG. 11B.

In some of these embodiments, the second AI model may utilize AI techniques such as alternating least square (ALS) with implicit feedback (e.g., relationship data described above) with a learning library (e.g., a Spark Machine Learning Library) or some filtering techniques (e.g., collaborative filtering, joint learning, etc.) to find client-specific (e.g., personalized) patterns or matches for the particular client. Alternating least squares (ALS) factorizes a given matrix R into two factors U (e.g., a row vector) and V (e.g., a column vector) such that R≈UTV. The unknown row dimension may be provided as a parameter to the ALS algorithm and may be called latent factors.

One of the advantages of ALS is that real-world data may be often bimodal (e.g., created by a joint interaction between two types of entities). For example, a client rating a product may be affected by both the client characteristics (e.g., affinity to some characteristics or attributes) and the product characteristics (e.g., its connections to one or more of those characteristics/attributes). This type of data may be represented as a matrix, of which each dimension represents one of the entity types. Co-clustering (or biclustering) is a data mining technique that relates to a simultaneous clustering of the rows and columns of a matrix. Some embodiments use Matrix Factorization (MF) to solve co-clustering problems (e.g., for collaborative recommender systems). For example, matrix factorization assumes a matrix of ratings given by m clients to n products. Applying the matrix factorization on the aforementioned matrix R may end up factorizing the matrix R into two matrices such that their multiplication approximates R. The new quantity, k, introduced by the operation of matrix factorization serves as both U's and P's dimensions. This new quantity denotes the rank of the factorization.

The second AI model may generate its predictions by using a cost function. In some embodiments where matrix factorization or collaborative filtering is used to factorize a matrix R into U and P as described above, the cost function may be defined as: cost function=$\|R-U \times PT\|2+(\|U\|2+\|P\|2)$. The first term in the above cost function, $\|R-U \times PT\|2$ denotes the Mean Square Error (MSE) distance measure between the original rating matrix R and its approximation, while the second term is a regularization term that is added to govern a generalized solution (e.g., to prevent overfitting to some local noisy effects on ratings).

The above may be achieved by using alternating least squares that involve a two-step iterative optimization process. In each iteration, ALS fixes P and solves for U, and following that ALS fixes U and solves for P. Because the solution may be unique and may guarantee a minimal MSE, the cost function may, in each step, either decrease or stay unchanged, but never increase. Alternating between the two steps guarantees reduction of the cost function, until convergence. Some other embodiments may use singular value decomposition (SVD) which may provider stronger guarantees than matrix factorization in some embodiments.

At 1114B, the second AI model may be optionally calibrated. In some embodiments, the second AI model may be calibrated by executing the second AI model over a validation dataset that is distinguishable from one or more training datasets used in training the second AI model or the one or more testing datasets used in testing the second AI model. In some embodiments where calibration is performed, the calibration may include receiving labeled data (e.g., ground truths) and/or adjustment data for the skin scan result and/or the ranked list of products. In some embodiments, client's selection data (or non-selection data indicating client's selecting none from the list), purchase data (or non-purchase indicating no purchases were made), and/or client's subsequent interaction data (e.g., interactions in future time) may also be received and utilized in calibrating the second AI model.

An accuracy or error measure of one or more rankings of the plurality of products may be determined based at least in part upon the adjustment data, labeled data, client's selection data (or non-selection data indicating client's selecting none from the list), purchase data (or non-purchase indicating no purchases were made), and/or client's subsequent interaction data. The accuracy or error measure may be propagated backward through the second AI model to distribute the accuracy or error measure to various levels or portions of the second AI model based at least in part on, for example, the gradient pertaining to the accuracy or error measure (e.g., by using a gradient descent algorithm such as the momentum or heavy ball algorithm, the stochastic gradient descent algorithm, fast gradient algorithms such as the optimized gradient method (OGM), the fast proximal gradient method (FPGM), etc., the forward-backward algorithms, or any other suitable algorithms that may be used in or as an extension of training artificial intelligence networks.

Figure 11C:
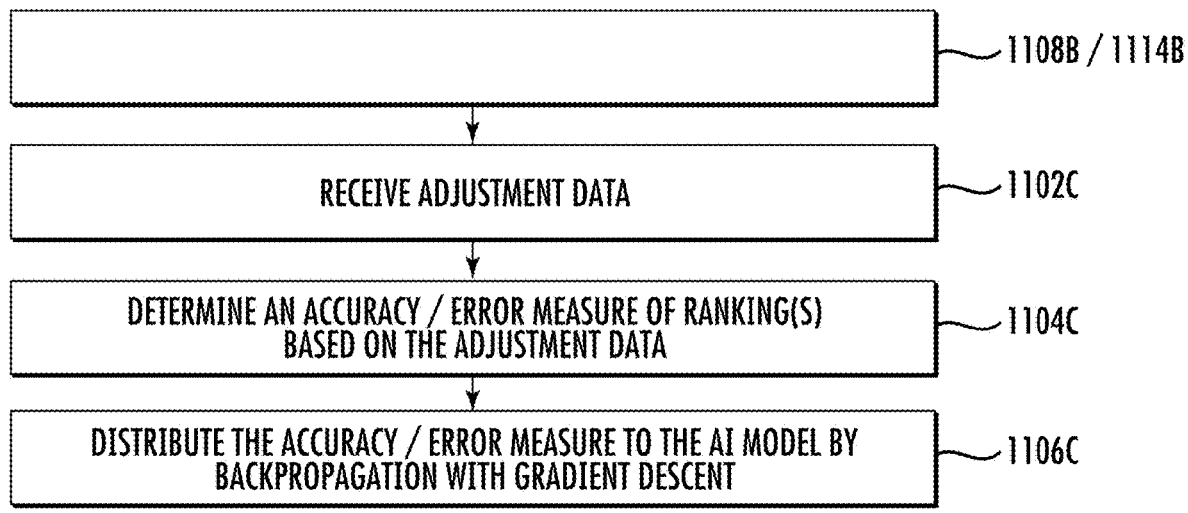
FIG. 11C illustrates more details about a portion of example high-level block diagram for a method or system for cosmetic product matching and recommendation using artificial intelligence techniques illustrated in FIG. 11B in some embodiments.

FIG. 11C illustrates more details about a portion of example high-level block diagram for a method or system for cosmetic product matching and recommendation using artificial intelligence techniques illustrated in FIG. 11B in some embodiments. More specifically, FIG. 11C illustrates more details about calibration 1108B or 1114B in FIG. 11B. In these embodiments, adjustment data may be received at 1102C. The adjustment data may include, for example but not limited to, adjusted data to the scan result (e.g., adjusted shade, hue, and/or saturation values), adjusted product ranking, labeled data, adjustment data for the skin scan result and/or the ranked list of products, client's selection data (or non-selection data indicating client's selecting none from the list), purchase data (or non-purchase indicating no purchases were made), and/or client's subsequent interaction data (e.g., interactions in future time).

An accuracy or error measure pertaining to the prediction or predictions by an AI model (e.g., the first AI model or the second AI model described above with reference to FIG. 11B) may be determined at 1104C based at least in part upon the adjustment data, labeled data, client's selection data (or non-selection data indicating client's selecting none from the list), purchase data (or non-purchase indicating no purchases were made), and/or client's subsequent interaction data. At 1106C, the accuracy or error measure may be distributed to the AI model (e.g., the first AI model or the second AI model described above) by, for example, back-propagating the accuracy or error measure through various levels or portions of the AI model based at least in part on, for example, the gradient pertaining to the accuracy or error measure (e.g., by using a gradient descent algorithm such as the momentum or heavy ball algorithm, the stochastic gradient descent algorithm, fast gradient algorithms such as the optimized gradient method (OGM), the fast proximal gradient method (FPGM), etc., the forward-backward algorithms, or any other suitable algorithms that may be used in or as an extension of training artificial intelligence networks.

Figure 11D:
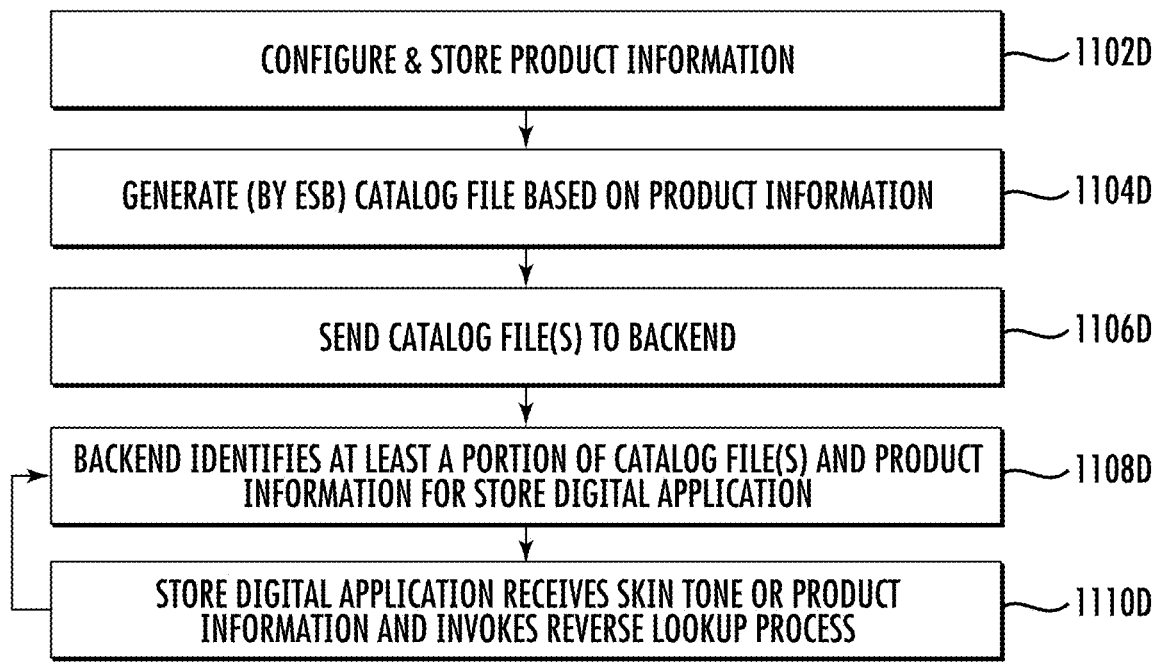
FIG. 11D illustrates an example data setup for a process or system for cosmetic product matching and recommendation using artificial intelligence techniques in one or more embodiments.

FIG. 11D illustrates an example data setup for a process or system for cosmetic product matching and recommendation using artificial intelligence techniques in one or more embodiments. In these one or more embodiments, product information pertaining to a plurality of cosmetic products may be configured and stored at 1102D. In some of these embodiments, the plurality of cosmetic products may include the products of the specific business entity that operates the system for cosmetic product matching and recommendation as well as the cosmetic products of the competitors of the aforementioned specific business entity.

In some of these embodiments, the product information may include, for example but not limited to, product identifiers such as a product stock keeping unit (SKU), bar code, QR code (quick response code), or other equivalent identifiers, color characteristics (e.g., color index in the CIELAB or CIELch color space), price, inventor status, client demographic distribution (e.g., by age, geographic locations, ethnicity, profession, etc.), skin care or skin health related information (e.g., targeting clients with acnes, etc.), sales records, or any other product information that may be utilized for business intelligence or analytics purposes, or any combinations thereof. In some of these embodiments, various pieces of data or information pertaining to each product of the plurality of products are correlated or associated with the corresponding color characteristics of the product at 1102D. In some embodiments, the color characteristics are defined in the CIELAB color space or CIELch color space. In these embodiments, any product color characteristics that are not represented in the aforementioned color space of choice may be exactly or approximately converted or transformed into the aforementioned color space of choice.

One or more catalog files may be generated or updated at 1104D (e.g., by an Enterprise Service Bus or ESB) based at least in part upon the product information. In some embodiments, a catalog file includes a data structure that further includes the identifier of each product of the plurality of products and its corresponding information or data. In some of these embodiments, a catalog file may be indexed by using a unique key (e.g., a key generated based on the SKU code, the manufacture/brand-product name, etc. to uniquely represent the plurality of products in an ordered manner in a catalog file) to facilitate more efficient look up and access.

A catalog file may include all or some commercial product information that enables the definition and mapping of product offering and may encompass certain sets of tools or references to such certain sets of tools that allow configuration of a product, a product service bundle, pricing, discounts, etc. in some embodiments. In some of these embodiments a catalog file includes a type of marketing collateral that lists product details that may be used to assist purchasers in making a purchase decision. A catalog file may include textual information as well as visual information such as one or more images of a product.

These one or more catalog files generated at 1104D or a may be transmitted at 1106D as a stream of data to the backend that comprises a platform having one or more servers or computing systems. The backend may identify at least a portion of a plurality of catalog files and product information for a store digital application at 1108D. A store digital application is a software tool that is installed upon a system for cosmetic product matching and recommendation at, for example, a cosmetic products retail site. The store digital application may enable the operator (e.g., a beauty advisor) to perform a skin tone scan that predicts a skin tone of a client as well as matching product recommendation and/or a skin guide scan that provides skin care recommendations with pertinent matching products, services, external treatment (e.g., by dermatologists or specialists), skin care instructions, etc.

A digital skin guide scan provides dermatologist-grade diagnosis results (e.g., a personalized recommendation for a specific client) that have been validated by various research and development (R&D) facilities and commercial entities in the medical fields. Although a skin guide scan may leverage the same or substantially functionalities provided by various methods or systems described herein, a skin guide scan may differ from a skin tone scan in that a skin guide scan pertains more to the health attributes or characteristics of a client's skin (or other parts of the client such as nails, hairs, etc.), whereas a skin tone scan pertains more to the complexion or appearance of a client's skin (or other parts of the client such as nails, hairs, etc.)

Further, a skin guide scan may focus on particular area or areas of concerns of a client, whereas a skin tone scan may focus on general area or areas of a plurality of clients. Further, a skin tone scan may focus more on the color attributes (e.g., LAB color index or value) and whether there exist one or more features such as hairs, moles, freckles, wrinkles, fine lines, etc. on the skin (for exclusion for skin tone or undertone color prediction and/or for separate color prediction of such one or more features), whereas a skin guide scan may focus on some attributes (e.g., physical attributes such as size, shape, etc.) of the aforementioned one or more features in addition to or in place of the aforementioned color attributes. In some embodiments, a scan may include both a skin tone scan and a skin guide scan while in some other embodiments, a skin tone scan and a skin guide scan may be two separate scan sessions.

A store digital application may receive the skin tone of a particular client, skin condition of the particular client, or product information of a particular cosmetic product (e.g., the name of a particular cosmetic product) at 1110D an initiate a reverse lookup process (e.g., the reverse lookup described above with reference to FIG. 10) to determine one or matching cosmetic products and provide a personalized recommendation for the particular client as described herein. In some embodiments, the skin tone of a particular client may be provided by the client (e.g., showing the skin tone color index or value) or by a skin tone scan session. The skin condition of a particular client may also be provided by the client (e.g., showing the skin condition information) or by a skin guide scan session. The product information of a particular cosmetic product (e.g., a competing product from a different manufacturer or brand) may be provided by the specific client who desires to try the matching cosmetic product which is determined by the aforementioned reverse lookup process.

In some embodiments, the backend may transmit the one or more catalog files or a smaller subset thereof to a system for cosmetic product matching and recommendation deployed at a cosmetic product retail site so that the reverse lookup process may be performed locally with the store digital application and the transmitted catalog file or files or a smaller portion thereof. In some other embodiments, the one or more catalog files are hosted remotely in a storage accessible by the backend and/or the store digital applications.

Moreover, a store digital application may act as a terminal to transmit received information as well as a request or query to perform a reverse lookup process for the received information to the backend that performs the reverse lookup process to obtain results and transmits the results back to the store digital application that initially sent the request or query in some embodiments. In some other embodiments, a store digital application may be configured to include all the requisite software modules, services, etc. as well as the catalog file or files so as to perform a reverse lookup process locally.

In yet other embodiments, a store digital application may function in tandem with the backend in such a way that the store digital application may perform a smaller portion of a reverse lookup process while the backend performs the remaining portion of the reverse lookup process. For example, the system for cosmetic product matching and recommendation may host thereupon a portion of the catalog file or files for the cosmetic products produced by the manufacturer or business entity that operates the system for cosmetic product matching and recommendation. The system nevertheless does not include a local copy of the portion of the catalog file or files for competitors' cosmetic products. Therefore, a reverse lookup for the cosmetic products produced by the business entity may be performed entirely locally on the system for cosmetic product matching and recommendation, whereas a reverse lookup for a competitor's cosmetic products is performed remotely by or through the backend.

Figure 11E:
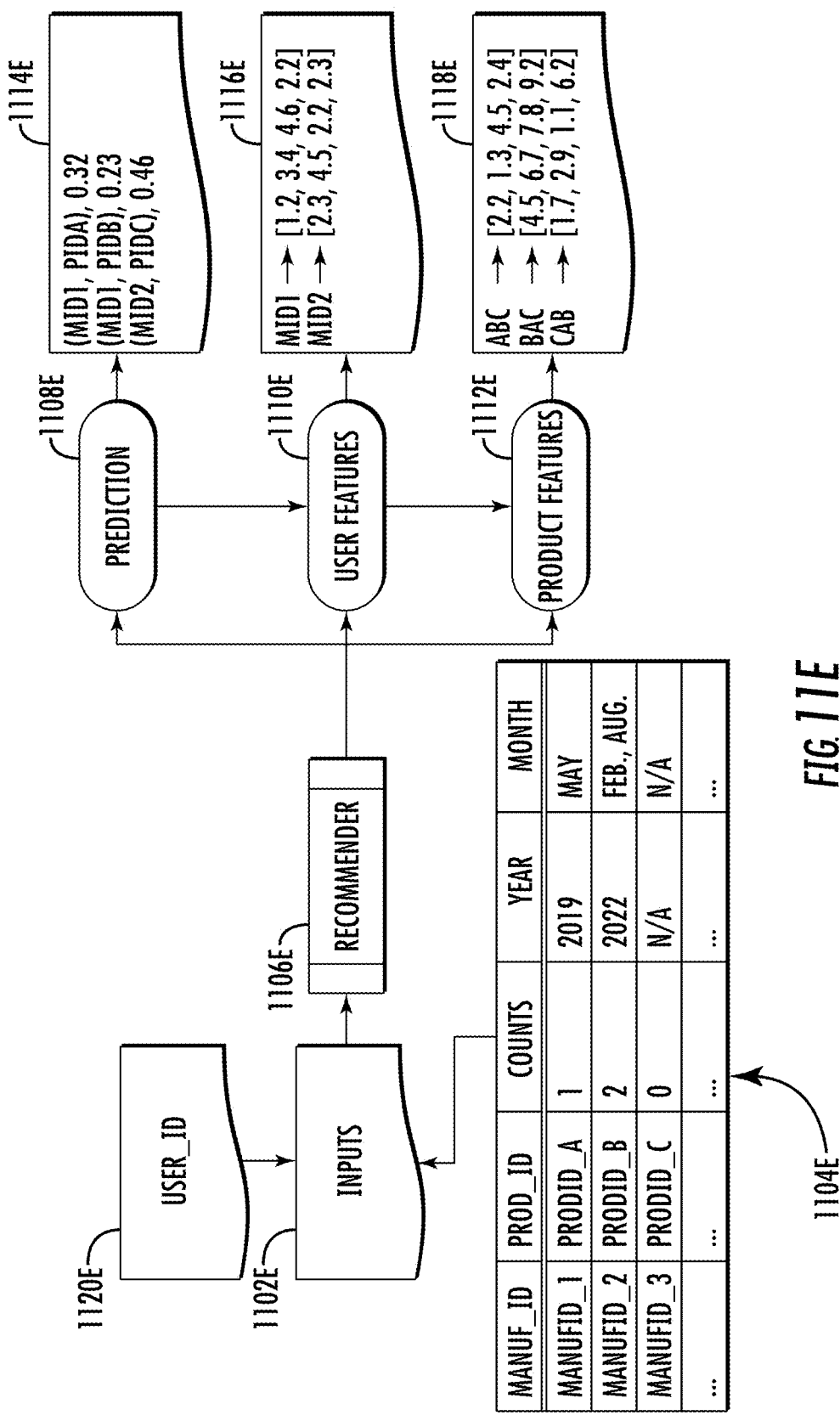
FIG. 11E illustrates an example recommender system that receives example inputs including data for personalized ranked products from a first level filtering model in a hierarchical or nested filtering network and re-ranks these ranked products using the recommender system as a second level filtering model in one or more embodiments.

FIG. 11E illustrates an example recommender system that receives example inputs including data for personalized ranked products from a first level filtering model in a hierarchical or nested filtering network and re-ranks these ranked products using the recommender system as a second level filtering model in one or more embodiments.

Figure 11F:
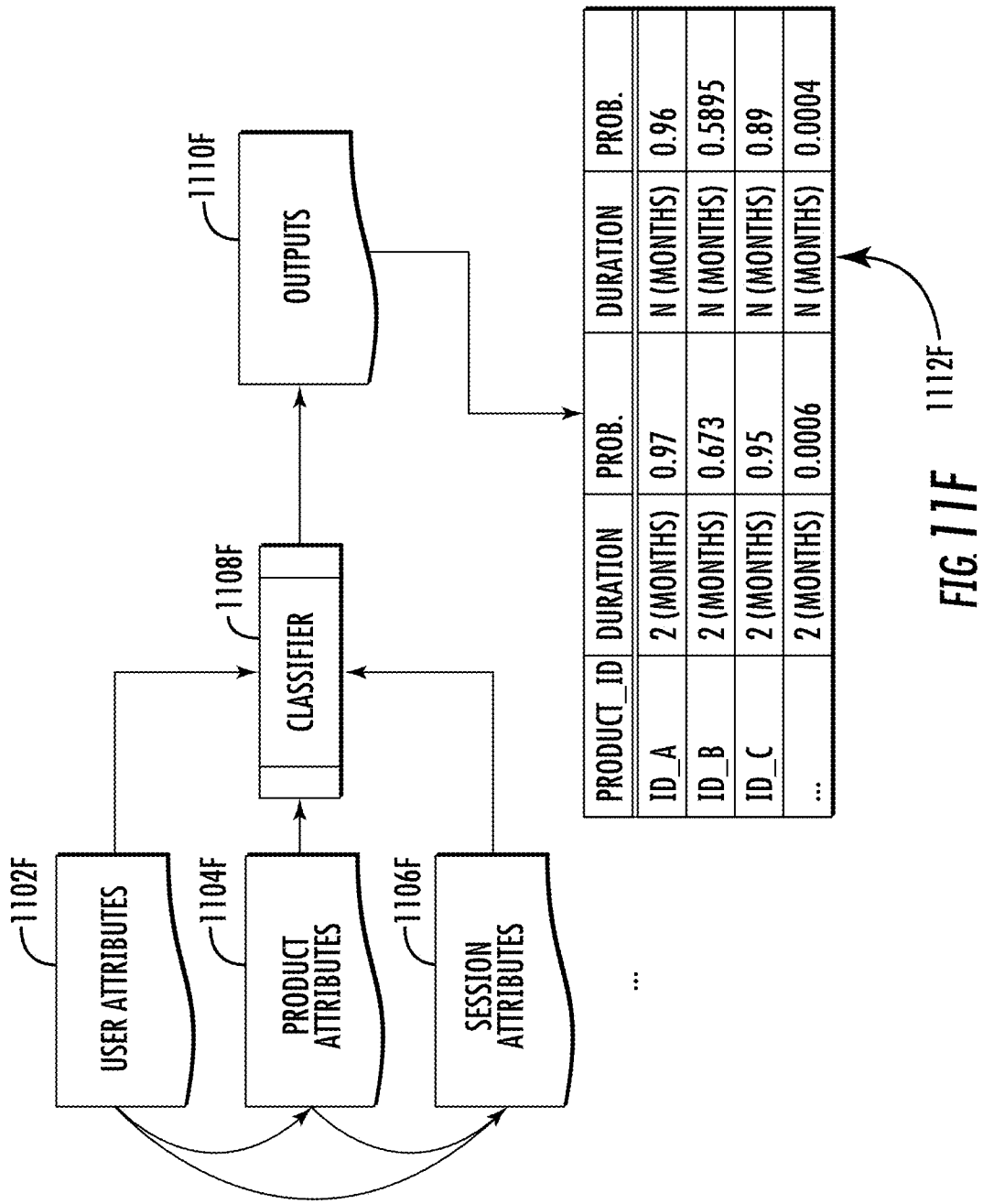
FIG. 11F illustrates an example recommender system that receives example inputs including data for personalized ranked products from a first level filtering model in a hierarchical or nested filtering network and re-ranks these ranked products using the recommender system as a second level filtering model to predict respective customer affinities for a plurality of products in one or more embodiments.

FIG. 11F illustrates an example recommender system that receives example inputs including data for personalized ranked products from a first level filtering model in a hierarchical or nested filtering network and re-ranks these ranked products using the recommender system as a second level filtering model to predict respective customer affinities for a plurality of products in one or more embodiments. In these embodiments, the example recommender system 1106E receives inputs 1102E that comprises the client identifier of a client 1120E and a list of ranked products 1104E comprising information such as manufacturer's identifier of a product, the identifier of the product, counts (e.g., quantities purchased), the temporal information (e.g., year, month, and/or date on which the respective count of the product was purchased, or any other suitable or appropriate information as described herein).

The recommender 1106E processes the input 1102E to generate a prediction at 1108E. An example prediction 1114E includes, for example, a predicted purchase or selection probability for the particular client with respect to each of one or more recommended cosmetic products. For example, 1114E illustrates that the particular client has a probability of 0.32 to purchase the recommended cosmetic product that corresponds to manufacturer ID1 and product ID A, a probability of 0.23 to purchase the recommended cosmetic product that corresponds to manufacturer ID_2 and product ID_B, a probability of 0.46 to purchase the recommended cosmetic product that corresponds to manufacturer ID_2 and product ID_C, and so forth.

The recommender 1106E may further process the input 1102E to generate one or more byproducts such as a client feature representation 1110E (e.g., a client feature vector) and/or a product feature representation 1112E (e.g., a product feature vector) by using one or more techniques described herein (e.g., quantization, embedding, and others)

FIG. 11F illustrates an example recommender system that receives example inputs including data for personalized ranked products from a first level filtering model in a hierarchical or nested filtering network and re-ranks these ranked products using the recommender system as a second level filtering model to predict respective customer affinities for a plurality of products in one or more embodiments. In these embodiments, a classifier 1108F may receive inputs such as one or more user attributes or characteristics 1102F (e.g., client identifier, client skin condition, client skin type, client skin concern or concerns, client skin tone index or value, ethnicity, age or age range, profession, loyalty or affinity, or others), one or more product attributes or characteristics 1104F (e.g., product identifier, price, availability, product color characteristics, etc.), and/or one or more session attributes or characteristics (e.g., store identifier, store location, time and/or date of scan, etc.).

The classifier 1108F may then generate an output 1110F based at least in part upon the input. In some embodiments, the classifier 1108F may generate a list of one or more matching cosmetic products as well as a prediction of how likely a client may purchase each of the one or more matching cosmetic products which one or more projected temporal durations. For example, the output 1112F may include the information showing that for the cosmetic product with the identifier "ID_A," a client (e.g., a particular client who has requested a cosmetic product matching and recommendation service) may have the probability (ranging from 0 to 1) of 0.97 to purchase the cosmetic product within two months and the probability of 0.96 to purchase the cosmetic product within N months.

The same client may have the probability of 0.673 to purchase the cosmetic product with identifier "ID_B" within two months and the probability of 0.5895 to purchase the cosmetic product within N months. The same client may have the probability of 0.95 to purchase the cosmetic product with identifier "ID_C" within two months and the probability of 0.89 to purchase the cosmetic product within N months. The same client may have the probability of 0.0006 to purchase the cosmetic product with identifier "ID_D" within two months and the probability of 0.0004 to purchase the cosmetic product within N months. The output 1112F may be sorted based on, for example, one or more columns. For example, the output 1112F may be sorted based on the probability values for the shortest temporal duration in some embodiments. In some other embodiments, the output 1112F may be sorted based on the weighted probability values for the temporal durations predicted by the classifier 1108F. Yet in other embodiments, the output 1112F may be first sorted based on the probability values for one temporal duration and then sorted based on the probability values for another temporal duration.

FIG. 12A illustrates some example configuration variables as well as their respective values and descriptions for a system for cosmetic product matching and recommendation in one or more embodiments. More specifically, these example configuration variables may include the offset value or starting point offset ("1Offset") for the L* values for the CIELAB color space; the size of distance of L* per segment ("1SubsementSize"); the size of distance of L* per subsegment ("1SubSegmentSize"); the link depth segments to ("lSegmentGroping"); the starting point offset for C* in the CIELAB color space ("cOffset"); the distance or size of C* per segment ("cSegmentSize"); the maximum C* per segment ("cSegmentMax"); the starting point or offset for h* of the CIELAB color space ("hOffset"); and the distance or size of h* per segment ("hSegmentSize"). FIG. 12A further illustrates some examples values for the aforementioned example configuration variables that may be referenced in the description below.

Figure 12B:
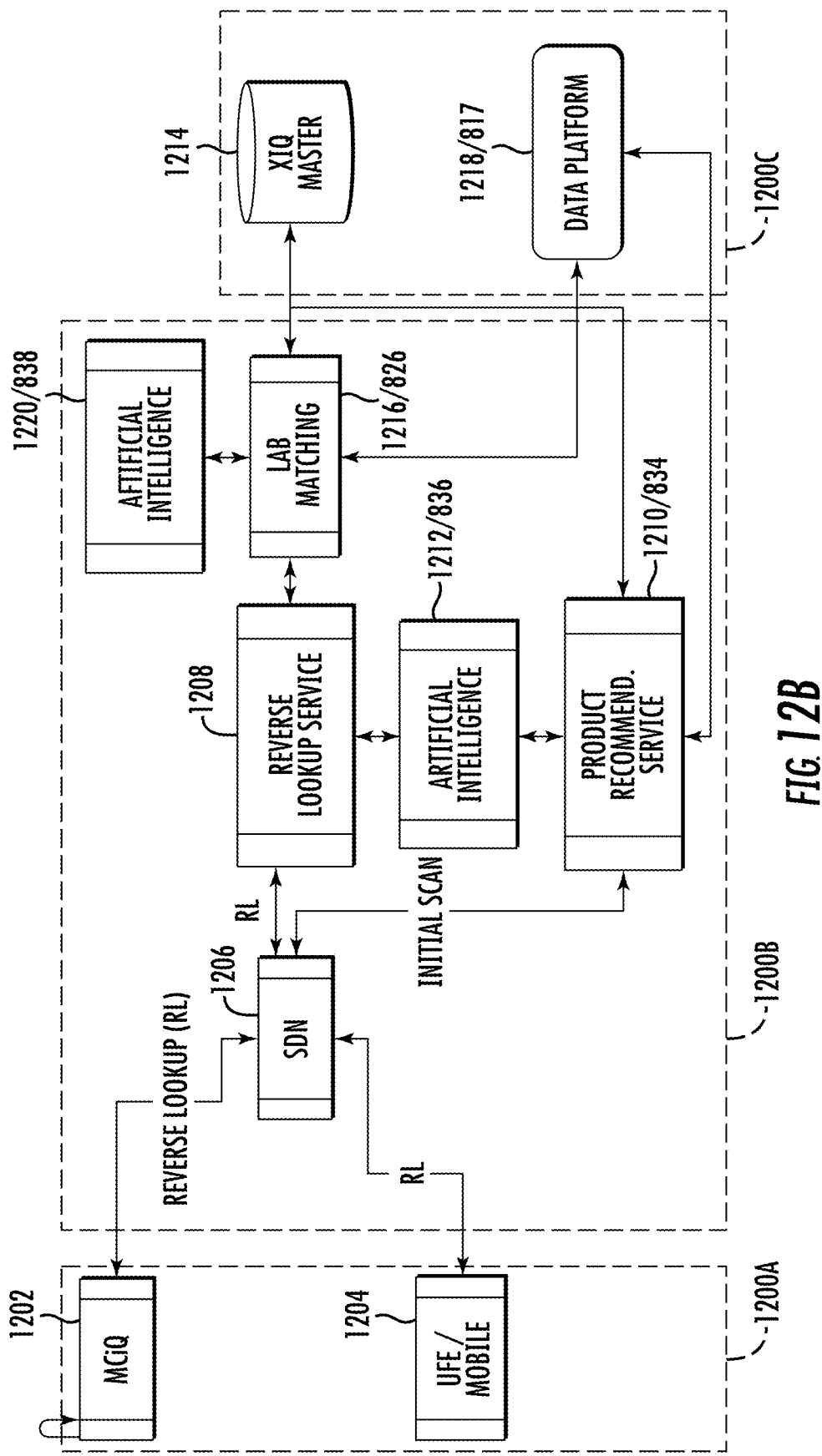
FIG. 12B illustrates an example high-level block diagram for a method or system that is provided as software as a service, infrastructure, and/or platform as a service for performing a reverse lookup for cosmetic product matching and recommendation in one or more embodiments.

FIG. 12B illustrates an example high-level block diagram for a method or system that is provided as software as a service, infrastructure, and/or platform as a service for performing a reverse lookup for cosmetic product matching and recommendation in one or more embodiments. In these embodiments, the method or system includes three platforms—the source platform 1200A, the middleware platform 1200B, and the target platform 1200C. The source platform 1200A may include an offline module 1202 which may provide, for example, services for an existing reverse lookup for cosmetic products by using CIELAB color space data (e.g., an existing mobile color IQ index or value representing the skin tone of a particular client). The source platform 1200A may further include an online module 1204 which scans the skin of a particular client with a store digital application (e.g., a store digital application described above having a unified frontend or UFE) or with a client mobile computing device having an image capturing capability.

The target platform 1200C may include a data platform (e.g., reference numeral 817 described above and/or 1218) and a master database or knowledge base storing data or information described here and denoted as XIQ Master 1214 in FIG. 12B. The middleware platform 1200B includes a development network 1206 that comprises a plurality of application programming interfaces (APIs) to interface with mobile applications (e.g., store digital application, mobile apps on different operation systems of mobile computing devices, etc.) The development network 1206 interfaces with the aforementioned offline module 1202 and the online module 1204 to receive requests or queries for the reverse lookup service and provide results back to the requesting modules or devices.

Moreover, the development network 1206 is further operatively coupled to a reverse lookup process or service 1208 (which may be implemented as a monolithic application, a set of services, or a collection of loosely connected microservices) for reverse lookup. The reverse lookup process or service 1208 receives the data from the source platform 1202 (e.g., one or more offline modules 1202, one or more online modules 1204, or a combination of one or more offline modules 1202 and one or more online modules 1204) via the corresponding APIs of the development network 1206 for respective reverse lookup services that respectively determine one more matching cosmetic products to provide respective recommendations. More specifically, the reverse lookup process or service 1208 is operatively coupled to a matching model (e.g., 1216 or 826 in FIG. 8) that determines one or more matching cosmetic products based at least in part upon the input data received from the reverse lookup service 1208. In some embodiments, the matching model (1216 or 826) may be operatively coupled to an artificial intelligence model 1220 (or 838 in FIG. 8) that may be trained for feature recognition and classification (e.g., predicting the color index or color code for a skin tone of a client) to facilitate the determination of matching cosmetic products by the matching model (1216 or 826).

The reverse lookup process or service 1208 may also be operatively coupled to an AI model (e.g., 1212 or 836 in FIG. 8) that utilizes various artificial intelligence techniques as described herein to facilitate the cosmetic product recommendation tasks. In some embodiments, the artificial intelligence model 1212 (or 836 in FIG. 8) that may be trained for recommendation tasks (e.g., providing general and/or personalized product, service, or other instructional recommendations). Further, the middleware platform 1200B may include an artificial intelligence model 1212 (or 836 in FIG. 8) that generates predicted, general and/or personalized recommendations based at least on the input (e.g., input relayed from the reverse lookup process or service 1208). The artificial intelligence model 1212 (or 836) may be trained as a recommender as described herein to facilitate the tasks for predicted general and/or personalized recommendations by the product recommendation process or service (1210 or 834).

The target platform 1200C may include a master database or knowledge base 1214 that stores thereupon master data such as static or runtime libraries, schemas, etc. to support (e.g., read/subscription operations and/or write/publication operations) for the matching process or service (1216 or 826) and the product recommendation process or service (1210 or 834). The target platform 1200C may further include a data platform 1218 (or 817 in FIG. 8) that receive data (e.g., a particular user's data such as the particular user's preference for shade, the particular user's purchase and/or return histories, the particular user's skin concern or concerns, the particular user's skin condition and/or type, the particular user's product/brand affinities, etc.) from the data platform 1218 (or 817) to generate a personalized recommendation for a particular user or other artificial intelligence models (e.g., the AI model 1220 in FIG. 12B or 838 in FIG. 8 for matching processes or services) described herein.

Figure 12C:
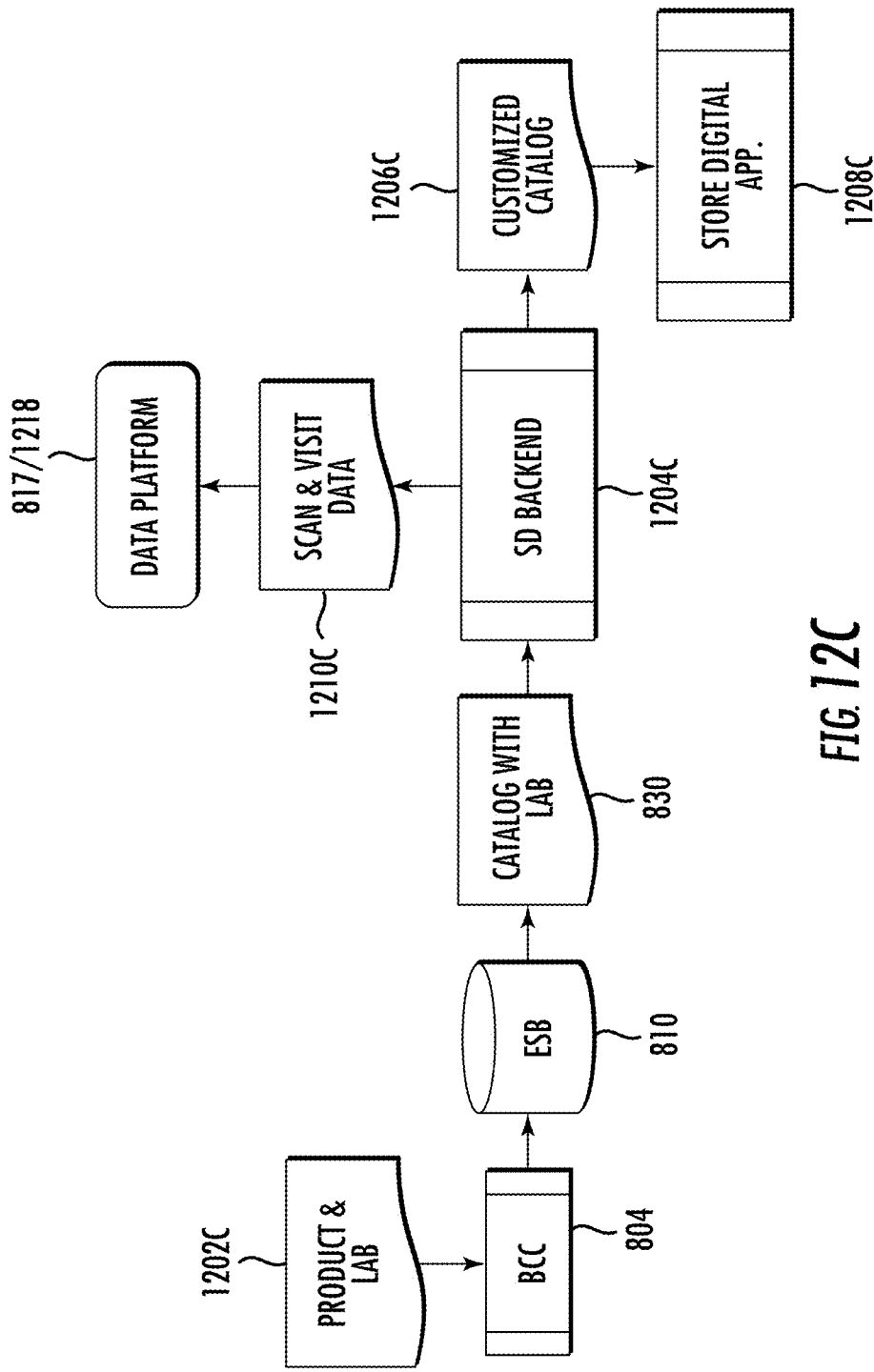
FIG. 12C illustrates a high-level block diagram for an example data setup for the method or system for performing a reverse lookup for cosmetic product matching and recommendation illustrated in FIG. 12B in one or more embodiments.

FIG. 12C illustrates a high-level block diagram for an example data setup for the method or system for performing a reverse lookup for cosmetic product matching and recommendation illustrated in FIG. 12B in one or more embodiments. More specifically, a business control center (BCC) process or module that is identical or similar to 804 in FIG. 8 may receive product information of a plurality of cosmetic products and their respective color characteristics 1202C. In some of these embodiments, the product information of a plurality of cosmetic products may be correlated with or linked to their respective color characteristics in a structured or unstructured manner in the form of one or more catalog files in an enterprise service bus (ESB) database or knowledge base 810.

The enterprise service bus (ESB) database or knowledge base 810 may provide, among other data, the one or more catalog files 830 to the store digital (SD) backend 1204C that correlates the one or more catalog files 830 with the data pertaining to skin tone scans or skin guide scans 1210C to store the correlated results in a data platform 1218 (or 817 in FIG. 8). The store digital backend 1204C may also transmit all of the one or more catalog files associated with the respective color data of the plurality of cosmetic products to one or more store digital applications 1208C (e.g., a store digital application in a system for cosmetic product matching and recommendations deployed to one or more cosmetic product retail sites).

In some of these embodiments, the store digital backend 1204C may customize a smaller subset of the one or more catalog files 830 and transmits the smaller subset to a system for cosmetic product matching and recommendation deployed at a cosmetic product retail site so that the store digital application included in the system may perform at least some of the reverse lookup tasks may locally with the transmitted smaller subset of catalog file or files. In some other embodiments, the one or more catalog files are hosted remotely in a storage accessible by the backend 1204C and/or the store digital application or applications 1208C.

Figures 13A, 13B:
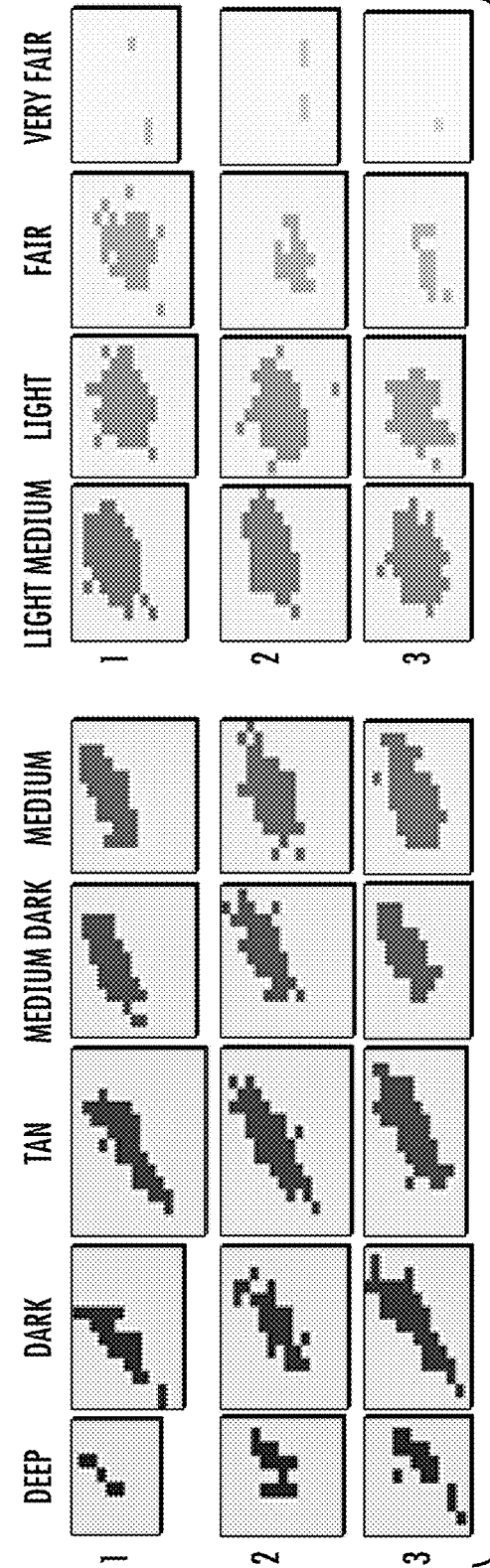
FIG. 13A illustrates an example depth table having nine levels of depths and their corresponding value ranges that may be utilized in a method or system for cosmetic product matching and recommendation in one or more embodiments.
FIG. 13B illustrates example graphical representations of the nine levels of depths illustrated in FIG. 13A in one or more embodiments.

FIG. 13A illustrates an example depth table having nine levels of depths and their corresponding value ranges that may be utilized in a method or system for cosmetic product matching and recommendation in one or more embodiments. As described above, various techniques described herein capture skin tones with at least three characteristics-depth (lightness or L* values), undertone (modeled by the a*b*-plane or the a* and b* values in the CIELAB color space or the c and h values in the CIELch color space), and saturation (e.g., brilliance modeled by the a*b*-plane or the a* and b* values or modeled by chroma or c value, where a more saturated color is represented by a point far away from the lightness axis, and a less saturated color is closer to the lightness axis). In some embodiments, the depth information may be represented by the lightness value (or L* value), the undertone may be represented by the a*b*-plane in the LAB color space, and the saturation may also be represented by the a*b*-plane (e.g., a* (green-red) and b* values (blue-yellow)) in the CIELAB color space or the c values (relative saturation or chroma) in the CIELch color space. In contrast, the current state of the art approaches at best capture depth and undertone, but not saturation, and thus under represent skin tones among people.

In some embodiments, the depth may be modeled with nine levels; undertone may be modeled with three levels each having seven (7) sublevels; and hue may be modeled by various techniques described herein with seven levels. These levels and sublevels for undertone and hue will be described below in greater details. FIG. 13A illustrates some example nine levels for the depth information or data.

More specifically, FIG. 13A illustrates that the depth of skin tones may be partitioned or divided into nine segments. These nine segments may range from the darkest "deep" (segment 1) to the lightest "very fair" (segment 9) with seven additional segments-"dark" (segment 2), "tan" (segment 3), "medium dark" (segment 4), "medium" (segment 5), "medium" (segment 5), "light medium" (segment 6), "light" (segment 7), and "fair" (segment 8)—ranging from darker depth to lighter depth. It shall be noted that these embodiments illustrated in FIG. 13A partition the depth of skin tones into nine segments although other embodiments may partition the depth of skin tones into more or fewer than nine segments. Further, FIG. 13A illustrates some example ranges of the lightness values (L values). For example, L values smaller than 27 may be categorized as deep; L values smaller than 34.5 and greater than or equal to 27 may be categorized as dark; etc.

The following equation may be used to determine depth in, for example, a store digital application or a mobile color IQ app:

TABLE C

```
1Segment = ceiling (
( lValue - lOffset ) / lSegmentSize
)
if ( lSegment < 1 ) {
lSegment = 1
} else if ( lSegment > lSegmentsMax ) {
lSegment = lSegmentsMax
}
The following example is the application of the above equation to an example Lch values of
(60.28, 31.14, 61.25)
lSegment = ceiling (
(60.28 - 19.25) / 7 5
)
lSegment = 6
if ( 6 < 1 ) {
lSegment = 1
} else if ( 6 < 9 ) {
lSegment = 9
} lSegment = 6
In some embodiments, a depth level may be further divided or partitioned into a plurality of
sublevels by using the example equation below:
If ( lValue < lOffset) {
1SubSegment = 1
} else if (lValue > lOffset + ( lSegmentSize * lSegmentsMax ) ) {
1SubSegment = lSegmentSize / 1SubSegmentSize
} else {
1SubSegment = ceiling ( 1SubSegment = ceiling ( (lValue - (lOffset + (lSegment -1) *
lSegmentSize ) ) / 1SubSegmentSize
)
}
```

FIG. 13B illustrates example graphical representations of the nine levels of depths illustrated in FIG. 13A in one or more embodiments. It shall be noted that these graphical representations merely schematically show some example depths while the lightness or darkness in these graphical representations may or may not necessarily be accurately or truthfully representing the depths utilized in various embodiments described herein due to computer graphics reproductions.

Figures 13C, 13D:
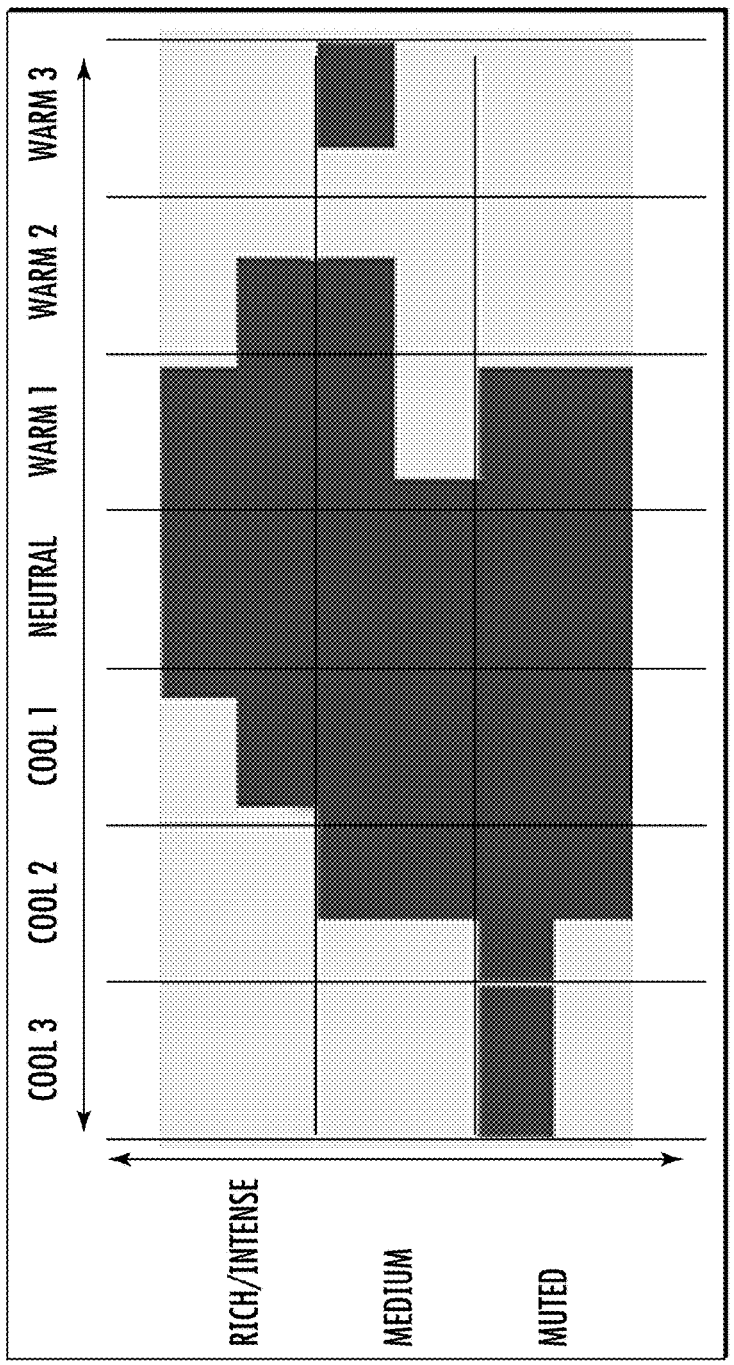
FIG. 13C illustrates an example chroma table having three levels of saturation and their corresponding value ranges and some additional information that may be utilized in a method or system for cosmetic product matching and recommendation in one or more embodiments.
FIG. 13D illustrates some graphical examples showing interactions between hue and saturation in a two-dimensional grid in one or more embodiments.

FIG. 13C illustrates an example chroma table having three levels of saturation and their corresponding value ranges and some additional information that may be utilized in a method or system for cosmetic product matching and recommendation in one or more embodiments. As described above, chroma relates to saturation that may be modeled by three levels using the a*b*-plane or the a* and b* values in the CIELAB color space or using the chroma or c value in the CIELch color space that is similar to CIELAB but in polar coordinates, where a more saturated color is represented by a point far away from the lightness (L) axis, and a less saturated color is closer to the lightness (L) axis. It shall be noted that due to the adoption of the LAB or Lch color space, red is considered cooler while yellow is considered warmer.

In these example three levels, chroma c value smaller than 18 may be categorized as low saturation or muted; chroma c value greater than or equal to 18 and smaller than 30 may be categorized as medium saturation or medium; and chroma c value greater than or equal to 30 may be categorized as high saturation, rich, or intense. One or more of these three levels may be further divided into a plurality of sublevels (e.g., seven sublevels). It shall be noted that although FIG. 13C illustrates three levels and describes seven sublevels, other embodiments may use different numbers of levels and/or different numbers of sublevels for a level.

TABLE D

```
The following formulae may be used to determine saturation
based on the c value.
cSegment = ceiling
( cValue - cOffset[ ]Group] ) / cSegmentSize[1Group]
)
if ( cSegment < 1 ) {
cSegment = 1
} else if ( cSegment > cSegmentsMax ) {
cSegment = cSegmentsMax
}
```

FIG. 13D illustrates some graphical examples showing interactions between hue and saturation in a two-dimensional grid in one or more embodiments. In these embodiments illustrated in FIG. 13D, the saturation is divided into three levels-muted, medium, rich/intense from less saturated to more saturated. Further, FIG. 13D illustrates that each of the three levels is further divided into seven sublevels-cool 3, cool 2, cool 1, neutral, warm 1, warm 2, and warm 3. The subdivision of a level into a plurality of sublevels (N) may be uniformly performed where each sublevel corresponds to approximately 1/N of the c value range in some embodiments. In some other embodiments, the subdivision may be performed for a level to partition the level into non-uniform sublevels.

FIG. 13E illustrates an example hue table that may be utilized in a method or system for cosmetic product matching and recommendation in one or more embodiments. As described above, hue relates to color may be modeled by various techniques described herein with three levels each also having seven (7) sublevels.

For example, hue may be modeled by various techniques described herein with seven levels. These seven levels in the example hue table illustrated in FIG. 13F include "high pink" corresponding to H values (e.g., H values in the CIELch color space) smaller than 44; "medium pink" corresponding to H values greater than or equal to 44 and smaller than 49; "low pink" corresponding to H values greater than or equal to 49 and smaller than 54; "neutral" corresponding to H values greater than or equal to 54 and smaller than 59; "low yellow" corresponding to H values greater than or equal to 59 and smaller than 64; "medium yellow" corresponding to H values greater than or equal to 64 and smaller than 69; and "high yellow" corresponding to H values smaller than 69. For purpose of skin tones, red is considered cooler, and yellow is considered warmer with respect to hue.

In some embodiments, hue relates to color, and color temperature may be determined based on hue according to the table below:

TABLE E

```
hSegment = ceiling (
( hValue – hOffset[ ]Group] ) / hSegmentSize[1Group]
)
if ( hSegment < 1) { hSegment = 1
} else if ( hSegment > hSegmentsMax ) { hSegment = hSegmentsMax
}
```

FIG. 13F illustrates an example hue table that may be utilized in a method or system for cosmetic product matching and recommendation in one or more embodiments. As described above, undertone may be modeled with three levels each having seven (7) sublevels using, for example, the a* and b* values in the CIELAB color space. Undertone may be modeled with three levels shown as "cSegment 1," "cSegment 2," and "cSegment 3" (intensity 1, intensity 2, and intensity 3). Each of the three levels may be further partitioned into seven sublevels show as "hSegment" from 1 through 7 (cool 3, cool 2, cool 1, neutral, warm 1, warm 2, and warm 3). FIG. 13F further illustrates the English identifier and French identifier for each sublevel.

In these embodiments illustrated in FIG. 13F, a correct undertone value may be determined using the aforementioned cSegment and hSegment variables using the following.

TABLE F

```
cSegment = ceiling
( cValue – cOffset[1Group] ) / cSegmentSize[1Group]
)
if ( cSegment < 1 ) {
cSegment = 1
} else if ( cSegment > cSegmentsMax ) {
cSegment = cSegmentsMax
}
hSegment = ceiling (
( hValue – hOffset[1Group] ) / hSegmentSize[1Group]
)
if ( hSegment < 1) { hSegment = 1
} else if ( hSegment > hSegmentsMax ) { hSegment = hSegmentsMax
}
```

FIGS. 13G-13H illustrate three example undertone table that may be jointly utilized in a method or system for cosmetic product matching and recommendation in one or more other embodiments. In these embodiments, undertone is modeled with three levels corresponding to the "cSegment" values of 1, 2, and 3. Each level may be further partitioned into seven sublevels corresponding to the "hSegment" values of 1 through 7. FIGS. 13G-H further illustrate the English identifier for each sublevel. In some embodiments, the method or system described herein first determine which undertone table of the three undertone tables 1302G, 1304G, and 1306G is to be used. Once the undertone table is determined, the method or system further use the cSegment and hSegment to determine the correct row in the undertone table for the correct under tone value. In one embodiment, the correct undertone value may be determined by using the following.

TABLE G

```
1Group = 1SegmentGrouping(1Segment)
cSegment = ceiling
( cValue – cOffset[1Group] ) / cSegmentSize[1Group]
)
if ( cSegment < 1 ) {
cSegment = 1
} else if ( cSegment > cSegmentsMax ) {
cSegment = cSegmentsMax
}
hSegment = ceiling (
( hValue – hOffset[1Group] ) / hSegmentSize[1Group]
)
if ( hSegment < 1) { hSegment = 1
} else if ( hSegment > hSegmentsMax ) { hSegment = hSegmentsMax
}
```

Figure 14A:
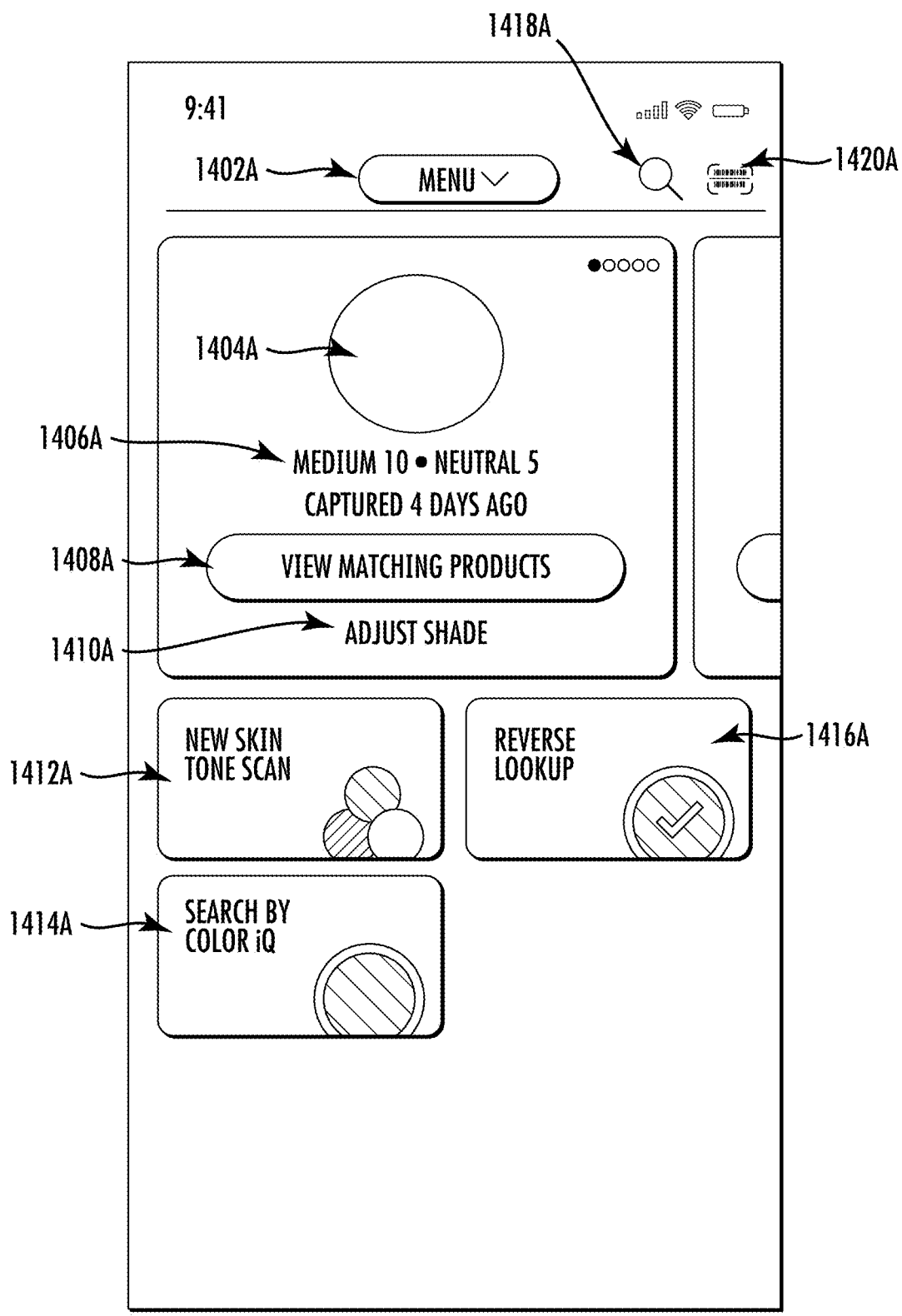
FIG. 14A illustrates an example home screen of a mobile color IQ app that may be installed on a mobile computing device in one or more embodiments.
Figure 14B:
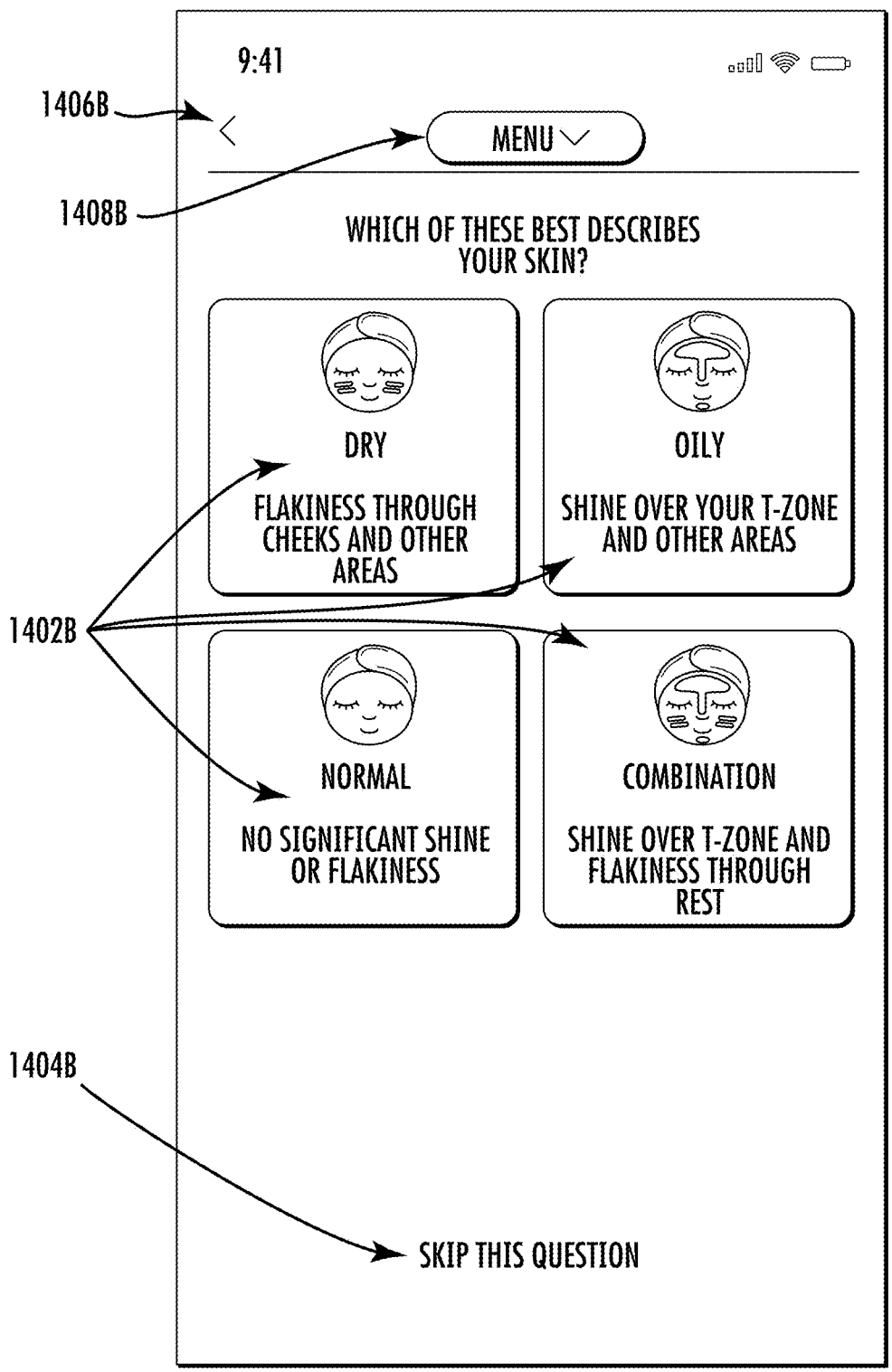
FIG. 14B illustrates an example user interface for a client interview process to collect various pieces of data or information that may be utilized in subsequent product matching and recommendation service or services in one or more embodiments.
Figure 14C:
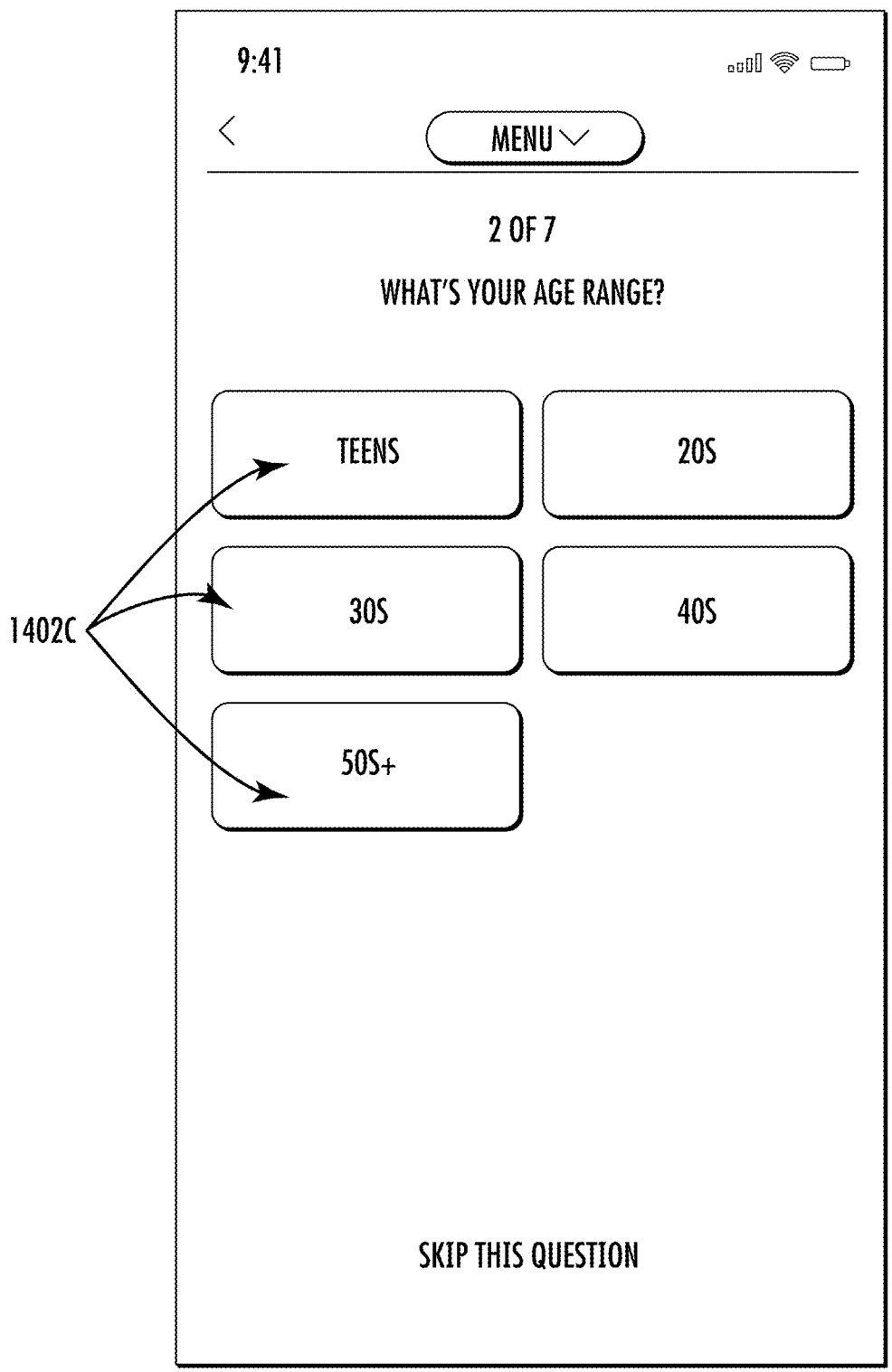
FIG. 14C illustrates an example user interface for a client interview process to collect various pieces of data or information that may be utilized in subsequent product matching and recommendation service in one or more embodiments.
Figure 14D:
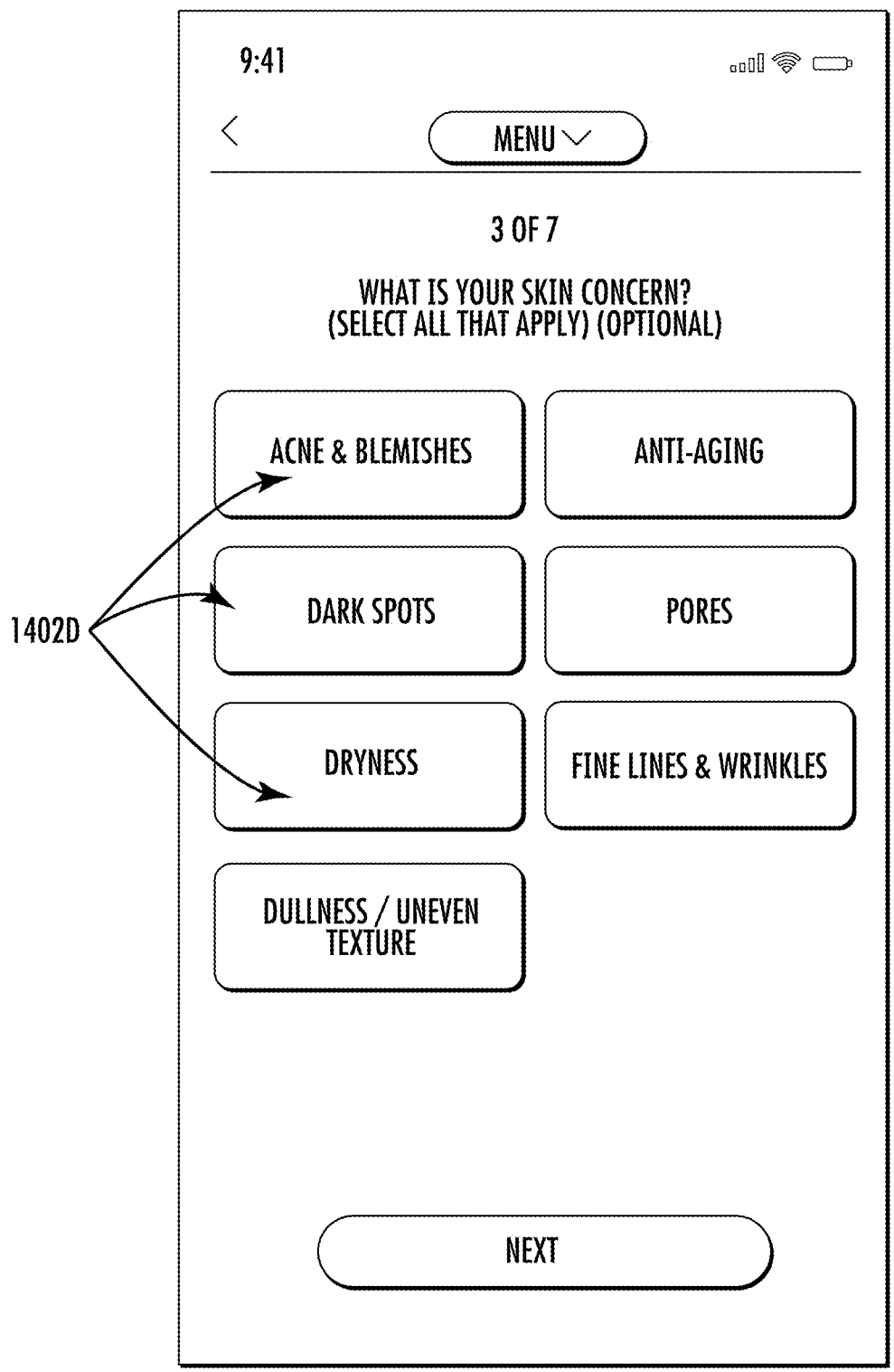
FIG. 14D illustrates an example user interface for a client interview process to collect various pieces of data or information that may be utilized in subsequent product matching and recommendation service or services in one or more embodiments.
Figure 14E:
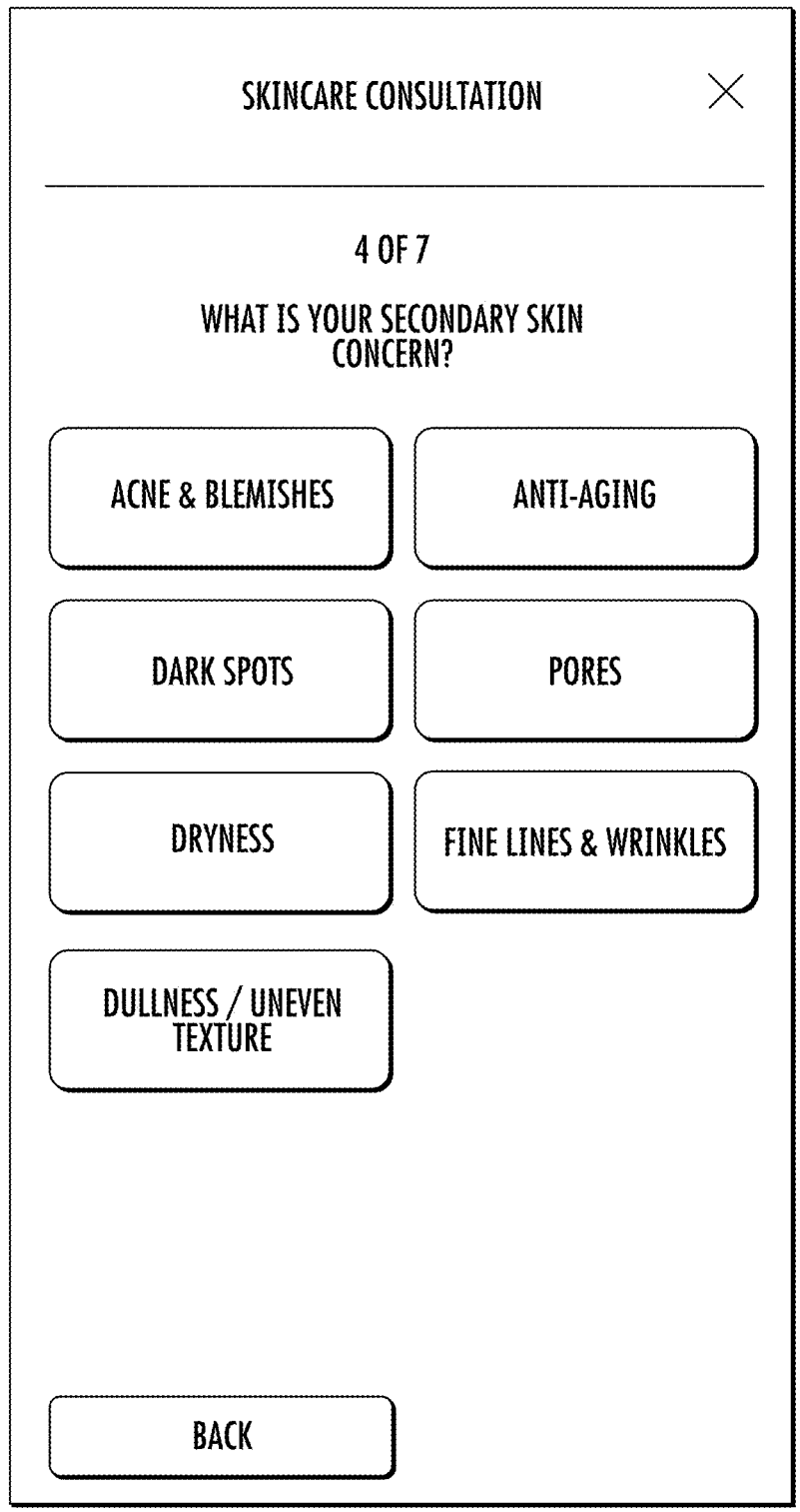
FIG. 14E illustrates an example user interface for a client interview process to collect various pieces of data or information that may be utilized in subsequent product matching and recommendation service or services in one or more embodiments.
Figure 14F:
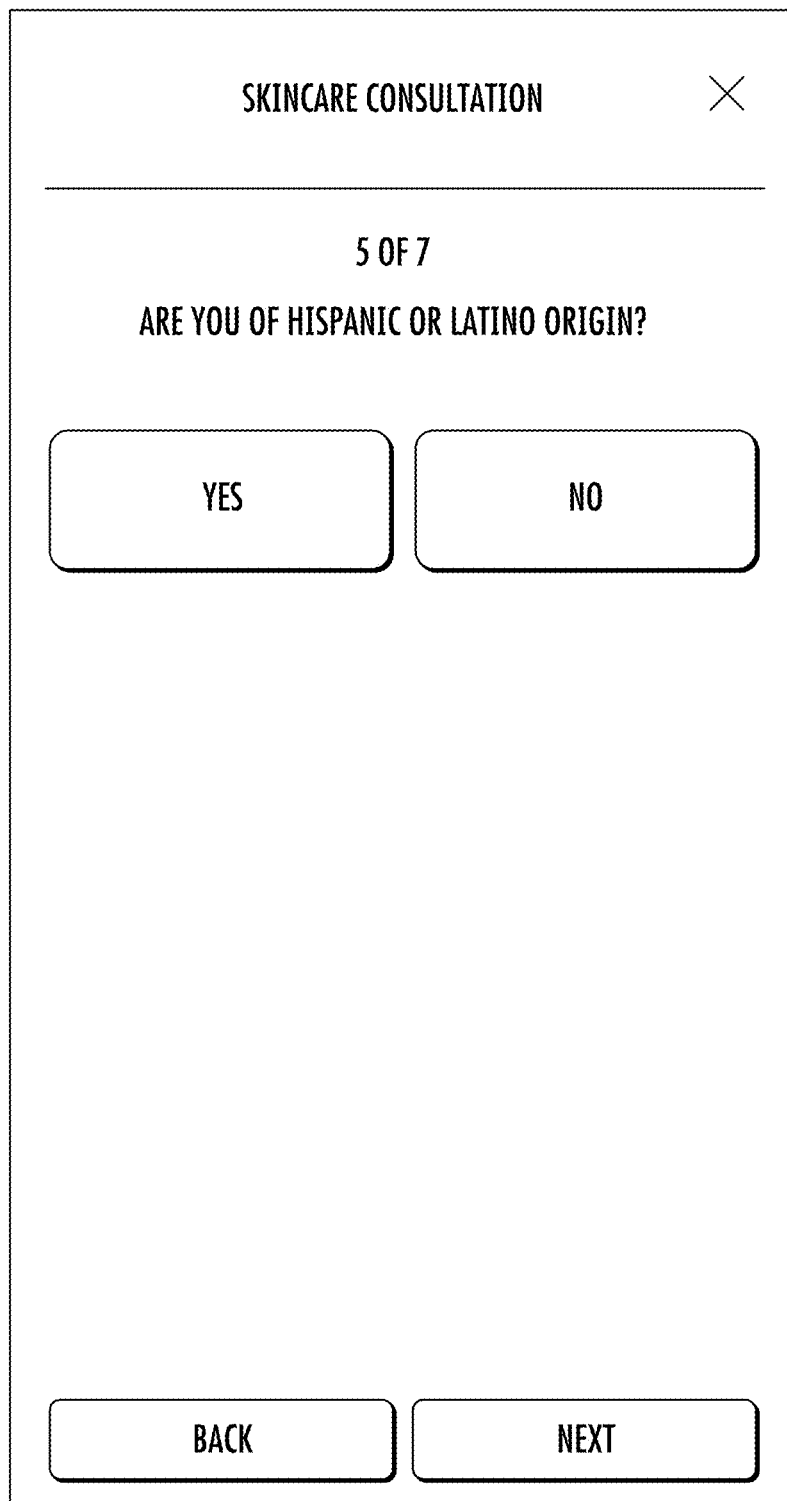
FIG. 14F illustrates an example user interface for a client interview process to collect various pieces of data or information that may be utilized in subsequent product matching and recommendation service or services in one or more embodiments.
Figure 14I:
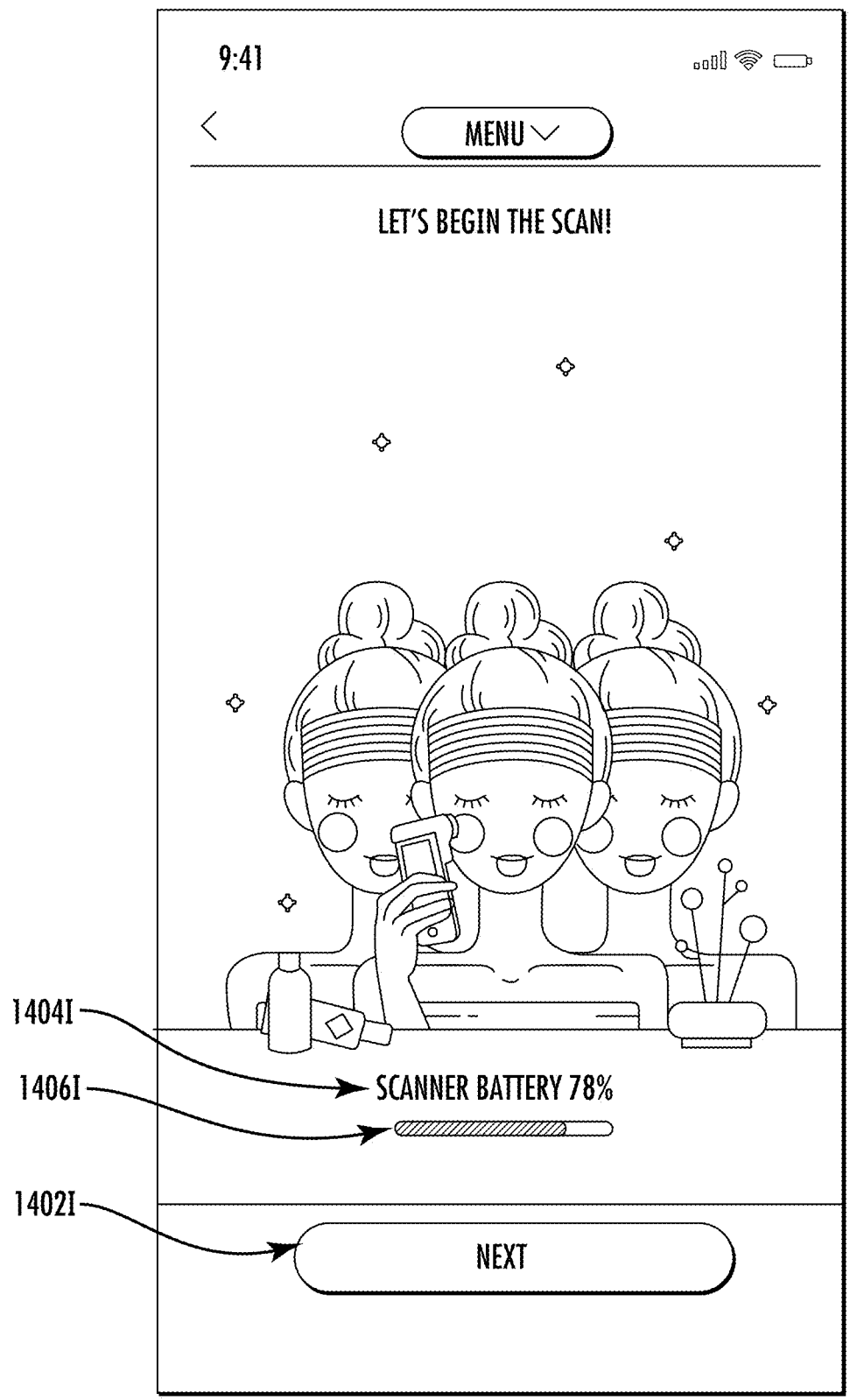
FIG. 14I illustrates an example user interface for preparing for a skin scan session to obtain scan results for subsequent product matching and recommendation service or services in one or more embodiments.
Figure 14J:
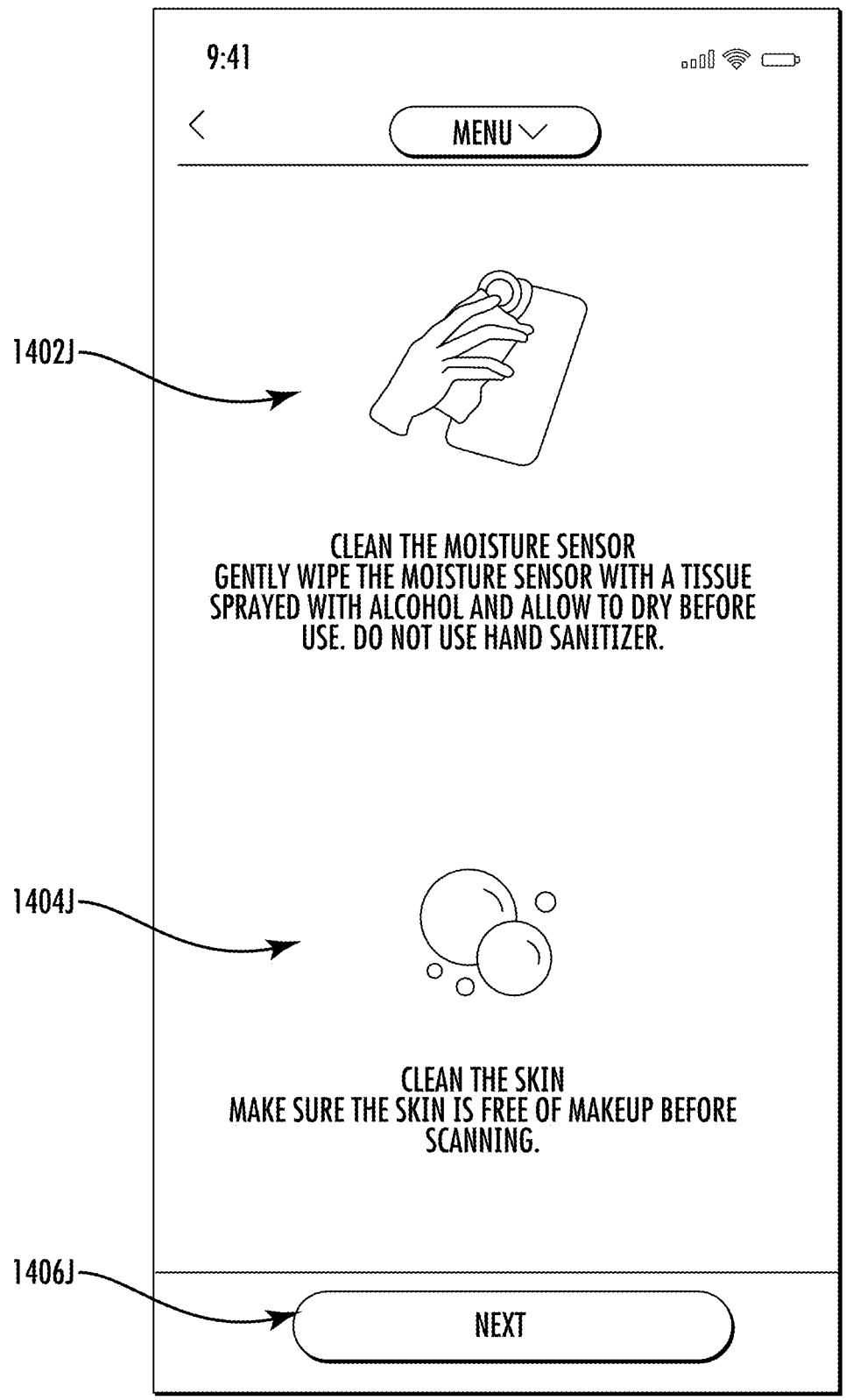
FIG. 14J illustrates an example user interface showing instructions for beginning a skin scan for a particular area of a client's skin in one or more embodiments.
Figure 14K:
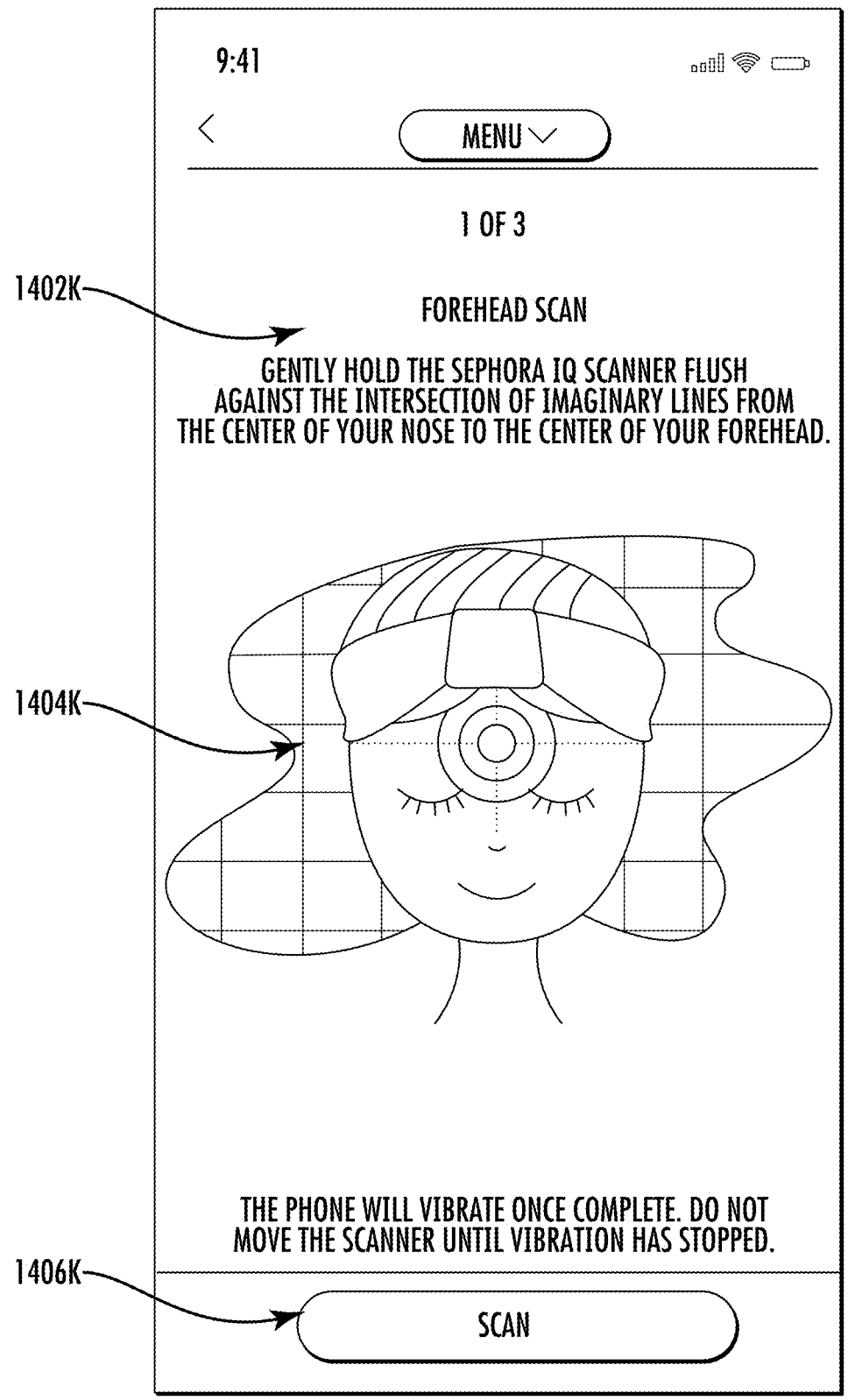
FIG. 14K illustrates an example user interface showing some skin scan results in one or more embodiments.
Figure 14M:
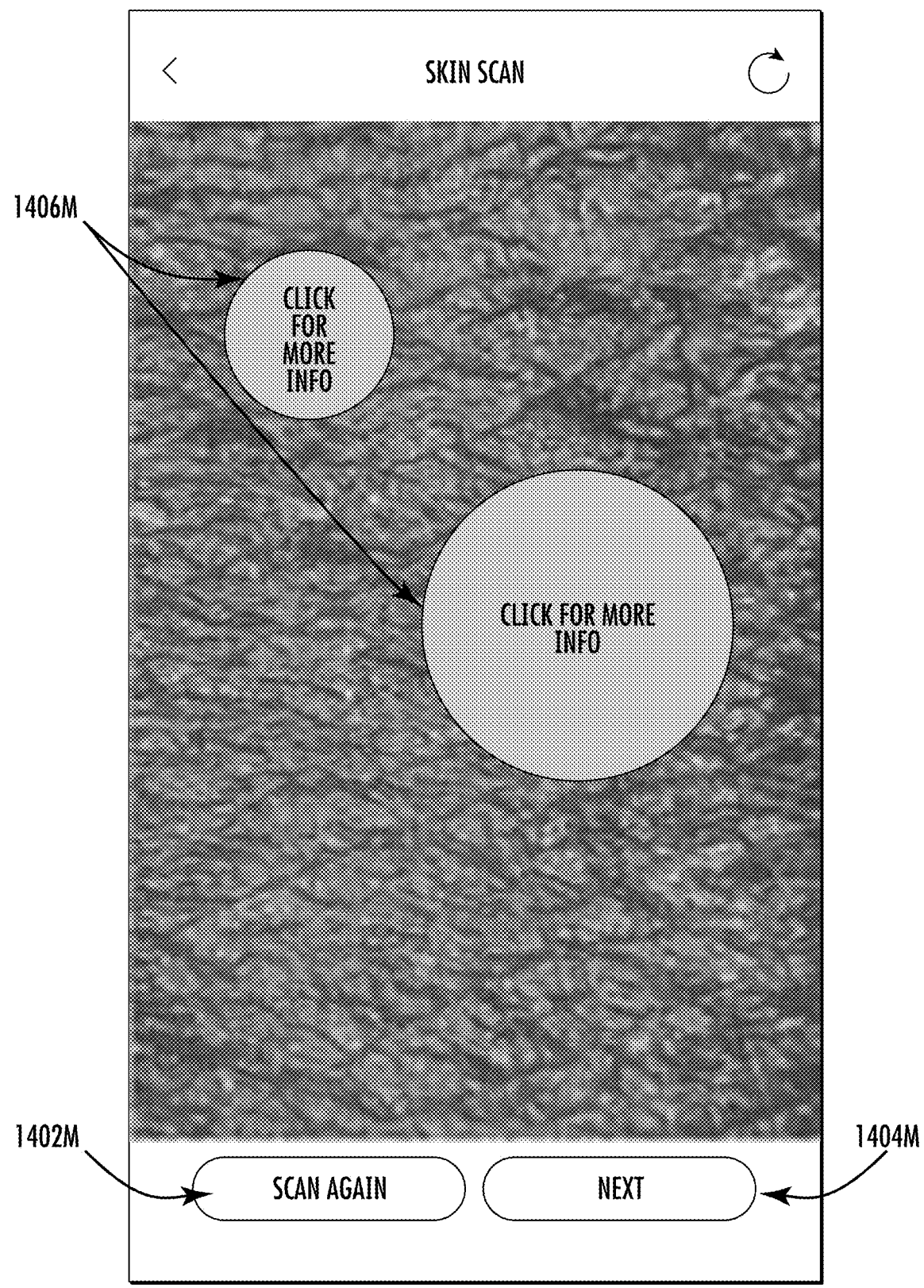
FIG. 14M illustrates an example scan image in one or more embodiments.
Figure 14N:
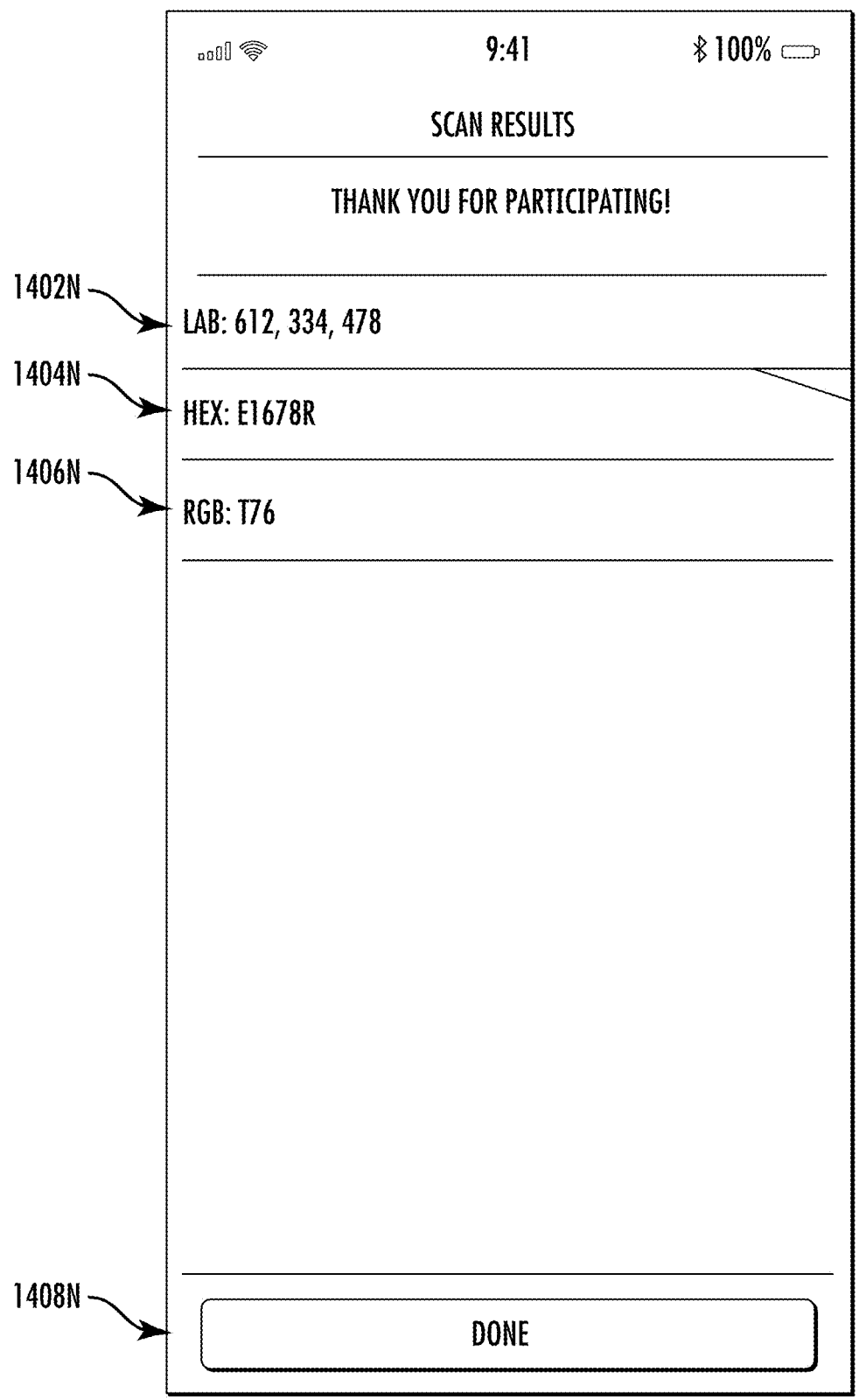
FIG. 14N illustrates example scan results in one or more embodiments.
Figure 140:
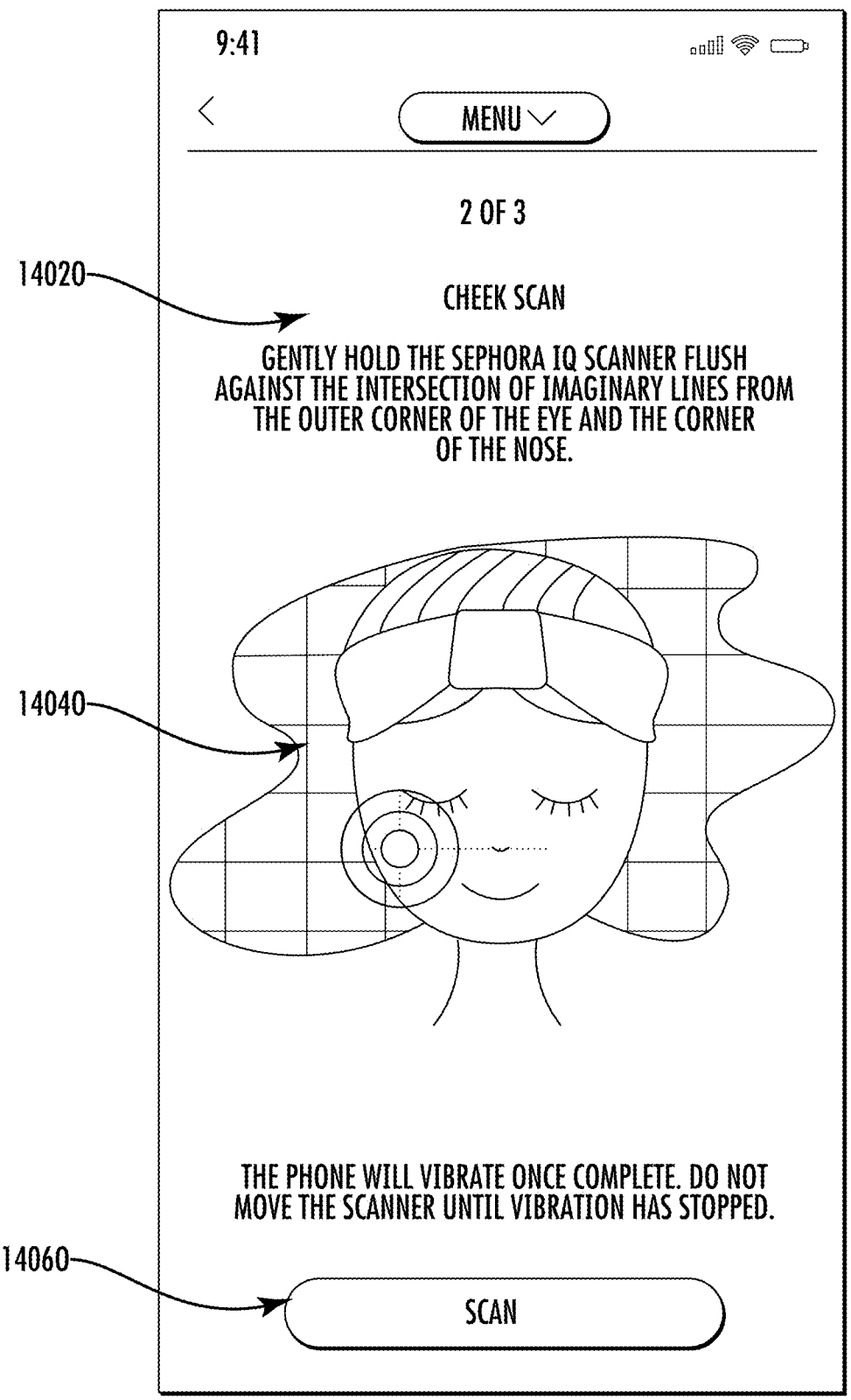
Figure 14P:
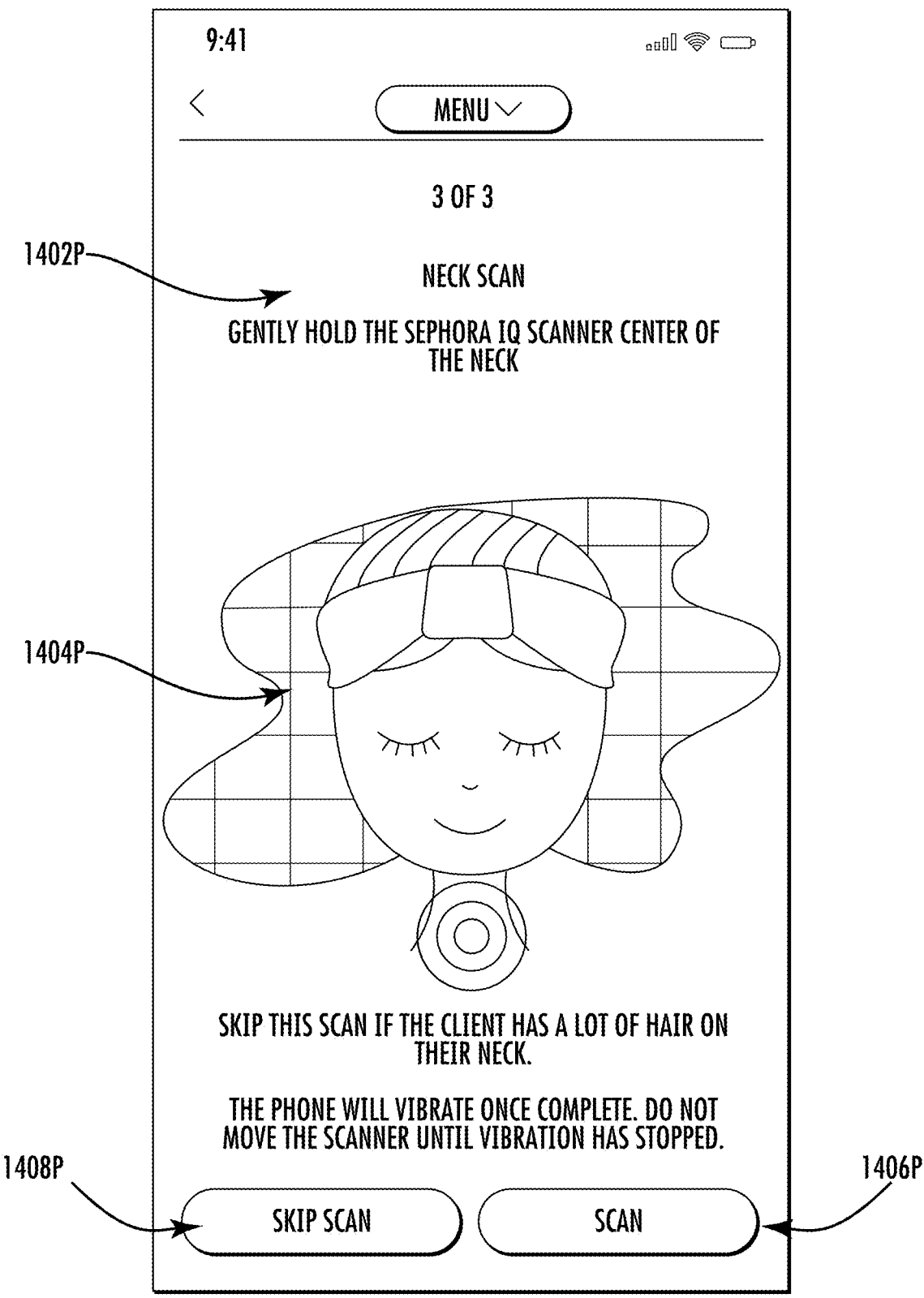
FIG. 14P illustrates an example user interface screen that includes textual and/or graphical information and/or instructions to guide a client to more correctly place a scanning device for a second particular area of a client's skin and/or how to perform the scan for the second particular area with a scanning device for the selected skin scan in one or more embodiments.
Figure 14Q:
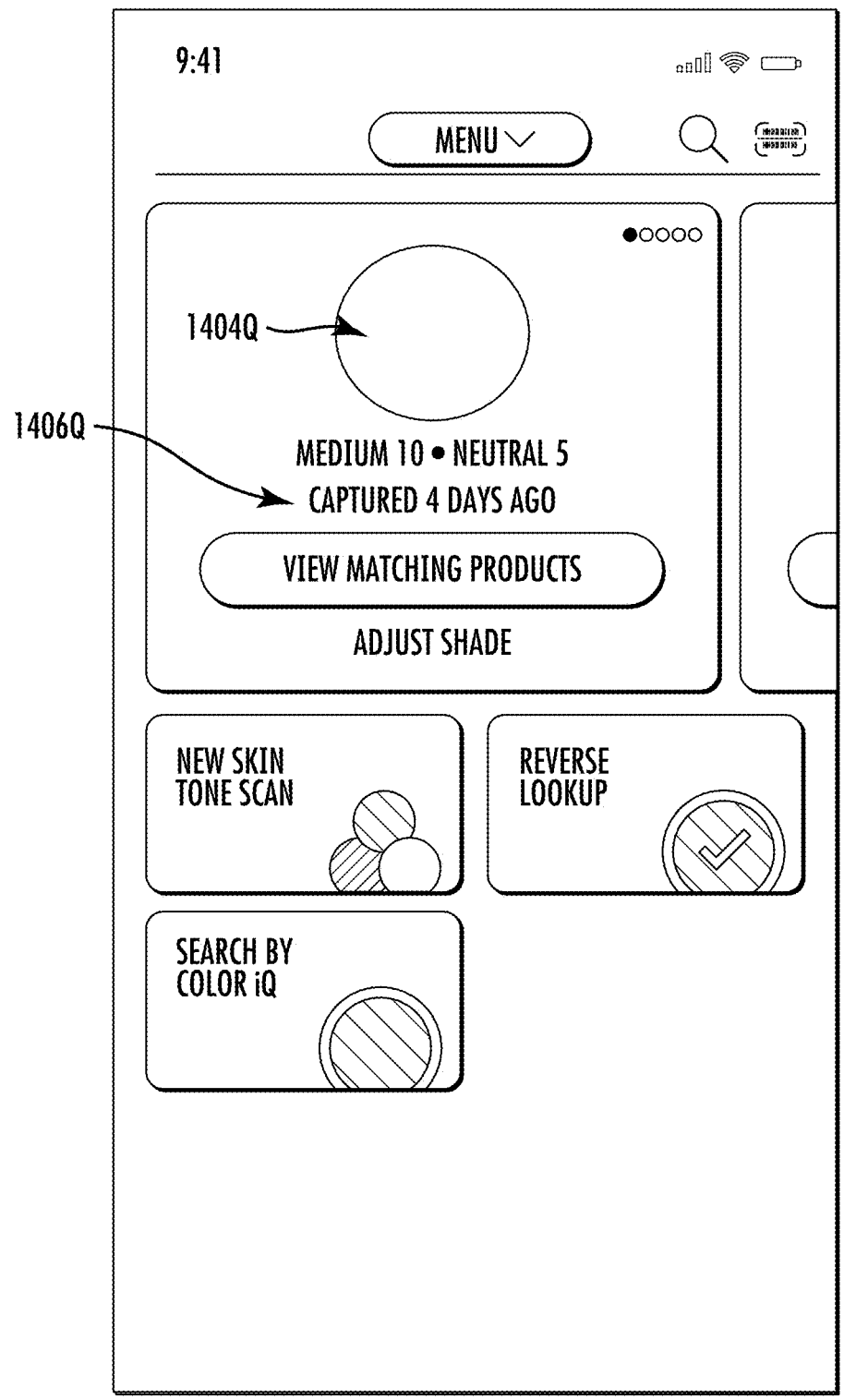
FIG. 14Q illustrates a screen of an example user interface when a client clicks on an interactable widget in FIG. 14N to finish the current skin scan session.
Figure 14R:
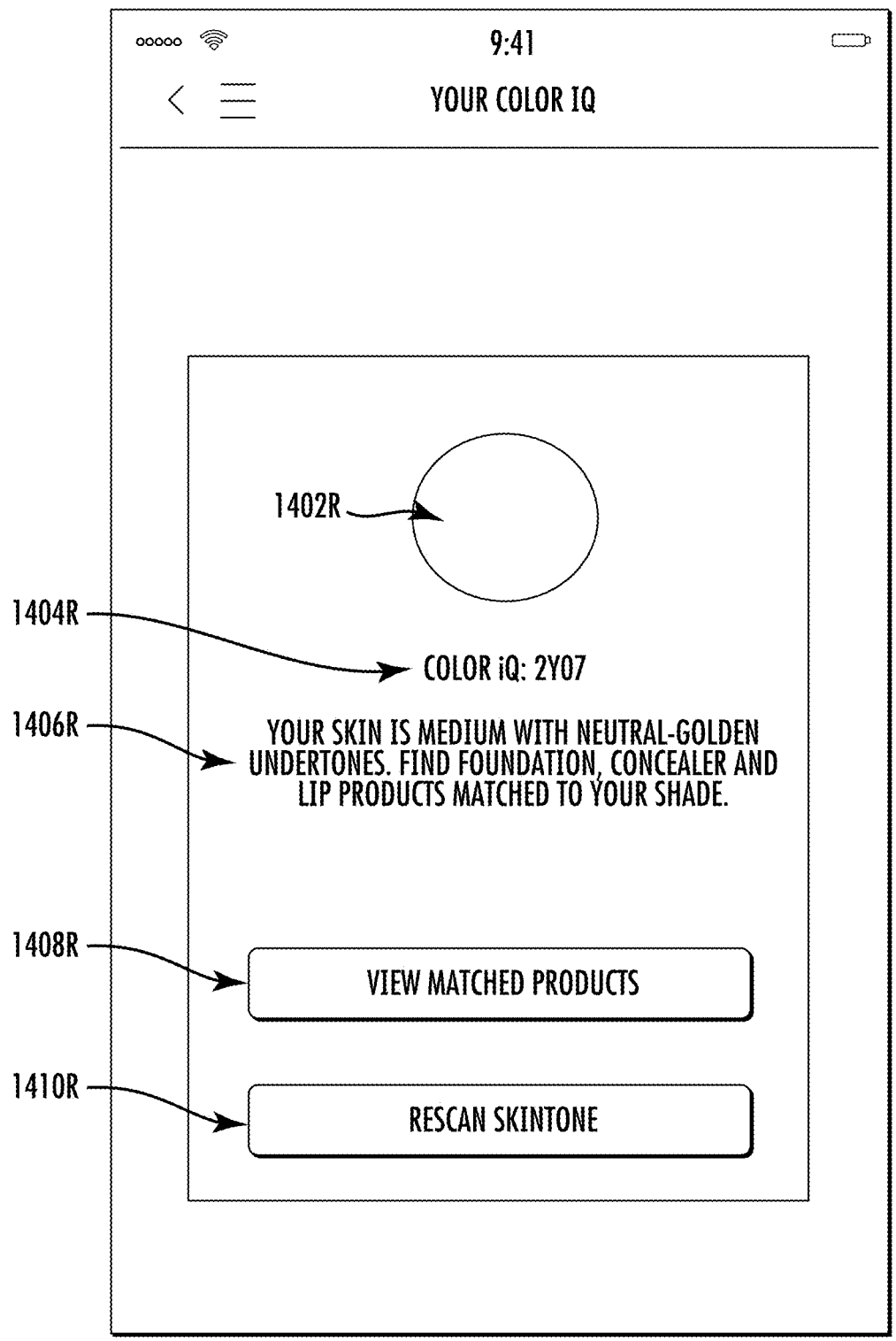
FIG. 14R illustrates another scan result screen showing scan results of a skin tone scan session for a client in one or more embodiments.
Figure 14S:
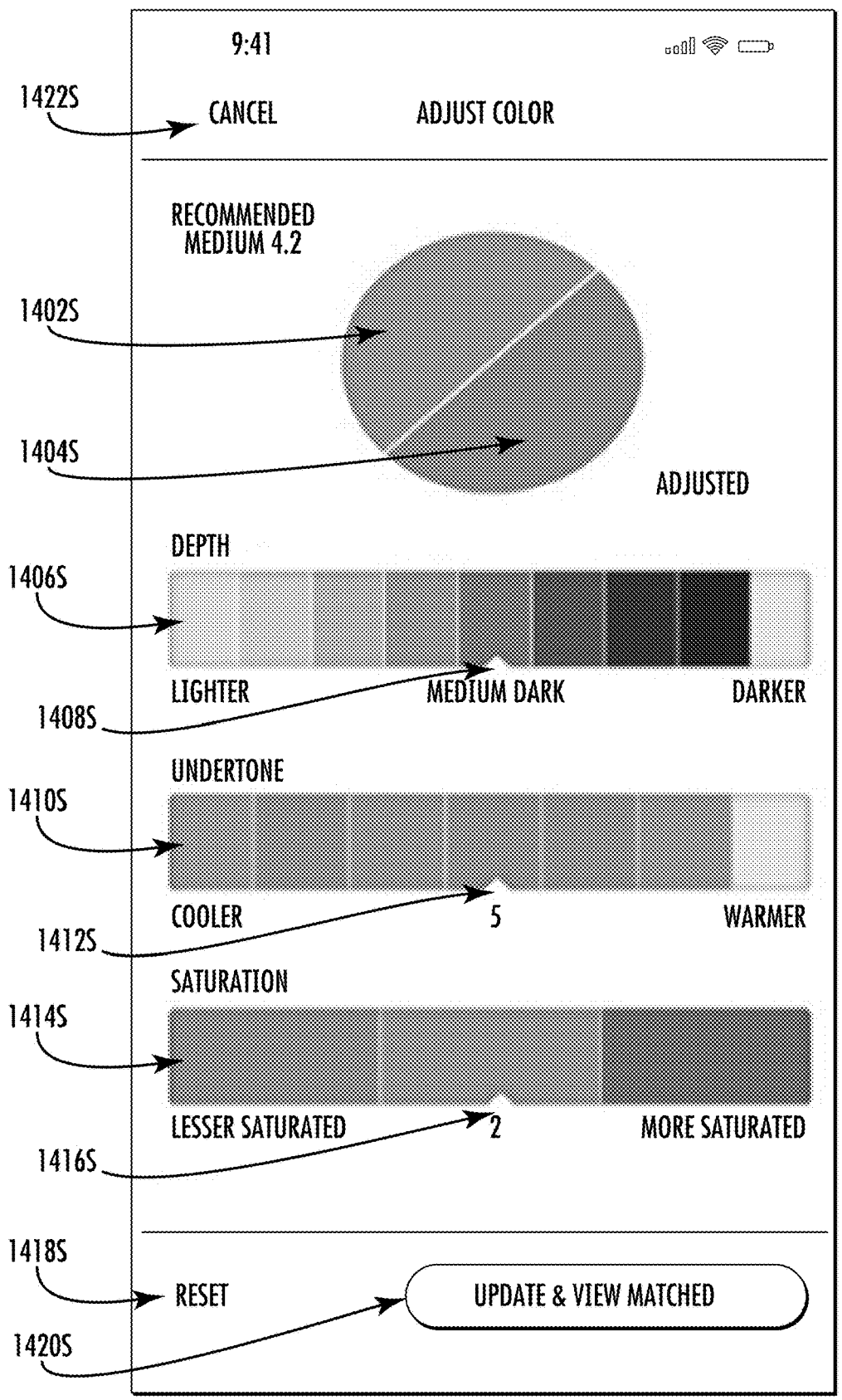
FIG. 14S illustrates an example user interface for adjusting skin tone color attributes of a color index or value in one or more embodiments.
Figure 14T:
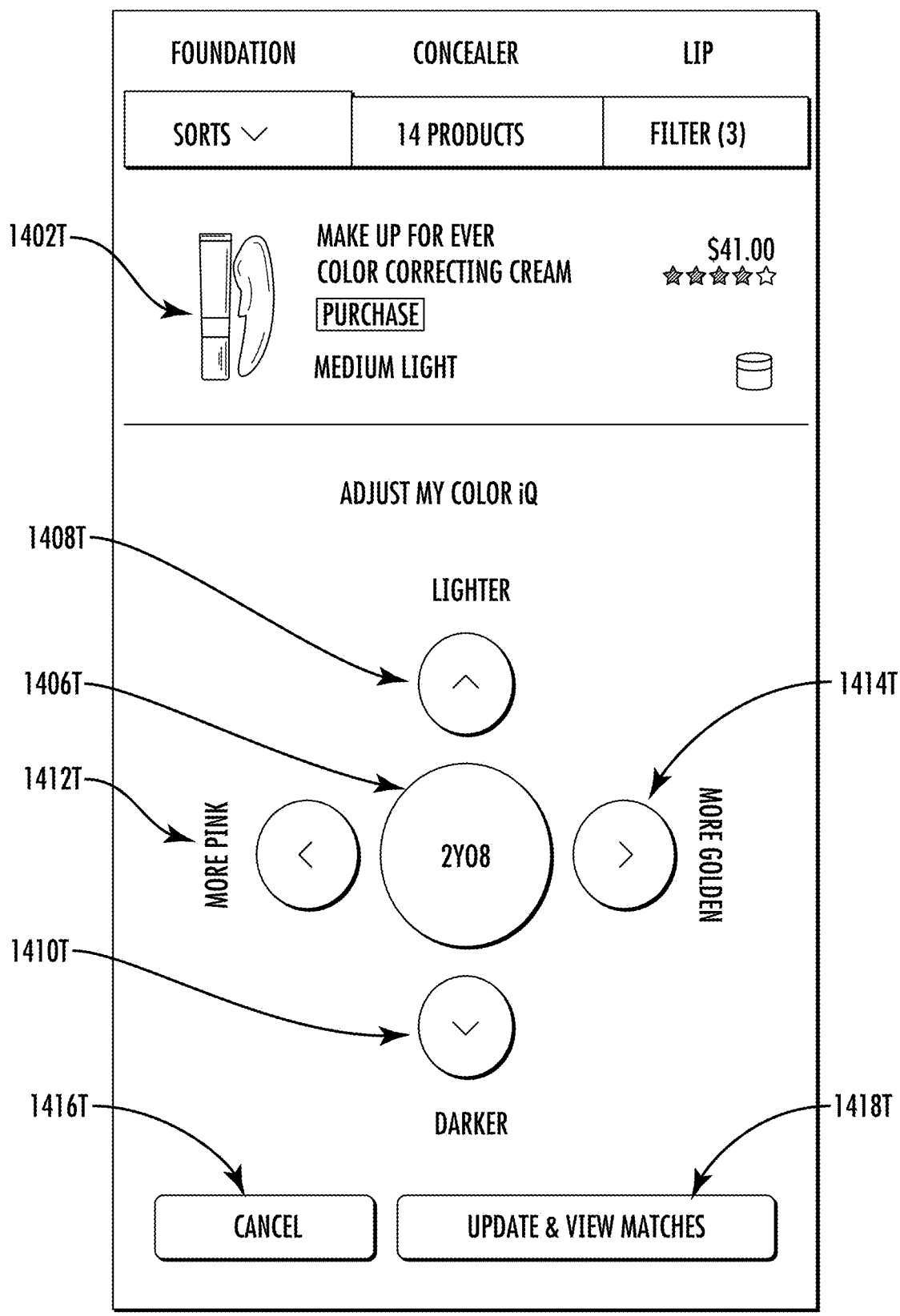
FIG. 14T illustrates another example user interface screen in one or more embodiments.
Figure 14U:
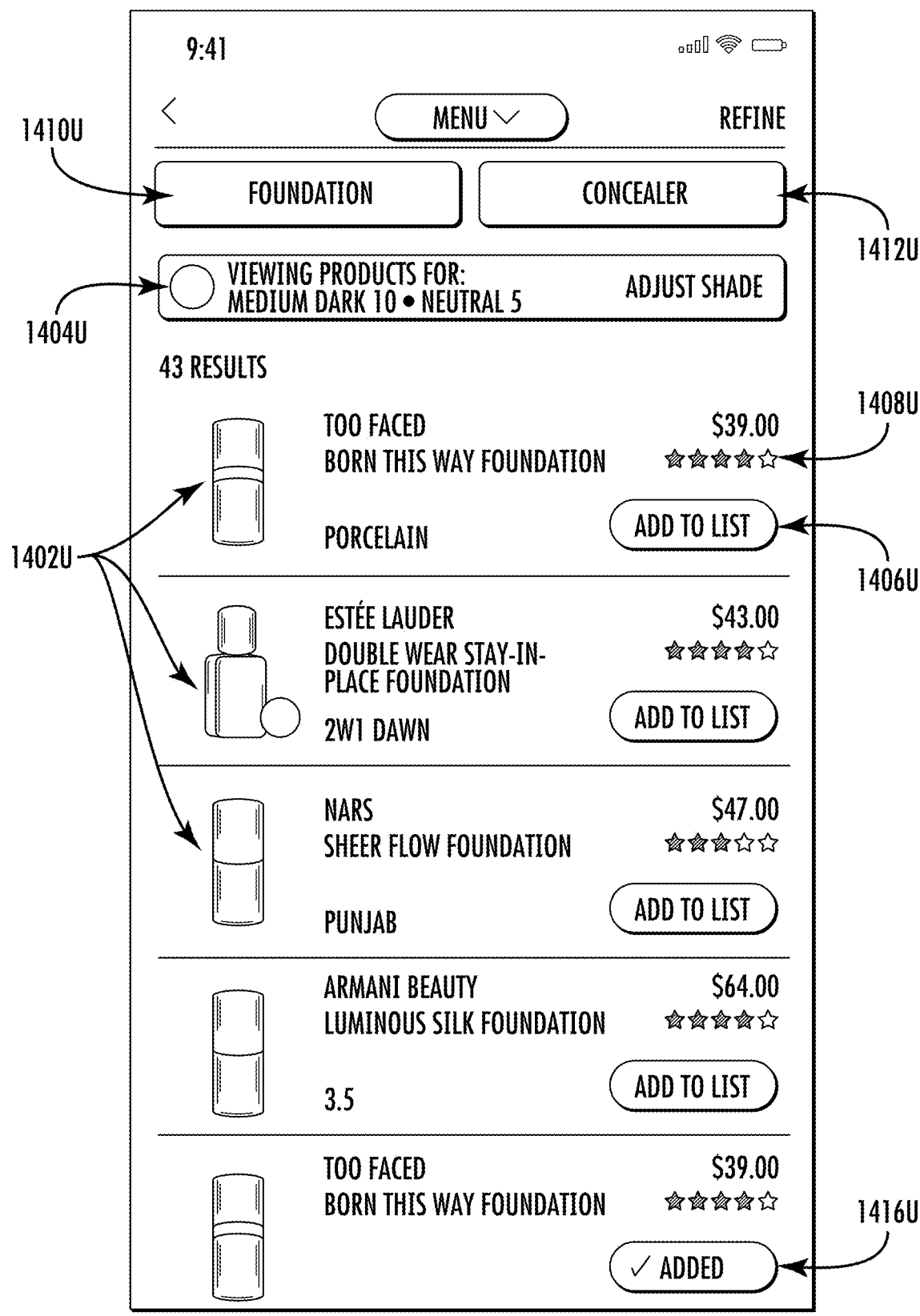
FIG. 14U illustrates an example user interface screen showing a list of predicted matching products or a list of personalized, recommended products in some embodiments.
Figure 14V:
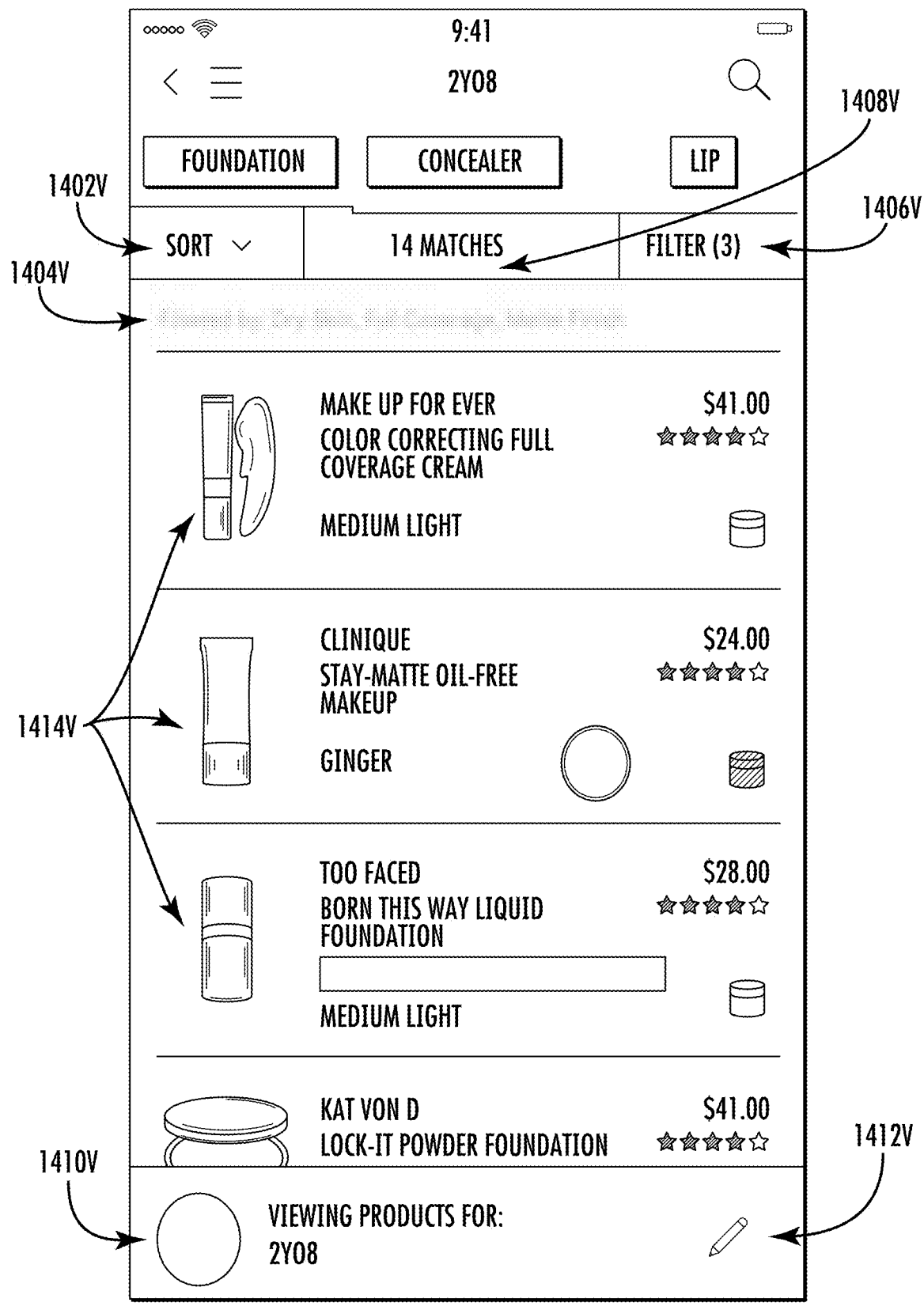
FIG. 14V illustrates another example user interface screen showing more options that may be implemented in an example user interface in one or more embodiments.
Figure 14W:
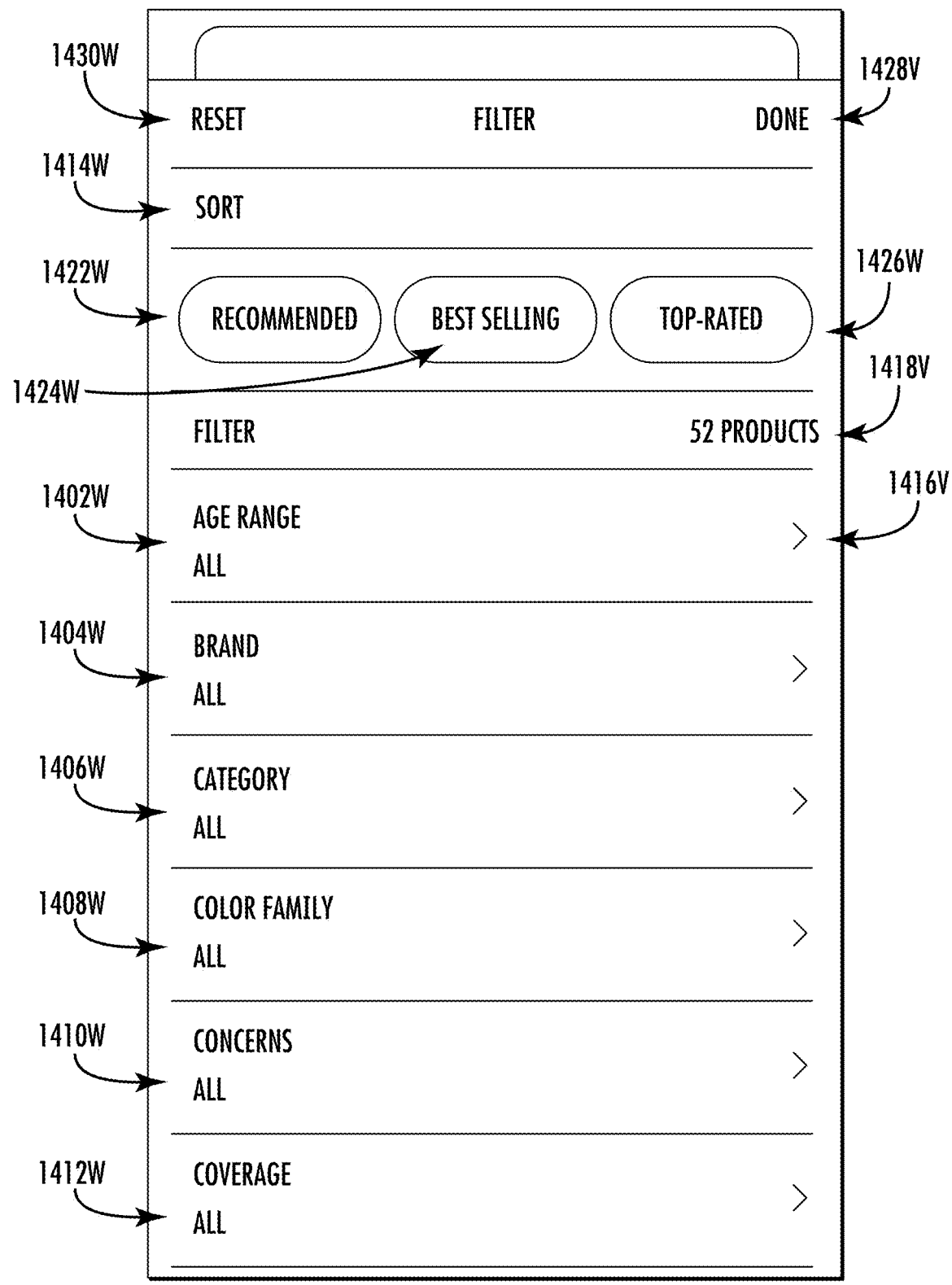
FIG. 14W illustrates another example user interface screen that lists some example filtering criteria in one or more embodiments.
Figure 14X:
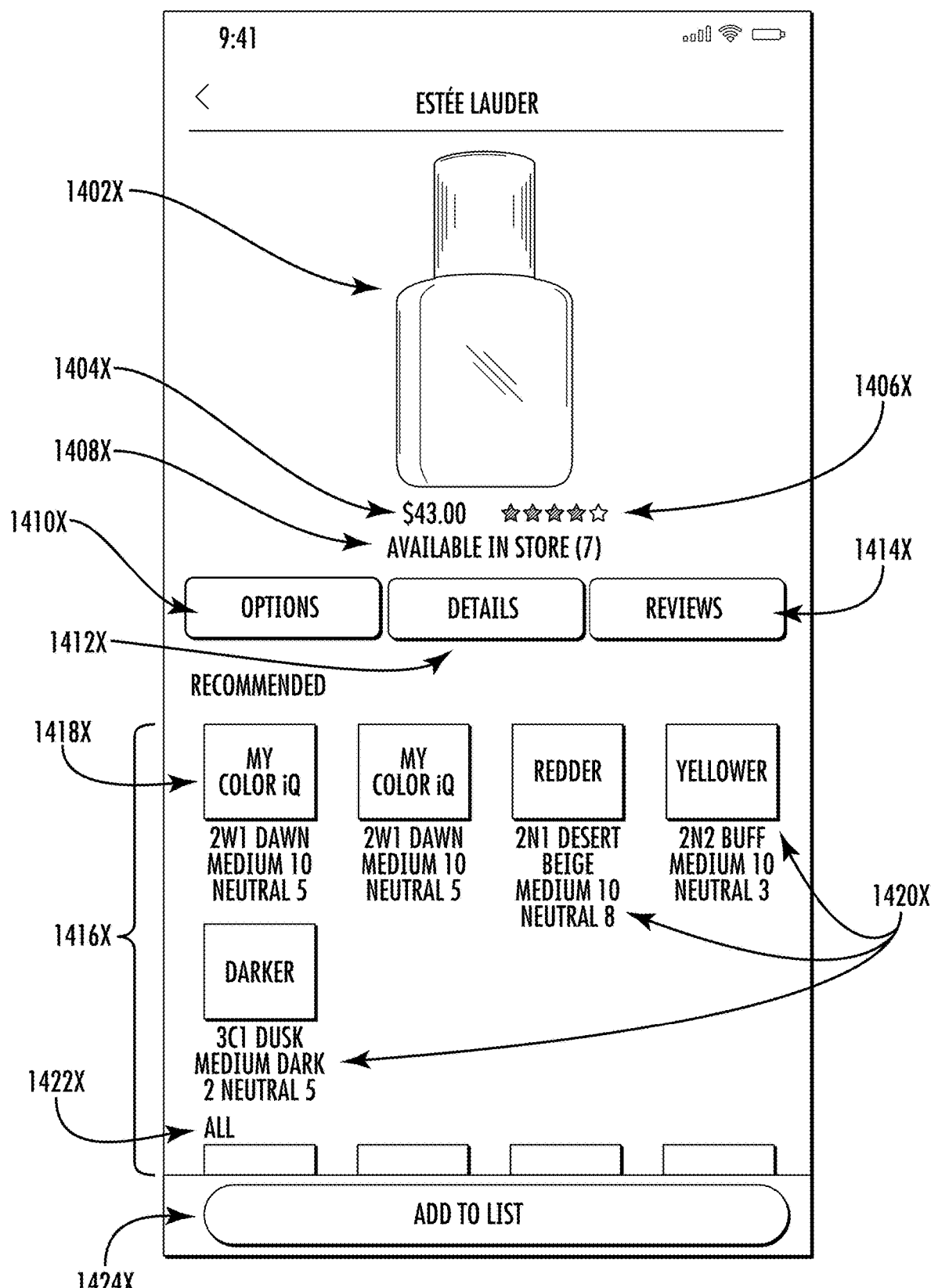
FIG. 14X illustrates an example product detail screen showing detailed information of a cosmetic product such as a predicted matching cosmetic product or a personalized, recommended cosmetic product in one or more embodiments.
Figure 14Y:
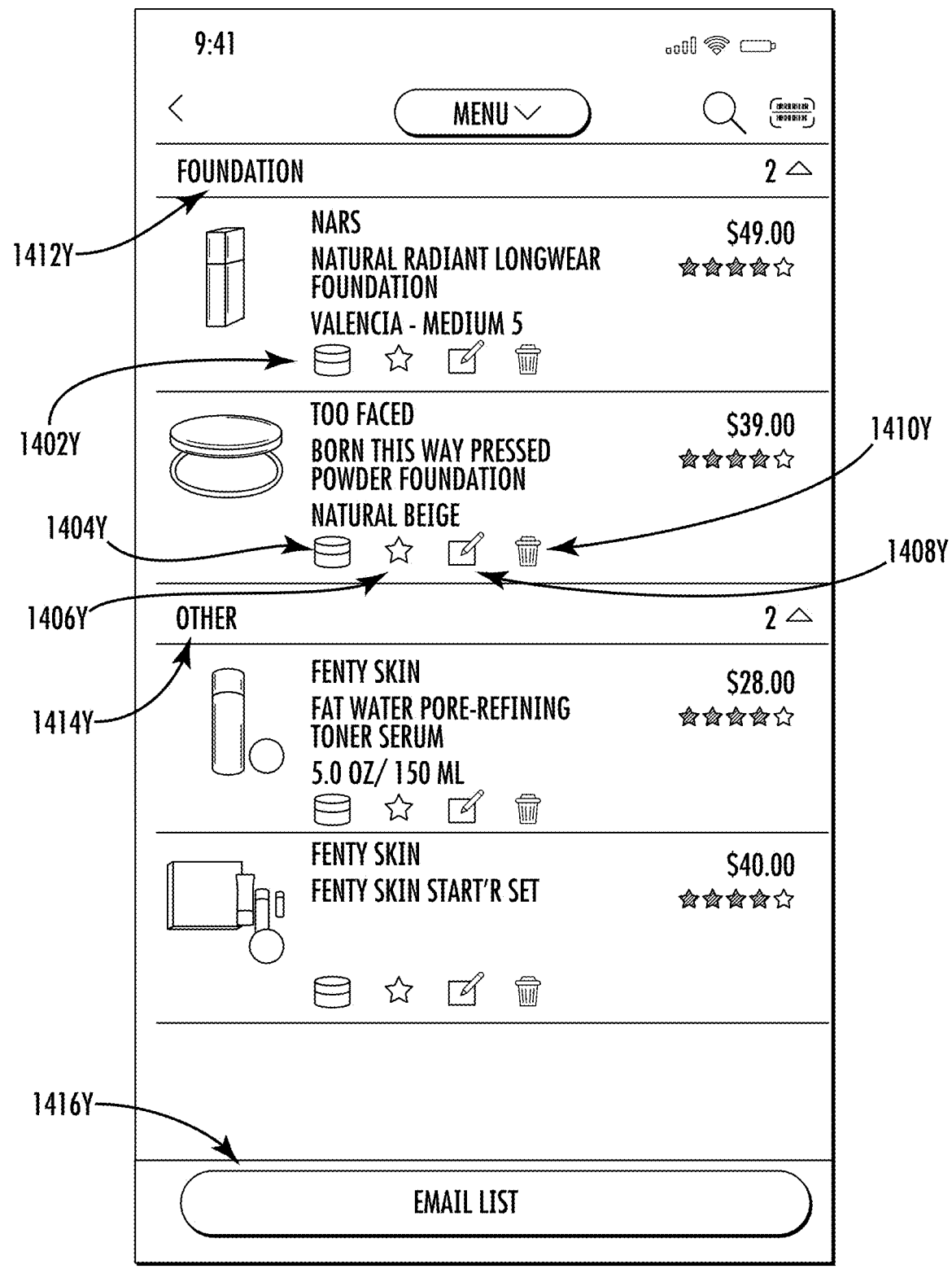
FIG. 14Y illustrates another example user interface screen showing a list of selected cosmetic products in one or more embodiments.
Figure 14Z:
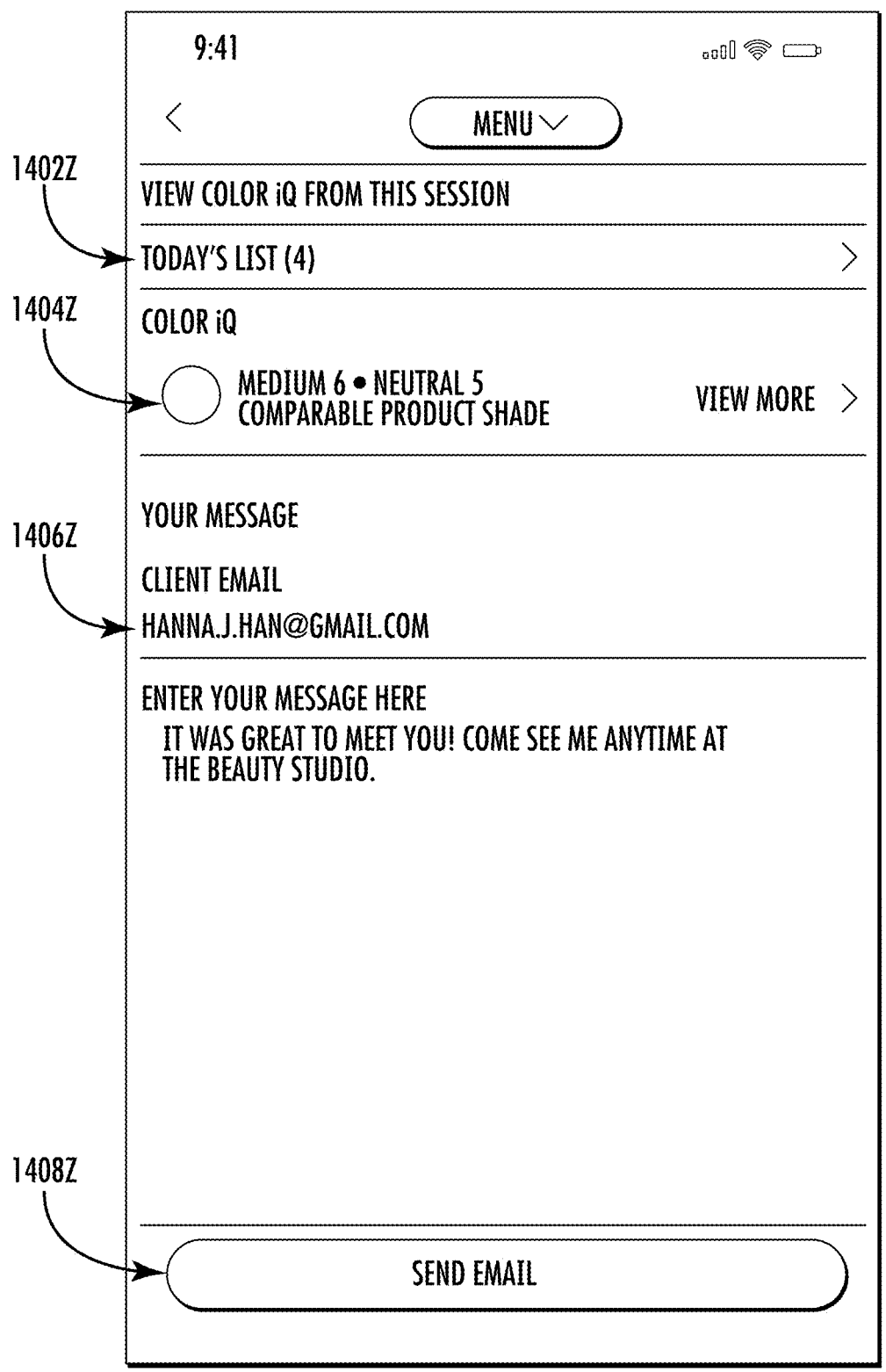
FIG. 14Z illustrates another example user interface screen showing the contents of a communication screen after a client interacted with an interactable widget illustrated in FIG. 14Y in one or more embodiments.
Figure 14A:
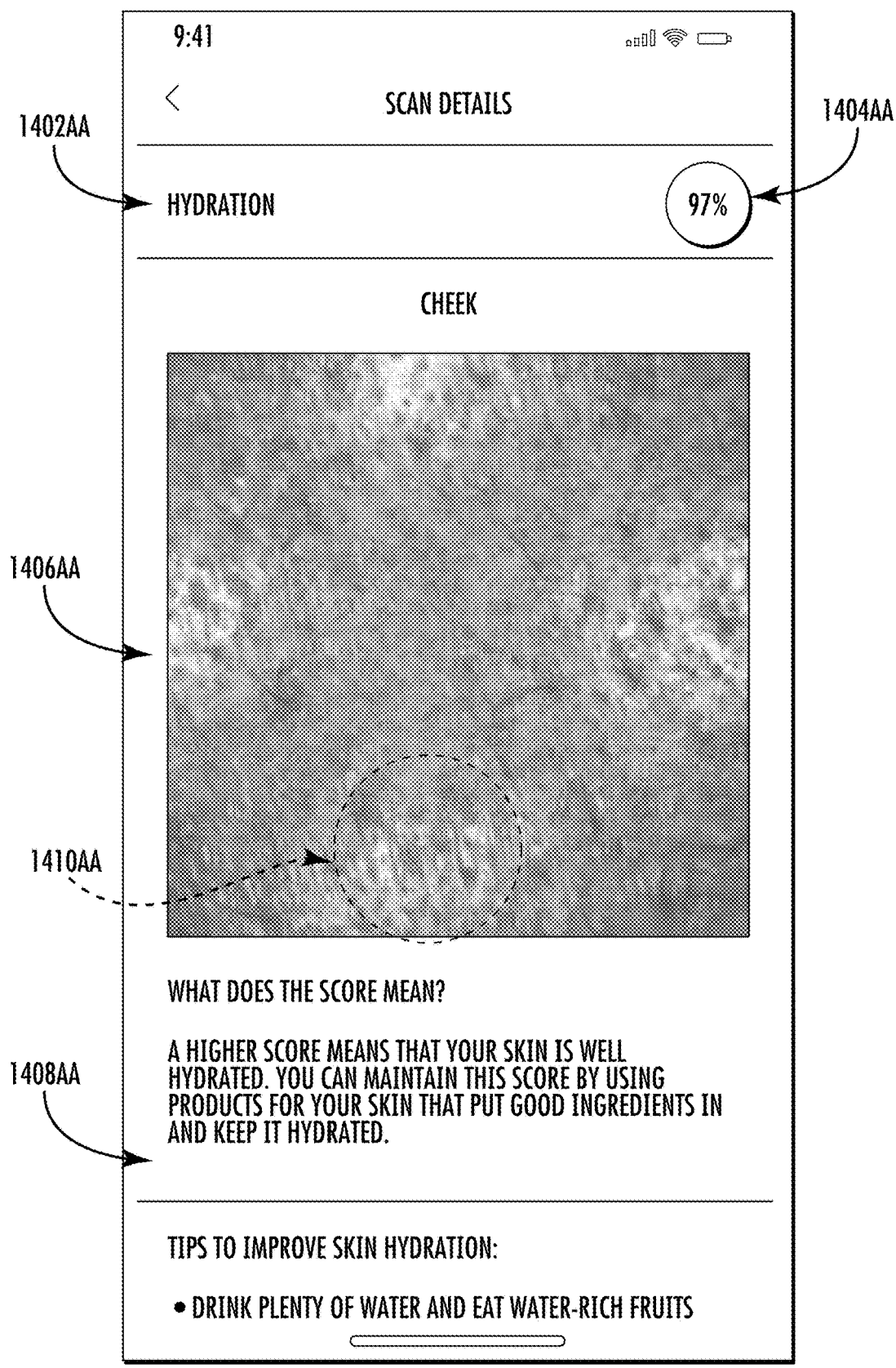
Figure 14A:
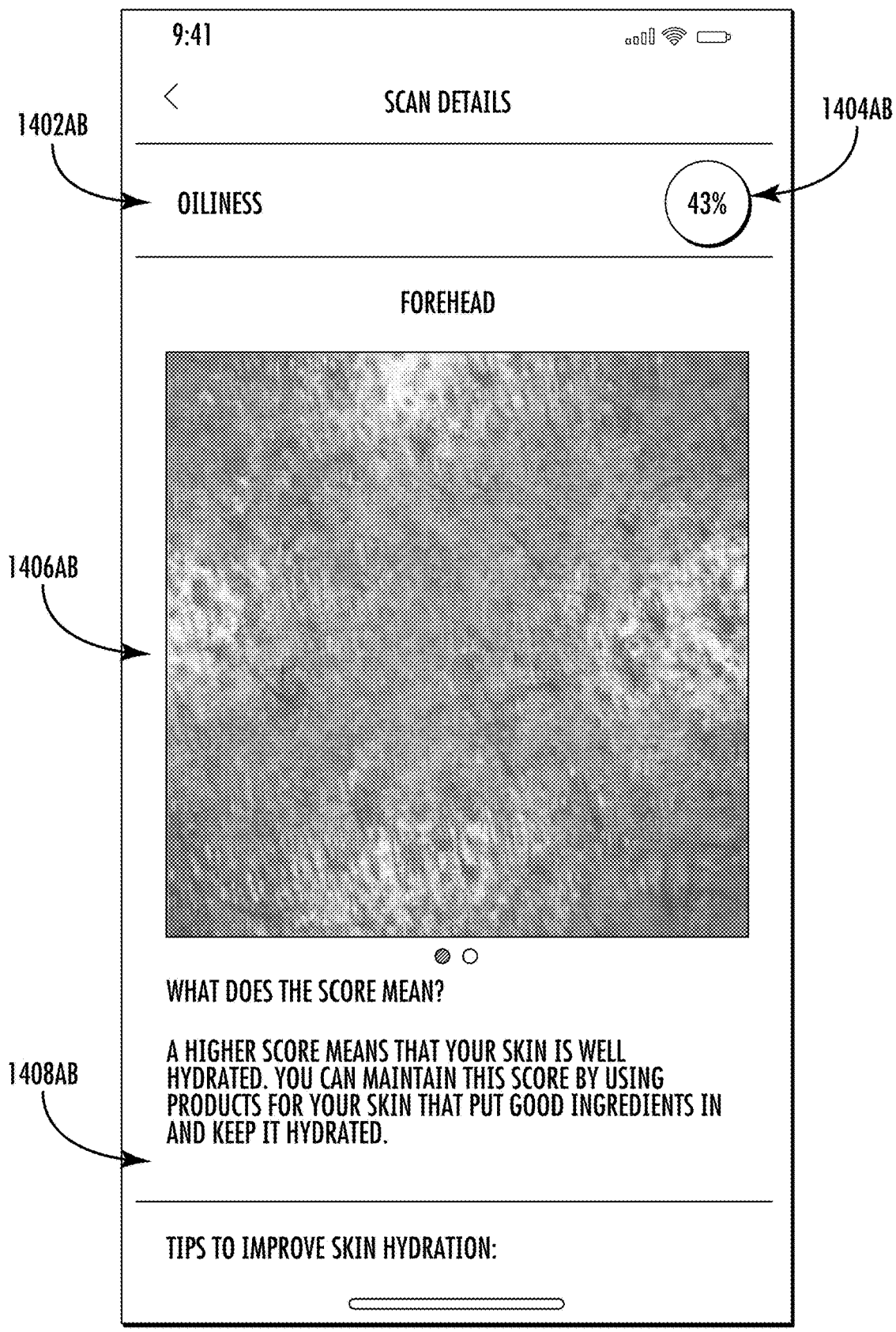
Figure 14A:
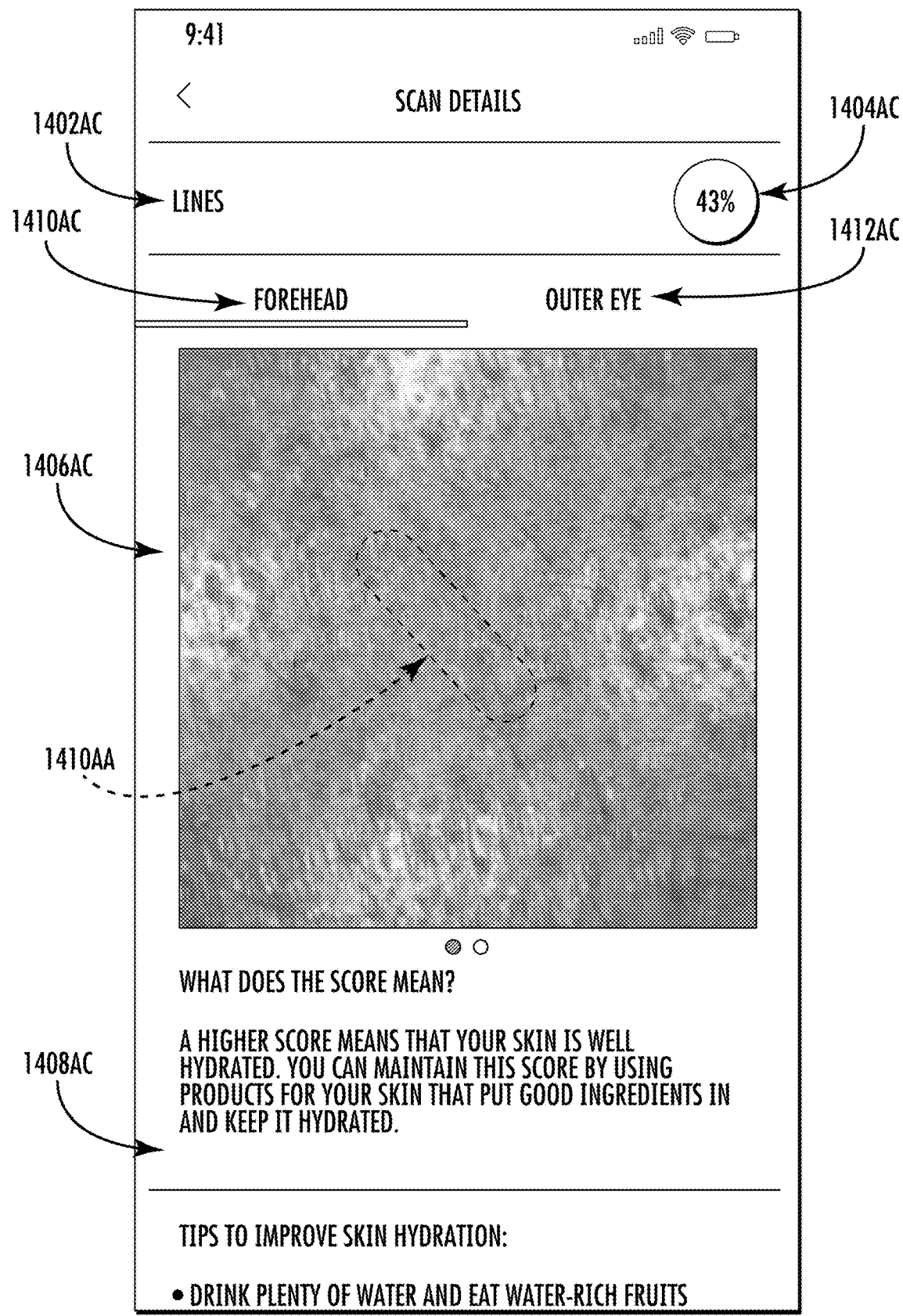
Figure 14A:
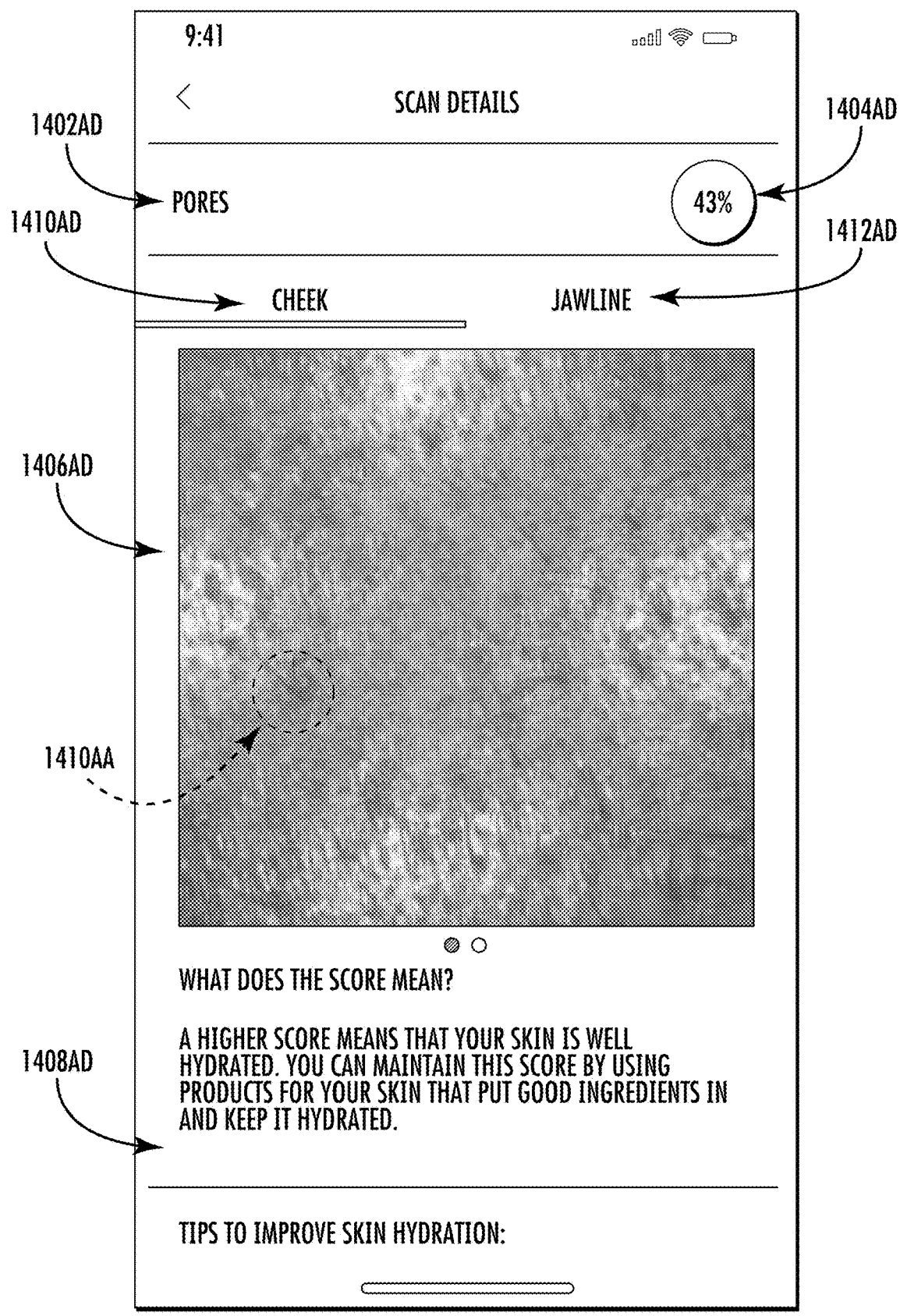
Figure 14A:
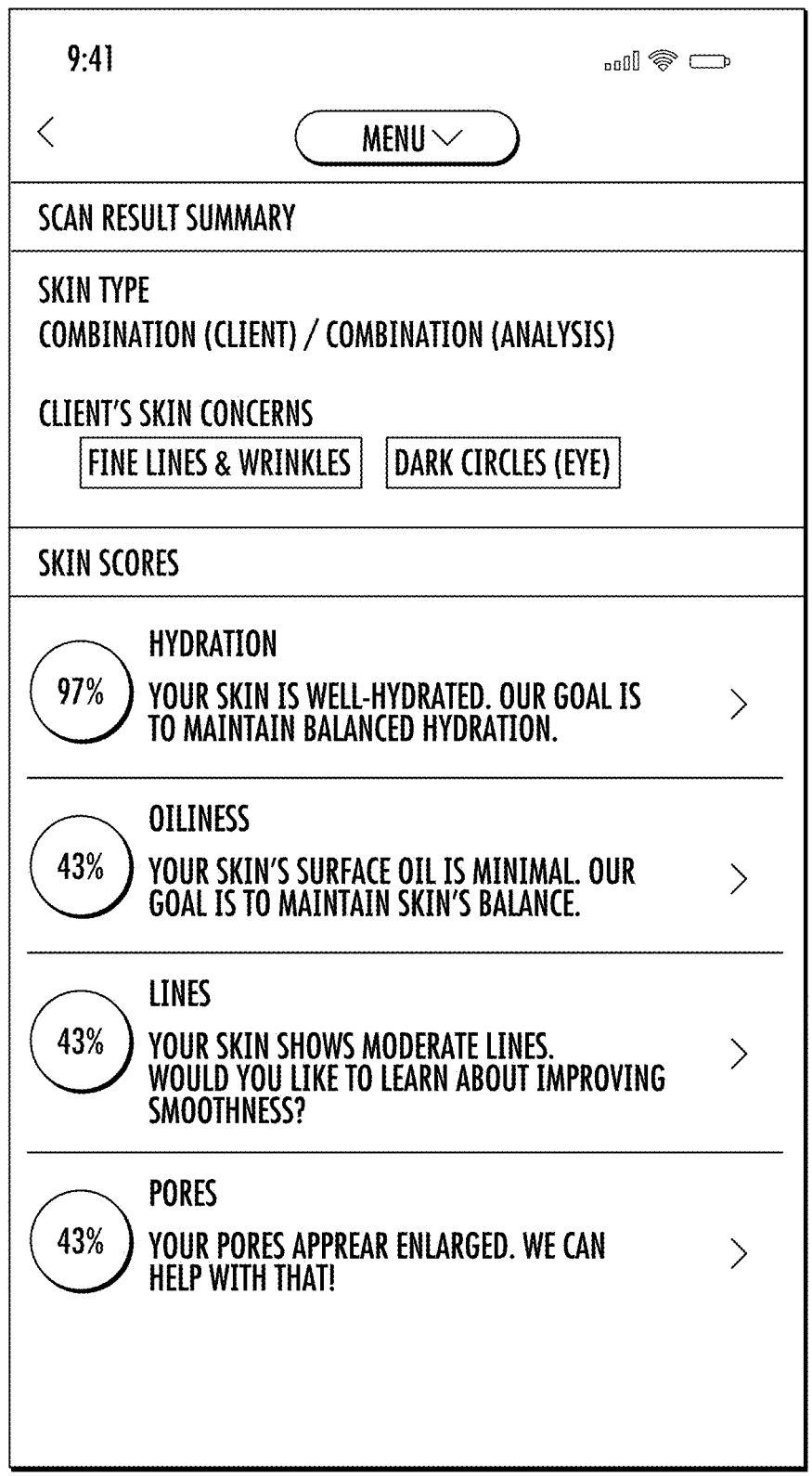
Figure 14A:
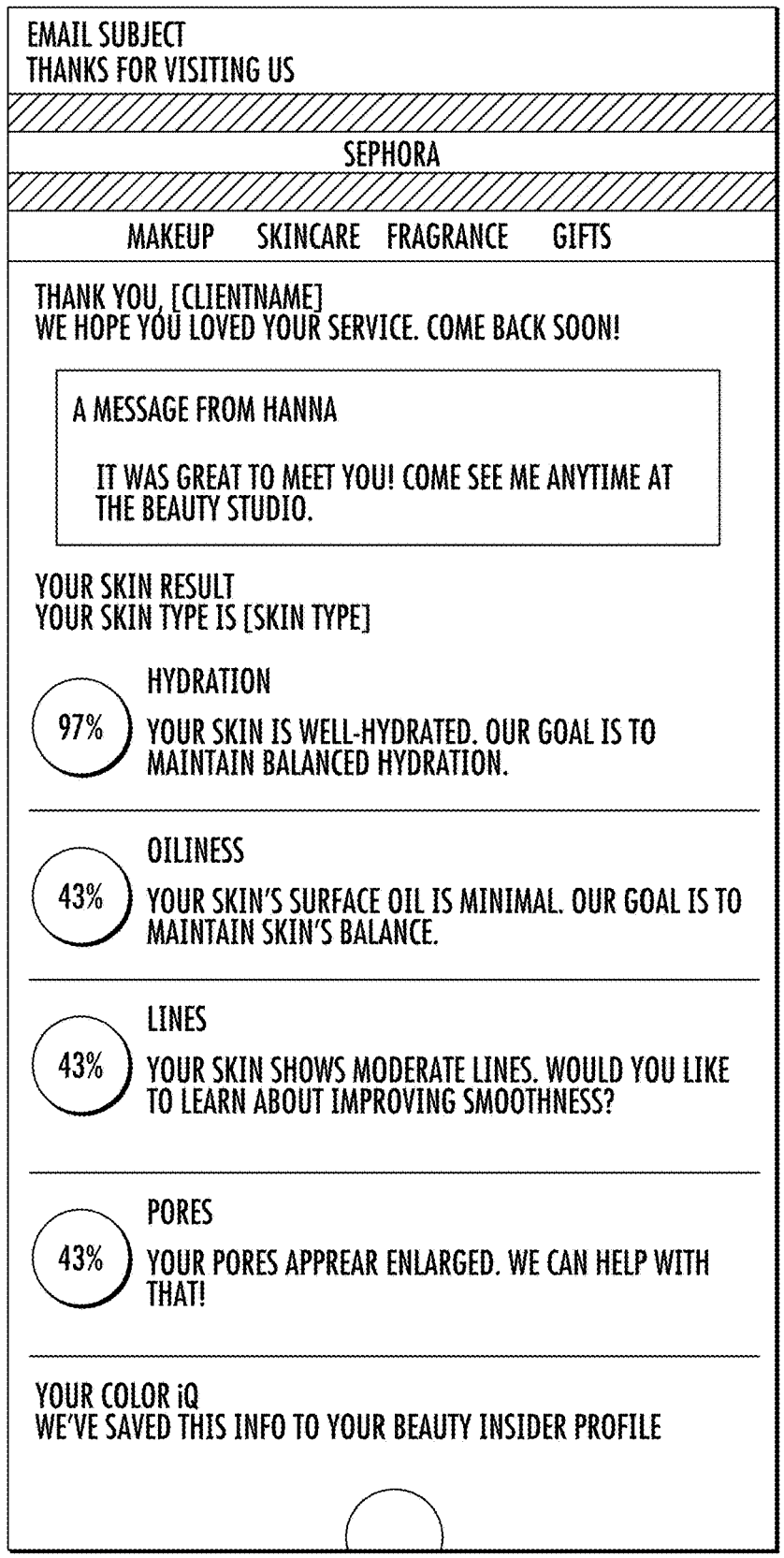

FIGS. 14A-14Z illustrates some simplified example user interface design and/or user experience design in one or more embodiments. More specifically, FIG. 14A illustrates an example home screen of a mobile color IQ app that may be installed on a mobile computing device in one or more embodiments. In these one or more embodiments, the example graphical user interface illustrated in FIG. 14A includes a pull-down menu 1402A providing a list of commands for executing respective functions, a search widget 1418A, and a code scanner widget 1420A.

A widget includes an application, or a component of an interface that enables a user to perform a function or access a service in some embodiments. A widget represents an element of a graphical user interface (GUI) that displays information or provides a specific way for a user to interact with, for example, the operating system of a computing device or an application in some embodiments. In addition or in the alternative, a widget may be an applet intended to be used within an application or web pages and represents a generic type of software application comprising portable code intended for one or more different software platforms. A widget may also include a graphical widget (e.g., a graphical control element or control) in a graphical user interface where a control is one or more software components that a user interacts with through direct manipulation to read or write information about an application.

The search widget 1418A, when interacted upon by a client, invokes a search module that presents an interface for the client to enter a search query and searches internal, local storage and/or remotely accessible storage to find the query result, and returns at least some of the query results to the client by presenting the at least some of the equerry result in the example user interface. The code scanner widget 1420A, when interacted upon, invokes a code scanner application, applet, module, service, or a set of microservices that scans a code of a cosmetic product and identifies, either alone or in conjunction with other processes, modules, services, or microservices, information for the cosmetic product. In some embodiments, such information may include, for example, general product information, product attributes (e.g., brand, price), customer profile attributes, prior customer purchases, prior customer replenishment purchases, client returns, customer affinities (e.g., brand loyalty), advisor suggestions or recommendations pertaining to the cosmetic product, skin tones or undertones that the particular cosmetic product exactly or approximately matches, skin types, skin conditions, or skin concerns to which the cosmetic product pertain or fits, or any combination of these.

The example user interface may further include an actionable widget 1412A which, when interacted upon, invokes a new skin tone scan session or a new skin guide scan session, an actionable widget 1414A which, when interacted upon, invokes a search module that allows a client or prospective client to search for information (e.g., matching cosmetic products, recommended cosmetic products, general product information, or others) based at least in part upon a color index or value provided by the client or prospective client, and/or a actionable widget 1416A which, when interacted upon, invokes a reverse lookup process for a client or prospective client to perform a reverse lookup that finds information pertaining to matching products or services based on the client's input.

The example user interface may further include a display area that displays graphical (1404A) and/or textual (1406A) of a scan result. For example, the example user interface may display a graphical representation 1404A that illustrates the color attribute or attributes (e.g., color index or value) and/or at least a representative portion of a scanned result (e.g., a portion of a scanned area showing the skin tone, the undertone, the skin condition, the existence of recognized objects such as freckles, skin health concerns, etc. in the display area. In addition or in the alternative, the display area may also present the color attribute or attributes such as the predicted color index or value 1406A.

Moreover, the example user interface may further include an actionable widget 1408A which, when interacted upon, retrieves and displays information pertaining to matching product or products based on the graphical (1404A) and/or the textual (1406A) information of the scan result. In addition or in the alternative, the example user interface may further include an actionable widget 1410A which, when interacted upon, invokes an adjustment process that allows the user of the example user interface to adjust the color attribute or attributes of the scan result. In an example where a CIELAB color space is adopted, the aforementioned adjustment process enables the user to adjust, for example, the L value, the a* value, and/or the b* value by either entering a different value to override the predicted value or by using one or more graphical sliders that respectively include an indicator for the predicted value and allows the user to move the indicator along the slider to change color attribute value or values while providing real-time or nearly real-time textual and/or graphical response to indicate the altered color attribute or attributes and/or the resulting skin tone.

FIG. 14B illustrates an example user interface for a client interview process to collect various pieces of data or information that may be utilized in subsequent product matching and recommendation service or services in one or more embodiments. More specifically, the example user interface presents a question asking the client to provide the skin type such as dry, oily, normal, or a combination thereof (e.g., certain subareas are oily while certain other subareas of the skin is normal). The example user interface may include a plurality of types of skin types 1402B with respective graphical and/or textual illustrations and/or explanations or instructions for a client to correctly identify his/her skin type in response to the interview inquiry.

In addition or in the alternative, the example user interface may include an actionable widget 1404B which, when interacted upon, allows a client to skip this question or even to skip the entire interview process. Further, the example user interface may include a backward navigation widget that allows the client to navigate back to the previous screen in the example user interface. A pull-down menu 1408B may also be included in the example user interface to allow the client to quickly navigate to other sections or functions (e.g., begin scan, home, reverse lookup, search, or others) provided by the store digital application or the mobile color IQ app to which the example user interface pertains.

FIG. 14C illustrates an example user interface for a client interview process to collect various pieces of data or information that may be utilized in subsequent product matching and recommendation service or services in one or more embodiments. More specifically, the example user interface presents a question asking the client to provide his/her age or age range. The example user interface may include a plurality of types of age ranges 1402C with respective graphical and/or textual illustrations and/or explanations/instructions for a client to indicate his or her age in response to the interview inquiry. It shall be noted that some example age ranges are illustrated in FIG. 14C although other age ranges or even specific age (e.g., a specific age entered by a client in the example user interface) may also be used.

In addition or in the alternative, the example user interface may include an actionable widget which, when interacted upon, allows a client to skip this question or even to skip the entire interview process. Further, the example user interface may include a backward navigation widget that allows the client to navigate back to the previous screen in the example user interface. A pull-down menu may also be included in the example user interface to allow the client to quickly navigate to other sections or functions (e.g., begin scan, home, reverse lookup, search, etc.) provided by the store digital application or the mobile color IQ app to which the example user interface pertains.

FIG. 14D illustrates an example user interface for a client interview process to collect various pieces of data or information that may be utilized in subsequent product matching and recommendation service or services in one or more embodiments. More specifically, the example user interface presents a question asking the client to provide his/her skin concern or concerns. The example user interface may include a plurality of types of example concerns 1402D with respective graphical or textual illustrations and/or explanations/instructions for a client to indicate his/her skin concern or concerns in response to the interview inquiry. In some embodiments, the skin concern or concerns indicated by a client may be validated by one or more AI modules described herein.

For example, an AI module may recognize features from a scanned image (e.g., an image during a skin tone scan session or a skin guide scan session, or combination, that provides additional information such as matching products, services, external treatment (e.g., by dermatologists or specialists), skin care instructions, or others) and validate or confirm the skin concern or concerns with the recognized features. In some embodiments where the recognized features do not reflect a skin concern indicated by a client, the example user interface may provide further screen or screens or instructions to as the client to, for example, perform a scan session at or near the area showing the aforementioned skin concern. In some embodiments where the method or system still cannot validate or confirm the skin concern after analyzing the newly performed scan result, the newly performed scan result may be used to further fine tune, train, or retrain the pertinent AI module or modules to improve the accuracy of the pertinent AI module or modules.

It shall be noted that some example skin concerns are illustrated in FIG. 14D although user interface may also provide an input field for a client to enter his/her skin concern or concerns that is not listed in the example skin concerns 1402D in some embodiments. In these embodiments, the skin concern manually entered by client may be processed by an artificial intelligence module that is either installed locally on a mobile computing device or is provided as a service that invokes a remote system for further processing. The AI module may recognize and predict the meanings of the manually entered skin concern for subsequent processing. For example, the AI module may recognize and predict the meanings of the manually entered skin concern by applying natural language processing that recognizes the content and meanings of the skin concern via, for example, a recurrent neural network (RNN) and further by finding cosmetic product or products that is developed to address the skin concern via, for example, the various AI modules described here for product matching and recommendations.

FIG. 14E illustrates an example user interface for a client interview process to collect various pieces of data or information that may be utilized in subsequent product matching and recommendation service or services in one or more embodiments. More specifically, the example user interface presents a question asking the client to provide his/her secondary skin concern or concerns. This example user interface provides identical or similar functionalities as that illustrated in FIG. 14D although for a different, secondary skin concern which will be weighted slightly lower than the skin concern or concerns that a client indicated in the example user interface shown in FIG. 14D for the purpose of cosmetic product matching and recommendation.

FIG. 14F illustrates an example user interface for a client interview process to collect various pieces of data or information that may be utilized in subsequent product matching and recommendation service or services in one or more embodiments. More specifically, the example user interface presents a question asking the client to indicate whether the client is of Middle Eastern, Hispanic, or Latino origin. As described above, olive undertone represents medium tones in, for example middle eastern and Hispanic persons and has been observed across all depths (e.g., warm, neutral, cool), not just medium tones. Nonetheless, the current state-of-the-art approaches do not address olive undertones. In some of these embodiments where a client indicates his/her Middle Eastern, Hispanic, or Latino origin, the method or system may invoke the pertinent portion of the code and libraries that address olive undertones.

In some other embodiments where a client indicates that he or she is not of the Middle Eastern, Hispanic, or Latino origin, the method or system may suppress the pertinent portion of the code and libraries that address olive undertones in order to conserve computational resources. For example, the method or system may skip the code sections, the routines, the subroutines, or library files specific to olive undertones and/or filter out (as a pre-filtering step) products that is specific to olive undertones in these latter embodiments.

FIG. 14G illustrates an example user interface for a client interview process to collect various pieces of data or information that may be utilized in subsequent product matching and recommendation service or services in one or more embodiments. More specifically, the example user interface presents a question asking the client to indicate his or her ethnicity (e.g., Caucasian/White, African American/Black, East Asian, South Asian/Indian, Middle Eastern, Pacific Islander, Native American/American Indian, and/or Other/Prefer Not to Say). In some of these embodiments where a client indicates his or her ethnicity, the method or system may invoke the pertinent portion of the code, library file or files, or product or products that addresses the specific ethnicity.

FIG. 14H illustrates an example user interface for a client interview process to collect various pieces of data or information that may be utilized in subsequent product matching and recommendation service or services in one or more embodiments. More specifically, the example user interface presents a question asking the client to indicate his or her preferred foundation brands or product or products. It shall be noted that although FIG. 14H uses foundation as an example in these illustrated embodiments, other embodiments may ask for other types of cosmetic products such as concealers, lips products, other skin care products, etc.

In some embodiments, the example user interface presents a question asking the client to provide his or her preference for coverage (e.g., cover all or part of exposed skin areas, cover some or all blemishes, cover lightly with some tint, or others), his/her preference for clean products, and/or his/her preference for sun protection, etc. In some embodiments, the example user interface presents a question asking the client to provide his/her preference for how the client appears after applying the product. Some example choices may include matte or shine-free all day, natural or on-makeup appearance, or radiant, etc. In some embodiments, the example user interface presents a question asking the client to provide the client's preference for the formula of products. Some example choices may include liquid, powder, cream, stick, or others. The example user interface may present an option for a client to skip each question or a choice of "don't care" for each question.

FIG. 14I illustrates an example user interface for preparing for a skin scan session to obtain scan results for subsequent product matching and recommendation service or others in one or more embodiments. More specifically, the example user interface presents a screen that includes an actionable widget 1402I which, when interacted upon, invokes or initiates a skin scan session (e.g., a skin tone scan session, a skin guide scan session, or others) In some embodiments, the example user interface may also present multiple types of skin scans (e.g., a skin tone scan session, a skin guide scan session, or others) for a client to choose from and invoke the corresponding components and/or modules to facilitate the selected scan.

In some embodiments, the example user interface may also include the battery status 1404I that shows the textual (1404I) and/or graphical information (1406I) pertaining to the charge level of the battery of the scanning device (e.g., a scanning device of a system for cosmetic product matching and recommendation described herein, a mobile computing device, etc.) In some of these embodiments, the example user interface may further provide a warning if it is determined that the remaining battery charge may not be sufficient to sustain the utilization of various components and/or modules for the selected scan.

FIG. 14J illustrates an example user interface showing instructions for beginning a skin scan for a particular area of a client's skin in one or more embodiments. More specifically, the example user interface presents a screen that includes textual and/or graphical information and/or instructions 1402J to clean the scanning device to prepare for the selected skin scan. Such instructions may include, for example, textual or graphical (e.g., images or videos) instructions or information pertaining to how and where to clean a scanning device.

The example user interface may further present textual and/or graphical information and/or instructions 1404J to clean the scanning device to prepare for the selected skin scan. Such instructions may include, for example, textual and/or graphical (e.g., images or videos) instructions or information pertaining to how and where to clean one or more areas of the skin for the selected skin scan. In some embodiments, the example user interface may also include an interactable widget 1406J for advancing to the next screen.

FIG. 14K illustrates an example user interface showing some skin scan results in one or more embodiments. More specifically, the example user interface presents a screen that includes textual (1402K) and/or graphical (1404K) information and/or instructions to show the user where to place a scanning device for a first particular area of a client's skin and/or how to perform the scan for the first particular area with a scanning device for the selected skin scan. In the example illustrated in FIG. 14K, the first particular area is the forehead area for the selected skin scan. In some embodiments, the example user interface may also include an interactable widget 1406K for begin the scan for the first particular area. In some embodiments, the app may provide an audio, visual, or haptic feedback to inform the client that a scan is complete (e.g., one or more images have been captured).

FIG. 14M illustrates an example scan image in one or more embodiments. In some embodiments, the lens used in scanning the client's skin includes a telephoto lens having a magnification power (e.g., optical magnification power, digital magnification power, or optical and digital magnification power, or others) greater than one to capture finer details of a client's skin. In some other embodiments, the lens used in scanning the client's skin may include a macro lens for creating close-up, macro images, a wide-angle lens, a standard lens (e.g., lens having focal length or lengths falling between 35 millimeters and 85 millimeters, or a specialty lens such a fisheye lens, a tilt shift lens, an infrared lens, etc.

A lens may be a fixed-focal length lens having a single focal length value in some embodiments or a variable focal length having a range of focal length values in some other embodiments. Different lenses may have different fields of view. For lenses having larger fields of view, the client's skin may be scanned only once per target area (e.g., forehead area, cheek area, neck area, or others) For lenses having smaller fields of view, the client's skin may be scanned more than once per target area to obtain a better representation of a reasonably large skin area for subsequent processing. In some of these embodiments, the example user interface may place a interactable marker 1406M at or around an area of interest in the captured scan result so that when the client clicks on the interactable marker 1406M, additional information such as what the system predicts this area of the skin to be, the explanation therefor, skin care information for this particular area of the skin, etc. In some embodiments, the example user interface may further include an interactable widget 1402M for a client to re-scan the same skin area (e.g., the first particular area described above) and/or another interactable widget 1404M to advance to the next screen.

FIG. 14N illustrates example scan results in one or more embodiments. In some embodiments, scan results may include the skin tone color index or value 1402N. In some of these embodiments adopting the CIELAB color space, the skin tone color index or value may include the L value, the a* value, and the b* value of the predicted skin tone for the particular client. Scan results may include another index 1404N such as the hex code that corresponds to the skin tone color index or value 1402N. In some of these embodiments, scan results may also include the predicted skin tone color in one or more different color spaces such as the RGB color space 1406N or any other suitable color space. The example user interface may further provide one or more interactable widgets for a client to finish the current skin scan (e.g., "DONE" 1408N), to transmit scan results or a portion thereof (e.g., via email), to redo the same scan, to select a different skin scan, etc.

FIG. 14O illustrates an example user interface screen that includes textual and/or graphical information and/or instructions to guide a client to more correctly place a scanning device for a second particular area of a client's skin and/or how to perform the scan for the second particular area with a scanning device for the selected skin scan in one or more embodiments. In the example illustrated in FIG. 14O, the second particular area is the check area or areas for the selected skin scan. In some embodiments, the example user interface may also include an interactable widget 14060 for begin the scan for the second particular area and an optional, interactable widget (not shown) to skip the skin scan session for a particular area. In some embodiments, the app may provide an audio, visual, and/or haptic feedback to inform the client that a scan is complete (e.g., one or more images have been captured).

FIG. 14P illustrates an example user interface screen that includes textual and/or graphical information and/or instructions to guide a client to more correctly place a scanning device for a second particular area of a client's skin and/or how to perform the scan for the second particular area with a scanning device for the selected skin scan in one or more embodiments. More specifically, the example user interface presents a screen that includes textual (1402P) and/or graphical (1404P) information and/or instructions to show the user where to place a scanning device for a third particular area of a client's skin and/or how to perform the scan for the third particular area with a scanning device for the selected skin scan. In the example illustrated in FIG. 14P, the third particular area is the cheek area or areas for the selected skin scan. In some embodiments, the example user interface may also include an interactable widget 1406P for begin the scan for the third particular area and an optional, interactable widget (not shown) to skip the skin scan session for a particular area. In some embodiments, the app may provide an audio, visual, and/or haptic feedback to inform the client that a scan is complete (e.g., one or more images have been captured).

FIG. 14Q illustrates a screen of an example user interface when a client clicks on, for example, "DONE" 1408N in FIG. 14N to finish the current skin scan session. One difference between the example user interface in FIG. 14Q and the example user interface in FIG. 14A is that the graphical (1404Q) and/or textual (1406Q) of a scan result in FIG. 14Q may be refreshed to display the latest scan results whereas the graphical (1404A) and/or textual (1406A) of a scan result in FIG. 14A may be refreshed to display the previous scan results (e.g., the immediately previous scan results).

FIG. 14R illustrates another scan result screen showing scan results of a skin tone scan session for a client in one or more embodiments. In these embodiments illustrated in FIG. 14R, the scan results may include a graphical representation 1402R showing the predicted skin tone color of the scan, a textual description 1404R showing the color index or value (e.g., color iQ having the value 2Y07 in FIG. 14R), and/or the description 1406R explaining more details about the predicted skin tone color index or value for the particular client. In some embodiments, the example user interface illustrated in FIG. 14R may further include an interactable widget 1408R which, when interacted upon, invokes various processes or modules for the product matching services and recommendations. In some embodiments, the example user interface illustrated in FIG. 14R may include another interactable widget 1410R which, when interacted upon, restarts a scan session.

FIG. 14S illustrates an example user interface for adjusting skin tone color attributes of a color index or value (e.g., a predicted color index or value obtained from a skin tone scan session or provided by a client) in one or more embodiments. More specifically, the example user interface includes a depth slider 1406S having a depth indicator 1408S that can be moved along a range of continuous or discreet (e.g., a fixed number of depth values or intervals such as the multiple levels of depth levels described above) depth values from a lighter depth value to a darker depth value with a corresponding graphical representation for each of a plurality of representative depth values. The depth indicator 1408S may also be associated with a dynamic display of current depth value or designator (e.g., "medium dark" as shown in FIG. 14S, a numeric, a hex value, or an index for the current depth value).

The example user interface may further include an undertone slider 1410S having an undertone indicator 1412S that can be moved along a range of continuous or discreet (e.g., a fixed number of undertone values or intervals such as the multiple levels of undertone levels described above) undertone values from a cooler undertone value to a warmer undertone value with a corresponding textual or graphical representation for each of a plurality of representative undertone values. The undertone indicator 1412S may also be associated with a dynamic display of current undertone value or designator (e.g., "5" as shown in FIG. 14S, a hex value, a textual description, or an index for the current undertone value).

The example user interface may further include a saturation slider 1414S having a saturation indicator 1416S that can be moved along a range of continuous or discreet (e.g., a fixed number of saturation values or intervals such as the multiple levels of saturation levels described above) saturation values from a less saturated saturation value to a more saturated saturation value with a corresponding textual or graphical representation for each of a plurality of representative saturation values. The saturation indicator 1416S may also be associated with a dynamic display of current saturation value or designator (e.g., "2" as shown in FIG. 14S, a hex value, a textual description, or an index for the current saturation value).

The example user interface may further include graphical representation that shows a first graphical representation 1402S of the recommended skin tone before any adjustment with any of the aforementioned sliders (1406S, 1410S, and 1414S) as well as a second graphical representation 1404S of the skin tone showing the adjusted skin tone. The first graphical representation 1402S and the second graphical representation 1404S may be arranged in close proximity for easier comparison between the predicted skin tone (1402S) and adjusted skin tone (1404S).

The example user interface may further an interactable widget 1418S to reset all adjustment or adjustments to revert the aforementioned three indicators (1408S, 1412S, and 1416S) to those corresponding to the predicted skin tone in some embodiments. In some other embodiments, each interaction with the widget 1418 resets the immediate prior adjustment of an indicator of a slider. The example user interface may also include another interactable widget 1420S to update the skin tone with the adjusted value or values and to show matching cosmetic product or products. In addition or in the alternative, the example user interface may include an interactable widget 1422S to cancel any adjustments made and revert to the previous screen, the app home screen, or the scan result screen.

FIG. 14T illustrates another example user interface screen in one or more embodiments. In this example, the user interface screen may show, in a display portion 1402T, a specific matching cosmetic product (e.g., a product selected by a client from a list of recommended cosmetic products) with corresponding product information (e.g., description, color index or value, price, rating, etc.) The cosmetic product in the display portion 1402T may be dynamically linked to the adjustment display portion in the example user interface that includes the textual (e.g., the skin tone color iQ value or index) and/or graphical representation (e.g., a display of the color corresponding to the skin tone) of a predicted skin tone or an adjusted skin tone (e.g., an adjusted skin tone by manipulating one or more sliders in FIG. 14S) so that when skin tone value or index is altered, a corresponding product that is similar (e.g., similar in functions or purposes of the product, similar price, similar rating, or any combinations thereof) to the cosmetic product for the predicted skin tone (e.g., skin tone before adjustments with the widgets in the example user interface in FIG. 14T).

The example user interface may further include one or more pairs of interactable widgets where each pair of interactable widgets allow adjustment of the skin tone value or index 1406T in both directions. For example, the example user interface may include a first pair of interactable widgets 1412T and 1414T to adjust the skin tone 1406T between yellower (or golden as shown in FIG. 14T) and pinker values. For example, interactable widget 1412T, when interacted upon, may provide adjustment for h-segment values towards pink and away from yellow while interactable widget 1414T, when interacted upon, may provide adjustment for h-segment values towards yellow and away from pink.

The example user interface may include a second pair of interactable widgets 1408T and 1410T to adjust the skin tone 1406T between lighter and darker values. For example, interactable widget 1408T, when interacted upon, may provide adjustment for L-segment values towards lighter and away from darker while interactable widget 1410T, when interacted upon, may provide adjustment for L-segment values towards darker values and away from lighter values. In some embodiments, the product display portion 1402T may be dynamically refreshed with updated product and information with any adjustment made with any of the interactable widgets for adjusting skin tone values (e.g., 1408T 1410T, 1412T, and/or 1412T). The example user interface may include an interactable widget 1416T to cancel any adjustments and another interactable widget 1418T to accept the adjustment, update the data, and view matching products or a list of matching products.

FIG. 14U illustrates an example user interface screen showing a list of predicted matching products or a list of personalized, recommended products in some embodiments. The list of cosmetic products (e.g., a list of matching cosmetic products or a list of personalized, recommended cosmetic products) 1402U may correspond to the color index or value 1404U in the example user interface and include one or more products of the manufacturer that develops and owns the matching and recommendation method or system described herein, one or more products from one or more competitors of the aforementioned manufacturer, etc. For each cosmetic product in the list 1402U, the example user interface may further include corresponding other information for the cosmetic product. Such other information may include, for example, the name or identifier of the cosmetic product, the price of the cosmetic product, users' or professional rating of the cosmetic product, a brief description of the product, an image of the cosmetic product, or any other suitable information that may help a client to make a purchase decision.

In some of these embodiments, the rating 1408U associated with a cosmetic product in the list 1402U may be implemented as an interactable widget which, when interacted upon, brings up more detailed information about the rating. Such more detailed information may include, for example, professional review or reviews, individual users' ratings, statistics of the individual users' ratings, or any other information or data pertaining to the rating 1408U. For example, such more detailed information may include demographic distributions of the rating 1408U or its individual components (e.g., the number or percentage of clients in their respective age ranges, ethnicity group, etc. gave the product a one-star rating, the same for clients in different demographic groups, and others) In another example, the more detailed information may include individual rating's distribution (e.g., the number or percentage of clients for each individual rating) that are aggregated into the rating 1408U shown in the example user interface. In some of these embodiments, each individual rating may also be interactable to bring up even more detailed information such as more detailed demographic distribution or distributions pertaining to the specific rating.

In some embodiments, each cosmetic product in the list may be represented by an interactable widget which, when interacted upon by a client, brings up more information (e.g., more detailed information about the cosmetic product, more images of the cosmetic product, video or videos about the cosmetic product, or others) In some of these embodiments, the interactable widget may be implemented by, for example, associating a link to a display area used by the cosmetic product (e.g., the image display portion, the textual description portion, etc.) or an object pertaining to the cosmetic product so that when the display area or object is interacted upon, the interaction invokes the link that in turn brings up the aforementioned more information. Each cosmetic product may further be associated with a first interactable widget 1406U for a client to add the cosmetic product to a list (e.g., a list for emailing product information to the client, a list of cosmetic products for comparison, a list of cosmetic products for purchase, or others) The first interactable widget 1406U, when interacted upon, automatically changes its appearance to indicate that the corresponding cosmetic product has been added to the list. For example, for cosmetic products that have not been added to the list, the first interactable widget 1406U may display "Add to List" and automatically changes to "Added" 1416U when a cosmetic product has been added to the list.

The example user interface may further include interactable widgets that respectively correspond to different types of cosmetic products for a client to select. When a client selects a specify type of cosmetic products, the list of cosmetic products 1402A may be automatically refreshed to show the corresponding cosmetic products that the method or the system predicts or recommends. For example, the example user interface may include a first widget 1410U for a client to select foundation products, a second widget 1412U for a client to select concealer products, etc. In some embodiments, the example user interface may implement such product type selection in other manners such as a pull-down list, radio buttons, etc. to facilitate cosmetic product type selection.

FIG. 14V illustrates another example user interface screen showing more options that may be implemented in an example user interface in one or more embodiments. Compared with the example user interface illustrated in FIG. 14U described immediately above, the example user interface in these one or more embodiments may further include a sort widget 1402V which, when interacted upon, presents a list of sort criteria from which a client may select one or more sort criteria (e.g., first sort by criterion A, then sort by criterion B, etc.) to sort the list of predicted matching or recommended cosmetic products 1414V. The list of sort criteria may include, for example, price, manufacturer, rating, one or more demographic group affinities (e.g., preferred or mostly purchased by one or more certain age ranges, one or more ethnicity groups, and others), popularity or quantities sold, and others.

As described above, sorting may be performed in a hierarchical or nested manner in some embodiments. For example, a client may select a first sorting criterion that the client values the most, a second sorting criterion that the client values less, and a third sorting criterion that the client values even less where different combinations of the same sorting criteria may result in different results. The method or system described herein may then first sort the list of products 1414V according to the first sorting criterion to generate a first sorted list which is then subject to the second sorting criterion, and so on and so forth.

The example user interface may further include a first filtering widget 1406V which, when interacted upon, presents a list of filtering criteria from which a client may select one or more filtering criteria (e.g., first filter by criterion A, then filter by criterion B, etc.) to filter the list of predicted matching or recommended cosmetic products 1414V into a filtered list. The example user interface may include a total number of matches 1408V that may be statically tied to the total number of cosmetic products (e.g., total number products of a specific product type such as foundations, concealers, and others or total number of products of all product types, etc.) or may be dynamically refreshed based at least in part on the filtering. Each product (e.g., matching product, predicted product, recommended product, or others) may be associated with usage or application guide information (e.g., what time or times to use the product, the recommended frequency of using the product such as how many times a day or a week, etc., detailed application guide, etc.), and such usage or application guide information may be presented in the example user interface screen pertaining to the product or included in the email or message to the client for whom the product is predicted or recommended.

The list of filtering criteria may be inclusive (e.g., products of selected filtering criterion/criteria are included in the list 1414V) in some embodiments or exclusive (e.g., products of selected filtering criterion/criteria are excluded in the list 1414V) in some other embodiments. The list of filtering criteria may include, for example, price or price range, manufacturer, rating, one or more demographic group affinities (e.g., preferred or mostly purchased by one or more certain age ranges, one or more ethnicity groups, etc.), popularity or quantities sold (e.g., best-selling products), recommended product or products, one or more skin tones or one or more skin tone ranges that the cosmetic products are known to produce desirable effects, ingredients such as specific ingredients, types of ingredients such as "organic only," and others, toxicity levels, or any other suitable criteria, or any combinations thereof, or others.

As described above, filtering may be performed in a hierarchical or nested manner in some embodiments. For example, a client may select a first filtering criterion that the client values the most, a second filtering criterion that the client values less, and a third filtering criterion that the client values even less where different combinations of the same filters may result in different results. The method or system described herein may then first filter the list of products 1414V according to the first filtering criterion to generate a first filtered list which is then subject to the second filtering criterion, and so on and so forth. Different combinations of the same filtering criteria may or may not necessarily produce the same final filtered list. For example, the aforementioned filtering criterion may be assigned a heavier weight or subject to exact or more strictly controlled fuzzy matching requirement so that only products that adhere to the exact or more strictly controlled fuzzy matching requirement will be part of the first filtered list because the first filter criterion represents what a client requires or desires more. The aforementioned second filtering criterion may be assigned a less heavy weight or subject to not as exact or not as strictly controlled fuzzy matching requirement so that more products in the first filtered list will be part of the second filtered list.

FIG. 14W illustrates another example user interface screen that lists some example filtering criteria in one or more embodiments. These example filtering criteria include, for instance, age or age range 1402W, brand or manufacturer 1404W, category 1406W (e.g., cosmetic product types such as foundation, concealer, lips products, skin care products, or others), color family 1408W (e.g., saturation levels, depth levels, and/or undertone levels described above), skin concerns 1410W (e.g., products for specific skin concerns), coverage 1412W (e.g., spot coverage, area coverage, or others), or any other suitable criteria, or any combinations thereof.

A filtering criterion may have a default value or selection requirement such as "ALL" that includes all products. In some embodiments, a filtering criterion may be associated with an interactable widget 1416W which, when interacted upon, provides a list of options for a client to select. With the filtering criteria determined, the method or system described herein may apply the filtering criteria to a list of products (e.g., a list of predicted matching products, a list of recommended products, etc.) to generate a filtered list of products and may further indicate the filtering results 1418W (e.g., a total number or other visual cue of products remaining in the filtered list) in the example user interface screen.

The example user interface screen may further include sorting functions 1414W and a set of sorting criteria (1422W, 1424W, 1426W, or others) For example, a client may sort a list of product by "Recommended" 1422W that sorts products (e.g., a list of predicted matching products, a list of recommended products, etc.) based at least on, for example, the respective recommendation scores of the products, by "Best Selling" 1424W that sorts products based at least on, for example, the respective sales records of the products, by "Top-Rated" 1426W that sorts products based at least on, for example, the respective user reviews and/or professional review or reviews of the products, or any other suitable or appropriate sorting criterion or criteria, or any combinations thereof.

The example user interface may also include a reset widget 1430W to reset one, some, or all actions performed in the example user interface screen illustrated in FIG. 14W. For example, a client may interact with the reset widget to reset the immediate prior action performed on the example user interface screen so that an option (e.g., a selection of a filtering criterion) is reset to its immediate prior value or setting, or select which one or more specific actions to reset to default, or reset all actions performed and revert all options to their original, default value. The example user interface screen may also include an interactable widget 1428W to indicate that the configuration of filtering criteria and sorting criteria is complete so the example user interface screen returns to a prior screen from which the example user interface screen in FIG. 14W was initiated or to the home screen.

FIG. 14X illustrates an example product detail screen showing detailed information of a cosmetic product such as a predicted matching cosmetic product or a personalized, recommended cosmetic product in one or more embodiments. The detailed information may include on-screen display of or one or more links to, for example but not limited to, one or more images 1402X of the product and/or packaging of the product, price 1404X, user and/or professional review or reviews 1414X, user and/or professional rating or ratings 1406X, more detailed description of the product such as compositions, ingredients, health-related information, usage or application guide, color attributes, skin type, condition or conditions, or concern or concerns fit for this particular product, demographic distribution of clients, endorsement information, inventory status 1408X (e.g., quantity, in-stock, pre-order, out-of-order, backorder, etc.) that may leverage location data from a global positioning system (GPS) of a mobile computing device, or any other information related to the product, etc., or any combination.

Any such information may be implemented on-screen, as respective interactable widgets the interactions of which bring up the respective information, or as one or more links to the information. In addition or in the alternative, the information may be arranged in a hierarchical or nested manner where a second piece of information (e.g., users' reviews) may be implemented at one level below a first piece of information (e.g., ratings 1406X).

The example user interface screen illustrated in FIG. 14X may further include an interactable widget 1412X which, when interacted upon, displays some or all of the more detailed information in a pop-up window in the example user interface screen illustrated in FIG. 14X or in a separate screen (not shown) that not only displays the more detailed information but may also provide a navigation widget to navigate to the example product detail screen illustrated in FIG. 14X. In addition or in the alternative, the example user interface screen illustrated in FIG. 14X may further include another interactable widget 1410X which, when interacted upon, brings up additional options pertaining to the specific product. Such additional options may include various sizes of the same product for a client to choose from, different quantities for the client to purchase, combos including the specific product and one or more different product or one or more services, other offers and/or discounts, etc.

The example user interface screen illustrated in FIG. 14X may further include a list of quick-change widgets 1416X which, when interacted upon, changes the current skin tone color index or value (1418X) to a different color index or value (1420X) and invokes a process that identifies a corresponding, equivalent product that corresponds to the different color index or value 1420X. For example, these quick-change widgets 1416X may include a first widget to make the skin tone color index or value darker, a second widget to make the skin tone color index or value lighter (e.g., L value in CIELAB color space), a third widget to make the skin tone color index or value more towards yellow (e.g., b* value in CIELAB color space), a fourth widget to make the skin tone color index or value more towards blue (e.g., b* value in CIELAB color space), a fifth widget to make the skin tone color index or value more towards green (e.g., a* value in CIELAB color space), and/or a sixth widget to make the skin tone color index or value more towards red (e.g., a* value in CIELAB color space), or any combinations thereof.

In some embodiments, each interaction (e.g., by touching a widget on a touch-sensitive screen) changes the skin tone color index or value by one or more levels or sublevels as described above with reference to FIG. 13A. The example user interface screen illustrated in FIG. 14X may further include another interactable widget 1422X which, when interacted upon, invokes a process that brings up additional adjustment capabilities. For example, some embodiments may include widgets 1416X for coarse adjustments of skin tone color index or value (e.g., each interaction of widget or widgets 1416X results in a change in multiple levels or sublevels) and additional, finer adjustments of skin tone color index or value by interacting with the widget 1422 (e.g., each interaction of widget 1422X results in a change in one or a few sublevels). The example user interface screen illustrated in FIG. 14X may further include another interactable widget 1424X that allows a client to add the product on display with the desired or default quantity to the list for comparison, review, or purchase.

FIG. 14Y illustrates another example user interface screen showing a list of selected cosmetic products in one or more embodiments. For example, various methods or systems described herein may present a list of predicted matching cosmetic products and/or a list of personalized, recommended cosmetic product to a user, and the user may select (e.g., by adding a specific product to the list using the interactable widget 1424X in FIG. 14X) one or more products from one or more lists. FIG. 14Y illustrates such cosmetic products selected by a client. The list of products may be grouped by product types such as a first group for foundation products 1412Y, a second group for other products 1414Y, a third group for concealer product, etc. In some embodiments, each product may be displayed or associated with some or all of the detailed product information (e.g., price, review or review, rating or ratings, and others) described above with reference to FIG. 14X.

In addition or in the alternative, a product listed in the list as shown in FIG. 14Y may further be displayed with a tray of interactable widgets 1402Y. This tray of widgets 1402Y may include a first widget 1404Y to display additional information about the specific product with which the tray 1404Y is associated, a second widget 1406Y for marking a specific product to a favorite or interested product list or marking for storing the product information for future reference, a third widget 1408Y for annotating (e.g., by adding textual or graphical annotations with on-screen virtual keyboard or hand writing and/or sketch pad) at least some of the product information of the specific product, a fourth widget 1410Y for scratching a specific product from the list of client-selected products, any other suitable, appropriate, desired, or required widgets pertaining to a specific product, or any combinations thereof, etc. The example user interface screen illustrated in FIG. 14Y may further include an interactable widget 1416Y which, when interacted upon, invokes an email client for the client to email or text the list of client-selected products, some or all of the aforementioned information, and/or some or all of the current or prior skin scan results to a designated e-mail address or mobile phone number capable of receiving multi-media messages.

FIG. 14Z illustrates another example user interface screen showing the contents of a communication screen after a client interacted with, for example the interactable widget 1416Y illustrated in FIG. 14Y and described above in one or more embodiments. In some embodiments, the example user interface screen illustrated in FIG. 14Z includes an expandable list 1402Z. The expandable list 1402Z may be interacted upon to show, for example, detailed information about the product or products included in the expandable list such as the detailed information described above with reference to FIG. 14X and/or 14Y.

The example user interface screen illustrated in FIG. 14Z may further include the results 1404Z of current skin scan or scans (e.g., skin tone scan and/or skin guide scan in the same session of the store digital app or the mobile color iQ app or for the same scan session). The results 1404Z may be interacted upon to bring up more detailed scan results such as skin tone color index or value, a predicted list of matching cosmetic and/or skin care products, a personalized list of recommended cosmetic and/or skin care products, more detailed product information for at least some products in the aforementioned lists, and/or personalized recommendations pertaining to skin care and/or treatment, or any combinations thereof.

A client may then enter an email address or a phone number of a mobile communication device that is capable of receiving messages (e.g., multi-media messages for the multi-media contents in the aforementioned information or results) in the provided field 1406Z and click on or touch the interactable widget 1408Z to send some or all of the aforementioned detailed information or results to the designated mobile phone number or email address.

FIG. 14AA illustrates another example user interface screen showing the results of a skin guide scan session in one or more embodiments. More specifically, FIG. 14AA illustrates the hydration analysis result of a skin guide scan in the check area of a client. In these one or more embodiments, the results screen includes the type of analysis 1402AA ("Hydration") as well as the hydration level ("97%") 1404AA. The example user interface screen further includes the scan image or a portion thereof or a processed (e.g., magnified and/or enhanced) scan image or a portion thereof 1406AA that may be further annotated with static annotation (e.g., a circle) indicating an area of concern that results in the scan results or interactable widget 1410AA around an area of concern for the particular scan. In some embodiments, an interaction with the interactable widget 1410AA may bring up further information, instructions, explanations, recommendations, etc. for this area of concern. Moreover, the example user interface screen may further include explanations, instructions, recommendations of products, services, or potential external treatments by specialists, tips, or any other suitable information 1408AA pertaining to the scan result.

FIG. 14AB illustrates another example user interface screen showing the results of a skin guide scan session in one or more embodiments. More specifically, FIG. 14AB illustrates the oiliness analysis result of a skin guide scan in the forehead area of a client (although other areas may also be scanned). In these one or more embodiments, the results screen includes the type of analysis 1402AB ("Oiliness") as well as the oiliness level ("43%") 1404AB. The example user interface screen further includes the scan image or a portion thereof or a processed (e.g., magnified and/or enhanced) scan image or a portion thereof 1406AB. In some embodiments, the example user interface screen in FIG. 14AB may further include explanations, instructions, recommendations of products, services, or potential external treatments by specialists, tips, or any other suitable information 1408AB pertaining to the scan result.

FIG. 14AC illustrates another example user interface screen showing the results of a skin guide scan session in one or more embodiments. More specifically, FIG. 14AC illustrates the lines analysis result of a skin guide scan in the forehead area of a client. In these one or more embodiments, the results screen includes the type of analysis 1402AC ("Lines") as well as the percentage level ("43%") 1404AC showing fine lines in the area of scan. The example user interface screen further includes the scan image or a portion thereof or a processed (e.g., magnified and/or enhanced) scan image or a portion thereof 1406AC that may be further annotated with static annotation (e.g., a circle) indicating an area of concern that results in the scan results or interactable widget 1410AC around an area of concern for the particular scan. FIGS. 14AE and 14AF respectively illustrate summary screens of a skin guide scan session in an example user interface in one or more embodiments.

In some embodiments, an interaction with the interactable widget 1410AC may bring up further information, instructions, explanations, recommendations, etc. for this area of concern. Moreover, the example user interface screen may further include explanations, instructions, recommendations of products, services, or potential external treatments by specialists, tips, or any other suitable information 1408AC pertaining to the scan result. Further, the scan is not limited to only one area of the client's skin. In some embodiments, multiple areas may be scanned, and the example user interface screen shows the results for these multiple areas in separate screens or tabs. For example, the example user interface screen may include a tab for a forehead scan 1410AC, an outer eye area scan 1412AC, etc.

FIG. 14AD illustrates another example user interface screen showing the results of a skin guide scan session in one or more embodiments. More specifically, FIG. 14AD illustrates the pores analysis result of a skin guide scan in the cheek area of a client. In these one or more embodiments, the results screen includes the type of analysis 1402AD ("Pores") as well as the percentage level ("43%") 1404AD showing pores of a certain size of above in the area of scan. The example user interface screen further includes the scan image or a portion thereof or a processed (e.g., magnified and/or enhanced) scan image or a portion thereof 1406AD that may be further annotated with static annotation (e.g., a circle) indicating an area of concern that results in the scan results or interactable widget 1410AD around an area of concern for the particular scan.

In some embodiments, an interaction with the interactable widget 1410AD may bring up further information, instructions, explanations, recommendations, etc. for this area of concern in addition to 1408AD. Moreover, the example user interface screen may further include explanations, instructions, recommendations of products, services, or potential external treatments by specialists, tips, or any other suitable information 1408AD pertaining to the scan result. Further, the scan is not limited to only one area of the client's skin. In some embodiments, multiple areas may be scanned, and the example user interface screen shows the results for these multiple areas in separate screens or tabs. For example, the example user interface screen may include a tab for a check scan 1410AD, a jawline area scan 1412AD, and others.

Figure 15A:
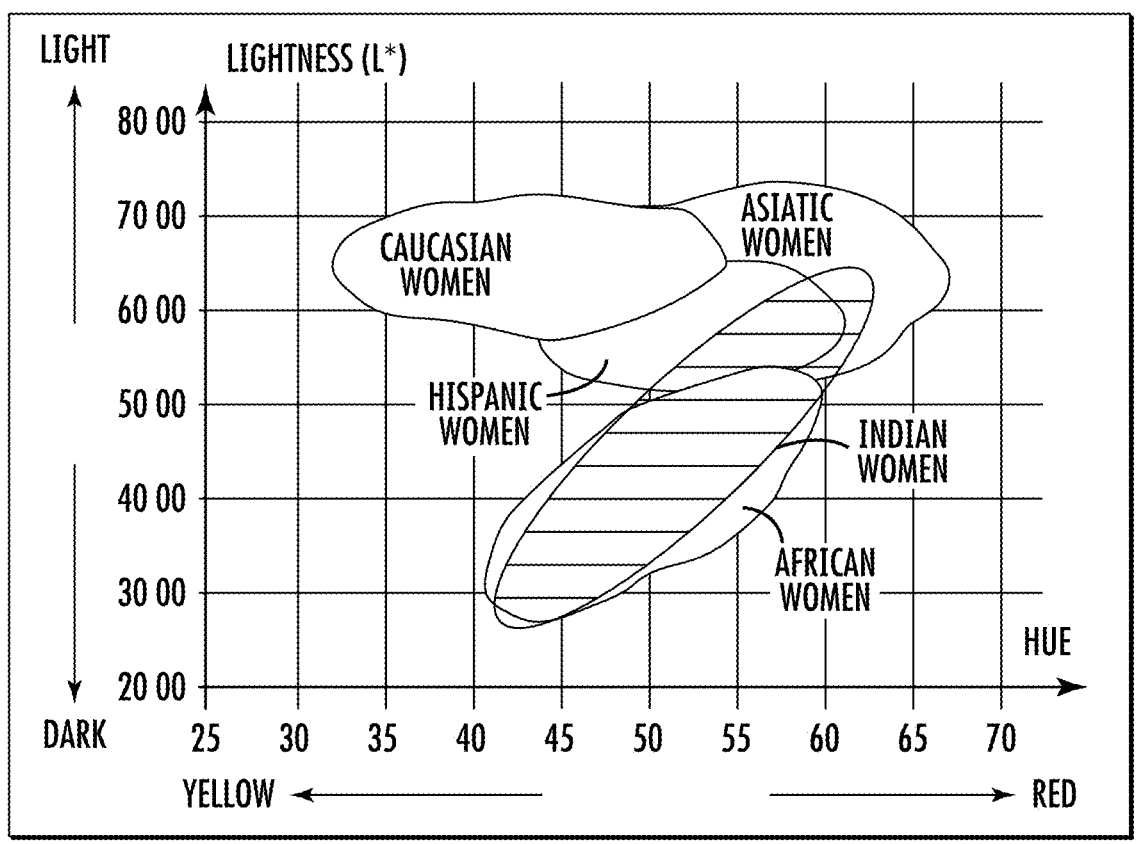
FIG. 15A illustrates an example of a foundation space with respect to hue and depth in one or more embodiments.

FIG. 15A illustrates an example of a skin tone space with respect to hue and depth (lightness) in one or more embodiments. As it can be seen from the respective distributions of different ethnicities, Caucasian skin tones are primarily with the region having the lightness values between 57-72 and the hue values between 34 to 58. The state-of-the-art methods for determining skin tones and undertones were developed in the 1970s or 1980s and, as a reflection of historical times then, was centered almost entirely around Caucasian skin tones. FIG. 15A shows that the lightness spread between high 20s to low 70s and the hue spread between low 30s to high 60s. As a result, the current state-of-the-art techniques (e.g., techniques referencing Pantone® color chart) merely provides about 100 or more skin tones and undertones and thus under-represent even Caucasian skin tones and undertones.

As evidenced in FIG. 15A, most of the skin tones are not represented the current state-of-the-art skin tones in cosmetic products despite the fact that cosmetic products have long become a global phenomenon. Various techniques described herein expand the coverage for skin tones and undertones to more than 5,000 different tones to not only provide better coverage for the much wider spread skin tones and undertones provided by the current state-of-the-art techniques but also more accurately represent the fine nuances and distinctions in the skin tones and undertones of various people in order to provide better cosmetic product matching and recommendation services for people around the world.

FIG. 15B illustrates an example comparison between a new foundation library utilized in one or more embodiments described herein and a conventional, industry-standard foundation library. More specifically, FIG. 15B illustrates a comparison between the new skin tone and undertone library and the current state-of-the-art foundation library 1504.

The new skin tone and undertone library provides more than 5,000 distinct color indices or values for product matching and recommendation, whereas the current state-of-the-art foundation library 1504 (e.g., library built upon Pantone® color chart) provides merely 110 color values. Moreover, each color value in the current state-of-the-art foundation library comprises multiple skin tone shades and foundation colors and is thus not useful for a specific client. To further exacerbate the aforementioned shortcomings, the current state-of-the-art foundation library only considers color (e.g., hue). Nonetheless, color is not the only attribute that impacts foundation or undertone preference and/or recommendation. Therefore, the current state-of-the-art foundation library is deficient in at least the aforementioned aspects.

Figure 16A:
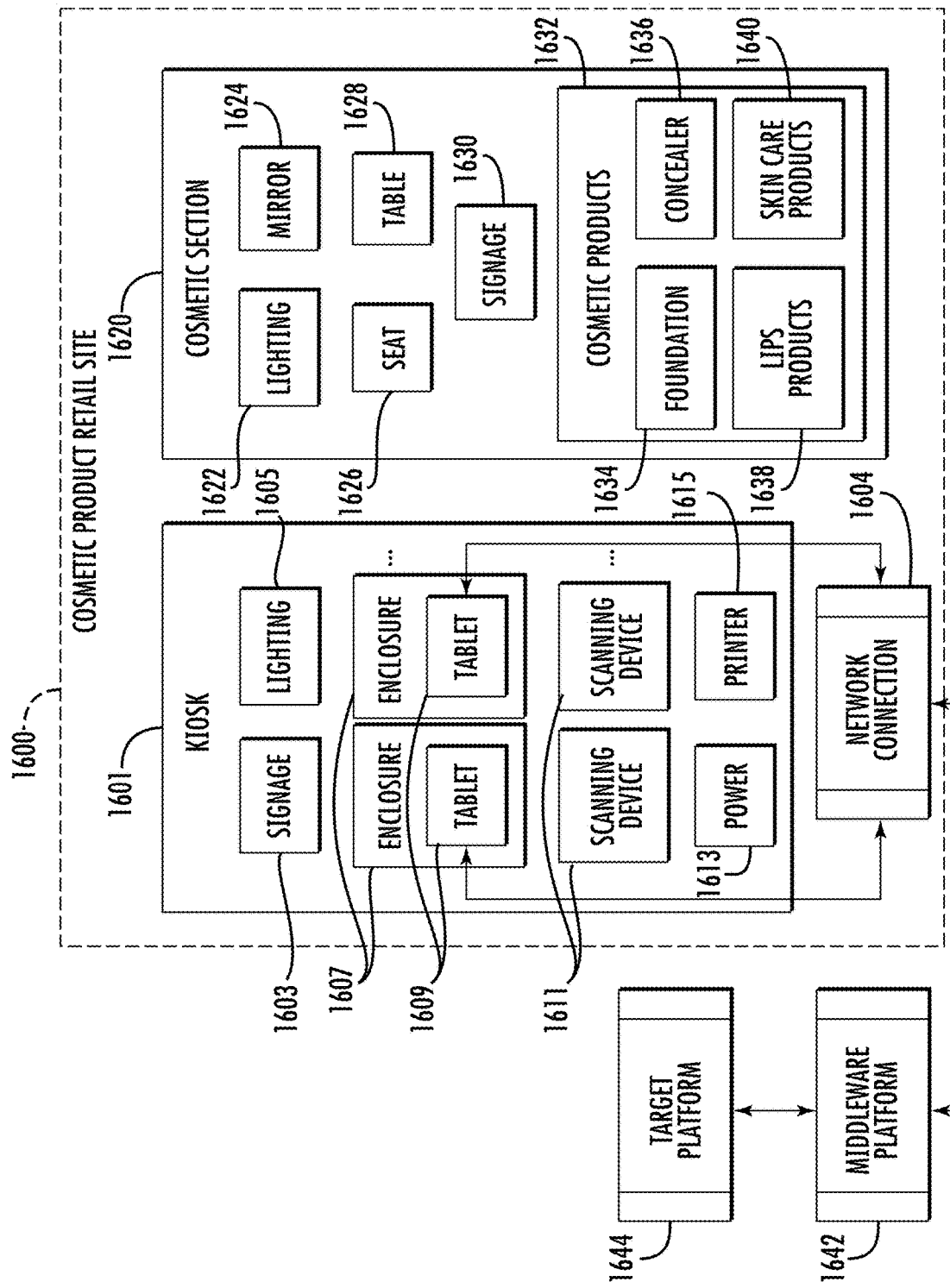
FIG. 16A illustrates a simplified block diagram of a kiosk or station of a system for cosmetic product matching and recommendation in one or more embodiments.

FIG. 16A illustrates a simplified block diagram of a kiosk or station of the system for cosmetic product matching and recommendation in one or more embodiments. The system may include the kiosk (or station or other system) 1601 and some or all of the components in the backend system (e.g., the middle platform 800B and the target platform 800C in FIG. 8A) to leverage various processes, services, and/or microservices (e.g., a first module or model may be implemented as a monolithic software application, a second module or model may be implemented as a collection of services, a third module or model may be implemented as a collection of microservices, etc.) In summary, the system receives inputs from the components in the source platform (e.g., 800A in FIG. 8A), invokes various processes such as the processes performed by the artificial intelligence model or models, the matching service, the product recommendation service, etc. described above with reference to FIGS. 8A-8B to predict a list of matching products or a personalized list of one or more recommendations. The system may further include other components such as the model that performs a mapping between product information and color information, the product catalog service, catalog file or files, various databases and/or knowledge bases, the redistribution layer, or the data platform that support the aforementioned artificial intelligence model or models, the matching service, the product recommendation service, etc. to facilitate the prediction of matching product or products and recommendations.

In some embodiments, a kiosk (or station) 1601 may be part of or located within a larger retail site 1603 that may have more than one kiosk. The retail store may include multiple retailers selling a variety of products, such as in a large department store. The retail store may also include a network connection (e.g., a wireless network connection) 1604. The network connection 1604 connects the mobile computing devices 1609 to the middleware platform 1642 (e.g., 1200B in FIG. 12B) that is in turn operatively coupled to the target platform 1644 (e.g., 1200C in FIG. 12B) described above for performing various processes, services, microservices, etc. described herein. The kiosk includes signage 1603 including information regarding how the system works. For example, the system may describe the benefits of the system, how the system allows selection of proper cosmetic products for a customer, and a brief summary of a methodology of the system. In another implementation, the signage includes brochures or other informational materials that explains the system.

The kiosk may have a counter (or horizontal surface) and a vertical surface (or wall). There may be chairs. Typically, a kiosk is a stationary structure, without wheels, fixed at a location such as a retail site or store. However, in other implementation, a kiosk may include wheels so it may be moved to another location as needed, and the wheels locked to prevent from rolling. The kiosk has a cord that is connected to an electrical outlet to provide power for the components of the kiosk. This cord is typically hidden beneath an enclosure of the booth, to prevent customers tripping over the cord.

In a specific implementation, the kiosk or station may include one or more mobile computing devices (e.g., tablet computers) 1609 in one or more respective enclosures 1607. In other implementation, a kiosk or station may include any number of mobile computing devices, more or fewer than two, such as 1, 3, 4, or more. When a particular store has higher levels of customer traffic, a kiosk may have greater number of mobile computing devices 1609 to handle the anticipated demand. Also, to increase the number of mobile computing devices, there may be multiple kiosks in a store.

The enclosures 1607 are designed to hold the tablet 1609 and protect the mobile computing device 1609 (e.g., from falling onto the floor, theft, or other hazards). The enclosures 1607 may also include a power mechanism so that the mobile computing device 1609 may be charged while the device is in the enclosure. The mobile computing device 1609 may be connected on the wireless network or wired network of the retail site 1600, if one is available. Although mobile computing devices 1609 are specifically discussed in this application, it should be understood that other types computing devices may be used instead, such as desktop computers, notebook computers, smartphones, point of sale (POS) devices, and many others.

In an implementation, the enclosure 1607 includes an arm attached to the kiosk. The arm holds the enclosure and the mobile computing device 1609 viewing surface at a specific angle with respect to the ground surface. For example, with the tablet viewing screen facing upwards, the tablet may be held at approximately 15, 20, 25, 30, 35, 40, 45, or more degrees with respect to the ground. The mobile computing device 1609 is also held above the ground at a specific height. For example, the mobile computing device 1609 may be held at 76, 89, 102, 115, 128, 140, or more centimeters above the ground. Generally, as the height of the mobile computing device 1609 increases, the mobile computing device 1609 may be held at a lower angle (lower number of degrees) with respect to the ground. This allows the mobile computing device 1609 to be used by customers in a variety of positions (e.g., standing, sitting in a chair, sitting in a stool, or other position) while in a comfortable position.

In another implementation, the mobile computing device 1609 angle is an adjustable angle so that clients may adjust the angle when using the mobile computing device 1609. This may be done with the mobile computing device 1609 attached to the kiosk 1601 or temporarily removed from the kiosk 1601. For example, the mobile computing device 1609 is removable from the kiosk 1601 while still in the enclosure 1607. A cable or other device may tether the mobile computing device 1609 to the kiosk 1601 and prevent it from being taken away too far from the kiosk 1601.

In one implementation, the kiosk 1601 includes two scanning devices 1611. The scanning devices 1611 are handheld, and may be used wirelessly. Other implementations of the kiosk 1601 may include more or fewer scanning devices 1611. In other implementation, the kiosk or station 1601 may include any number of scanning devices, more or fewer than two, such as 1, 3, 4, 5, 6, 7, 8, or more. Typically, there are an equal number of scanning devices to the number of mobile computing devices 1609. However, in some implementations, there are fewer scanning device 1611 than mobile computing devices 1609, such as two mobile computing devices 1609 and one scanner 1611, three mobile computing devices 1609 and two scanners 1611, four mobile computing devices 1609 and two scanners 1611, or any other combinations. In other implementations, there are more scanning device 1611 than mobile computing devices 1609, such as two mobile computing devices 1609 and three scanners 1611, three mobile computing devices 1609 and six scanners 1611, four mobile computing devices 1609 and five scanners 1611, or any other combinations.

By adding more mobile computing devices 1609 or scanning devices 1611, more clients may interact with the kiosk 1601 at a given time. By removing mobile computing devices 1609 or scanning devices 1611, a smaller space for the kiosk 1601 is necessary, as well as less maintenance and energy requirements. The kiosk 1601 also includes a power receptacle 1613. The power receptacle 1613 includes an electrical connection so that the mobile computing devices 1609 or scanning device 1611 may be powered or recharged at the kiosk 1601. The kiosk 1601 optionally includes a printer 1615. The printer 1615 may print relevant information for the clients, such as their skin tone identifier or cosmetic products they may be interested in. The kiosk 1601 includes lighting 1605 that illuminates at least one or more portions of the kiosk 1601. This may include illuminating the signage and mobile computing devices 1609 areas.

The kiosk 1601 may be included with an optional cosmetic section 1620. With this section, a beauty advisor or other professional may assist a client or prospective client in trying the cosmetic products suggested by the system in store, before purchase. This section includes cosmetic products, materials, and related items for the customer's trial experience. This includes lighting 1622, mirror 1624, and seat 1626. A table or counter may also be included. The table may be specially designed with drawers of depressions for holding samples and other cosmetic products. The table may include an area to place beauty supplies currently being used. The cosmetic section includes signage 1630 advertising the specific retailer associated with the kiosk 1601 (e.g., the assignee Sephora).

Cosmetic section 1620 may also include cosmetic products 1632. Some examples of these cosmetic products include foundations 1634, concealers 1636, lips products 1638, skin care products 1640, etc. In an implementation, the kiosk 1601 is customized to a geographical location of the kiosk 1601. This means that depending on where the kiosk 1601 is installed, the information on the kiosk is presented in the local language. The system may support French, Chinese, Korean, Japanese, Arabic, Hindi, Russian, German, Italian, or other languages. Signage, the tablet application, and other parts of the systems described may be adapted to use localized languages.

Figure 16B:
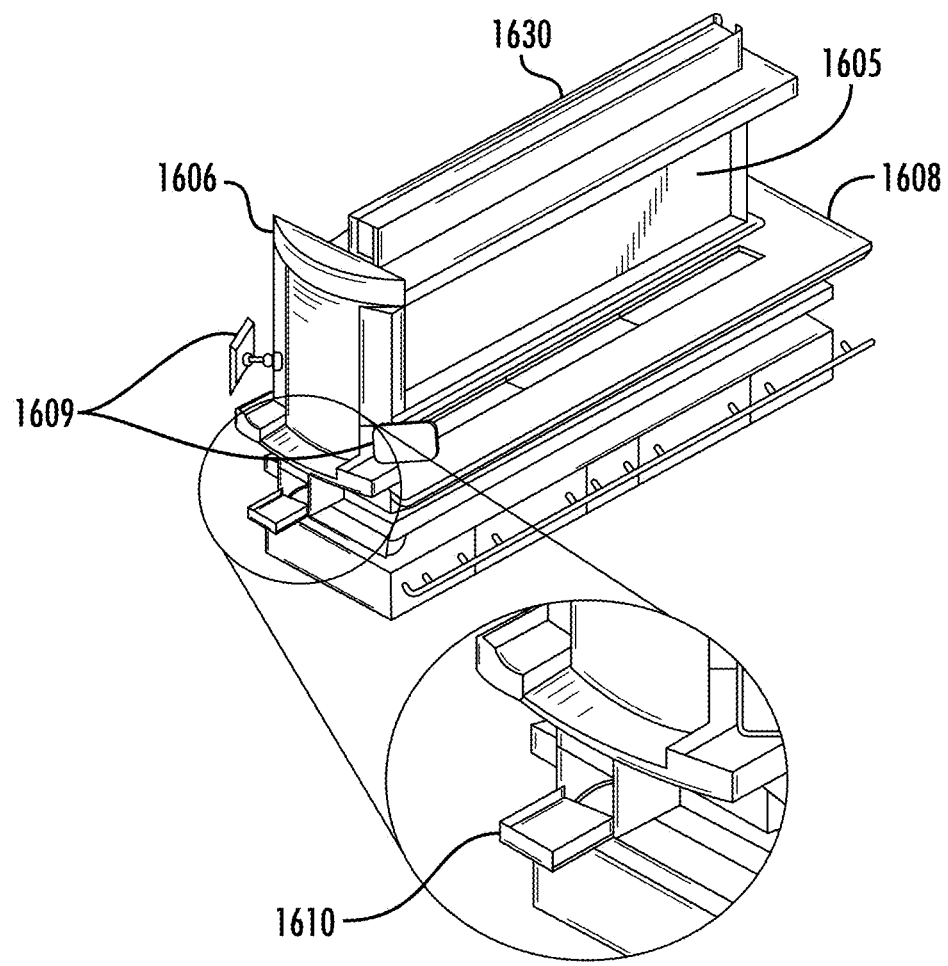
FIG. 16B illustrates a perspective view of an embodiment of a kiosk of a system for cosmetic product matching and recommendation in one or more embodiments.
Figure 16C:
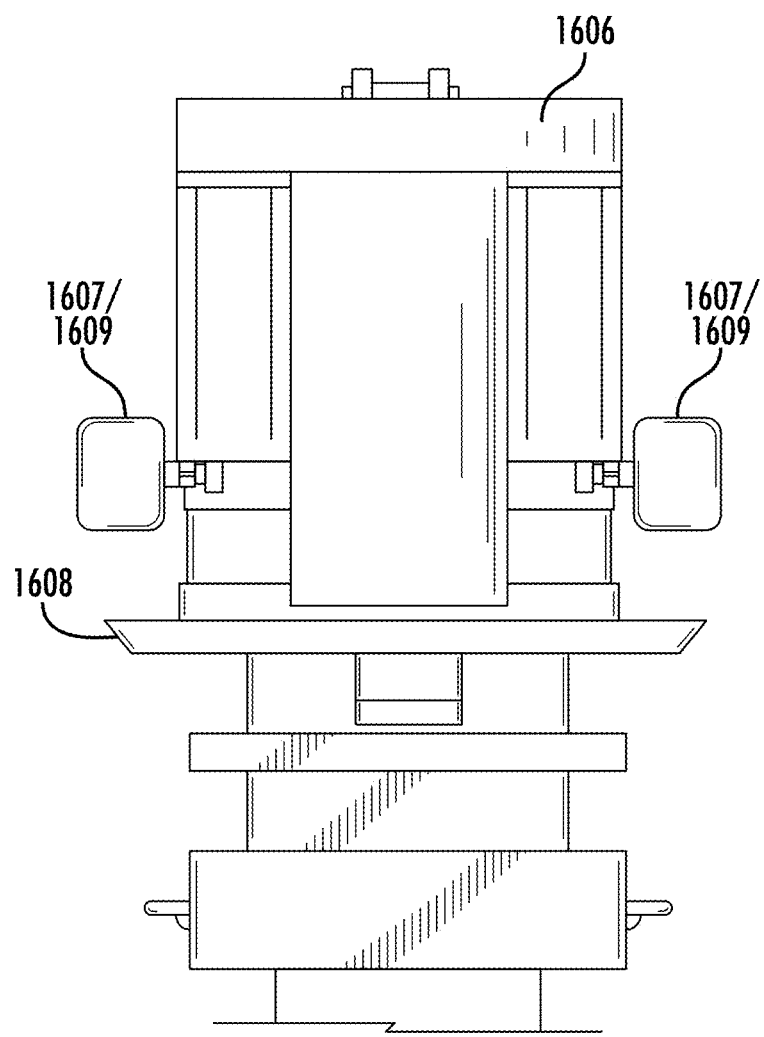
FIG. 16C illustrates a front view of the embodiment of a kiosk of a system for cosmetic product matching and recommendation in one or more embodiments.
Figure 16D:
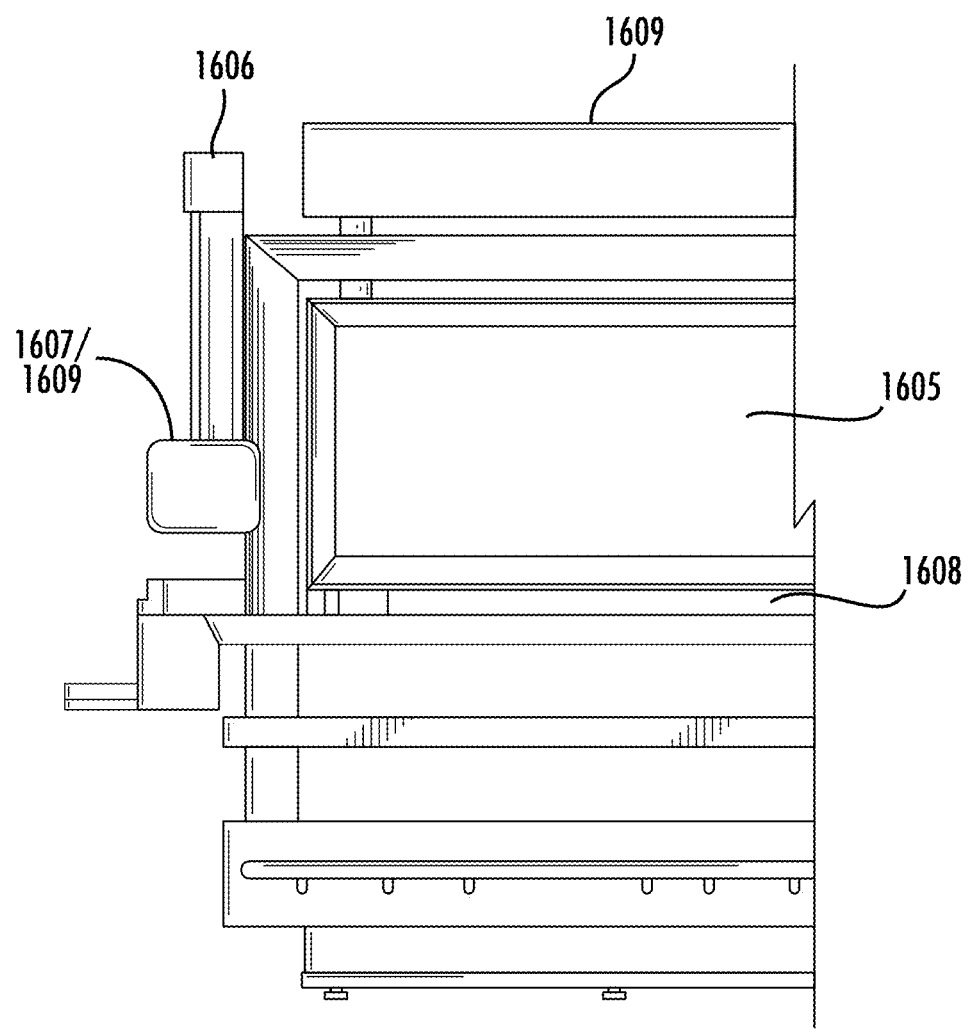
FIG. 16D illustrates a side view of the embodiment of a kiosk of a system for cosmetic product matching and recommendation in one or more embodiments.

FIG. 16B shows a perspective view of an embodiment of a kiosk of the system. FIG. 16C shows a front view of the embodiment of the kiosk of the system. FIG. 16D shows a side view of the embodiment of the kiosk of the system. In this embodiment of the kiosk, the kiosk includes an endcap unit 1606 to a cosmetic section. The endcap unit 1604 may be inserted to an end of the cosmetic section and secured (e.g., using bolts) onto the cosmetic section. The endcap unit 1604 includes at least one tablet 1609 (e.g., two tablets 1609) and signage 1603.

The cosmetic section includes a mirror 1605 and counter or table 1608. The mirror does not necessarily extend along the entire length of the counter, but enough to allow clients to see themselves with their products. A base of the endcap unit 1606 may partially or entirely rest on top of the counter or table 1608. This may help support the weight of the endcap unit 1606 when used with the cosmetic section. While the signage 1630 for the cosmetic section includes a signage 1630 specific to a retailer of the kiosk (e.g., Sephora's "Beauty Studio"), the signage of the endcap unit 1603 includes signage specific to the system (e.g., "Sephora Matching Color IQ"). The endcap unit 1606 includes a compartment 1610 that may be used to hold items for use with the system, such as scanning devices of the system when they are not in use.

Figure 17A:
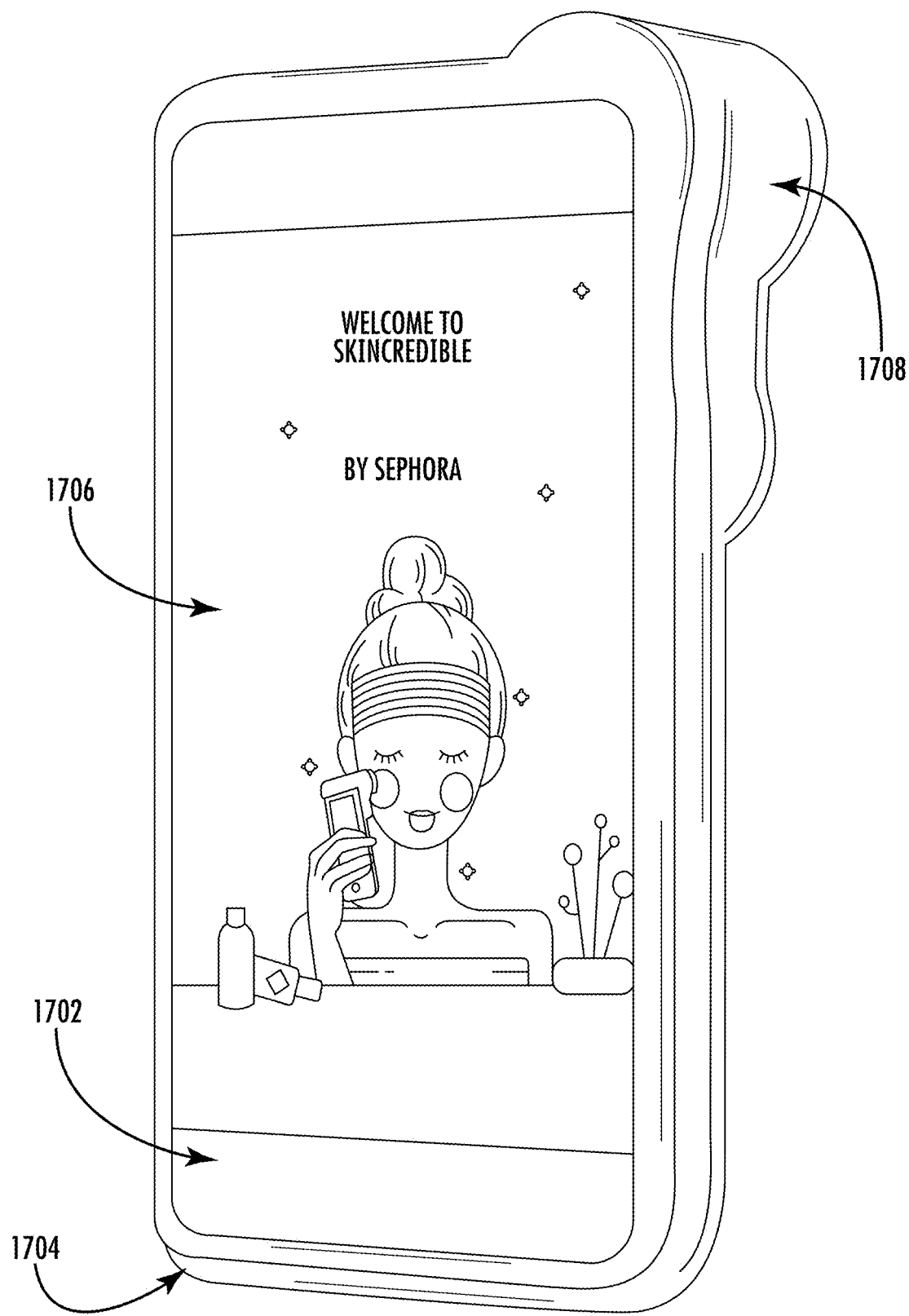
FIG. 17A illustrates a front view of a mobile computing device integrated with a sensor assembly for performing a skin scan in one or more embodiments.

FIG. 17A illustrates a front view of scanning device for performing a skin scan in one or more embodiments. In these one or more embodiments, the scanning device illustrated in FIG. 17A includes a mobile computing device 1702 integrated with a sensor assembly which is described in greater details with reference to FIG. 17B. The mobile computing device 1702 may include a mobile phone, a tablet, or a digital assistant, etc. that is capable of executing an app 1706 (e.g., the aforementioned mobile color iQ app).

The sensor assembly may be integrated within an enclosure 1704 that also accommodates the mobile computing device 1702. For example, the enclosure 1704 may be a device-specific smart phone case with the additional feature 1708 (e.g., a bulged portion as shown in FIG. 17A) that accommodates at least the sensor assembly. In these embodiments, the enclosure 1704 may be devised in such a way to exhibit no or minimal blockage of the on-screen display of the mobile computing device 1702 so that all contents displayed on the screen of the mobile computing device 1702 may still be visible and/or interacted upon after placing the mobile computing device 1702 into the enclosure 1704.

The additional feature 1708 may be devised to align the one or more lenses of the mobile computing device with one or more corresponding lenses in the sensor assembly. In some of these embodiments, the one or more corresponding lenses in the sensor assembly housed in the additional feature 1708 may comprises one or more optical lenses such as a fixed-focal length or variable focal length spherical lens such as a telephoto lens, a macro lens, or a normal lens. In some of these embodiments, a lens of the one or more lenses in the sensor assembly may be aligned with a separate lens of the mobile computing device so that the lens and the separate lens are stacked up in such a way that the stacked-up lenses produce a higher magnification power. For example, a lens having 3× magnification power in the sensor assembly and a separate lens having 2× magnification power, when stacked properly, produce 3×2=6× magnification power. Further, in these embodiments, the entrance pupil of the separate lens on the mobile computing device accommodates the images (or light beams) projected from the separate lens of the sensor assembly to avoid vignetting. In addition or in the alternative, a lens of the aforementioned one or more corresponding lenses in a sensor assembly may include stacked-up lenses (e.g., a pair of teleconverters, a pair of macro lenses, etc.) that not only provides greater magnification power form the stacked-up lenses but may also be aligned with a lens of the mobile computing device to further enhance the greater magnification power. In these embodiments, supplementing or enhancing the magnification power of a camera lens of a mobile computing device by stacking up another lens in the aforementioned sensor assembly also increases the minimum focal distance. As described herein, the focal distance may be addressed by the height or thickness of the protrusion (e.g., 1708 in FIG. 17A) and/or by the software development kit (SDK) that enhances the sharpness of images captured through such stack-up lenses.

In some other embodiments, the one or more corresponding lenses may comprise an optical lens with zero power (e.g., 0.00 glasses) and sufficient optical clarity to allow the one or more corresponding lenses of the mobile computing device to capture images through these one or more corresponding, zero-power lenses with reduced, minimal, or no distortion in geometry or colors. In these later embodiments, the scanning device illustrated in FIG. 17A effectively utilizes the lens(es) of the mobile computing device to capture images for skin scans although it shall be noted that the one or more corresponding lenses in the former embodiments are responsible for capturing images for skin scans. In some of these latter embodiments, the aforementioned optical lens with zero power may not be required so that the enclosure includes one or more openings for the one or more corresponding lenses of the mobile computing device to see through and hence capture images.

Figure 17B:
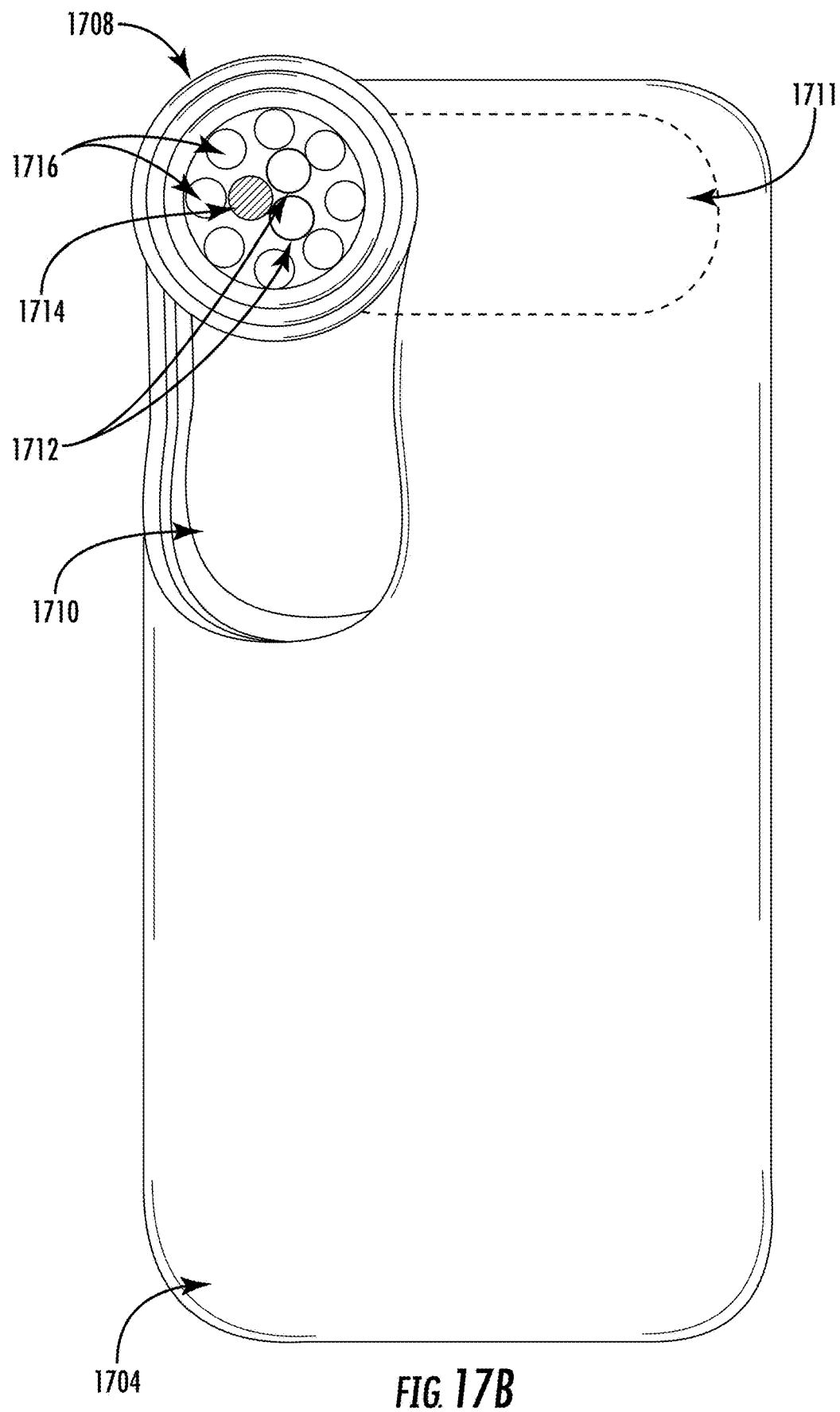
FIG. 17B illustrates a back view of the mobile computing device integrated with a sensor assembly for performing a skin scan illustrated in FIG. 17A in one or more embodiments.

In some embodiments, some or all of the one or more lenses and/or the one or more corresponding lenses may be protected by an optical lens with zero power. The optical lens with zero power not only serves to protect the lens(es) from directly contacting a user's skin but also serves as an anchor or a reference plane or reference point to place the outer surface of the optical lens with zero power against the user's skin for scanning purposes with a proper focal distance in some embodiments. In these embodiments, the one or more lenses or the one or more corresponding lenses may be deemed as being placed against the user's skin for the case of explanation and description. It shall be noted that although FIG. 17A and FIG. 17B illustrate a scanning device with an enclosure that accommodates the aforementioned sensor assembly, the sensor assembly may be separate instrument (e.g., a wand) including the aforementioned sensor assembly in some embodiments. In these embodiments, the separate instrument may be connected to a mobile computing device (e.g., a mobile phone on which the aforementioned mobile color IQ app is installed) or another computing device (e.g., a computer located at a retail store) via wired connection (e.g., via a USB or Ethernet cable) or wireless connection (e.g., Bluetooth®, NFC, Wi-Fi, or any other suitable wireless connections) to facilitate the transmission of instructions and/or data between the separate instrument and the mobile computing device or another computing device. In some embodiments, the separate instrument may include at least one sensor (e.g., an image sensor) having a plurality of sensor elements that stores the data (e.g., pixel data of an image, hydration data, etc.) captured by the sensor assembly and also a controller (e.g., a processor) that performs at least some processing tasks. For instance, the aforementioned controller may check the quality of an image captured by the separate instrument such as whether the image is in focus. In addition or in the alternative, the controller may perform a sharpening algorithm provided by a software development kit or SDK in the sensor assembly to bring an out-of-focus image back to a sharp image as described above.

In some other embodiments, the separate instrument may transmit captured data (e.g., image pixel data in a raw format or a compressed format) to a connected mobile computing device or another connected computing device that performs image processing tasks locally or invokes one or more remotely hosted services to perform such image processing tasks so that the separate instrument acts as a data capturing instrument without having any provisions to perform post-capture processing tasks. In some embodiments where the sensor assembly is housed in an enclosure that also accommodates a mobile computing device as illustrated in FIGS. 17A-17B or is a separate instrument as described immediately above, the connection between a sensor assembly and a mobile computing device (or another computing device) may also provide the capability to update various components (e.g., driver or drivers, the aforementioned SDK, firmware, etc.) of the sensor assembly via the connected mobile computing device (or another connected computing device).

FIG. 17B illustrates a back view of the mobile computing device integrated with a sensor assembly for performing a skin scan illustrated in FIG. 17A in one or more embodiments. More particularly, FIG. 17B illustrates more details about the additional feature 1708 as well as the exposed part of the sensor assembly (e.g., portion of the sensor assembly not covered by the additional feature 1708 of the enclosure 1702. In some embodiments, the additional feature 1708 of the enclosure 1702 includes an elongated portion 1710 that extends along the length direction of the enclosure 1702 or the mobile computing device 1704. In some other embodiments, the additional feature 1708 of the enclosure 1702 includes an elongated portion 1711 that extends along the width direction or any other direction between the length direction and the width direction of the enclosure 1702 or the mobile computing device 1704.

The additional feature 1708 includes an aperture or opening that exposes one or more sensors or other components of the sensor assembly. For example, the sensor assembly may include one or more lenses 1712, a moisture sensor 1714, or any other types of sensors that may be used for skin scan, or any combinations thereof in some embodiments. In these embodiments, the additional feature 1708 may include an aperture to allow the one or more lenses 1712 to capture images through the aperture and/or to allow the moisture sensor to contact the skin of a user. In some embodiments, the additional feature 1708 protrudes from the back of the enclosure 1702 with a thickness that may be devised in such a way that not only for protecting the one or more lenses (e.g., the aforementioned one or more lenses of the mobile computing device or the one or more corresponding lenses of the sensor assembly) from being contaminated (e.g., touching a user's skin) but also for allowing the one or more lenses to properly focus on the skin area of interest.

In addition or in the alternative, the additional feature 1708 protrudes from the back of the enclosure 1702 with a thickness that may be devised in such a way that when the back side of the additional feature 1708 contacts a user's skin, the spacing between the back side of the additional feature 1708 and the moisture sensor provides sufficient contact for the moisture sensor to detect the hydration level of the skin area, unless a user misuses the scanning device by, for example, forcibly pressing the scanning device hard against the skin area.

The aperture in the additional feature 1708 may also allow one or more light sources 1716 to illuminate the skin area for the one or more lens 1712 to capture the image of the skin area. These one or more light sources 1716 may illuminate the skin area to assist auto-focus of the one or more lenses 1712 and/or to provide lit up the skin area of interest for image capture. In some embodiments, the one or more light sources 1716 may include a UVA light source with a wavelength in the range of 315-400 nm and/or a UVB light source with a wavelength in the range of 280-315 nm to illuminate a skin area of interest in order to produce, for example, corneform and proprioni bacteria florescence, if any, for a skin guide scan that produces dermatologist grade results.

The sensor assembly may include a power source (e.g., a battery), a communication chip (e.g., a Bluetooth® or wireless communication chip) to communicate with the mobile communicating device 1702 in some embodiments. In various embodiments illustrated in FIGS. 17A-17B, the system (e.g., a kiosk system deployed at a retail site carrying body care or skin care products or services) may a banner or signage describing textual or graphical information pertaining to determination of skin shades for body care products or services to clients as well as a mobile computing device comprising a memory, a processor operatively coupled to the memory, a display operatively coupled to the processor, and one or more sensors that capture data from an area on a body of a client and transmit the data as a data stream to the processor that processes the data for display on the display.

In addition, the memory of the mobile computing device stores thereupon a sequence of instructions which, when executed by the processor of the mobile computing device, causes execution of a set of acts on the mobile computing device or on one or more remote computing systems, the set of acts comprising receiving, at the mobile computing device, an input pertaining to a body complexion characteristic of the client, wherein the body complexion characteristic is captured by the mobile computing device or derived from the data captured by the mobile computing device; invoking execution of a first artificial intelligence model that predicts a body complexion index at least by executing an extraction service on at least the input to obtain an extraction result and by executing a classification service on the extract result, wherein the body complexion index includes a color index having a plurality of values in a L*A*B* color space or a Lch color space; invoking execution of a second artificial intelligence model that predicts a list of products or services at least by executing a recommendation service based at least in part upon the body complexion index for the client; and displaying, in the user interface of the mobile computing device, information pertaining to the list of products or services.

Some of these embodiments may further include a sensor assembly that further comprises the one or more sensors in the mobile computing device; a wireless communication integrated circuit that connects the sensor assembly with the mobile computing device via, for example, Bluetooth, Wi-Fi, NFC (near field communication protocol), or other suitable wireless communication protocols; input/output electronic circuitry that is operatively coupled to the wireless communication wireless communication integrated circuit to receive input data or instructions from the mobile computing device and to transmit captured data to the mobile communication device; a rechargeable battery that powers at least the wireless communication wireless communication integrated circuit and the input/output (I/O) electronic circuitry; and one or more light sources that are operatively coupled to at least one of the one or more sensors in the sensor assembly and provide a plurality of functions including illuminating a subject area of a body of the client. In some of the immediately preceding embodiments, the one or more light sources comprise a UVA light source emitting first light having a first wavelength in a first range of 315 nm to 400 nm or a UVB light source emitting a second light having a second wavelength in a second range of 280 nm to 315 nm.

In addition or in the alternative, the system in these latter embodiments may further include an enclosure or case that houses the mobile computing device and comprises a first extruded portion extending for a first height from a back side of the enclosure or case and having a first opening that exposes the one or more sensors; a second opening on a front side of the enclosure or case that exposes the display; and a second extruded portion extending for a second height from the back side of the enclosure or case and having a second height from the back side of the enclosure or case that is removably attached to the mobile computing device.

In some of these embodiments, the first extruded portion includes a first compartment that houses at least the one or more sensors and the one or more light sources of the sensor assembly, the second extruded portion includes a second compartment that houses at least one of the wireless communication integrated circuit, the input/output electronic circuitry, or the rechargeable battery, the second extruded portion further comprises a connector that is electrically connected to the rechargeable battery for recharging the rechargeable battery, and the first height is greater than the second height. In some embodiments, the connector for recharging the rechargeable battery may be placed at other locations based at least in part upon the arrangement of components in the sensor assembly.

In some embodiments, the one or more sensors include a telephoto lens having a fixed or variable focal length. The first height is determined based at least in part upon the fixed or variable focal length of the telephoto lens, and the telephoto lens, when a distant end of the first extruded portion opposing the front side of the enclosure or case is in contact with the area on the body of the client, focuses on the area and allows light reflected from the area to be captured by the mobile computing device through the telephoto lens.

In some other embodiments, the one or more sensors include a telephoto lens having a fixed or variable focal length; and the telephoto lens, when a distant end of the first extruded portion opposing the front side of the enclosure or case is in contact with the area on the body of the client, allows light reflected from the area to be captured by the mobile computing device through the telephoto lens to capture an out-of-focus image.

In some embodiments, the system may further comprise an erasable and reprogrammable read-only memory storing thereupon computer program code which, when executed, causes performance of a set of image processing tasks on the out-of-focus image, wherein the set of image processing tasks includes at least one of a sharping mask, an unsharp mask task applying one or more unsharp masks, a shake reduction task, a smart sharpening task, a manual, adjustable sharpening task using a plurality of radius parameters, or an artifact suppression task. In some embodiments, the one or more sensors further comprise a first sensor that is of a contactless type or a contact type and measures a moisture level or one or more conditions of the area on the body of the client.

In some of these embodiments, the first sensor of the contact type comprises a capacitance-based sensor, a conductance-based sensor, an impedance-based sensor, or an electrostatic sensor including a thin silicone sheet covering multiple thin metallic films. The first sensor of the contactless type comprises an electrostatic sensor including a thin silicone sheet and a thin metallic film, an infrared spectroscope-based sensor, or an attenuated total reflection-Fourier transform-based sensor. In some of these immediately preceding embodiments, the first sensor is of the contact type, and the first height of the first extruded portion, when a distant end of the first extruded portion opposing the front side of the enclosure or case is in contact with the area on the body of the client, allows at least a portion of the area on the body of the client to contact the first sensor with a contact pressure that further allows for measuring the moisture level or the one or more conditions of the area on the body of the client.

In addition or in the alternative, the first sensor is of the contactless type, and the first height of the first extruded portion, when a distant end of the first extruded portion opposing the front side of the enclosure or case is in contact with the area on the body of the client, defines a distance between the first sensor and the area on the body of the client to allow the first sensor to capture moisture data or condition data for measuring the moisture level or the one or more conditions of the area on the body of the client in a contactless manner.

In some embodiments, the mobile computing device in the system illustrated in FIGS. 17A-17B may further comprise a first artificial intelligence model that predicts a predicted body characteristic of the area on the body of the client for providing body care to the client; and a second artificial intelligence model that generates a predicted list of products or services for the body care at least by executing a recommendation service on the predicted list of products or services.

In some embodiments, the mobile computing device further comprises a communication integrated circuit that connects the mobile computing device to connect in a wired or wireless manner to a plurality of remote computing devices, and the plurality of remote computing devices comprises a first remote computing device hosting a first artificial intelligence model that predicts a predicted body characteristic of the area on the body of the client for providing body care to the client; the first remote computing device or a second remote computing device hosting a second artificial intelligence model that generates a predicted list of products or services for the body care at least by executing a recommendation service on the predicted list of products or services; and a data lake that is integrated with a plurality of application programming interfaces across multiple computing nodes and multiple mobile computing devices including the mobile computing device and stores multiple types of data for predicting the predicted list of products or services by the first artificial intelligence model and for predicting the personalized recommendation by the second artificial intelligence model.

In some of the immediately preceding embodiments, the mobile computing device further comprises the communication integrated circuit that connects the mobile computing device to connect in the wired or wireless manner to the plurality of remote computing devices, and the plurality of remote computing devices comprises the first remote computing device, the second remote computing device, or a third remote computing device hosting a product catalog service that is operatively coupled to the plurality of mobile computing devices, the first artificial intelligence model, and the second artificial intelligence model, wherein the product catalog service operatively coupled to the first artificial intelligence model to receive first inputs from the plurality of mobile computing devices or a product catalog database, and the product catalog service operatively coupled to the first artificial intelligence model to generate the predicted body characteristic of the part of the body of the client based at least in part on the first inputs received from the plurality of mobile computing devices or the product catalog database.

In some of these embodiments, the product catalog service operatively coupled to the second artificial intelligence model to receive second inputs from the plurality of mobile computing devices or a product catalog database. Moreover, the product catalog service operatively coupled to the second artificial intelligence model to generate the predicted list of products or services for the body care based at least in part on the second inputs received from the plurality of mobile computing devices or the product catalog database.

In some embodiments, the mobile computing device further comprises a communication integrated circuit that connects the mobile computing device to connect in a wired or wireless manner to a plurality of remote computing services, and the plurality of remote computing services comprises a business control center database; a mapping service that is operatively coupled to the business control center database to correlate product information with body care information into correlated product and body care data at least by performing a mapping between the product information of a plurality of body care products in the business control center database and the body care information, wherein the body care information comprises color space data in the L*A*B* color space or a Lch color space; and an enterprise service bus that comprises a correlation database or correlation knowledge base and stores the correlated product and body care data generated by the mapping service.

In some embodiments, the mobile computing device further comprises a communication integrated circuit that connects the mobile computing device to connect in a wired or wireless manner to a plurality of remote computing services, and the plurality of remote computing services comprises a product ingestion processor that distributes inputs received from a correlation database or correlation knowledge base of an enterprise service bus among a distributed processing system that comprises a plurality of stream processing nodes; and a product or user experience management model operatively coupled to the product ingestion processor, wherein the inputs comprise correlated product and body care data that is generated by correlating product information of a plurality of products with body care information, the body care information comprises color space data of a L*A*B* color space or a Lch color space, and the plurality of stream processing nodes respectively processes corresponding streams of the inputs into one or more catalog files.

In some embodiments, the memory of the mobile computing device storing thereupon the sequence of instructions which, when executed by the processor of the mobile computing device, causes execution of the set of acts on the mobile computing device or on one or more remote computing systems. The set of acts further comprises presenting preparation instructions in the display for preparing for a body scan session, wherein the preparation instructions comprise a first preparation instruction to prepare the mobile computing device for the body scan session; presenting preparation instructions in the display for preparing for a body scan session, wherein the preparation instructions comprise a first preparation instruction to prepare the mobile computing device for the body scan session; capturing, by the mobile computing device, body complexion characteristic data for the area on the body of the client, wherein receiving the input comprising receiving, at the computing system, a body complexion index captured by a sensor of a scanning device, and the body complexion index comprises a body tone color index or value for a subject area of a body of the client, and the body tone color index or value for the subject area comprises a plurality of color attribute values in a L*A*B* color space of a Lch color space.

In some embodiments where the memory of the mobile computing device storing thereupon the sequence of instructions which, when executed by the processor of the mobile computing device, causes execution of the set of acts on the mobile computing device or on one or more remote computing systems, the set of acts further comprises receiving, at the user interface, an adjustment instruction that alters a value of a first attribute of a plurality of attributes of the body complexion index into an adjusted value, wherein the body complexion index comprises a body tone color index or value for a subject area of a body of the client, and the plurality of attributes comprises a first attribute pertaining to lightness of the body complexion characteristic of the client, a second attribute pertaining to saturation of the body complexion characteristic of the client, and a third attribute pertaining to undertone of the body complexion characteristic of the client.

This description has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A system comprising:

a banner or signage describing textual or graphical information pertaining to determination of skin shades for body care products or services to clients;

a mobile computing device comprising a memory, a processor operatively coupled to the memory, a display operatively coupled to the processor, and one or more sensors that capture data from an area on a body of a client and transmit the data as a data stream to the processor that processes the data for display on the display; and the memory of the mobile computing device storing thereupon a sequence of instructions which, when executed by the processor of the mobile computing device, causes execution of a set of acts on the mobile computing device or on one or more remote computing systems, the set of acts comprising:

receiving, at the mobile computing device, an input pertaining to a body complexion characteristic of the client, wherein the body complexion characteristic is captured by the mobile computing device or derived from the data captured by the mobile computing device;

invoking execution of a first artificial intelligence model that predicts a body complexion index at least by executing an extraction service on at least the input to obtain an extraction result and by executing a classification service on the extraction result, wherein the body complexion index includes a color index having a plurality of values in a L*a*b* color space or a ligthness, chroma, and hue (LCh) color space;

invoking execution of a second artificial intelligence model that predicts a list of products or services at least by executing a recommendation service based at least in part upon the body complexion index for the client; and displaying, in a user interface of the mobile computing device, information pertaining to the list of products or services.

2. The system of claim 1 further comprising a sensor assembly that further comprises:

the one or more sensors in the mobile computing device;

a wireless communication integrated circuit that connects the sensor assembly with the mobile computing device;

input/output (I/O) electronic circuitry that is operatively coupled to the wireless communication integrated circuit to receive input data or instructions from the mobile computing device and to transmit captured data to the mobile communication device;

a rechargeable battery that powers at least the wireless communication integrated circuit and the input/output (I/O) electronic circuitry; and one or more light sources that are operatively coupled to at least one of the one or more sensors in the sensor assembly and provide a plurality of functions including illuminating the area on the body of the client.

3. The system of claim 2, wherein the one or more light sources comprise an ultraviolet (UVA) light source emitting a first light having a first wavelength in a first range of 315 nanometers to 400 nanometers or an ultraviolet (UVB) light source emitting a second light having a second wavelength in a second range of 280 nanometers to 315 nanometers.

4. The system of claim 2 further comprising an enclosure or case that houses the mobile computing device and comprises:

a first extruded portion extending for a first height from a back side of the enclosure or case and having a first opening that exposes the one or more sensors;

a second opening on a front side of the enclosure or case that exposes the display; and a second extruded portion extending for a second height from the back side of the enclosure or case and having the second height from the back side of the enclosure or case that is removably attached to the mobile computing device.

5. The system of claim 4 wherein the first extruded portion includes a first compartment that houses at least the one or more sensors and the one or more light sources of the sensor assembly, the second extruded portion includes a second compartment that houses at least one of the wireless communication integrated circuit, the input/output (I/O) electronic circuitry, or the rechargeable battery, the second extruded portion further comprises a connector that is electrically connected to the rechargeable battery for recharging the rechargeable battery, and the first height is greater than the second height.

6. The system of claim 4 wherein the one or more sensors include a telephoto or macro lens having a fixed or variable focal length, the first height is determined based at least in part upon the fixed or variable focal length of the telephoto or macro lens, and the telephoto or macro lens, when a distal end of the first extruded portion opposing the front side of the enclosure or case is in contact with the area on the body of the client, focuses on the area and allows light reflected from the area to be captured by the mobile computing device through the telephoto or macro lens.

7. The system of claim 4 wherein the one or more sensors include a telephoto or macro lens having a fixed or variable focal length, and the telephoto or macro lens, when a distal end of the first extruded portion opposing the front side of the enclosure or case is in contact with the area on the body of the client, allows light reflected from the area to be captured by the mobile computing device through the telephoto or macro lens to capture an out-of-focus image.

8. The system of claim 7 further comprising an erasable and reprogrammable read-only memory storing thereupon computer program code which, when executed, causes performance of a set of image processing tasks on the out-of-focus image, wherein the set of image processing tasks includes at least one of a sharpening mask, an unsharp mask task applying one or more unsharp masks, a shake reduction task, a smart sharpening task, a manual, adjustable sharpening task using a plurality of radius parameters, or an artifact suppression task.

9. The system of claim 4 wherein the one or more sensors further comprise a first sensor that is of a contactless type or a contact type and measures a moisture level or one or more conditions of the area on the body of the client.

10. The system of claim 4 wherein the first sensor of the contact type comprises:

a capacitance-based sensor, a conductance-based sensor, or a first electrostatic sensor including a first thin silicone sheet covering multiple thin metallic films, or the first sensor of the contactless type comprises:
a a second electrostatic sensor including a second thin silicone sheet and a thin metallic film,
an infrared spectroscope-based sensor, or
an attenuated total reflection-Fourier transform-based sensor.

11. A method of providing personalized body care for a client in a user interface, comprising:
displaying, in a user interface of a computing device, an instructional display portion comprising one or more textual or graphical instructions pertaining to preparing for a body scan for body care of a client;
displaying, in the user interface, a scan initiation display portion that comprises a scan initiation widget which, when interacted by the client, invokes execution of a scan process and an analysis process for a respective body area of the client;
executing the body scan at least by transmitting a signal and a stream of data to a scanning device, based at least in part on a client interaction with the scan initiation widget;
displaying, in the user interface, a scan result display portion comprising interactable textual or graphical information pertaining to a result of the body scan for the body care; and
displaying, in the user interface, a plurality of adjustment widgets in an adjustment display portion of the user interface, wherein
at least one adjustment widget of the plurality of adjustment widgets, when interacted upon by the client, transforms a color index or value into a transformed color index or value by altering at least one color attribute of a plurality of color attributes in a L*a*b* color space or a lightness, chroma, and hue (LCh) color space, and
the plurality of color attributes includes a first color attribute, a second color attribute, and a third color attribute that pertains to a complexion of the respective body area in the result of the body scan in the L*a*b* color space or the LCh color space.

12. The method of claim 11 wherein the first color attribute pertains to lightness of the complexion and comprises a first value for a first color component of three color components in the L*a*b* color space or the LCh color space, a second color attribute pertains to undertone of the complexion of the client and comprises a second value for a second color component or a third color component of the three color components in the L*a*b* color space or the LCh color space, and a third color attribute pertains to saturation of the complexion of the client and comprises a third value for the second color component or the third color component of the three color components in the L*a*b* color space or the LCh color space.

13. The method of claim 11 further comprising:
displaying, in the user interface, an interview display portion comprising a response widget which, when interacted upon by the client, identifies a response of the client to an interview question that pertains to the body care and is displayed in the interview display portion, wherein the interview question pertains to whether ethnicity of the client is of a Hispanic or Middle Eastern origin or to whether the complexion pertains to an olive undertone.

14. The method of claim 11 wherein
the body scan comprising a plurality of body scans of respective body areas of the client, and
the body scan of a respective body area comprises capturing an image of the respective body area and predicting a characteristic of the respective body area at least by performing an analysis process on the image.

15. The method of claim 11, wherein
the scan process captures an image of the respective body area of the client, and
the analysis process predicts one or more characteristics of the respective body area at least by performing an analysis on the image using one or more artificial intelligence models.

16. The method of claim 15, wherein
the one or more characteristics comprise a body tone color index or value one or more body features in the respective body area, and
the one or more body features in the respective body area including a first image feature recognized as a hair on the respective body area, a second image feature recognized as a freckle on the respective body area, a third image feature recognized as a wrinkle on the respective body area, or a fourth image feature recognized as a color spot other than freckles.

17. The method of claim 16 wherein
the result of the body scan comprises a list of one or more predicted matching products or a list of one or more predicted recommendations, and
a predicted recommendation in the list of one or more predicted recommendations comprises an interactable product widget for a product in the list of one or more predicted matching products that is predicted by using at least one of the one or more artificial intelligence models.

18. The method of claim 14 wherein
the result of the body scan comprises a body tone color index or value that is predicted with at least one artificial intelligence model of the one or more artificial intelligence models that analyzes the image of the respective body area in the image.

19. The method of claim 11 wherein
the body scan includes at least one of a body tone scan or a digital body guide scan,
the body tone scan includes a skin tone scan, a nail tone scan, or a hair guide scan, and
the digital body guide scan includes a skin guide scan, a hair guide scan, or a nail guide scan.

20. The method of claim 11, further comprising:
identifying a plurality of colors in the L*a*b* color space or the LCh color space in a color chart or file;
reducing a plurality of colors into a reduced set of colors;
determining the result of the body scan for the body care using only the reduced set of colors; and
displaying, in the scan result display portion in the user interface, the result of the body scan.

* * * * *